US011124498B2

(12) United States Patent
Fischbach et al.

(10) Patent No.: US 11,124,498 B2
(45) Date of Patent: Sep. 21, 2021

(54) COMPOSITIONS AND METHODS FOR MODULATING PROTEASE ACTIVITY

(71) Applicants: THE REGENTS OF THE UNIVERSITY OF CALIFORNIA, Oakland, CA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Michael A. Fischbach, San Francisco, CA (US); Chun-Jun Guo, San Francisco, CA (US); Christopher A. Voigt, Belmont, MA (US); Fang-Yuan Chang, Somerville, MA (US); Jon Clardy, Boston, MA (US); Thomas Wyche, Chelsea, MA (US)

(73) Assignees: THE REGENTS OF THE UNIVERSITY OF CALIFORNIA, Oakland, CA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/462,460

(22) PCT Filed: Nov. 15, 2017

(86) PCT No.: PCT/US2017/061840
§ 371 (c)(1),
(2) Date: May 20, 2019

(87) PCT Pub. No.: WO2018/097999
PCT Pub. Date: May 31, 2018

(65) Prior Publication Data
US 2020/0048227 A1 Feb. 13, 2020

Related U.S. Application Data

(60) Provisional application No. 62/426,012, filed on Nov. 23, 2016.

(51) Int. Cl.
| C07D 403/14 | (2006.01) |
| C07C 237/20 | (2006.01) |
| C07D 403/12 | (2006.01) |
| C07C 323/60 | (2006.01) |
| C07D 241/18 | (2006.01) |
| C07D 241/12 | (2006.01) |
| C07D 403/06 | (2006.01) |

(52) U.S. Cl.
CPC .......... *C07D 403/14* (2013.01); *C07C 237/20* (2013.01); *C07C 323/60* (2013.01); *C07D 241/12* (2013.01); *C07D 241/18* (2013.01); *C07D 403/06* (2013.01); *C07D 403/12* (2013.01)

(58) Field of Classification Search
CPC .. C07D 403/14; C07D 403/12; C07D 241/18; C07D 241/12; C07D 403/06; C07C 237/20; C07C 323/60
USPC ........................................................ 514/255
See application file for complete search history.

(56) References Cited

U.S. PATENT DOCUMENTS

| 4,472,380 | A | 9/1984 | Harris et al. |
| 6,251,917 | B1 | 6/2001 | Lubisch et al. |
| 2007/0232527 | A1 | 10/2007 | Ghosal et al. |
| 2008/0004286 | A1 | 1/2008 | Wang et al. |
| 2013/0039930 | A1* | 2/2013 | Alitalo .................... A61P 35/00 424/174.1 |

OTHER PUBLICATIONS

L. Jayashankar et al., Analog based studies on Cathepsin B inhibitors for the treatment of Cancer, Internet Electronic Journal of Molecular Design, (2009), 8(3), 29-41.*
Takumi Watanabe et al., Synthesis of Boronic acid Derivatives of Tyropeptin Protease inhibitors, Bioorganic and Medicinal Chemistry Letters (2009), 19(8), 2343-2345.*
Adams, J. et al. (Feb. 17, 1998). "Potent and selective inhibitors of the proteasome: dipeptidyl boronic acids," *Bioorg Med Chem Lett* 8(4):333-338.
Aoyagi, T. et al. (Jun. 1969). "Leupeptins, new protease inhibitors from Actinomycetes," *J Antibiot* 22(6):283-286.
Aoyagi, T. et al. (Nov. 1969). "Biological activities of leupeptins," *J Antibiot* 22(11):558-568.
Backus, K.M. et al. (Jun. 23, 2016, e-published Jun. 15, 2016). "Proteome-wide covalent ligand discovery in native biological systems," *Nature* 534(7608):570-574.
Berge, S.M. et al. (Jan. 1977). "Pharmaceutical salts," *J Pharm Sci* 66(1):1-19.
Blättner, S. et al. (Sep. 15, 2016). "*Staphylococcus aureus* Exploits a Non-ribosomal Cyclic Dipeptide to Modulate Survival within Epithelial Cells and Phagocytes," *PLoS Pathog* 12(9):e1005857.
Donia, M.S. et al. (Sep. 11, 2014). "A systematic analysis of biosynthetic gene clusters in the human microbiome reveals a common family of antibiotics," *Cell* 158(6):1402-1414.
Donia, M.S. et al. (Jul. 24, 2015, e-published Jul. 23, 2015). "Human Microbiota. Small molecules from the human microbiota," *Science* 349(6246):1254766.

(Continued)

*Primary Examiner* — Tracy Vivlemore
*Assistant Examiner* — Ebenezer O Sackey
(74) *Attorney, Agent, or Firm* — Mintz, Levin, Cohn, Ferris, Glovsky and Popeo, P.C.; Kenneth E. Jenkins; Joohee Lee

(57) ABSTRACT

Disclosed herein, inter alia, are compositions for modulating protease activity and treating cancer.

20 Claims, 20 Drawing Sheets
Specification includes a Sequence Listing.

(56) References Cited

OTHER PUBLICATIONS

Franzosa, E.A. et al. (Jun. 3, 2014, e-published May 19, 2014). "Relating the metatranscriptome and metagenome of the human gut," *PNAS USA* 111(22):E2329-2338.

Fung, T.C. et al. (Jul. 2014). "Anatomical localization of commensal bacteria in immune cell homeostasis and disease," *Immunol Rev* 260(1):35-49.

Gosalbes, M.J. et al. (Mar. 8, 2011). "Metatranscriptomic approach to analyze the functional human gut microbiota," *PLoS One* 6(3):e17447.

Guo, C.J. et al. (Jan. 26, 2017, e-published Jan. 19, 2017). "Discovery of Reactive Microbiota-Derived Metabolites that Inhibit Host Proteases," *Cell* 168(3):517-526.

Hershberg, R.M. et al. (Jul. 1, 1997). "Intestinal epithelial cells use two distinct pathways for HLA class II antigen processing," *J Clin Invest* 100(1):204-215.

International Search Report dated Apr. 6, 2018, for PCT Application No. PCT/US2017/061840, filed Nov. 15, 2017, 5 pages.

Katunuma, N. (2011). "Structure-based development of specific inhibitors for individual cathepsins and their medical applications," Proc Jpn Acad Ser B 87:29-39.

Laine, D.I. et al. (Apr. 2010). "Inhibitors of cathepsin C (dipeptidyl peptidase I)," *Expert Opin Ther Pat* 20(4):497-506.

Lee, D.H. et al. (Oct. 1998). "Proteasome inhibitors: valuable new tools for cell biologists," *Trends Cell Biol* 8(10):397-403.

Lee, W.J. et al. (Jun. 2014, e-published May 16, 2014). "Gut microbiota-generated metabolites in animal health and disease," *Nat Chem Biol* 10(6):416-424.

MacDonald, J.C. et al. (1976). "$^{13}$C and Proton NMR Spectra of 2(1H)Pyrazinones," *Tetrahedron* 32:655-660.

Maslowski, K.M. et al. (Oct. 29, 2009). "Regulation of inflammatory responses by gut microbiota and chemoattractant receptor GPR43," *Nature* 461(7268):1282-1286.

Matsumoto, F. et al. (Mar. 14, 2008, e-published Dec. 31, 2007). "Cathepsins are required for Toll-like receptor 9 responses," *Biochem Biophys Res Commun* 367(3):693-699.

Medema, M.H. et al. (May 2013, e-published Feb. 14, 2013). "Detecting sequence homology at the gene cluster level with MultiGeneBlast," *Mol Biol Evol* 30(5):1218-1223.

Mehdi, S. et al. (Dec. 30, 1988). "Inhibition of the proteolysis of rat erythrocyte membrane proteins by a synthetic inhibitor of calpain," *Biochem Bioophys Res Commun* 157(3):117-1123.

Nayfach, S. et al. (Oct. 15, 2015, e-published Jun. 22, 2015). "MetaQuery: a web server for rapid annotation and quantitative analysis of specific genes in the human gut microbiome," *Bioinformatics* 31(20):3368-3370.

Nicholson, J.K. et al. (Jun. 8, 2012, e-published Jun. 6, 2016). "Host-gut microbiota metabolic interactions," *Science* 336(6086):1262-1267.

Nielsen, H.B. et al. (Aug. 2014, e-published Jul. 6, 2014). "Identification and assembly of genomes and genetic elements in complex metagenomic samples without using reference genomes," *Nat Biotechnol* 32(8):822-828.

Obata, T. et al. (Apr. 20, 2010, e-published Apr. 1, 2010). "Indigenous opportunistic bacteria inhabit mammalian gut-associated lymphoid tissues and share a mucosal antibody-mediated symbiosis," *PNAS USA* 107(16):7419-7424.

Otto, H.H. et al. (Feb. 5, 1997). "Cysteine Proteases and Their Inhibitors," *Chem Rev* 97(1):133-172.

Park, B. et al. (Dec. 2008). "Proteolytic cleavage in an endolysosomal compartment is required for activation of Toll-like receptor 9," *Nat Immunol* 9(12):1407-1414.

Quan, J. et al. (Jul. 30, 2009). "Circular polymerase extension cloning of complex gene libraries and pathways," *PLoS One* 4(7):e6441.

Reuter, K. et al. (Dec. 1999). "Crystal structure of the surfactin synthetase-activating enzyme sfp: a prototype of the 4'-phosphopantetheinyl transferase superfamily," *EMBO J* 18(23):6823-6831.

Rosenberger, C.M. et al. (May 2003). "Phagocyte sabotage: disruption of macrophage signalling by bacterial pathogens," *Nat Rev Mol Cell Biol* 4(5):385-396.

Siklos, M. et al. (Nov. 2015, e-published Sep. 26, 2015). "Cysteine proteases as therapeutic targets: does selectivity matter? A systematic review of calpain and cathepsin inhibitors," *Acta Pharm Sin B* 5(6):506-519.

Thompson, R.C. et al. (Jan. 1973). "Use of peptide aldehydes to generate transition-state analogs of elastase," *Biochemistry* 12(1):47-51.

Weerapana, E. et al. (Dec. 9, 2010, e-published Nov. 17, 2010). "Quantitative reactivity profiling predicts functional cysteines in proteomes," *Nature* 468(7325):790-795.

Westerik, J.O. et al. (Dec. 25, 1972). "Aldehydes as inhibitors of papain," *J Biol Chem* 247(24):8195-8197.

Woo, J-T. et al. (Jul. 20, 1995). "Peptidyl aldehyde derivatives as potent and selective inhibitors of cathepsin L," *Bioorganic & Medicinal Chemistry Letters* 5(14):1501-1504.

Written Opinion dated Apr. 6, 2018, for PCT Application No. PCT/US2017/061840, filed Nov. 15, 2017, 5 pages.

Wyatt, M.A. et al. (Aug. 2013, e-published Jan. 2, 2013). "Optimizing dimodular nonribosomal peptide synthetases and natural dipeptides in an *Escherichia coli* heterologous host," *Biochem Cell Biol* 91(4):203-208.

Wyatt, M.A. et al. (Nov. 5, 2012, e-published Oct. 15, 2012). "Heterologous expression and structural characterisation of a pyrazinone natural product assembly line," *Chembiochem* 13(16):2408-2415.

Zimmerman, M. et al. (Sep. 24, 2010). "A family of pyrazinone natural products from a conserved nonribosomal peptide synthetase in *Staphylococcus aureus*," *Chem Biol* 17(9):925-930.

\* cited by examiner

| | Cat B | Cat L | Cat C | Cat S | Calpain I | Proteasome | Trypsin | Chymotrypsin |
|---|---|---|---|---|---|---|---|---|
| | 2.8 | 0.006 | 0.5 | 2 | 1.0 | >30 | N/O | N/O |
| | 46.0 | 0.006 | 8 | 0.9 | 1.5 | >30 | N/O | N/O |
| | 9.4 | 0.005 | >20 | 0.6 | N/O | >30 | N/O | N/O |
| 16 | 0.38 | N/O | 0.37 | 0.013 | 1.3 | 2.8 | N/O | >30 |

FIG. 6A
FIG. 6B
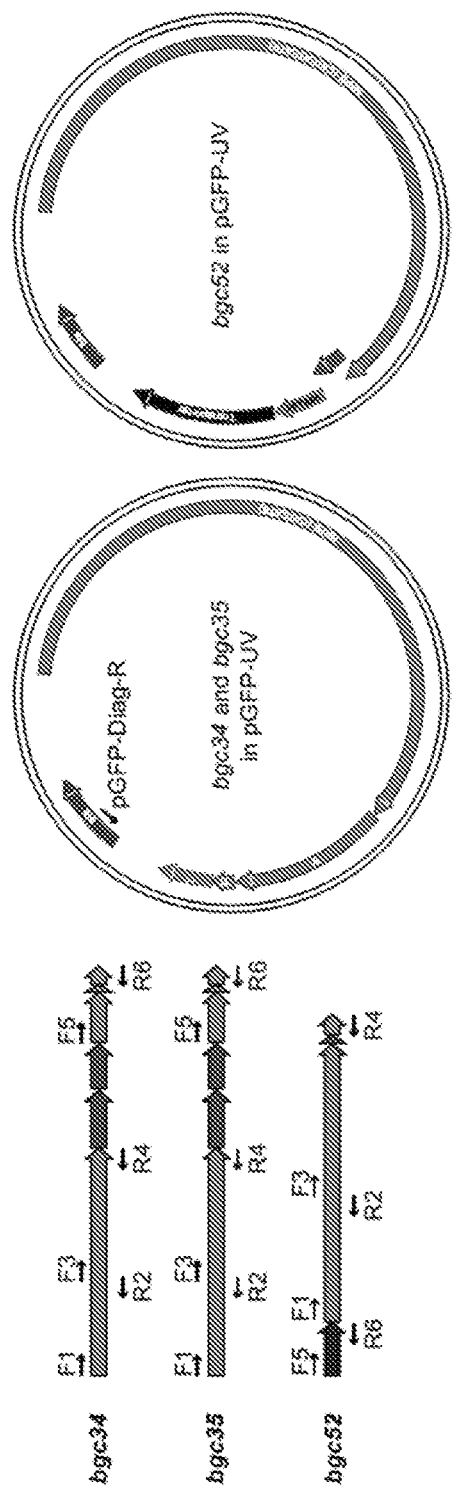
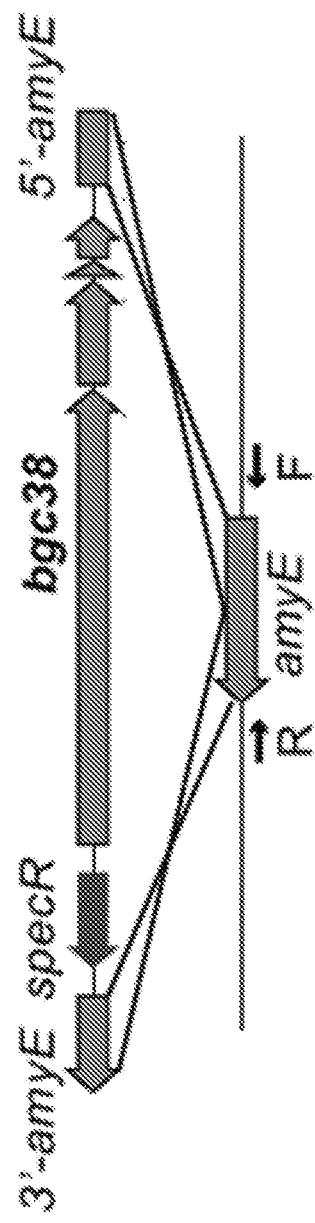

i. Reaction EIC(+) 249.16, 229.13, 231.15 ii. Bgc52 EIC(+) 229.13 iii. Reaction EIC(+) 263.18, 243.15, 245.17 iv. Bgc52 EIC(+) 243.15 v. Reaction EIC(+) 297.16, 277.13, 279.15 vi. Bgc35 EIC(+) 277.13

Time (min)

SEQUENCE LISTING

<160> NUMBER OF SEQ ID NOS: 35

<210> SEQ ID NO 1
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 1
cacacaggaa acagctatgg attttggagg gataacagt          39

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
cagcaccagc tcaataaaca          20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 3
tgtttattga gctggtgctg                                              20

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
ttgccttccc ccttctca                                                18

<210> SEQ ID NO 5
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 5
taagacgtga aaggggggaa ggcaaaaaat gaagaattttt ccacg                 45

<210> SEQ ID NO 6
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 6
accggcgctc agttggaatt caagcatttt cataataaa                         39

<210> SEQ ID NO 7
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 7
cacacaggaa acagctatgc ataatagaca gcgtctcc                          38

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
gccaataagc gtaatccaga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gggacgtgga ttatctggat                                              20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
ccgcccgctt tagtgggcat                                          20

<210> SEQ ID NO 11
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 11
atgcccacta aagcgggcgg atgaaaaatt tcccgcgca                     39

<210> SEQ ID NO 12
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 12
accggcgctc agttggaatt cactgtgttt cgtaatgaa                     39

<210> SEQ ID NO 13
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 13
cacacaggaa acagctatga aaatattaa tgaaagg                        37

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
agagatgtac catcggcaac                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
tggaccttca ccacattgtt                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 16
tcatacataa atatcgtcga                                                    20

<210> SEQ ID NO 17
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 17
tcgacgatat ttatgtatga atggaagaga gaaataacag                              40

<210> SEQ ID NO 18
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 18
accggcgctc agttggaatt caaaaagata ttatggtatt at                           42

<210> SEQ ID NO 19
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 19
cagtcagtgg tctcacatat ggctgccgcg cg                                      32

<210> SEQ ID NO 20
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 20
cagtcagtgg tctcaaagtc gacaagcttg cggcc                                   35

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
tgcatgtgtc agaggttttc                                                    20

<210> SEQ ID NO 22
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 22
cctggtgccg cgcggcagcc atatgcataa tagacagcgt ctccctgagg g                 51
```

<210> SEQ ID NO 23
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 23
gagtgcggcc gcaagcttgt cgacttattc accggaaaaa agtccggc          48

<210> SEQ ID NO 24
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 24
gtcgacaagc ttgcggccg                                           19

<210> SEQ ID NO 25
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 25
catatggctg ccgcgcgg                                            18

<210> SEQ ID NO 26
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 26
cctggtgccg cgcggcagcc atatgcataa tagacagcgt ctccctgagg g       51

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 27
tgtgggcttt gccgcgttta ccc                                      23

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
ttgcagacgg aaagaaccgc                                          20

<210> SEQ ID NO 29
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 29
catgatgttt gccatttta tagtggaaag                                    30

<210> SEQ ID NO 30
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 30
ttggcggtac acagtacc                                                18

<210> SEQ ID NO 31
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 31
catagctgtt tcctgtgtga aattg                                        25

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 32
cctgcgccgg aggaaaag                                                18

<210> SEQ ID NO 33
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 33
ggcggggaaa aggaagcg                                                18

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
aactggacac atggaaacac                                              20

<210> SEQ ID NO 35
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 35
ccgctccagc tttattgt                                                18

COMPOSITIONS AND METHODS FOR MODULATING PROTEASE ACTIVITY

CROSS-REFERENCES TO RELATED APPLICATIONS

This application is the national stage filing under USC 371 of international application PCT/US2017/061840, filed Nov. 15, 2017, which claims the benefit of U.S. Provisional Application No. 62/426,012, filed Nov. 23, 2016, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. OD007290, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-590N01US_ST25.txt, created May 19, 2019, 7,450 bytes, machine format IBM-PC, MS Windows operating system, is hereby incorporated by reference.

BACKGROUND

The human microbiome contains genome information of thousands of microorganisms which reside on the surface or inside a human body. In the past decade, significant progress has been achieved in sequencing and assembling the genome information of these human-associated isolates. Numerous biosynthetic gene clusters (BGCs) in bacterial genome sequences are harbored in human microbiota, encoding a large variety of small molecules like ribosomally synthesized and post-translationally modified peptides (RiPPS), polysaccrides, polyketides (PKS), and nonribosomal peptides (NRPS). NRPs are a group of natural products biosynthesized by modular NRP synthetases (NRPSs). Limited numbers of NRPSs have been found to be related to any microbial host interaction. Understanding the small molecule products of these genetic elements represent large gaps in our knowledge of what the microbiota are capable of producing, and moreover represent potential therapeutics. Disclosed herein, inter alia, are solutions to these and other problems in the art.

BRIEF SUMMARY OF THE INVENTION

In an aspect is provided a compound, or pharmaceutically acceptable salt thereof, having the formula:

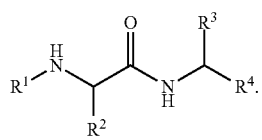

(I)

$R^1$ is independently hydrogen, halogen, —C(O)$R^{1C}$, —C(O)—OR$^{1C}$, —C(O)NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, and $R^{1C}$ are each independently hydrogen, —CF$_3$, —CI$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ are independently an amino acid side chain. $R^4$ is —C(O)H, or —B(OH)$_2$. In embodiments, when $R^4$ is —B(OH)$_2$, $R^1$ is not

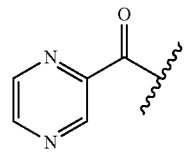

In an aspect is provided a compound, or pharmaceutically acceptable salt thereof, having the formula:

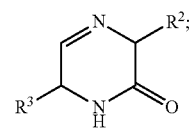

(IIa)

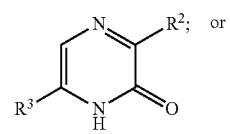

(IIb)

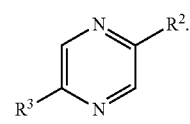

(IIc)

$R^2$ and $R^3$ are independently an amino acid side chain.

In an aspect is provided a pharmaceutical composition comprising a compound as described herein and a pharmaceutically acceptable excipient.

In an aspect is provided a method of treating cancer, the method including administering to a subject in need thereof an effective amount of a compound as described herein.

In an aspect is provided a method of inhibiting protease activity, the method including contacting the protease with a compound as described herein.

In an aspect is provided a method of inhibiting cathepsin activity, the method including contacting the cathepsin with a compound as described herein.

In an aspect is provided a method of reducing cathepsin activity, the method including contacting the cathepsin with a compound as described herein.

In another aspect, there is provided a method of reducing a harmful bacterial load of a subject in need thereof. The method includes administering to the subject an effective amount of a compound as described herein and embodiments thereof disclosed herein.

In another aspect, there is provided a method of promoting growth of a microbial population in a subject in need thereof. The method includes administering to the subject an effective amount of a compound as described herein and embodiments thereof disclosed herein.

In embodiments, the microbial population is beneficial to the subject's health relative (e.g., gastrointestinal health, reduces risk of acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases, malnutrition, or obesity) to the absence administering the compound.

BRIEF DESCRIPTION OF THE DRAWINGS

FIG. 2B: HPLC or LC-MS profiles showing the production of each molecule in Escherichia coli or Bacillus subtilis. From top left, E. coli DH10β (Ec); and Ec expressing bgc34, bgc35, and bgc52, as detected by UV absorption at 300 nm. B. subtilis 168 sfp+ (Bs); and Bs expressing bgc38 and bgc39, as detected by UV absorption at 360 nm. E. coli BAP1 (Ec) and Ec expressing bgc33; extracted ion chromatograms for the indicated masses are shown. FIG. 2C: In vitro reconstitution of the bgc35 NRPS. From top right, HPLC profiles of organic extracts of the reaction without adding the enzyme (negative control) and the complete in vitro reaction (bgc35 iv), as detected by UV absorption at 300 nm. Below are authentic standards of compounds 4 and 2, and extracted ion chromatograms at the indicated masses showing production of compounds 4 and 2 in the reaction. The numbering of the peaks in (FIG. 2B) and (FIG. 2C) corresponds to the small molecules shown in (FIG. 2A).

FIG. 3A: A biosynthetic scheme for the pathways encoded by the gut NRPS clusters. A C-terminal reductase (R) domain catalyzes nicotinamide-dependent reduction of the thioester, releasing a free dipeptide aldehyde that has a half-life of hours under physiological conditions, and exists in equilibrium with the cyclic imine. In the presence of oxygen, this dihydropyrazinone oxidizes irreversibly to the pyrazinone. Results from a panel of in vitro protease inhibition assays using free-amino and N-acylated dipeptide aldehydes discovered in this study. $IC_{50}$ values are shown in µM. Cat=cathepsin; N/O=no inhibition observed under these experimental conditions. Data for the corresponding N-Boc protected dipeptide aldehydes and pyrazinones are shown in FIGS. 11A-11B. Competitive isoTOP-ABPP identifies CTSL as a target of the bgc35 product Phe-Phe-H. The heat map (FIG. 3C) shows all cathepsin cysteines, including both catalytic and non-catalytic detected in isoTOP-ABPP experiments where the THP-1 membrane fraction was subjected to the indicated concentrations of the Phe-Phe-H aldehyde. Note that cysteines on the same tryptic peptide cannot be differentiated and are indicated together, e.g. C135/138. The graphs (FIG. 3D) show the MS1 chromatographic peak ratios (R values) for all peptides identified from the THP1 membrane fraction treated with 25 µM Phe-Phe-H. The black squares indicate cysteines with R values >5 and the line indicates the R value >5 threshold. Heatmap shows all cathepsin cysteines, including both catalytic and non-catalytic detected in isoTOP-ABPP experiments where the THP-1 membrane fraction was subjected to the indicated concentrations of the Phe-Phe-H aldehyde. Note that cysteines on the same tryptic peptide cannot be differentiated and are indicated together, e.g. C135/138.

FIGS. 6A-6B. The schemes for molecular genetic cloning and diagnostic PCR. FIG. 5A: BGCs34, 35, and 52 were synthesized via assembling of three fragments (F1+R2, F3+R4, F5+R6) and pGFP-UV vector. Transformants were selected on LB+Carb plates and were initially screened by diagnostic PCR using primer set F5+pGFP-Diag-R. FIG. 5B: an example of how those BGCs optimized for B. subtilis 168 are transformed into the host strain. pMSD is constructed in a manner in which the targeted BGC is inserted into 5'-amyE and 3'-amyE. Upon transformation, the targeted BGC, for example bgc38, and the spectinomycin resistant gene specR are inserted at the amyE locus of B. subtilis via homologous recombination. Diagnostic PCRs were performed using primer set BS_amyE_F+ BS_amyE_R, which anneal just outside the amyE locus. If a single copy of BGC is inserted, the PCR fragment amplified from a correct transformant will be different in size from the fragment amplified if amyE is intact.

Figure 1:
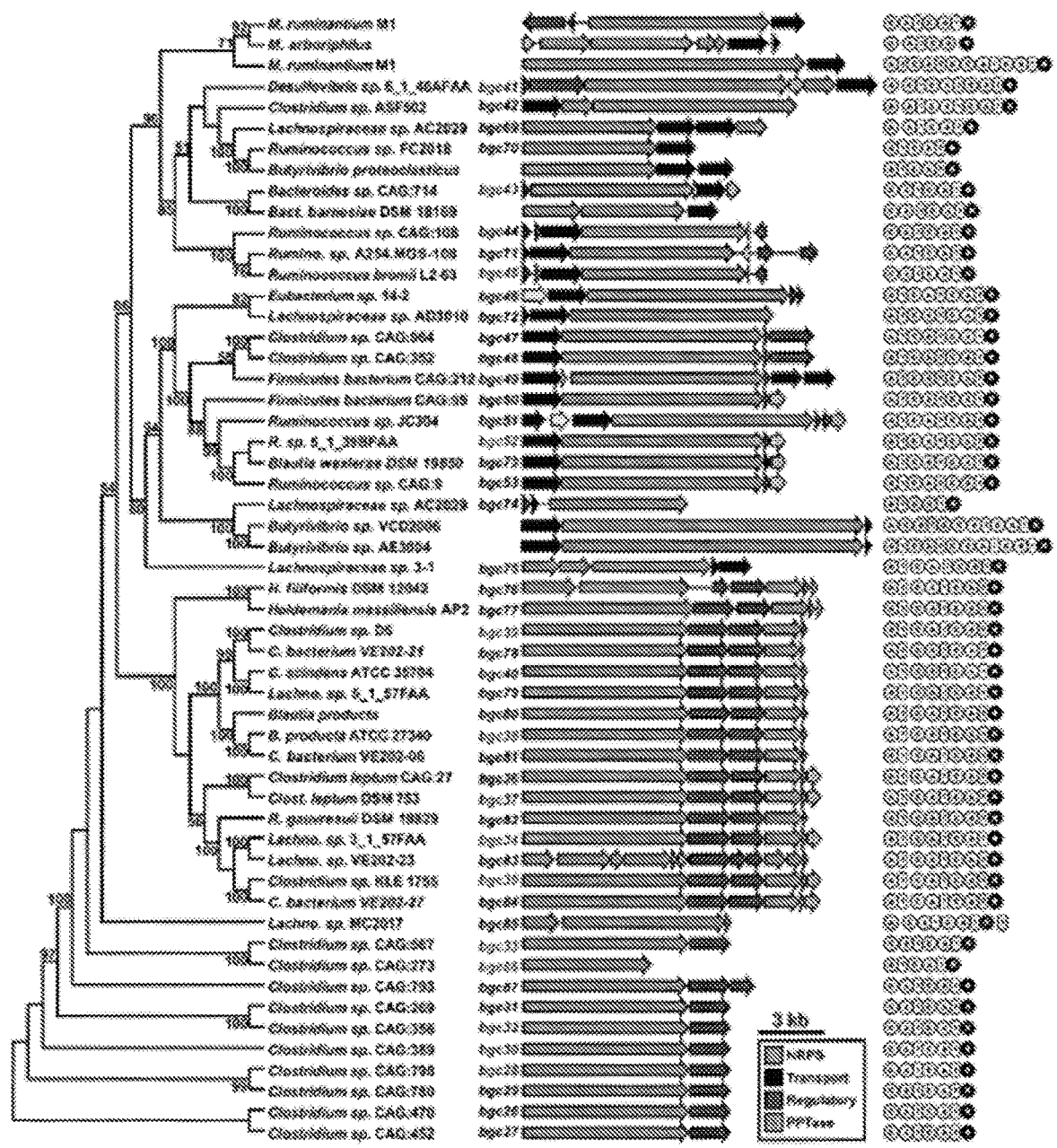
FIG. 1. Phylogenetic analysis of a family of NRPS BGCs found exclusively in gut isolates. Shown on the left is a phylogenetic tree (maximum parsimony, MEGA6) based on the large NRPS gene of the 47 BGCs in the family. Numbers next to the branches represent the percentage of replicate trees in which this topology was reached using a bootstrap test of 1000 replicates. The BGCs characterized experimentally where products were obtained include bgc52, bgc39, bgc38, bgc 34, bgc34, bgc35, bgc33, and bgc86. Experimentally characterized but no products observed include bgc28, bgc30, bgc32, bgc37, bgc45, bgc43, and bgc41. The domain organization of the NRPS enzyme(s) are shown to the right of each cluster (A, adenylation domain; C, condensation domain: T, thiolation domain; R, reductase domain). BGCs without an index number were discovered from non-human (e.g., rumen) gut bacterial isolates.

[M+H]$^+$ m/z found 421.2517, calcd for $C_{23}H_{37}N_2O_3S$ 421.2525; vi. n=7, HRESIMS [M+H]$^+$ m/z found 435.2670, calcd for $C_{24}H_{39}N_2O_3S$ 435.2681; vii. n=8, HRESIMS [M+H]$^+$ m/z found 449.2834, calcd for $C_{25}H_{41}N_2O_3S$ 449.2838; viii. n=9, HRESIMS [M+H]$^+$ m/z found 463.2989, calcd for $C_{26}H_{43}N_2O_3S$ 463.2989; ix. n=10, HRESIMS [M+H]$^+$ m/z found 477.3144, calcd for $C_{27}H_{45}N_2O_3S$ 477.3151; x. n=11, HRESIMS [M+H]$^+$ m/z found 491.3307, calcd for $C_{28}H_{47}N_2O_3S$ 491.3304.

Figure 10:
Figure 10:
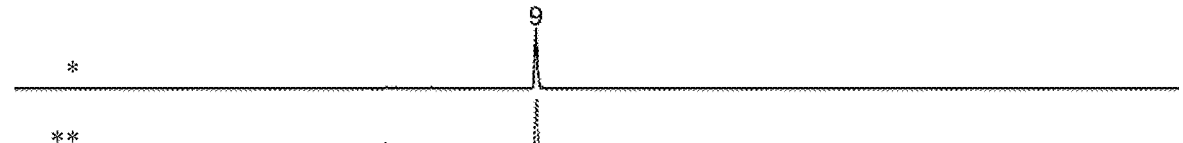
Figure 10:
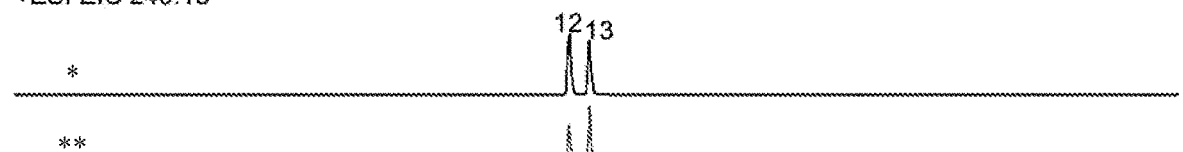
Figure 10:
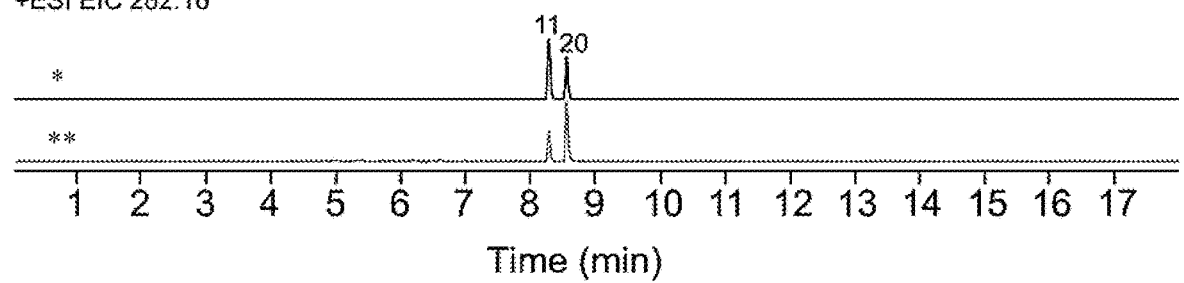

FIG. 10. The same set of pyrazinones are produced by *Ruminococcus* sp. 5_1_39BFAA, the native host of bgc52. The compounds produced by *E. coli*+bgc52 can also be found in the culture extract of R. sp. 5_1_39BFAA. *: Extracted ion chromatogram of *E. coli* DH10B_bgc52 culture; **: Extracted ion chromatogram of *R.* sp. 5_1_39BFAA culture. The numbering of the peaks in the figure corresponds to the natural products shown in FIG. 6.

Figure 11A:
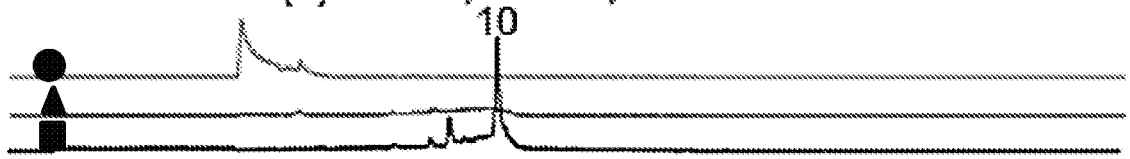
Figure 11A:
Figure 11A:
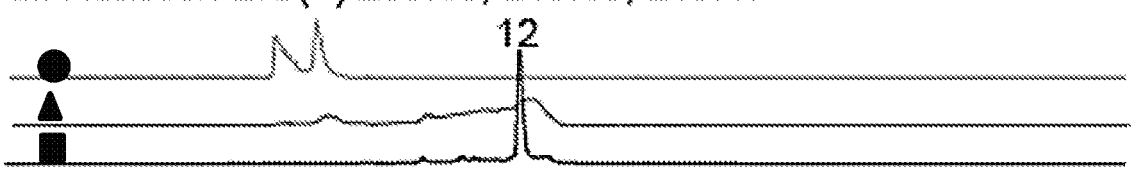
Figure 11A:
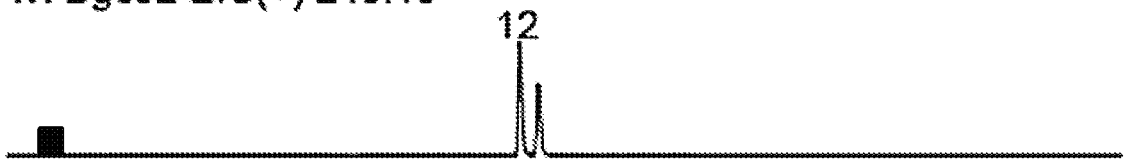
Figure 11A:
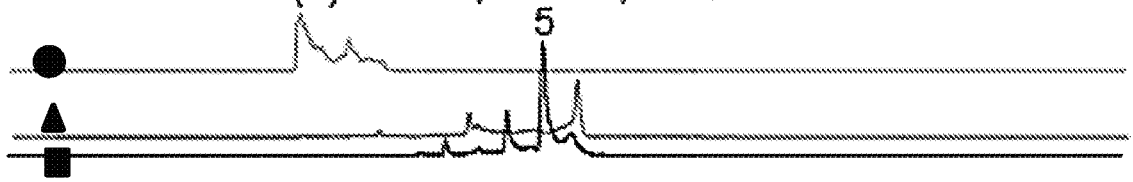
Figure 11A:
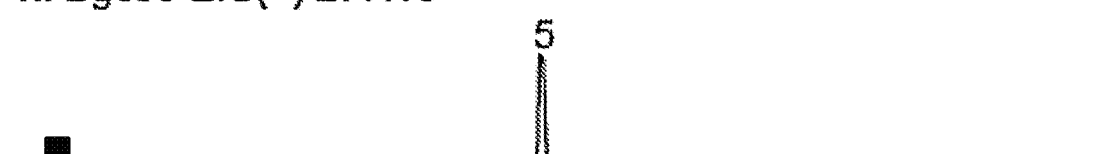
Figure 11B:
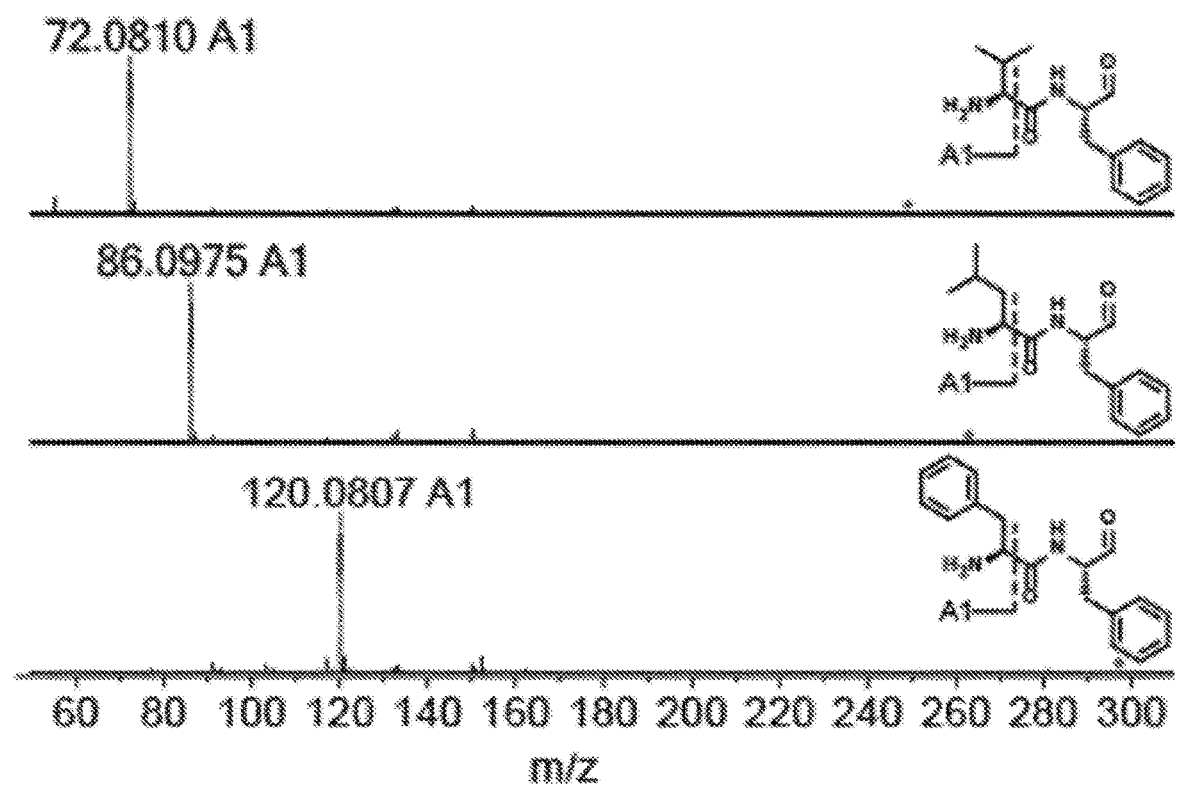
Figure 11C:
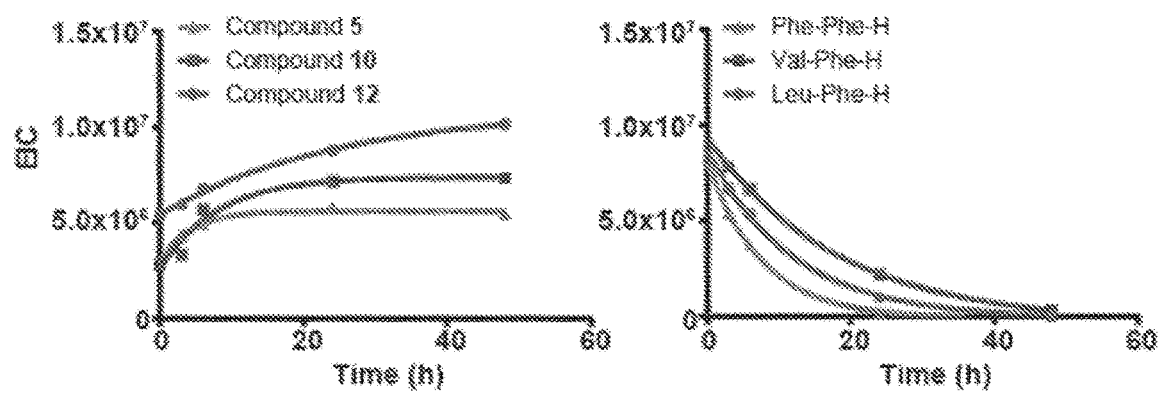

FIGS. 11A-11C. HRMS analysis of TFA deprotection reactions and HRMS-MS analysis of peptide aldehydes. FIG. 11A: i. EIC (+) of 249.16 (Val-Phe-H, shown in in circle), 229.13 (compound 10, square), and 231.15 (corresponding imine form, triangle); ii. EIC (+) of 229.13 (compound 10) from EA extracts of bacterial culture; iii. EIC (+) of 263.18 (Leu-Phe-H, red), 243.15 (compound 12, black), and 245.17 (corresponding imine form, green); iv. EIC (+) of 243.15 (compound 12) from EA extracts of bacterial culture; v. EIC (+) of 297.16 (Phe-Phe-H, shown in red), 277.13 (compound 5, black), and 279.15 (corresponding imine form, green); vi. EIC (+) of 277.13 (compound 5) from EA extracts of bacterial culture. FIG. 11B: HRMS-MS fragmentation pattern of Val-Phe-H, Leu-Phe-H, and Phe-Phe-H. FIG. 11C: Stability measurement of dipeptide aldehydes in the experiment. The stability of dipeptide aldehydes is measured by (1) the rate of pyrazinone (5, 10, and 12) accumulation examined by the area under curve (AUC) of EIC (+) and (2) the rate of the dipeptide aldehyde disappearance as determined by the AUC of EIC (+).

Figure 12A:
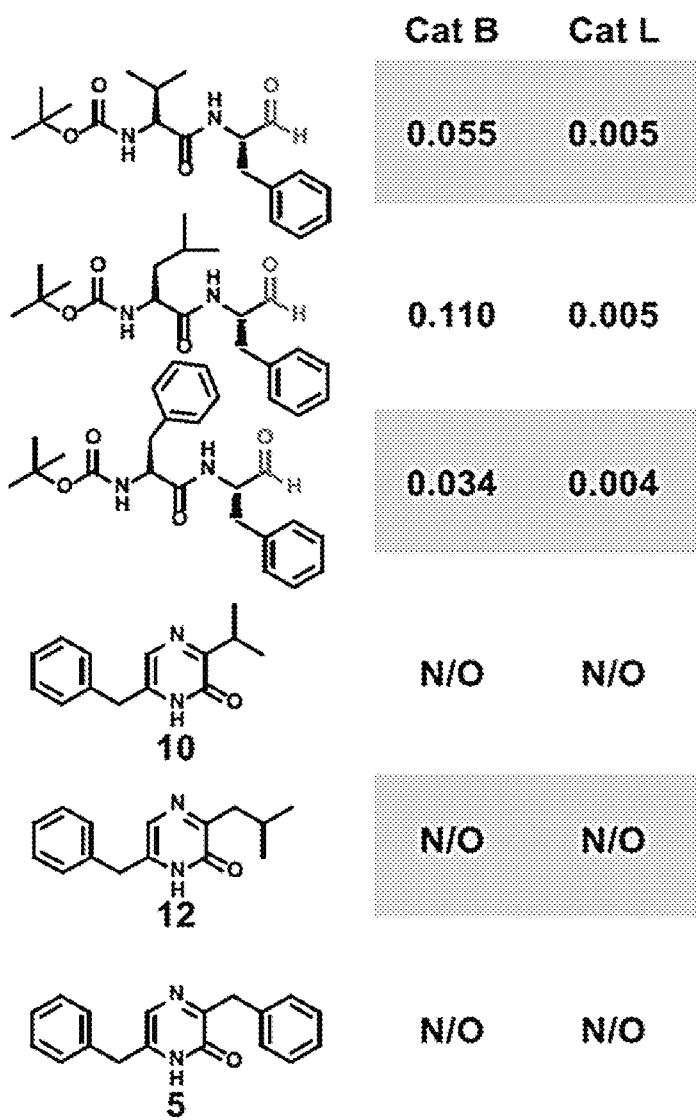
Figure 12B:
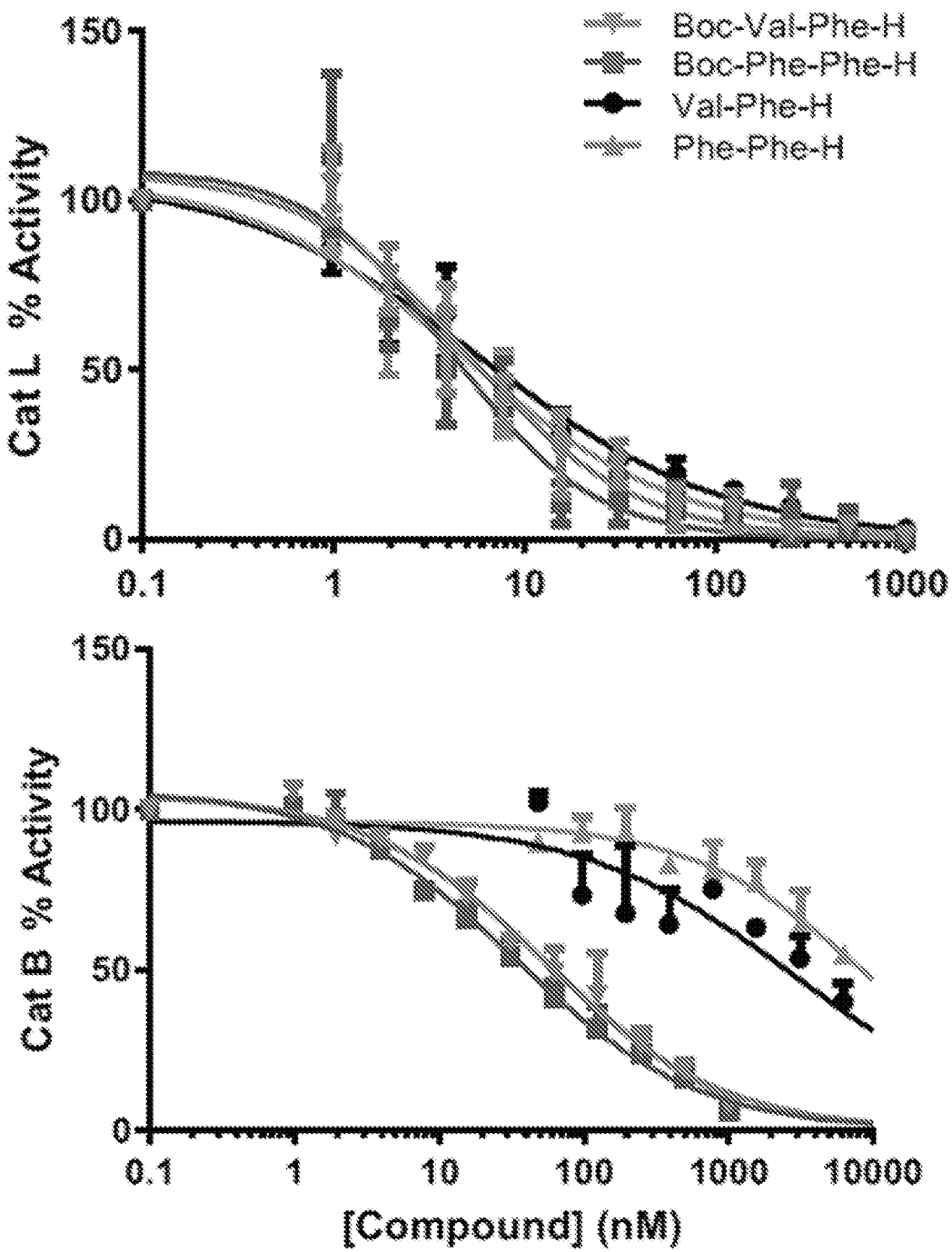

FIGS. 12A-12B. Protease inhibition activity of Boc-protected peptide aldehydes and corresponding pyrazinones. FIG. 12A: IC$_{50}$ values obtained in in vitro cathepsin B and cathepsin L inhibition assays using Boc-protected peptide aldehydes and pyrazinones. IC$_{50}$ values are shown in µM. N/O=no inhibition observed. FIG. 11B: Inhibition curves of Val-Phe-H, Phe-Phe-H, and their Boc-protected peptide aldehydes against cathepsins B and L. The Boc-protected molecules could efficiently inhibit both cathepsin B and cathepsin L with IC$_{50}$ values at nM range. The deprotected molecules could efficiently inhibit cathepsin L (IC$_{50}$ at nM range) but not cathepsin B (IC$_{50}$ at µM range).

Figure 13:
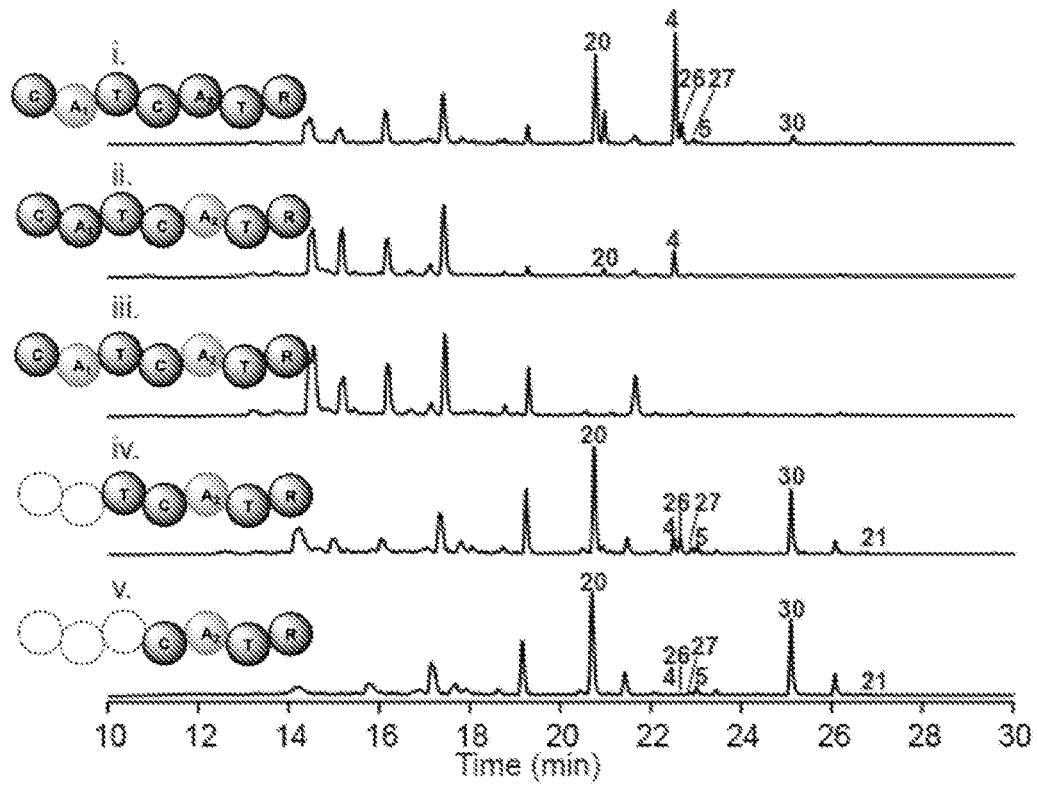

FIG. 13. Point mutation and protein truncation analysis of the NRPS in bgc35. HPLC profiles of the point mutants heterologously expressing bgc35 (i) D686A, (ii) D1713A, (iii) D686A and D1713A, (iv) bgc35 NRPS from which C and A$_1$ have been excised, (v) bgc35 NRPS from which C, A$_1$, and T$_1$ have been excised, as detected by UV at 300 nm.

Figure 14:
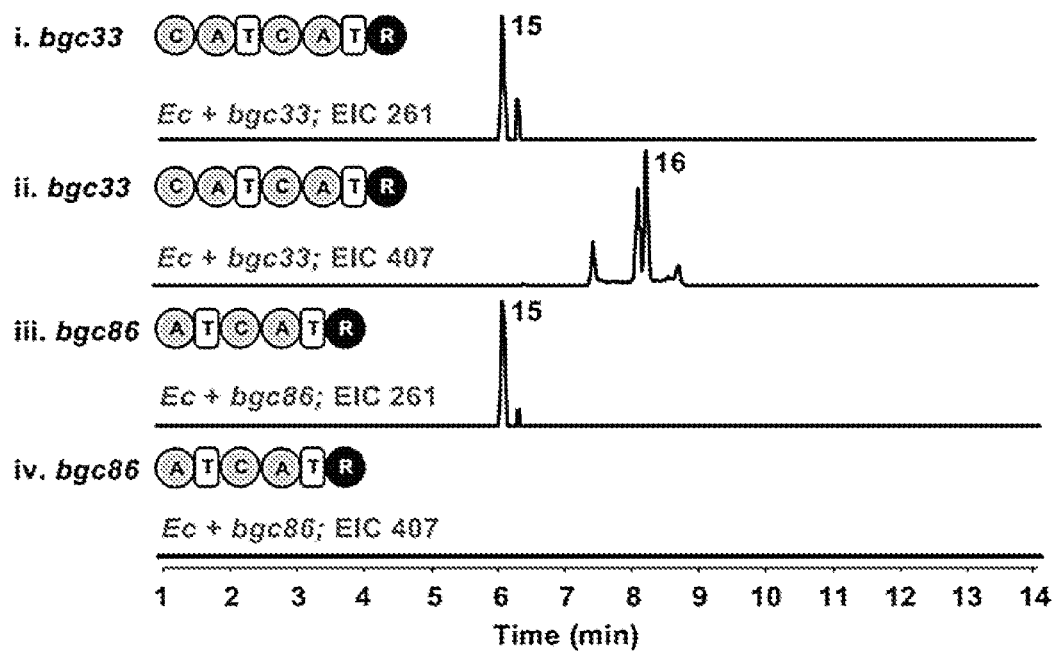

FIG. 14. The first condensation domain of bgc33 participates in N-acylation of compound 16. The gene clusters bgc33 and bgc86 are closely related and differ only by the absence of the first condensation domain (FIG. 1). Under the same cloning, fermentation, and extraction conditions as bgc33, bgc86-harboring *E. coli* BAP1 produced the pyrazinone 15 (i and iii), but not the acylated 16 (ii and iv).

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include adesignated number of carbon atoms (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "∼" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

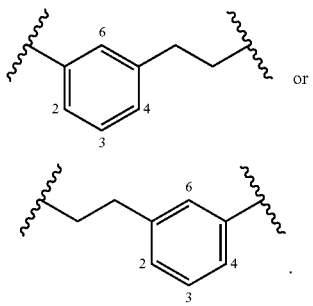

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cyclalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O) NR"NR'"R"", —CN, —NO$_2$, —R', —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing, relative to a control (e.g., the absence of the inhibitor) the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemia, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "lymphoma" refers to a neoplasm of the hematopoietic and lymphoid tissues (e.g., blood, bone marrow, lymph, or lymph tissues). Non-limiting examples of lymphoma include B-acute lymphoblastic lymphoma, non-Hodgkin's lymphomas (e.g., Burkitt's, Small Cell, and Large Cell lymphomas), or Hodgkin's lymphoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of microbiome associated disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule relative to a control (e.g., the absence of the modulator). In some embodiments, a microbiome associated disease modulator is a compound that reduces the severity of one or more symptoms of a disease associated with microbiome imbalance (e.g. acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases (including Crohn's Disease (CD)), malnutrition, or obesity).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-diseaseassociated amount (e.g. by administering a compound or using a method as described herein), results in reduction of the disease or one or more disease symptoms.

The term "microbiome" (e.g., "human microbiome") refers, in the usual and customary sense, to the assemblage of microorganisms and genome information thereof which reside on the surface or inside a body (e.g., a human body). The term "microbiome imbalance" and the like refers to a disruption in the normal levels of microorganisms within a microbiome. A microbiome imbalance may be observed in a disease or disorder, e.g., acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases (including Crohn's Disease (CD)), malnutrition, obesity, or other diseases or disorders.

The terms "amino acid side chain" or "side chain of an amino acid" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the side chain of an amino acid is a monovalent functional substituent of that amino acid. For example, the side chain of the side chain of alanine is —CH$_3$; the side chain of isoleucine is

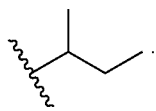 [SMILES: *C(C)CC]

the side chain of leucine is

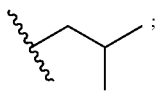 [SMILES: *CC(C)C]

the side chain of methionine is

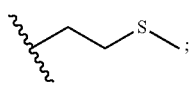 [SMILES: *CCSC]

the side chain of valine is

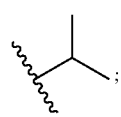 [SMILES: *C(C)C]

the side chain of phenylalanine is

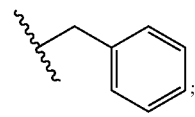 [SMILES: *Cc1ccccc1]

the side chain of tryptophan is

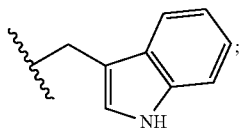 [SMILES: *Cc1c[nH]c2ccccc12]

the side chain of tyrosine is

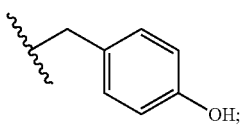 [SMILES: *Cc1ccc(O)cc1]

the side chain of asparagine is

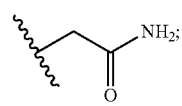

the side chain of cysteine is

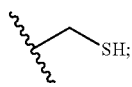

the side chain of glutamine is

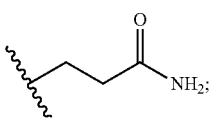

the side chain of serine is

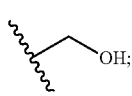 [SMILES: *CO]

the side chain of threonine is

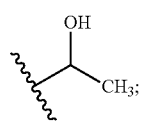

the side chain of aspartic acid is

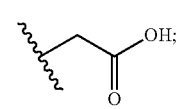 [SMILES: *CC(=O)O]

the side chain of glutamic acid is

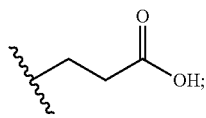 [SMILES: *CCC(=O)O]

the side chain of arginine is

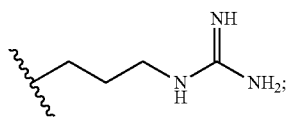 [SMILES: *CCCNC(=N)N]

the side chain of histidine is

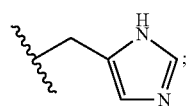 [SMILES: *Cc1cnc[nH]1]

the side chain of lysine is

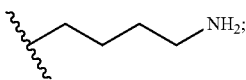 [SMILES: *CCCCN]

and the side chain of glycine is —H.

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2, 3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

Amino acids may be referred to herein by either their commonly known three letter symbols or by the one-letter symbols recommended by the IUPAC-IUB Biochemical Nomenclature Commission.

The term "cathepsin B" refers to the lysosomal cysteine protease involved in intracellular proteolysis. The term "cathepsin B" may refer to the nucleotide sequence or protein sequence of human cathepsin B (e.g., Entrez 1508, Uniprot P07858, RefSeq NM_001908, RefSeq NM_147780, RefSeq NM_147781, RefSeq NM_147782, RefSeq NM_147783, RefSeq NP_001304166, RefSeq NP_001899, RefSeq NP_680090, RefSeq NP_680091, or RefSeq NP_680092). The term "cathepsin B" includes both the wild-type form of the nucleotide sequences or proteins as well as any mutants thereof. In some embodiments, "cathepsin B" is wild-type cathepsin B. In some embodiments, "cathepsin B" is one or more mutant forms. The term "cathepsin B" XYZ refers to a nucleotide sequence or protein of a mutant cathepsin B wherein the Y numbered amino acid of cathepsin B that normally has an X amino acid in the wildtype, instead has a Z amino acid in the mutant. In embodiments, a cathepsin B is the human cathepsin B. In embodiments, the cathepsin B has the nucleotide sequence corresponding to reference number RefSeq NM_001908.4, RefSeq NM_147780.3, RefSeq NM_147781.3, RefSeq NM_147782.3, or RefSeq NM_147783.3. In embodiments, the cathepsin B has the nucleotide sequence corresponding to reference number RefSeq NM_001908.4. In embodiments, the cathepsin B has the nucleotide sequence corresponding to RefSeq NM_147780.3. In embodiments, the cathepsin B has the nucleotide sequence corresponding to RefSeq NM_147781.3. In embodiments, the cathepsin B has the nucleotide sequence corresponding to RefSeq NM_147782.3. In embodiments, the cathepsin B has the nucleotide sequence corresponding to RefSeq NM_147783.3. In embodiments, the cathepsin B has the protein sequence corresponding to RefSeq NP_001304166.1, RefSeq NP_001899.1, RefSeq NP_680090.1, RefSeq NP_680091.1, or RefSeq NP_680092.1. In embodiments, the cathepsin B has the protein sequence corresponding to RefSeq NP_001304166.1. In embodiments, the cathepsin B has the protein sequence corresponding to RefSeq NP_001899.1. In embodiments, the cathepsin B has the protein sequence corresponding to RefSeq NP_680090.1. In embodiments, the cathepsin B has the protein sequence corresponding to RefSeq NP_680091.1. In embodiments, the cathepsin B has the protein sequence corresponding to RefSeq NP_680092.1.

The term "cathepsin C" refers to the lysosomal exo-cysteine protease also referred to as dipeptidyl peptidase I (DPP-I). The term "cathepsin C" may refer to the nucleotide sequence or protein sequence of human cathepsin C (e.g., Entrez 1075, Uniprot P53634, RefSeq NM_148170, RefSeq NM_001114173, RefSeq NM_001814, RefSeq NP_001107645, RefSeq NP_001805, or RefSeq NP_680475). The term "cathepsin C" includes both the wild-type form of the nucleotide sequences or proteins as well as any mutants thereof. In some embodiments, "cathepsin C" is wild-type cathepsin C. In some embodiments, "cathepsin C" is one or more mutant forms. The term "cathepsin C" XYZ refers to a nucleotide sequence or protein of a mutant cathepsin C wherein the Y numbered amino acid of cathepsin C that normally has an X amino acid in the wildtype, instead has a Z amino acid in the mutant. In embodiments, a cathepsin C is the human cathepsin C. In embodiments, the cathepsin C has the nucleotide sequence corresponding to reference number RefSeq NM_148170.4, RefSeq NM_001114173.2, or RefSeq NM_001814.5. In embodiments, the cathepsin C has the nucleotide sequence corresponding to reference number RefSeq NM_148170.4. In embodiments, the cathepsin C has the nucleotide sequence corresponding to reference number RefSeq NM_001114173.2. In embodiments, the cathepsin C has the nucleotide sequence corresponding to reference number RefSeq NM_001814.5. In embodiments, the cathepsin C has the protein sequence corresponding to RefSeq NP_001107645.1, RefSeq NP_001805.3, or RefSeq NP_680475.1. In embodiments, the cathepsin C has the protein sequence corresponding to RefSeq NP_001107645.1. In embodiments, the cathepsin C has the protein sequence corresponding to RefSeq NP_001805.3.

In embodiments, the cathepsin C has the protein sequence corresponding to RefSeq NP_680475.1.

The terms "cathepsin L" or "cathepsin L1" refer to the lysosomal cysteine protease also referred to as CTSL or CTSL1. The term "cathepsin L" may refer to the nucleotide sequence or protein sequence of human cathepsin L (e.g., Entrez 1514, Uniprot P07711, Uniprot Q9HBQ7, RefSeq NM_001257971, RefSeq NM_001257972, RefSeq NM_001257973, RefSeq NM_001912, RefSeq NM_145918, RefSeq NP_001244900, RefSeq NP_001244901, RefSeq NP_001244902, RefSeq NP_00193, or RefSeq NP_666023). The term "cathepsin L" includes both the wild-type form of the nucleotide sequences or proteins as well as any mutants thereof. In some embodiments, "cathepsin L" is wild-type cathepsin L. In some embodiments, "cathepsin L" is one or more mutant forms. The term "cathepsin L" XYZ refers to a nucleotide sequence or protein of a mutant cathepsin L wherein the Y numbered amino acid of cathepsin L that normally has an X amino acid in the wildtype, instead has a Z amino acid in the mutant. In embodiments, a cathepsin L is the human cathepsin L. In embodiments, the cathepsin L has the nucleotide sequence corresponding to RefSeq NM_001257971.1, RefSeq NM_001257972.1, RefSeq NM_001257973.1, RefSeq NM_001912.4, or RefSeq NM_145918.2. In embodiments, the cathepsin L has the nucleotide sequence corresponding to RefSeq NM_001257971.1. In embodiments, the cathepsin L has the nucleotide sequence corresponding to RefSeq NM_001257972.1. In embodiments, the cathepsin L has the nucleotide sequence corresponding to RefSeq NM_001257973.1. In embodiments, the cathepsin L has the nucleotide sequence corresponding to RefSeq NM_001912.4. In embodiments, the cathepsin L has the nucleotide sequence corresponding to RefSeq NM_145918.2. In embodiments, the cathepsin L has the protein sequence corresponding to RefSeq NP_001244900.1, RefSeq NP_001244901.1, RefSeq NP_001244902.1, RefSeq NP_00193.1, or RefSeq NP_666023.1. In embodiments, the cathepsin L has the protein sequence corresponding to RefSeq NP_001244900.1. In embodiments, the cathepsin L has the protein sequence corresponding to RefSeq NP_001244901.1. In embodiments, the cathepsin L has the protein sequence corresponding to RefSeq NP_001244902.1. In embodiments, the cathepsin L has the protein sequence corresponding to RefSeq NP_00193.1. In embodiments, the cathepsin L has the protein sequence corresponding to RefSeq NP_666023.1.

The term "cathepsin S" refers to the lysosomal cysteine protease also referred to as CTSS. The term "cathepsin S" may refer to the nucleotide sequence or protein sequence of human cathepsin S (e.g., Entrez 1520, Uniprot P25774, RefSeq NM_004079, RefSeq NM_001199739, RefSeq NP_001186668, or RefSeq NP_004070). The term "cathepsin S" includes both the wild-type form of the nucleotide sequences or proteins as well as any mutants thereof. In some embodiments, "cathepsin S" is wild-type cathepsin S. In some embodiments, "cathepsin S" is one or more mutant forms. The term "cathepsin S" XYZ refers to a nucleotide sequence or protein of a mutant cathepsin S wherein the Y numbered amino acid of cathepsin S that normally has an X amino acid in the wildtype, instead has a Z amino acid in the mutant. In embodiments, a cathepsin S is the human cathepsin S. In embodiments, the cathepsin S has the nucleotide sequence corresponding to RefSeq NM_004079.4 or RefSeq NM_001199739.1. In embodiments, the cathepsin S has the nucleotide sequence corresponding to RefSeq NM_004079.4. In embodiments, the cathepsin S has the nucleotide sequence corresponding to RefSeq NM_001199739.1. In embodiments, the cathepsin S has the protein sequence corresponding to RefSeq NP_001186668.1 or RefSeq NP_004070.3. In embodiments, the cathepsin S has the protein sequence corresponding to RefSeq NP_001186668.1. In embodiments, the cathepsin S has the protein sequence corresponding to RefSeq NP_004070.3.

II. Compounds

In an aspect is provided a compound, or pharmaceutically acceptable salt thereof, having the formula:

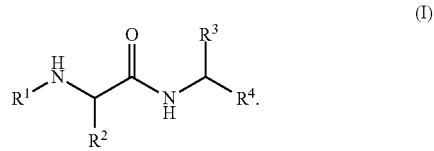

(I)

$R^1$ is independently hydrogen, halogen, —C(O)$R^{1C}$, —C(O)—O$R^{1C}$, —C(O)N$R^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, and $R^{1C}$ are each independently hydrogen, —CF$_3$, —CI$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^2$ and $R^3$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or an amino acid side chain. $R^4$ is —C(O)H, or —B(OH)$_2$. In embodiments, when $R^4$ is —B(OH)$_2$, $R^1$ is not

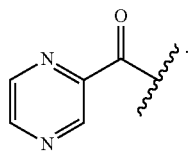 [SMILES: *C(=O)c1cnccn1]

In embodiments, the compound, or pharmaceutically acceptable salt thereof, has the formula:

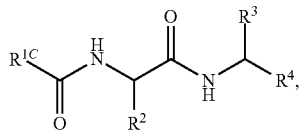
(Ia)

wherein $R^{1C}$, $R^2$, $R^3$, and $R^4$ are as described herein, including embodiments.

In embodiments, the compound, or pharmaceutically acceptable salt thereof, has the formula:

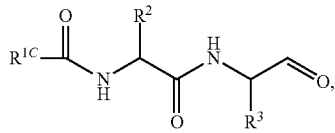
(Ib)

wherein $R^{1C}$, $R^2$, and $R^3$ are as described herein, including embodiments.

In embodiments, the compound, or pharmaceutically acceptable salt thereof, has the formula:

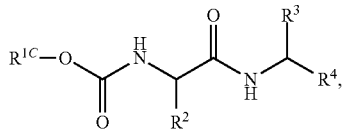
(Ic)

wherein $R^{1C}$, $R^2$, $R^3$, and $R^4$ are as described herein, including embodiments.

In embodiments, the compound, or pharmaceutically acceptable salt thereof, has the formula:

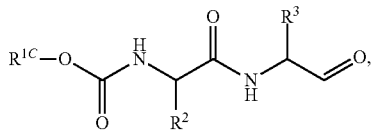
(Id)

wherein $R^{1C}$, $R^2$, and $R^3$ are as described herein, including embodiments.

In embodiments, the compound, or pharmaceutically acceptable salt thereof, has the formula:

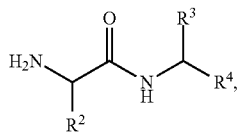
(Ie)

where $R^2$, $R^3$, and $R^4$ are as described herein, including embodiments.

In embodiments, the compound, or pharmaceutically acceptable salt thereof has the formula:

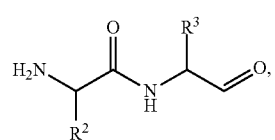
(If)

where $R^2$ and $R^3$ are as described herein, including embodiments.

In embodiments, the compound, or pharmaceutically acceptable salt thereof has the formula:

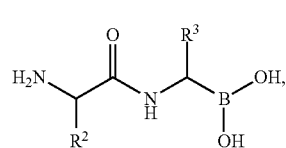
(Ig)

where $R^2$ and $R^3$ are as described herein, including embodiments.

In embodiments, $R^1$ is hydrogen, halogen, —C(O)$R^{1C}$, —C(O)—O$R^{1C}$, —C(O)N$R^{1A}R^{1B}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^1$ is independently hydrogen. In embodiments, $R^1$ is independently halogen. In embodiments, $R^1$ is independently —C(O)$R^{1C}$. In embodiments, $R^1$ is independently —C(O)—O$R^{1C}$. In embodiments, $R^1$ is independently —C(O)N$R^{1A}R^{1B}$. In embodiments, $R^1$ is independently substituted or unsubstituted alkyl (e.g., $C_1$-$C_8$, $C_1$-$C_6$, $C_1$-$C_4$, or $C_1$-$C_2$). In embodiments, $R^1$ is independently substituted alkyl (e.g., $C_1$-$C_8$, $C_1$-$C_6$, $C_1$-$C_4$, or $C_1$-$C_2$). In embodiments, $R^1$ is independently unsubstituted alkyl (e.g., $C_1$-$C_8$, $C_1$-$C_6$, $C_1$-$C_4$, or $C_1$-$C_2$). In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted isopropyl. In embodiments, $R^1$ is independently unsubstituted tert-butyl. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently substituted heteroalkyl (e.g., 2 to 8 membered, 2 to 6 membered, 4 to 6 membered, 2 to 3 membered, or 4 to 5 membered). In embodiments, $R^1$ is independently unsubstituted heteroalkyl (e.g., 2 to 8 membered, 2 to 6 membered, 4 to 6 membered, 2 to 3 membered, or 4 to 5 membered). In embodiments, $R^1$ is independently substituted or unsubstituted cycloalkyl (e.g., $C_3$-$C_8$, $C_3$-$C_6$, $C_4$-$C_6$, or $C_5$-$C_6$). In embodiments, $R^1$ is independently substituted cycloalkyl (e.g., $C_3$-$C_8$, $C_3$-$C_6$, $C_4$-$C_6$, or $C_5$-$C_6$). In embodiments, $R^1$ is independently unsubstituted cycloalkyl (e.g., $C_3$-$C_8$, $C_3$-$C_6$, $C_4$-$C_6$, or $C_5$-$C_6$). In embodiments, $R^1$ is independently substituted or unsubstituted heterocycloalkyl (e.g., 3 to 8 membered, 3 to 6 membered, 4 to 6 membered, 4 to 5 membered, or 5 to 6 membered). In embodiments, $R^1$ is independently substituted heterocycloalkyl (e.g., 3 to 8 membered, 3 to 6 membered, 4 to 6 membered, 4 to 5 membered, or 5 to 6 membered). In embodiments, $R^1$ is independently unsubstituted heterocycloalkyl (e.g., 3 to 8 membered, 3 to 6 membered, 4 to 6 membered, 4 to 5 membered, or 5 to 6 membered). In embodiments, $R^1$ is independently substituted or unsubstituted aryl (e.g., $C_6$-$C_{10}$ or phenyl). In embodiments, $R^1$ is independently substituted aryl (e.g., $C_6$-$C_{10}$ or phenyl). In embodiments, $R^1$ is independently unsubstituted aryl (e.g., $C_6$-$C_{10}$ or phenyl). In embodiments, $R^1$ is independently substituted or unsubstituted heteroaryl (e.g., 5 to 10 membered, 5 to 9 membered, or 5 to 6 membered). In embodiments, $R^1$ is independently substituted heteroaryl (e.g., 5 to 10 membered, 5 to 9 membered, or 5 to 6 membered). In embodiments, $R^1$ is independently unsubstituted heteroaryl (e.g., 5 to 10 membered, 5 to 9 membered, or 5 to 6 membered).

In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted butyl. In embodiments, $R^1$ is independently unsubstituted n-propyl. In embodiments, $R^1$ is independently unsubstituted iso-propyl. In embodiments, $R^1$ is independently unsubstituted n-butyl. In embodiments, $R^1$ is independently unsubstituted iso-butyl. In embodiments, $R^1$ is independently unsubstituted methoxy. In embodiments, $R^1$ is independently unsubstituted ethoxy. In embodiments, $R^1$ is independently unsubstituted propoxy. In embodiments, $R^1$ is independently unsubstituted butoxy.

In embodiments, $R^1$ is independently hydrogen, halogen, —C(O)$R^{1C}$, —C(O)—O$R^{1C}$, —C(O)N$R^{14}R^{1B}$, $R^5$-substituted or unsubstituted alkyl (e.g., $C_1$-$C_8$ alkyl, $C_1$-$C_6$ alkyl, or $C_1$-$C_4$ alkyl), $R^5$-substituted or unsubstituted heteroalkyl (e.g., 2 to 8 membered heteroalkyl, 2 to 6 membered heteroalkyl, or 2 to 4 membered heteroalkyl), $R^5$-substituted or unsubstituted cycloalkyl (e.g., $C_3$-$C_8$ cycloalkyl, $C_3$-$C_6$ cycloalkyl, or $C_5$-$C_6$ cycloalkyl), $R^5$-substituted or unsubstituted heterocycloalkyl (e.g., 3 to 8 membered heterocycloalkyl, 3 to 6 membered heterocycloalkyl, or 5 to 6 membered heterocycloalkyl), $R^5$-substituted or unsubstituted aryl (e.g., $C_6$-$C_{10}$ aryl, $C_{10}$ aryl, or phenyl), or $R^5$-substituted or unsubstituted heteroaryl (e.g., 5 to 10 membered heteroaryl, 5 to 9 membered heteroaryl, or 5 to 6 membered heteroaryl).

In embodiments, $R^1$ is $R^5$-substituted or unsubstituted alkyl (e.g., $C_1$-$C_8$ alkyl, $C_1$-$C_6$ alkyl, or $C_1$-$C_4$ alkyl). In embodiments, $R^1$ is $R^5$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl). In embodiments, $R^1$ is an unsubstituted $C_1$-$C_8$ alkyl. In embodiments, $R^1$ is an unsubstituted $C_1$-$C_6$ alkyl. In embodiments, $R^1$ is an unsubstituted $C_1$-$C_4$ alkyl. In embodiments, $R_1$ is an unsubstituted $C_2$-$C_8$ alkyl. In embodiments, $R^1$ is an unsubstituted $C_4$-$C_8$ alkyl. In embodiments, $R^1$ is an unsubstituted $C_4$ alkyl.

In embodiments, $R^1$ is $R^5$-substituted or unsubstituted methyl. In embodiments, $R^1$ is $R^5$-substituted or unsubstituted $C_2$ alkyl. In embodiments, $R^1$ is $R^5$-substituted or unsubstituted $C_3$ alkyl. In embodiments, $R^1$ is $R^5$-substituted or unsubstituted $C_4$ alkyl. In embodiments, $R^1$ is $R^5$-substituted or unsubstituted $C_5$ alkyl. In embodiments, $R^1$ is $R^5$-substituted or unsubstituted $C_6$ alkyl. In embodiments, $R^1$ is $R^5$-substituted or unsubstituted $C_7$ alkyl. In embodiments, $R^1$ is $R^5$-substituted or unsubstituted $C_8$ alkyl. In embodiments, $R^1$ is $R^5$-substituted methyl. In embodiments, $R^1$ is $R^5$-substituted $C_2$ alkyl. In embodiments, $R^1$ is $R^5$-substituted $C_3$ alkyl. In embodiments, $R^1$ is $R^5$-substituted $C_4$ alkyl. In embodiments, $R^1$ is $R^5$-substituted $C_5$ alkyl. In embodiments, $R^1$ is $R^5$-substituted $C_6$ alkyl. In embodiments, $R^1$ is $R^5$-substituted $C_7$ alkyl. In embodiments, $R^1$ is $R^5$-substituted $C_8$ alkyl. In embodiments, $R^1$ is an unsubstituted methyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl.

In embodiments, $R^1$ is $R^5$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^5$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl).

In embodiments, $R^1$ is $R^5$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^5$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^1$ is $R^5$-substituted or unsubstituted aryl (e.g., $C_6$-$C_{10}$ aryl, $C_{10}$ aryl, or phenyl). In embodiments, $R^1$ is $R^5$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl).

In embodiments, $R^1$ is $R^5$-substituted or unsubstituted heteroaryl (e.g., 5 to 10 membered heteroaryl, 5 to 9 membered heteroaryl, or 5 to 6 membered heteroaryl). In embodiments, $R^1$ is $R^5$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^{1A}$, is hydrogen, —$CF_3$, —$Cl_3$, —$CI_3$, —COOH, —$CONH_2$, —$CHF_2$, —$CHCl_2$, —$CHBr_2$, —$OCH_2F$, —$OCH_2Cl$, —$OCH_2I$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{1A}$ is independently substituted or unsubstituted alkyl (e.g., $C_1$-$C_8$, $C_1$-$C_6$, $C_1$-$C_4$, or $C_1$-$C_2$). In embodiments, $R^{1A}$ is independently substituted alkyl (e.g., $C_1$-$C_8$, $C_1$-$C_6$, $C_1$-$C_4$, or $C_1$-$C_2$). In embodiments, $R^{1A}$ is independently unsubstituted alkyl (e.g., $C_1$-$C_8$, $C_1$-$C_6$, $C_1$-$C_4$, or $C_1$-$C_2$). In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{10}$ or phenyl). In embodiments, $R^{1A}$ is independently substituted aryl (e.g., $C_6$-$C_{10}$ or phenyl). In embodiments, $R^{1A}$ is independently unsubstituted aryl (e.g., $C_6$-$C_{10}$ or phenyl). In embodiments, $R^{1A}$ is independently substituted or unsubstituted heteroaryl (e.g., 5 to 10 membered, 5 to 9 membered, or 5 to 6 membered). In embodiments, $R^{1A}$ is independently substituted heteroaryl (e.g., 5 to 10 membered, 5 to 9 membered, or 5 to 6 membered). In embodiments, $R^{1A}$ is independently unsubstituted heteroaryl (e.g., 5 to 10 membered, 5 to 9 membered, or 5 to 6 membered).

In embodiments, $R^{1A}$ is $R^{5A}$-substituted or unsubstituted alkyl (e.g., $C_1$-$C_8$ alkyl, $C_1$-$C_6$ alkyl, or $C_1$-$C_4$ alkyl). In embodiments, $R^{1A}$ is $R^{5A}$-substituted alkyl (e.g., $C_1$-$C_8$ alkyl, $C_1$-$C_6$ alkyl, or $C_1$-$C_4$ alkyl). In embodiments, $R^{1A}$ is an unsubstituted alkyl (e.g., $C_1$-$C_8$ alkyl, $C_1$-$C_6$ alkyl, or $C_1$-$C_4$ alkyl).

In embodiments, $R^{1A}$ is $R^{5A}$-substituted or unsubstituted methyl. In embodiments, $R^{1A}$ is $R^{5A}$-substituted or unsubstituted $C_2$ alkyl. In embodiments, $R^{1A}$ is $R^{5A}$-substituted or unsubstituted $C_3$ alkyl. In embodiments, $R^{1A}$ is $R^{5A}$-substituted or unsubstituted $C_4$ alkyl. In embodiments, $R^{1A}$ is $R^{5A}$-substituted or unsubstituted $C_{5B}$ alkyl. In embodiments, $R^{1A}$ is $R^{5A}$-substituted or unsubstituted $C_6$ alkyl. In embodiments, $R^{1A}$ is $R^{5A}$-substituted or unsubstituted $C_7$ alkyl. In embodiments, $R^{1A}$ is $R^{5A}$-substituted or unsubstituted $C_8$ alkyl. In embodiments, $R^{1A}$ is $R^{5A}$-substituted methyl. In embodiments, $R^{1A}$ is $R^{5A}$-substituted $C_2$ alkyl. In embodiments, $R^{1A}$ is $R^{5A}$-substituted $C_3$ alkyl. In embodiments, $R^{1A}$ is $R^{5A}$-substituted $C_4$ alkyl. In embodiments, $R^{1A}$ is $R^{5A}$-substituted $C_{5B}$ alkyl. In embodiments, $R^{1A}$ is $R^{5A}$-substituted $C_6$ alkyl. In embodiments, $R^{1A}$ is $R^{5A}$-substituted $C_7$ alkyl. In embodiments, $R^{1A}$ is $R^{5A}$-substituted $C_8$ alkyl. In embodiments, $R^{1A}$ is an unsubstituted methyl. In embodiments, $R^{1A}$ is an unsubstituted $C_2$ alkyl. In embodiments, $R^{1A}$ is an unsubstituted $C_3$ alkyl. In embodiments, $R^{1A}$ is an unsubstituted $C_4$ alkyl. In embodiments, $R^{1A}$ is an unsubstituted $C_{5B}$ alkyl. In embodiments, $R^{1A}$ is an unsubstituted $C_6$ alkyl. In embodiments, $R^{1A}$ is an unsubstituted $C_7$ alkyl. In embodiments, $R^{1A}$ is an unsubstituted $C_8$ alkyl.

In embodiments, $R^{1A}$ is $R^{5A}$-substituted or unsubstituted heteroalkyl (e.g., 2 to 8 membered heteroalkyl, 2 to 6 membered heteroalkyl, or 2 to 4 membered heteroalkyl). In embodiments, $R^{1A}$ is $R^{5A}$-substituted heteroalkyl (e.g., 2 to 8 membered heteroalkyl, 2 to 6 membered heteroalkyl, or 2 to 4 membered heteroalkyl). In embodiments, $R^{1A}$ is an unsubstituted heteroalkyl (e.g., 2 to 8 membered heteroalkyl, 2 to 6 membered heteroalkyl, or 2 to 4 membered heteroalkyl).

In embodiments, $R^{1A}$ is $R^{5A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is $R^{5A}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1A}$ is $R^{5A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is $R^{5A}$-substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1A}$ is $R^{5A}$-substituted or unsubstituted aryl (e.g., $C_6$-$C_{10}$ aryl, $C_{10}$ aryl, or phenyl). In embodiments, $R^{1A}$ is $R^{5A}$-substituted aryl (e.g., $C_6$-$C_{10}$ aryl, $C_{10}$ aryl, or phenyl). In embodiments, $R^{1A}$ is an unsubstituted aryl (e.g., $C_6$-$C_{10}$ aryl, $C_{10}$ aryl, or phenyl).

In embodiments, $R^{1A}$ is $R^{5A}$-substituted or unsubstituted heteroaryl (e.g., 5 to 10 membered heteroaryl, 5 to 9 membered heteroaryl, or 5 to 6 membered heteroaryl). In embodiments, $R^{1A}$ is $R^{5A}$-substituted heteroaryl (e.g., 5 to 10 membered heteroaryl, 5 to 9 membered heteroaryl, or 5 to 6 membered heteroaryl). In embodiments, $R^{1A}$ is an unsubstituted heteroaryl (e.g., 5 to 10 membered heteroaryl, 5 to 9 membered heteroaryl, or 5 to 6 membered heteroaryl).

In embodiments, $R^{1B}$, is hydrogen, $-CF_3$, $-Cl_3$, $-Cl_3$, $-CBr_3$, $-COOH$, $-CONH_2$, $-CHF_2$, $-CHCl_2$, $-CHI_2$, $-CHBr_2$, $-OCH_2F$, $-OCH_2Cl$, $-OCH_2I$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{1B}$ is independently substituted or unsubstituted alkyl (e.g., $C_1$-$C_8$, $C_1$-$C_6$, $C_1$-$C_4$, or $C_1$-$C_2$). In embodiments, $R^{1B}$ is independently substituted alkyl (e.g., $C_1$-$C_8$, $C_1$-$C_6$, $C_1$-$C_4$, or $C_1$-$C_2$). In embodiments, $R^{1B}$ is independently unsubstituted alkyl (e.g., $C_1$-$C_8$, $C_1$-$C_6$, $C_1$-$C_4$, or $C_1$-$C_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., $C_3$-$C_8$, $C_3$-$C_6$, $C_4$-$C_6$, or $C_5$-$C_6$). In embodiments, $R^{1B}$ is independently substituted cycloalkyl (e.g., $C_3$-$C_8$, $C_3$-$C_6$, $C_4$-$C_6$, or $C_5$-$C_6$). In embodiments, $R^{1B}$ is independently unsubstituted cycloalkyl (e.g., $C_3$-$C_8$, $C_3$-$C_6$, $C_4$-$C_6$, or $C_5$-$C_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., $C_6$-$C_{10}$ or phenyl). In embodiments, $R^{1B}$ is independently substituted aryl (e.g., $C_6$-$C_{10}$ or phenyl). In embodiments, $R^{1B}$ is independently unsubstituted aryl (e.g., $C_6$-$C_{10}$ or phenyl). In embodiments, $R^{1B}$ is independently substituted or unsubstituted heteroaryl (e.g., 5 to 10 membered, 5 to 9 membered, or 5 to 6 membered). In embodiments, $R^{1B}$ is independently substituted heteroaryl (e.g., 5 to 10 membered, 5 to 9 membered, or 5 to 6 membered). In embodiments, $R^{1B}$ is independently unsubstituted heteroaryl (e.g., 5 to 10 membered, 5 to 9 membered, or 5 to 6 membered).

In embodiments, $R^{1B}$ is $R^{5B}$-substituted or unsubstituted alkyl (e.g., $C_1$-$C_8$ alkyl, $C_1$-$C_6$ alkyl, or $C_1$-$C_4$ alkyl). In embodiments, $R^{1B}$ is $R^{5B}$-substituted alkyl (e.g., $C_1$-$C_8$ alkyl, $C_1$-$C_6$ alkyl, or $C_1$-$C_4$ alkyl). In embodiments, $R^{1B}$ is an unsubstituted alkyl (e.g., $C_1$-$C_8$ alkyl, $C_1$-$C_6$ alkyl, or $C_1$-$C_4$ alkyl).

In embodiments, $R^{1B}$ is $R^{5B}$-substituted or unsubstituted methyl. In embodiments, $R^{1B}$ is $R^{5B}$-substituted or unsubstituted $C_2$ alkyl. In embodiments, $R^{1B}$ is $R^{5B}$-substituted or unsubstituted $C_3$ alkyl. In embodiments, $R^{1B}$ is $R^{5B}$-substituted or unsubstituted $C_4$ alkyl. In embodiments, $R^{1B}$ is $R^{5B}$-substituted or unsubstituted $C_{5B}$ alkyl. In embodiments, $R^{1B}$ is $R^{5B}$-substituted or unsubstituted $C_6$ alkyl. In embodiments, $R^{1B}$ is $R^{5B}$-substituted or unsubstituted $C_7$ alkyl. In embodiments, $R^{1B}$ is $R^{5B}$-substituted or unsubstituted $C_8$ alkyl. In embodiments, $R^{1B}$ is $R^{5B}$-substituted methyl. In embodiments, $R^{1B}$ is $R^{5B}$-substituted $C_2$ alkyl. In embodiments, $R^{1B}$ is $R^{5B}$-substituted $C_3$ alkyl. In embodiments, $R^{1B}$ is $R^{5B}$-substituted $C_4$ alkyl. In embodiments, $R^{1B}$ is $R^{5B}$-substituted $C_{5B}$ alkyl. In embodiments, $R^{1B}$ is $R^{5B}$-substituted $C_6$ alkyl. In embodiments, $R^{1B}$ is $R^{5B}$-substituted $C_7$ alkyl. In embodiments, $R^{1B}$ is $R^{5B}$-substituted $C_8$ alkyl. In embodiments, $R^{1B}$ is an unsubstituted methyl. In embodiments, $R^{1B}$ is an unsubstituted $C_2$ alkyl. In embodiments, $R^{1B}$ is an unsubstituted $C_3$ alkyl. In embodiments, $R^{1B}$ is an unsubstituted $C_4$ alkyl. In embodiments, $R^{1B}$ is an unsubstituted $C_{5B}$ alkyl. In embodiments, $R^{1B}$ is an unsubstituted $C_6$ alkyl. In embodiments, $R^{1B}$ is an unsubstituted $C_7$ alkyl. In embodiments, $R^{1B}$ is an unsubstituted $C_8$ alkyl.

In embodiments, $R^{1B}$ is $R^{5B}$-substituted or unsubstituted heteroalkyl (e.g., 2 to 8 membered heteroalkyl, 2 to 6 membered heteroalkyl, or 2 to 4 membered heteroalkyl). In embodiments, $R^{1B}$ is $R^{5B}$-substituted heteroalkyl (e.g., 2 to 8 membered heteroalkyl, 2 to 6 membered heteroalkyl, or 2 to 4 membered heteroalkyl). In embodiments, $R^{1B}$ is an unsubstituted heteroalkyl (e.g., 2 to 8 membered heteroalkyl, 2 to 6 membered heteroalkyl, or 2 to 4 membered heteroalkyl).

In embodiments, $R^{1B}$ is $R^{5B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is $R^{5B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1B}$ is $R^{5B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is $R^{5B}$-substituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1B}$ is $R^{5B}$-substituted or unsubstituted aryl (e.g., $C_6$-$C_{10}$ aryl, $C_{10}$ aryl, or phenyl). In embodiments, $R^{1B}$ is $R^{5B}$-substituted aryl (e.g., $C_6$-$C_{10}$ aryl, $C_{10}$ aryl, or phenyl). In embodiments, $R^{1B}$ is an unsubstituted aryl (e.g., $C_6$-$C_{10}$ aryl, $C_{10}$ aryl, or phenyl).

In embodiments, $R^{1B}$ is $R^{5B}$-substituted or unsubstituted heteroaryl (e.g., 5 to 10 membered heteroaryl, 5 to 9 membered heteroaryl, or 5 to 6 membered heteroaryl). In embodiments, $R^{1B}$ is $R^{5B}$-substituted heteroaryl (e.g., 5 to 10 membered heteroaryl, 5 to 9 membered heteroaryl, or 5 to 6 membered heteroaryl). In embodiments, $R^{1B}$ is an unsubstituted heteroaryl (e.g., 5 to 10 membered heteroaryl, 5 to 9 membered heteroaryl, or 5 to 6 membered heteroaryl).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{1A}$ and $R^{1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 10 membered, 5 to 9 membered, or 5 to 6 membered).

In embodiments, $R^{1C}$, is hydrogen, —$CF_3$, —$Cl_3$, —$CI_3$, —$CBr_3$, —COOH, —$CONH_2$, —$CHF_2$, —$CHCl_2$, —$CHI_2$, —CHBr$_2$, —OCH$_2$F, —OCH$_2$Cl, —OCH$_2$I, substituted or unsubstituted alkyl (e.g., C$_1$-C$_{18}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl), substituted or unsubstituted heteroalkyl (e.g., 2 to 18 membered heteroalkyl, 2 to 14 membered heteroalkyl, 2 to 12 membered heteroalkyl, 2 to 10 membered heteroalkyl, 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{1C}$ is independently substituted or unsubstituted alkyl (e.g., C$_1$-C$_{18}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is independently substituted alkyl e.g., C$_1$-C$_{18}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is independently unsubstituted alkyl (e.g., C$_1$-C$_{18}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is independently unsubstituted methyl. In embodiments, R$^{1C}$ is independently unsubstituted ethyl. In embodiments, R$^{1C}$ is independently unsubstituted propyl. In embodiments, R$^{1C}$ is independently unsubstituted isopropyl. In embodiments, R$^{1C}$ is independently unsubstituted tert-butyl. In embodiments, R$^{1C}$ is independently substituted or unsubstituted heteroalkyl (e.g., 2 to 8 membered, 2 to 6 membered, 4 to 6 membered, 2 to 3 membered, or 4 to 5 membered). In embodiments, R$^{1C}$ is independently substituted heteroalkyl (e.g., 2 to 8 membered, 2 to 6 membered, 4 to 6 membered, 2 to 3 membered, or 4 to 5 membered). In embodiments, R$^{1C}$ is independently unsubstituted heteroalkyl (e.g., 2 to 8 membered, 2 to 6 membered, 4 to 6 membered, 2 to 3 membered, or 4 to 5 membered). In embodiments, R$^{1C}$ is independently substituted or unsubstituted cycloalkyl (e.g., C$_3$-C$_8$, C$_3$-C$_6$, C$_4$-C$_6$, or C$_5$-C$_6$). In embodiments, R$^{1C}$ is independently substituted cycloalkyl (e.g., C$_3$-C$_8$, C$_3$-C$_6$, C$_4$-C$_6$, or C$_5$-C$_6$). In embodiments, R$^{1C}$ is independently unsubstituted cycloalkyl (e.g., C$_3$-C$_8$, C$_3$-C$_6$, C$_4$-C$_6$, or C$_5$-C$_6$). In embodiments, R$^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{1C}$ is independently substituted heterocycloalkyl (e.g., 3 to 8 membered, 3 to 6 membered, 4 to 6 membered, 4 to 5 membered, or 5 to 6 membered). In embodiments, R$^{1C}$ is independently unsubstituted heterocycloalkyl (e.g., 3 to 8 membered, 3 to 6 membered, 4 to 6 membered, 4 to 5 membered, or 5 to 6 membered). In embodiments, R$^{1C}$ is independently substituted or unsubstituted aryl (e.g., C$_6$-C$_{10}$ or phenyl). In embodiments, R$^{1C}$ is independently substituted aryl (e.g., C$_6$-C$_{10}$ or phenyl). In embodiments, R$^{1C}$ is independently unsubstituted aryl (e.g., C$_6$-C$_{10}$ or phenyl). In embodiments, R$^{1C}$ is independently substituted or unsubstituted heteroaryl (e.g., 5 to 10 membered, 5 to 9 membered, or 5 to 6 membered). In embodiments, R$^{1C}$ is independently substituted heteroaryl (e.g., 5 to 10 membered, 5 to 9 membered, or 5 to 6 membered). In embodiments, R$^{1C}$ is independently unsubstituted heteroaryl (e.g., 5 to 10 membered, 5 to 9 membered, or 5 to 6 membered).

In embodiments, R$^{1C}$ is independently unsubstituted methyl. In embodiments, R$^{1C}$ is independently unsubstituted ethyl. In embodiments, R$^{1C}$ is independently unsubstituted propyl. In embodiments, R$^{1C}$ is independently unsubstituted butyl. In embodiments, R$^{1C}$ is independently unsubstituted n-propyl. In embodiments, R$^{1C}$ is independently unsubstituted isopropyl. In embodiments, R$^{1C}$ is independently unsubstituted n-butyl. In embodiments, R$^{1C}$ is independently unsubstituted iso-butyl. In embodiments, R$^{1C}$ is independently unsubstituted methoxy. In embodiments, R$^{1C}$ is independently unsubstituted ethoxy. In embodiments, R$^{1C}$ is independently unsubstituted propoxy. In embodiments, R$^{1C}$ is independently unsubstituted butoxy.

In embodiments, R$^{1C}$ is R$^{5C}$-substituted or unsubstituted alkyl (e.g., C$_1$-C$_{10}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is R$^{5C}$-substituted alkyl (e.g., C$_1$-C$_{10}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is an unsubstituted alkyl (e.g., C$_1$-C$_{18}$ alkyl, C$_1$-C$_{14}$ alkyl, C$_1$-C$_{12}$ alkyl, C$_1$-C$_{10}$ alkyl, C$_1$-C$_8$ alkyl, C$_1$-C$_6$ alkyl, or C$_1$-C$_4$ alkyl). In embodiments, R$^{1C}$ is an unsubstituted C$_1$-C$_{18}$ alkyl. In embodiments, R$^{1C}$ is an unsubstituted C$_1$-C$_{14}$ alkyl. In embodiments, R$^{1C}$ is an unsubstituted C$_1$-C$_{12}$ alkyl. In embodiments, R$^{1C}$ is an unsubstituted C$_1$-C$_{10}$ alkyl. In embodiments, R$^{1C}$ is an unsubstituted C$_1$-C$_8$ alkyl. In embodiments, R$^{1C}$ is an unsubstituted C$_1$-C$_6$ alkyl. In embodiments, R$^{1C}$ is an unsubstituted C$_1$-C$_4$ alkyl. In embodiments, R$^{1C}$ is an unsubstituted C$_2$-C$_8$ alkyl. In embodiments, R$^{1C}$ is an unsubstituted C$_4$-C$_8$ alkyl.

In embodiments, R$^{1C}$ is R$^{5C}$-substituted or unsubstituted methyl. In embodiments, R$^{1C}$ is R$^{5C}$-substituted or unsubstituted C$_2$ alkyl. In embodiments, R$^{1C}$ is R$^{5C}$-substituted or unsubstituted C$_3$ alkyl. In embodiments, R$^{1C}$ is R$^{5C}$-substituted or unsubstituted C$_4$ alkyl. In embodiments, R$^{1C}$ is R$^{5C}$-substituted or unsubstituted C$_{5B}$ alkyl. In embodiments, R$^{1C}$ is R$^{5C}$-substituted or unsubstituted C$_6$ alkyl. In embodiments, R$^{1C}$ is R$^{5C}$-substituted or unsubstituted C$_7$ alkyl. In embodiments, R$^{1C}$ is R$^{5C}$-substituted or unsubstituted C$_8$ alkyl. In embodiments, R$^{1C}$ is R$^{5C}$-substituted methyl. In embodiments, R$^{1C}$ is R$^{5C}$-substituted C$_2$ alkyl. In embodiments, R$^{1C}$ is R$^{5C}$-substituted C$_3$ alkyl. In embodiments, R$^{1C}$ is R$^{5C}$-substituted C$_4$ alkyl. In embodiments, R$^{1C}$ is R$^{5C}$-substituted C$_{5B}$ alkyl. In embodiments, R$^{1C}$ is R$^{5C}$-substituted C$_6$ alkyl. In embodiments, R$^{1C}$ is R$^{5C}$-substituted C$_7$ alkyl. In embodiments, R$^{1C}$ is R$^{5C}$-substituted C$_8$ alkyl. In embodiments, R$^{1C}$ is R$^{5C}$-substituted C$_9$ alkyl. In embodiments, R$^{1C}$ is R$^{5C}$-substituted C$_{10}$ alkyl. In embodiments, R$^{1C}$ is R$^{5C}$-substituted C$_{11}$ alkyl. In embodiments, R$^{1C}$ is R$^{5C}$-substituted C$_{12}$ alkyl. In embodiments, R$^{1C}$ is R$^{5C}$-substituted C$_{13}$ alkyl. In embodiments, R$^{1C}$ is R$^{5C}$-substituted C$_{14}$ alkyl. In embodiments, R$^{1C}$ is R$^{5C}$-substituted C$_{15}$ alkyl. In embodiments, R$^{1C}$ is R$^{5C}$-substituted C$_{16}$ alkyl. In embodiments, R$^{1C}$ is R$^{5C}$-substituted C$_{17}$ alkyl. In embodiments, R$^{1C}$ is R$^{5C}$-substituted C$_{18}$ alkyl. In embodiments, R$^{1C}$ is an unsubstituted methyl. In embodiments, R$^{1C}$ is an unsubstituted C$_2$ alkyl. In embodiments, R$^{1C}$ is an unsubstituted C$_3$ alkyl. In embodiments, R$^{1C}$ is an unsubstituted C$_4$ alkyl. In embodiments, R$^{1C}$ is an unsubstituted C$_{5B}$ alkyl. In embodiments, R$^{1C}$ is an unsubstituted C$_6$ alkyl. In embodiments, R$^{1C}$ is an unsubstituted C$_7$ alkyl. In embodiments, R$^{1C}$ is an unsubstituted C$_8$ alkyl. In embodiments, R$^{1C}$ is an unsubstituted C$_9$ alkyl. In embodiments, R$^{1C}$ is an unsubstituted C$_{10}$ alkyl. In embodiments, R$^{1C}$ is an unsubstituted C$_{11}$ alkyl. In embodiments, R$^{1C}$ is an unsubstituted C$_{12}$ alkyl. In embodiments, R$^{1C}$ is an unsubstituted C$_{13}$ alkyl. In embodiments, R$^{1C}$ is an unsubstituted C$_{14}$ alkyl. In embodiments, R$^{1C}$ is an unsubstituted C$_{15}$ alkyl. In embodiments, $R^{1C}$ is an unsubstituted $C_{16}$ alkyl. In embodiments, $R^{1C}$ is an unsubstituted $C_{17}$ alkyl. In embodiments, $R^{1C}$ is an unsubstituted $C_{18}$ alkyl.

In embodiments, $R^{1C}$ is $R^{5C}$-substituted or unsubstituted heteroalkyl (e.g., 2 to 8 membered heteroalkyl, 2 to 6 membered heteroalkyl, or 2 to 4 membered heteroalkyl). In embodiments, $R^{1C}$ is $R^{5C}$-substituted heteroalkyl (e.g., 2 to 8 membered heteroalkyl, 2 to 6 membered heteroalkyl, or 2 to 4 membered heteroalkyl). In embodiments, $R^{1C}$ is an unsubstituted heteroalkyl (e.g., 2 to 8 membered heteroalkyl, 2 to 6 membered heteroalkyl, or 2 to 4 membered heteroalkyl).

In embodiments, $R^{1C}$ is $R^{5C}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1C}$ is $R^{5C}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1C}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{1C}$ is $R^{5C}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1C}$ is $R^{5C}$-substituted heterocycloalkyl (e.g., 3 to 8 membered heterocycloalkyl, 3 to 6 membered heterocycloalkyl, or 5 to 6 membered heterocycloalkyl). In embodiments, $R^{1C}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{1C}$ is $R^{5C}$-substituted or unsubstituted aryl (e.g., $C_6$-$C_{10}$ aryl, $C_{10}$ aryl, or phenyl). In embodiments, $R^{1C}$ is $R^{5C}$-substituted aryl (e.g., $C_6$-$C_{10}$ aryl, $C_{10}$ aryl, or phenyl). In embodiments, $R^{1C}$ is an unsubstituted aryl (e.g., $C_6$-$C_{10}$ aryl, $C_{10}$ aryl, or phenyl).

In embodiments, $R^{1C}$ is $R^{5C}$-substituted or unsubstituted heteroaryl (e.g., 5 to 10 membered heteroaryl, 5 to 9 membered heteroaryl, or 5 to 6 membered heteroaryl). In embodiments, $R^{1C}$ is $R^{5C}$-substituted heteroaryl (e.g., 5 to 10 membered heteroaryl, 5 to 9 membered heteroaryl, or 5 to 6 membered heteroaryl). In embodiments, $R^{1C}$ is an unsubstituted heteroaryl (e.g., 5 to 10 membered heteroaryl, 5 to 9 membered heteroaryl, or 5 to 6 membered heteroaryl).

In embodiments, $R^2$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^2$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^2$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is substituted (e.g., substituted with a substituent group, a size-limited substituent group, or lower substituent group) or unsubstituted alkyl. In embodiments, $R^2$ is substituted (e.g., substituted with a substituent group, a size-limited substituent group, or lower substituent group) alkyl. In embodiments, $R^2$ is unsubstituted alkyl. In embodiments, $R^2$ is substituted or unsubstituted alkyl (e.g., $C_1$-$C_8$, $C_1$-$C_6$, $C_1$-$C_4$, or $C_1$-$C_2$). In embodiments, $R^2$ is substituted alkyl (e.g., $C_1$-$C_8$, $C_1$-$C_6$, $C_1$-$C_4$, or $C_1$-$C_2$). In embodiments, $R^2$ is unsubstituted alkyl (e.g., $C_1$-$C_8$, $C_1$-$C_6$, $C_1$-$C_4$, or $C_1$-$C_2$).

In embodiments, $R^2$ is substituted (e.g., substituted with a substituent group, a size-limited substituent group, or lower substituent group) or unsubstituted heteroalkyl. In embodiments, $R^2$ is substituted (e.g., substituted with a substituent group, a size-limited substituent group, or lower substituent group) heteroalkyl. In embodiments, $R^2$ is unsubstituted heteroalkyl. In embodiments, $R^2$ is substituted or unsubstituted heteroalkyl (e.g., 2 to 8 membered, 2 to 6 membered, 4 to 6 membered, 2 to 3 membered, or 4 to 5 membered). In embodiments, $R^2$ is substituted heteroalkyl (e.g., 2 to 8 membered, 2 to 6 membered, 4 to 6 membered, 2 to 3 membered, or 4 to 5 membered). In embodiments, $R^2$ is an unsubstituted heteroalkyl (e.g., 2 to 8 membered, 2 to 6 membered, 4 to 6 membered, 2 to 3 membered, or 4 to 5 membered).

In embodiments, $R^2$ is substituted (e.g., substituted with a substituent group, a size-limited substituent group, or lower substituent group) or unsubstituted cycloalkyl. In embodiments, $R^2$ is substituted (e.g., substituted with a substituent group, a size-limited substituent group, or lower substituent group) cycloalkyl. In embodiments, $R^2$ is an unsubstituted cycloalkyl. In embodiments, $R^2$ is substituted or unsubstituted cycloalkyl (e.g., $C_3$-$C_8$, $C_3$-$C_6$, $C_4$-$C_6$, or $C_5$-$C_6$). In embodiments, $R^2$ is substituted cycloalkyl (e.g., $C_3$-$C_8$, $C_3$-$C_6$, $C_4$-$C_6$, or $C_5$-$C_6$). In embodiments, $R^2$ is unsubstituted cycloalkyl (e.g., $C_3$-$C_8$, $C_3$-$C_6$, $C_4$-$C_6$, or $C_5$-$C_6$).

In embodiments, $R^2$ is substituted (e.g., substituted with a substituent group, a size-limited substituent group, or lower substituent group) or unsubstituted heterocycloalkyl. In embodiments, $R^2$ is substituted (e.g., substituted with a substituent group, a size-limited substituent group, or lower substituent group) heterocycloalkyl. In embodiments, $R^2$ is an unsubstituted heterocycloalkyl. In embodiments, $R^2$ is substituted or unsubstituted heterocycloalkyl (e.g., 3 to 8 membered, 3 to 6 membered, 4 to 6 membered, 4 to 5 membered, or 5 to 6 membered). In embodiments, $R^2$ is substituted heterocycloalkyl (e.g., 3 to 8 membered, 3 to 6 membered, 4 to 6 membered, 4 to 5 membered, or 5 to 6 membered). In embodiments, $R^2$ an unsubstituted heterocycloalkyl (e.g., 3 to 8 membered, 3 to 6 membered, 4 to 6 membered, 4 to 5 membered, or 5 to 6 membered).

In embodiments, $R^2$ is substituted (e.g., substituted with a substituent group, a size-limited substituent group, or lower substituent group) or unsubstituted aryl. In embodiments, $R^2$ is substituted (e.g., substituted with a substituent group, a size-limited substituent group, or lower substituent group) aryl. In embodiments, $R^2$ is an unsubstituted aryl. In embodiments, $R^2$ is substituted or unsubstituted aryl (e.g., $C_6$-$C_{10}$ or phenyl). In embodiments, $R^2$ is substituted aryl (e.g., $C_6$-$C_{10}$ or phenyl). In embodiments, $R^2$ is an unsubstituted aryl (e.g., $C_6$-$C_{10}$ or phenyl).

In embodiments, $R^2$ is substituted (e.g., substituted with a substituent group, a size-limited substituent group, or lower substituent group) or unsubstituted heteroaryl. In embodiments, $R^2$ is substituted (e.g., substituted with a substituent group, a size-limited substituent group, or lower substituent group) heteroaryl. In embodiments, $R^2$ is an unsubstituted heteroaryl. In embodiments, $R^2$ is substituted or unsubstituted heteroaryl (e.g., 5 to 10 membered, 5 to 9 membered, or 5 to 6 membered). In embodiments, $R^2$ is substituted heteroaryl (e.g., 5 to 10 membered, 5 to 9 membered, or 5 to 6 membered). In embodiments, $R^2$ is an unsubstituted heteroaryl (e.g., 5 to 10 membered, 5 to 9 membered, or 5 to 6 membered).

In embodiments, $R^2$ is substituted (e.g., substituted with a substituent group, a size-limited substituent group, or lower substituent group) or unsubstituted alkyl. In embodiments, $R^2$ is an alkyl substituted with a substituent group. In embodiments, $R^2$ is an alkyl substituted with a size-limited substituent group. In embodiments, $R^2$ is an alkyl substituted with a lower substituent group. In embodiments, $R^2$ is unsubstituted alkyl.

In embodiments, $R^2$ is substituted (e.g., substituted with a substituent group, a size-limited substituent group, or lower substituent group) or unsubstituted heteroalkyl. In embodiments, $R^2$ is a heteroalkyl substituted with a substituent group. In embodiments, $R^2$ is a heteroalkyl substituted with a size-limited substituent group. In embodiments, $R^2$ is a heteroalkyl substituted with a lower substituent group. In embodiments, $R^2$ is unsubstituted heteroalkyl.

In embodiments, $R^2$ is substituted (e.g., substituted with a substituent group, a size-limited substituent group, or lower substituent group) or unsubstituted cycloalkyl. In embodiments, $R^2$ is a cycloalkyl substituted with a substituent group. In embodiments, $R^2$ is a cycloalkyl substituted with a size-limited substituent group. In embodiments, $R^2$ is a cycloalkyl substituted with a lower substituent group. In embodiments, $R^2$ is unsubstituted cycloalkyl.

In embodiments, $R^2$ is substituted (e.g., substituted with a substituent group, a size-limited substituent group, or lower substituent group) or unsubstituted heterocycloalkyl. In embodiments, $R^2$ is a heterocycloalkyl substituted with a substituent group. In embodiments, $R^2$ is a heterocycloalkyl substituted with a size-limited substituent group. In embodiments, $R^2$ is a heterocycloalkyl substituted with a lower substituent group. In embodiments, $R^2$ is unsubstituted heterocycloalkyl.

In embodiments, $R^2$ is substituted (e.g., substituted with a substituent group, a size-limited substituent group, or lower substituent group) or unsubstituted aryl. In embodiments, $R^2$ is an aryl substituted with a substituent group. In embodiments, $R^2$ is an aryl substituted with a size-limited substituent group. In embodiments, $R^2$ is an aryl substituted with a lower substituent group. In embodiments, $R^2$ is unsubstituted aryl.

In embodiments, $R^2$ is substituted (e.g., substituted with a substituent group, a size-limited substituent group, or lower substituent group) or unsubstituted heteroaryl. In embodiments, $R^2$ is a heteroaryl substituted with a substituent group. In embodiments, $R^2$ is a heteroaryl substituted with a size-limited substituent group. In embodiments, $R^2$ is a heteroaryl substituted with a lower substituent group. In embodiments, $R^2$ is unsubstituted heteroaryl.

In embodiments, $R^3$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^3$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^3$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^3$ is substituted (e.g., substituted with a substituent group, a size-limited substituent group, or lower substituent group) or unsubstituted alkyl. In embodiments, $R^3$ is substituted (e.g., substituted with a substituent group, a size-limited substituent group, or lower substituent group) alkyl. In embodiments, $R^3$ is unsubstituted alkyl. In embodiments, $R^3$ is substituted or unsubstituted alkyl (e.g., $C_1$-$C_8$, $C_1$-$C_6$, $C_1$-$C_4$, or $C_1$-$C_2$). In embodiments, $R^3$ is substituted alkyl (e.g., $C_1$-$C_8$, $C_1$-$C_6$, $C_1$-$C_4$, or $C_1$-$C_2$). In embodiments, $R^3$ is unsubstituted alkyl (e.g., $C_1$-$C_8$, $C_1$-$C_6$, $C_1$-$C_4$, or $C_1$-$C_2$).

In embodiments, $R^3$ is substituted (e.g., substituted with a substituent group, a size-limited substituent group, or lower substituent group) or unsubstituted heteroalkyl. In embodiments, $R^3$ is substituted (e.g., substituted with a substituent group, a size-limited substituent group, or lower substituent group) heteroalkyl. In embodiments, $R^3$ is unsubstituted heteroalkyl. In embodiments, $R^3$ is substituted or unsubstituted heteroalkyl (e.g., 2 to 8 membered, 2 to 6 membered, 4 to 6 membered, 2 to 3 membered, or 4 to 5 membered). In embodiments, $R^3$ is substituted heteroalkyl (e.g., 2 to 8 membered, 2 to 6 membered, 4 to 6 membered, 2 to 3 membered, or 4 to 5 membered). In embodiments, $R^3$ is an unsubstituted heteroalkyl (e.g., 2 to 8 membered, 2 to 6 membered, 4 to 6 membered, 2 to 3 membered, or 4 to 5 membered).

In embodiments, $R^3$ is substituted (e.g., substituted with a substituent group, a size-limited substituent group, or lower substituent group) or unsubstituted cycloalkyl. In embodiments, $R^3$ is substituted (e.g., substituted with a substituent group, a size-limited substituent group, or lower substituent group) cycloalkyl. In embodiments, $R^3$ is an unsubstituted cycloalkyl. In embodiments, $R^3$ is substituted or unsubstituted cycloalkyl (e.g., $C_3$-$C_8$, $C_3$-$C_6$, $C_4$-$C_6$, or $C_5$-$C_6$). In embodiments, $R^3$ is substituted cycloalkyl (e.g., $C_3$-$C_8$, $C_3$-$C_6$, $C_4$-$C_6$, or $C_5$-$C_6$). In embodiments, $R^3$ is unsubstituted cycloalkyl (e.g., $C_3$-$C_8$, $C_3$-$C_6$, $C_4$-$C_6$, or $C_5$-$C_6$).

In embodiments, $R^3$ is substituted (e.g., substituted with a substituent group, a size-limited substituent group, or lower substituent group) or unsubstituted heterocycloalkyl. In embodiments, $R^3$ is substituted (e.g., substituted with a substituent group, a size-limited substituent group, or lower substituent group) heterocycloalkyl. In embodiments, $R^3$ is an unsubstituted heterocycloalkyl. In embodiments, $R^3$ is substituted or unsubstituted heterocycloalkyl (e.g., 3 to 8 membered, 3 to 6 membered, 4 to 6 membered, 4 to 5 membered, or 5 to 6 membered). In embodiments, $R^3$ is substituted heterocycloalkyl (e.g., 3 to 8 membered, 3 to 6 membered, 4 to 6 membered, 4 to 5 membered, or 5 to 6 membered). In embodiments, $R^3$ an unsubstituted heterocycloalkyl (e.g., 3 to 8 membered, 3 to 6 membered, 4 to 6 membered, 4 to 5 membered, or 5 to 6 membered).

In embodiments, $R^3$ is substituted (e.g., substituted with a substituent group, a size-limited substituent group, or lower substituent group) or unsubstituted aryl. In embodiments, $R^3$ is substituted (e.g., substituted with a substituent group, a size-limited substituent group, or lower substituent group) aryl. In embodiments, $R^3$ is an unsubstituted aryl. In embodiments, $R^3$ is substituted or unsubstituted aryl (e.g., $C_6$-$C_{10}$ or phenyl). In embodiments, $R^3$ is substituted aryl (e.g., $C_6$-$C_{10}$ or phenyl). In embodiments, $R^3$ is an unsubstituted aryl (e.g., $C_6$-$C_{10}$ or phenyl).

In embodiments, $R^3$ is substituted (e.g., substituted with a substituent group, a size-limited substituent group, or lower substituent group) or unsubstituted heteroaryl. In embodiments, $R^3$ is substituted (e.g., substituted with a substituent group, a size-limited substituent group, or lower substituent group) heteroaryl. In embodiments, $R^3$ is an unsubstituted heteroaryl. In embodiments, $R^3$ is substituted or unsubstituted heteroaryl (e.g., 5 to 10 membered, 5 to 9 membered, or 5 to 6 membered). In embodiments, $R^3$ is substituted heteroaryl (e.g., 5 to 10 membered, 5 to 9 membered, or 5 to 6 membered). In embodiments, $R^3$ is an unsubstituted heteroaryl (e.g., 5 to 10 membered, 5 to 9 membered, or 5 to 6 membered).

In embodiments, $R^3$ is substituted (e.g., substituted with a substituent group, a size-limited substituent group, or lower substituent group) or unsubstituted alkyl. In embodiments, $R^3$ is an alkyl substituted with a substituent group. In embodiments, $R^3$ is an alkyl substituted with a size-limited substituent group. In embodiments, $R^3$ is an alkyl substituted with a lower substituent group. In embodiments, $R^3$ is unsubstituted alkyl.

In embodiments, $R^3$ is substituted (e.g., substituted with a substituent group, a size-limited substituent group, or lower substituent group) or unsubstituted heteroalkyl. In embodiments, $R^3$ is a heteroalkyl substituted with a substituent group. In embodiments, $R^3$ is a heteroalkyl substituted with a size-limited substituent group. In embodiments, $R^3$ is a heteroalkyl substituted with a lower substituent group. In embodiments, $R^3$ is unsubstituted heteroalkyl.

In embodiments, $R^3$ is substituted (e.g., substituted with a substituent group, a size-limited substituent group, or lower substituent group) or unsubstituted cycloalkyl. In embodiments, $R^3$ is a cycloalkyl substituted with a substituent group. In embodiments, $R^3$ is a cycloalkyl substituted with a size-limited substituent group. In embodiments, $R^3$ is a cycloalkyl substituted with a lower substituent group. In embodiments, $R^3$ is unsubstituted cycloalkyl.

In embodiments, $R^3$ is substituted (e.g., substituted with a substituent group, a size-limited substituent group, or lower substituent group) or unsubstituted heterocycloalkyl. In embodiments, $R^3$ is a heterocycloalkyl substituted with a substituent group. In embodiments, $R^3$ is a heterocycloalkyl substituted with a size-limited substituent group. In embodiments, $R^3$ is a heterocycloalkyl substituted with a lower substituent group. In embodiments, $R^3$ is unsubstituted heterocycloalkyl.

In embodiments, $R^3$ is substituted (e.g., substituted with a substituent group, a size-limited substituent group, or lower substituent group) or unsubstituted aryl. In embodiments, $R^3$ is an aryl substituted with a substituent group. In embodiments, $R^3$ is an aryl substituted with a size-limited substituent group. In embodiments, $R^3$ is an aryl substituted with a lower substituent group. In embodiments, $R^3$ is unsubstituted aryl.

In embodiments, $R^3$ is substituted (e.g., substituted with a substituent group, a size-limited substituent group, or lower substituent group) or unsubstituted heteroaryl. In embodiments, $R^3$ is a heteroaryl substituted with a substituent group. In embodiments, $R^3$ is a heteroaryl substituted with a size-limited substituent group. In embodiments, $R^3$ is a heteroaryl substituted with a lower substituent group. In embodiments, $R^3$ is unsubstituted heteroaryl.

In embodiments, $R^2$ and $R^3$ are independently an amino acid side chain. In embodiments, the amino acid side chain is a side chain of a natural amino acid (e.g., alanine, arginine, asparagine, aspartic acid, cysteine, glutamine, glutamic acid, glycine (e.g., —H), histidine, isoleucine, leucine, lysine, methionine, phenylalanine, serine, threonine, tryptophan, tyrosine, or valine). In embodiments, the amino acid side chain is a side chain of a non-natural amino acid side-chain. In embodiments, $R^2$ and $R^3$ are independently an amino acid side chain of an L-amino acid.

In embodiments, $R^2$ is —H,

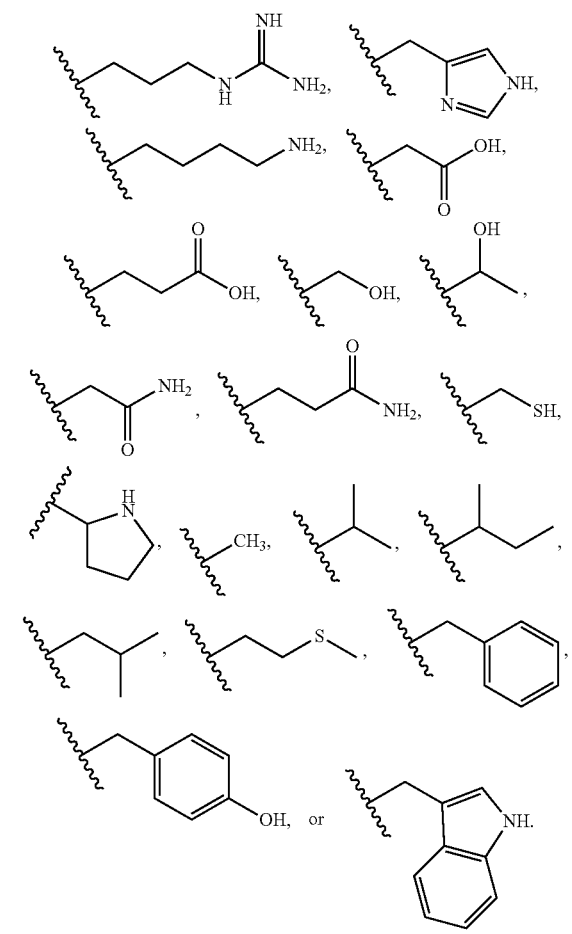

In embodiments, R² is —H. In embodiments, R² is
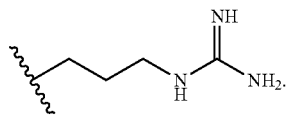 [SMILES: *CCCNC(=N)N]
In embodiments, R² is
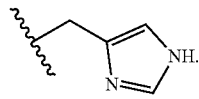 [SMILES: *Cc1c[nH]cn1]
In embodiments, R² is
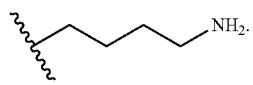 [SMILES: *CCCCN]
In embodiments, R² is
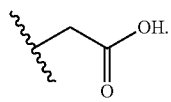
In embodiments, R² is
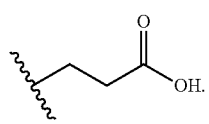
In embodiments, R² is
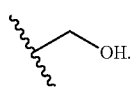 [SMILES: *CO]
In embodiments, R² is
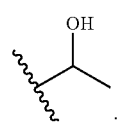 [SMILES: *C(C)O]
In embodiments, R² is
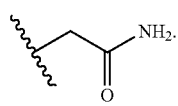
In embodiments, R² is
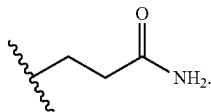 [SMILES: *CCC(N)=O]
In embodiments, R² is
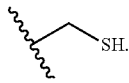
In embodiments, R² is
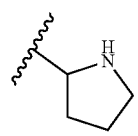
In embodiments, R² is
In embodiments, R² is
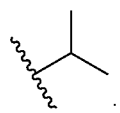 [SMILES: *C(C)C]
In embodiments, R² is
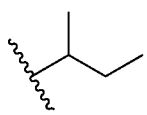
In embodiments, R² is
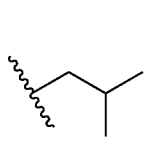
In embodiments, R² is
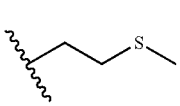

In embodiments, R² is
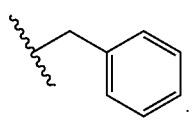
In embodiments, R² is
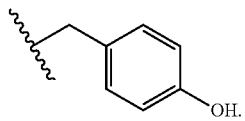
In embodiments, R² is
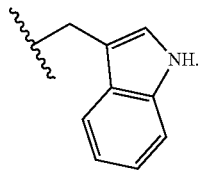 [SMILES: *Cc1c[nH]c2ccccc12]
In embodiments, R² is
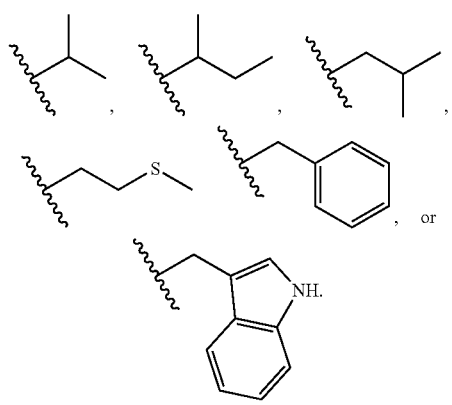
, or
In embodiments, R² is
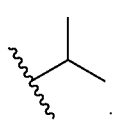
In embodiments, R² is
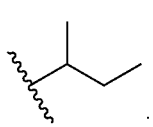 [SMILES: *C(C)CC]
In embodiments, R² is
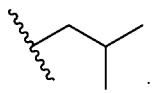 [SMILES: *CC(C)C]
In embodiments, R² is
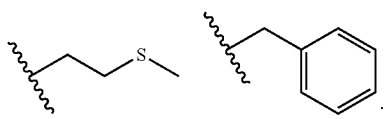
In embodiments, R² is or
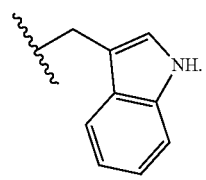 [SMILES: *Cc1c[nH]c2ccccc12]
In embodiments, R³ is —H,
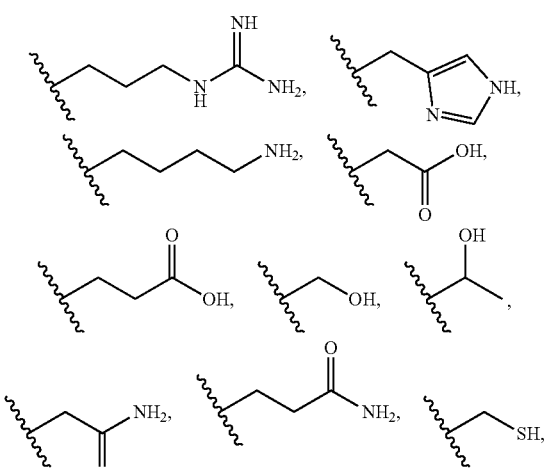
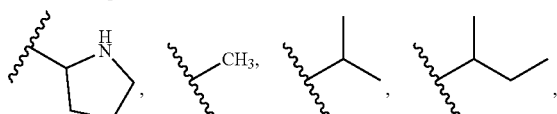
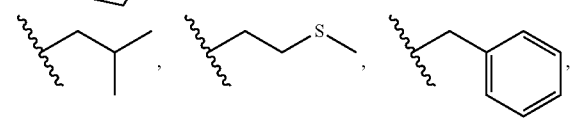
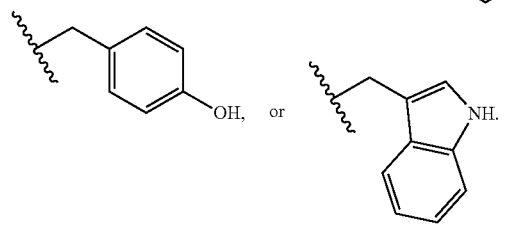

In embodiments, $R^3$ is —H. In embodiments, $R^3$ is

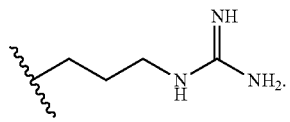 [SMILES: *CCCNC(=N)N]

In embodiments, $R^3$ is

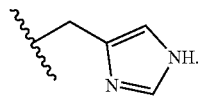

In embodiments, $R^3$ is

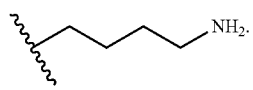

In embodiments, $R^3$ is

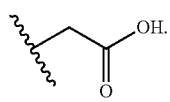

In embodiments, $R^3$ is

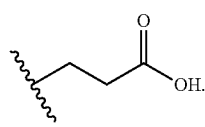 [SMILES: *CCC(=O)O]

In embodiments, $R^3$ is

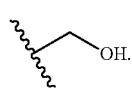

In embodiments, $R^3$ is

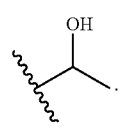

In embodiments, $R^3$ is

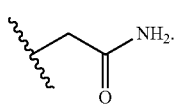

In embodiments, $R^3$ is

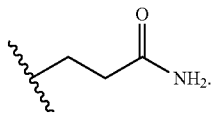 [SMILES: *CCC(N)=O]

In embodiments, $R^3$ is

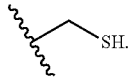

In embodiments, $R^3$ is

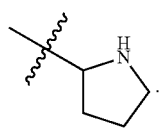

In embodiments, $R^3$ is

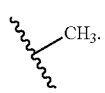

In embodiments, $R^3$ is

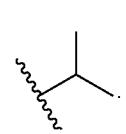

In embodiments, $R^3$ is

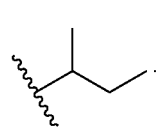

In embodiments, $R^3$ is

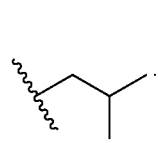

In embodiments, $R^3$ is

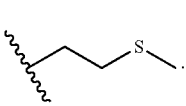 [SMILES: *CCSC]

In embodiments, R³ is
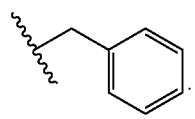
In embodiments, R³ is
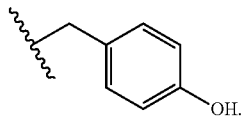 [SMILES: *Cc1ccc(O)cc1]
In embodiments, R³ is
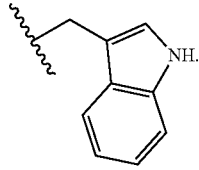
In embodiments, R³ is
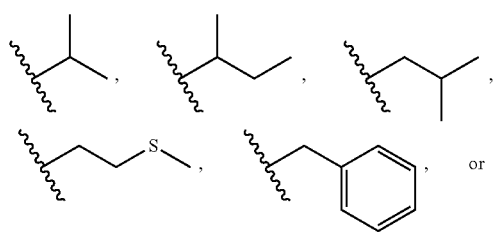
In embodiments, R³ is
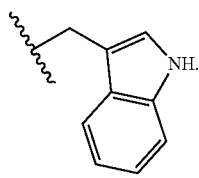 [SMILES: *Cc1c[nH]c2ccccc12]
In embodiments, R³ is
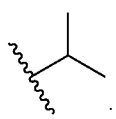
In embodiments, R³ is
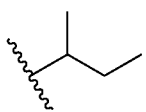
In embodiments, R³ is
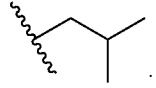 [SMILES: *CC(C)C]
In embodiments, R³ is
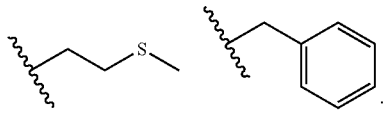
In embodiments, R³ is or
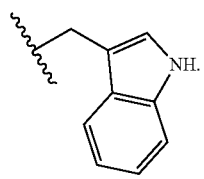 [SMILES: *Cc1c[nH]c2ccccc12]
In embodiments, R² is
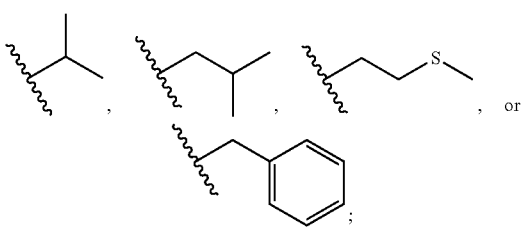
and R³ is
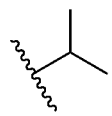 [SMILES: *C(C)C]
In embodiments, R² is
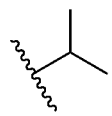 [SMILES: *C(C)C]
and R³ is
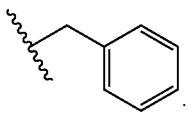 [SMILES: *Cc1ccccc1]

In embodiments, R² is

[isobutyl group structure]

and R³ is

[benzyl group structure].

In embodiments, R² is

[CH₂CH₂SCH₃ group structure]

and R³ is

[benzyl group structure].

In embodiments, R² is

[benzyl group structure]

and R³ is

[benzyl group structure].

In embodiments, R² is

[indol-3-ylmethyl group structure with NH]

and R³ is

[isopropyl, sec-butyl, isobutyl group structures], [benzyl group structure], or [indol-3-ylmethyl group structure with NH].

In embodiments, R² is

[indol-3-ylmethyl group structure with NH]

and R³ is

[isopropyl group structure].

In embodiments, R² is

[indol-3-ylmethyl group structure with NH]

and R³ is

[sec-butyl group structure].

In embodiments, R² is

[indol-3-ylmethyl group structure with NH]

and R³ is
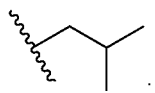 [SMILES: *CC(C)C]
In embodiments, R² is
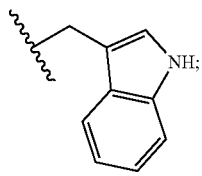 [SMILES: *Cc1c[nH]c2ccccc12]
and R³ is
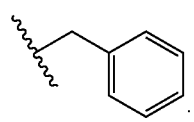
In embodiments, R² is
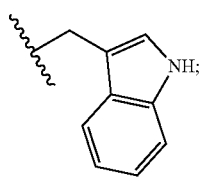 [SMILES: *Cc1c[nH]c2ccccc12]
and R³ is
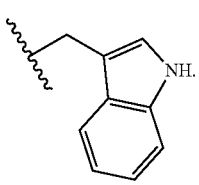 [SMILES: *Cc1c[nH]c2ccccc12]
In embodiments, R² is
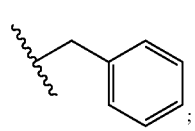 [SMILES: *Cc1ccccc1]
and R³ is
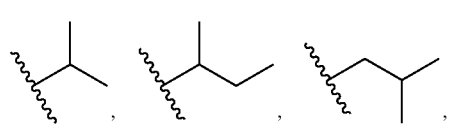
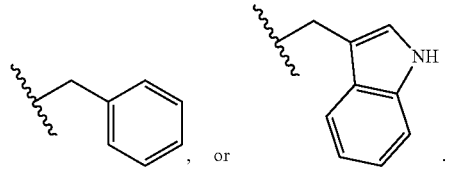, or
In embodiments, R² is
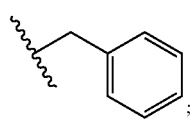 [SMILES: *Cc1ccccc1];
and R³ is
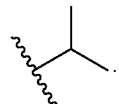 [SMILES: *C(C)C]
In embodiments, R² is
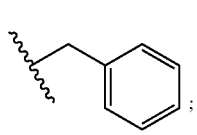;
and R³ is
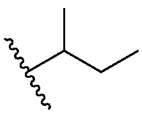
In embodiments, R² is
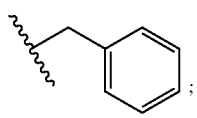;
and R³ is
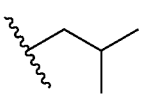
In embodiments, R² is
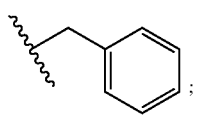;
and R³ is
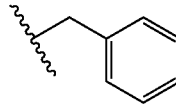

In embodiments, $R^2$ is

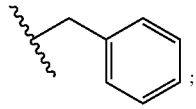;

and $R^3$ is

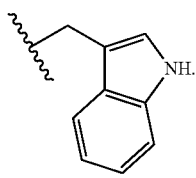 [SMILES: *Cc1c[nH]c2ccccc12]

In embodiments, $R^2$ is H,

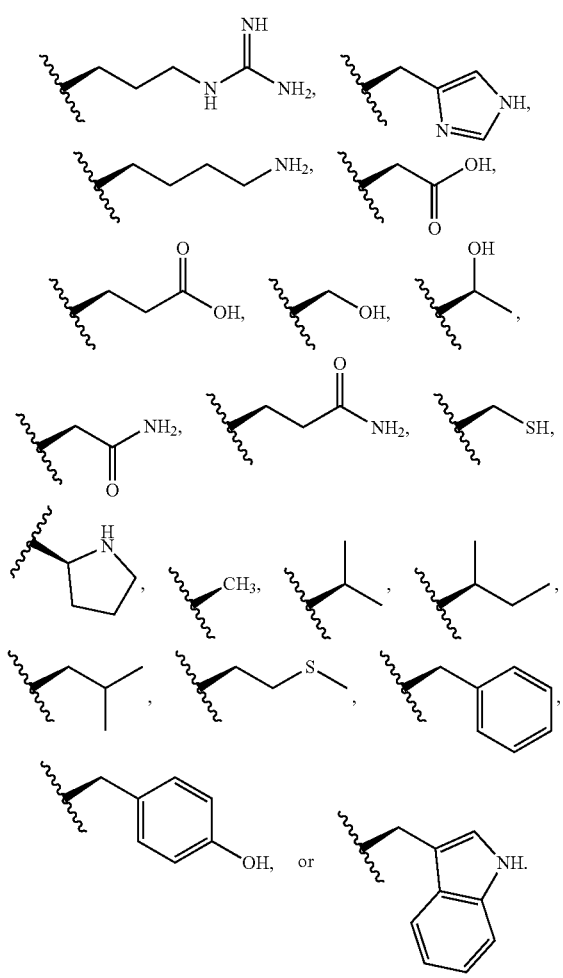

In embodiments, $R^3$ is H,

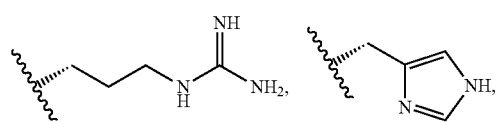

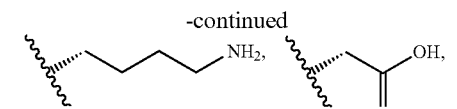

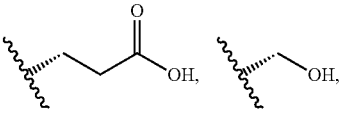

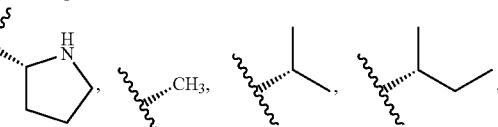

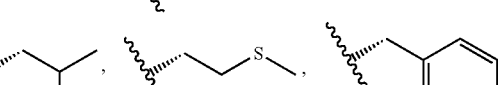

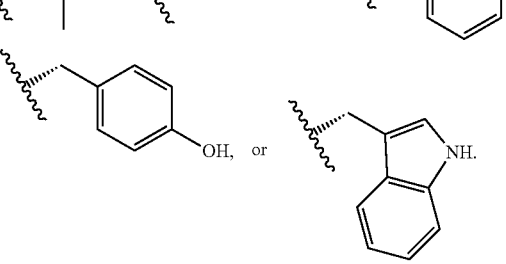

In embodiments $R^2$ and $R^3$ are independently a non-natural amino acid side-chain or a natural amino acid side-chain. In embodiments, $R^2$ is the side-chain of exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-βopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—Boc-Phe(4-Br)—Boc-D-Phe(4-Br)—Boc-D-Phe(3-Cl)—Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-(4-(trifluoromethyl)phenyl]acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, or Fmoc-β-(2-thienyl)-Ala-OH, 4-(Hydroxymethyl)-D-phenylalanine.

In embodiments, $R^3$ is the side-chain of exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl]acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, or Fmoc-β-(2-thienyl)-Ala-OH, 4-(Hydroxymethyl)-D-phenylalanine.

In embodiments, $R^2$ is a side chain of alanine and $R^3$ is a side chain of alanine. In embodiments, $R^2$ is a side chain of alanine and $R^3$ is a side chain of isoleucine. In embodiments, $R^2$ is a side chain of alanine and $R^3$ is a side chain of leucine. In embodiments, $R^2$ is a side chain of alanine and $R^3$ is a side chain of methionine. In embodiments, $R^2$ is a side chain of alanine and $R^3$ is a side chain of valine. In embodiments, $R^2$ is a side chain of alanine and $R^3$ is a side chain of phenylalanine. In embodiments, $R^2$ is a side chain of alanine and $R^3$ is a side chain of tryptophan. In embodiments, $R^2$ is a side chain of alanine and $R^3$ is a side chain of tyrosine. In embodiments, $R^2$ is a side chain of alanine and $R^3$ is a side chain of asparagine. In embodiments, $R^2$ is a side chain of alanine and $R^3$ is a side chain of cysteine. In embodiments, $R^2$ is a side chain of alanine and $R^3$ is a side chain of glutamine. In embodiments, $R^2$ is a side chain of alanine and $R^3$ is a side chain of serine. In embodiments, $R^2$ is a side chain of alanine and $R^3$ is a side chain of threonine. In embodiments, $R^2$ is a side chain of alanine and $R^3$ is a side chain of aspartic acid. In embodiments, $R^2$ is a side chain of alanine and $R^3$ is a side chain of glutamic acid. In embodiments, $R^2$ is a side chain of alanine and $R^3$ is a side chain of arginine. In embodiments, $R^2$ is a side chain of alanine and $R^3$ is a side chain of histidine. In embodiments, $R^2$ is a side chain of alanine and $R^3$ is a side chain of lysine. In embodiments, $R^2$ is a side chain of alanine and $R^3$ is a side chain of glycine (e.g., H). In embodiments, $R^2$ is a side chain of isoleucine and $R^3$ is a side chain of alanine. In embodiments, $R^2$ is a side chain of isoleucine and $R^3$ is a side chain of isoleucine. In embodiments, $R^2$ is a side chain of isoleucine and $R^3$ is a side chain of leucine. In embodiments, $R^2$ is a side chain of isoleucine and $R^3$ is a side chain of methionine. In embodiments, $R^2$ is a side chain of isoleucine and $R^3$ is a side chain of valine. In embodiments, $R^2$ is a side chain of isoleucine and $R^3$ is a side chain of phenylalanine. In embodiments, $R^2$ is a side chain of isoleucine and $R^3$ is a side chain of tryptophan. In embodiments, $R^2$ is a side chain of isoleucine and $R^3$ is a side chain of tyrosine. In embodiments, $R^2$ is a side chain of isoleucine and $R^3$ is a side chain of asparagine. In embodiments, $R^2$ is a side chain of isoleucine and $R^3$ is a side chain of cysteine. In embodiments, $R^2$ is a side chain of isoleucine and $R^3$ is a side chain of glutamine. In embodiments, $R^2$ is a side chain of isoleucine and $R^3$ is a side chain of serine. In embodiments, $R^2$ is a side chain of isoleucine and $R^3$ is a side chain of threonine. In embodiments, $R^2$ is a side chain of isoleucine and $R^3$ is a side chain of aspartic acid. In embodiments, $R^2$ is a side chain of isoleucine and $R^3$ is a side chain of glutamic acid. In embodiments, $R^2$ is a side chain of isoleucine and $R^3$ is a side chain of arginine. In embodiments, $R^2$ is a side chain of isoleucine and $R^3$ is a side chain of histidine. In embodiments, $R^2$ is a side chain of isoleucine and $R^3$ is a side chain of lysine. In embodiments, $R^2$ is a side chain of isoleucine and $R^3$ is a side chain of glycine (e.g., H). In embodiments, $R^2$ is a side chain of leucine and $R^3$ is a side chain of alanine. In embodiments, $R^2$ is a side chain of leucine and $R^3$ is a side chain of isoleucine. In embodiments, $R^2$ is a side chain of leucine and $R^3$ is a side chain of leucine. In embodiments, $R^2$ is a side chain of leucine and $R^3$ is a side chain of methionine. In embodiments, $R^2$ is a side chain of leucine and $R^3$ is a side chain of valine. In embodiments, $R^2$ is a side chain of leucine and $R^3$ is a side chain of phenylalanine. In embodiments, $R^2$ is a side chain of leucine and $R^3$ is a side chain of tryptophan. In embodiments, $R^2$ is a side chain of leucine and $R^3$ is a side chain of tyrosine. In embodiments, $R^2$ is a side chain of leucine and $R^3$ is a side chain of asparagine. In embodiments, $R^2$ is a side chain of leucine and $R^3$ is a side chain of cysteine. In embodiments, $R^2$ is a side chain of leucine and $R^3$ is a side chain of glutamine. In embodiments, $R^2$ is a side chain of leucine and $R^3$ is a side chain of serine. In embodiments, $R^2$ is a side chain of leucine and $R^3$ is a side chain of threonine. In embodiments, $R^2$ is a side chain of leucine and $R^3$ is a side chain of aspartic acid. In embodiments, $R^2$ is a side chain of leucine and $R^3$ is a side chain of glutamic acid. In embodiments, $R^2$ is a side chain of leucine and $R^3$ is a side chain of arginine. In embodiments, $R^2$ is a side chain of leucine and $R^3$ is a side chain of histidine. In embodiments, $R^2$ is a side chain of leucine and $R^3$ is a side chain of lysine. In embodiments, $R^2$ is a side chain of leucine and $R^3$ is a side chain of glycine (e.g., H). In embodiments, $R^2$ is a side chain of methionine and $R^3$ is a side chain of alanine. In embodiments, $R^2$ is a side chain of methionine and $R^3$ is a side chain of isoleucine. In embodiments, $R^2$ is a side chain of methionine and $R^3$ is a side chain of leucine. In embodiments, $R^2$ is a side chain of methionine and $R^3$ is a side chain of methionine. In embodiments, $R^2$ is a side chain of methionine and $R^3$ is a side chain of valine. In embodiments, $R^2$ is a side chain of methionine and $R^3$ is a side chain of phenylalanine. In embodiments, $R^2$ is a side chain of methionine and $R^3$ is a side chain of tryptophan. In embodiments, $R^2$ is a side chain of methionine and $R^3$ is a side chain of tyrosine. In embodiments, $R^2$ is a side chain of methionine and $R^3$ is a side chain of asparagine. In embodiments, $R^2$ is a side chain of methionine and $R^3$ is a side chain of cysteine. In embodiments, $R^2$ is a side chain of methionine and $R^3$ is a side chain of glutamine. In embodiments, $R^2$ is a side chain of methionine and $R^3$ is a side chain of serine. In embodiments, $R^2$ is a side chain of methionine and $R^3$ is a side chain of threonine. In embodiments, $R^2$ is a side chain of methionine and $R^3$ is a side chain of aspartic acid. In embodiments, $R^2$ is a side chain of methionine and $R^3$ is a side chain of glutamic acid. In embodiments, $R^2$ is a side chain of methionine and $R^3$ is a side chain of arginine. In embodiments, $R^2$ is a side chain of methionine and $R^3$ is a side chain of histidine. In embodiments, $R^2$ is a side chain of methionine and $R^3$ is a side chain of lysine. In embodiments, $R^2$ is a side chain of methionine and $R^3$ is a side chain of glycine (e.g., H). In embodiments, $R^2$ is a side chain of valine and $R^3$ is a side chain of alanine. In embodiments, $R^2$ is a side chain of valine and $R^3$ is a side chain of isoleucine. In embodiments, $R^2$ is a side chain of valine and $R^3$ is a side chain of leucine. In embodiments, $R^2$ is a side chain of valine and $R^3$ is a side chain of methionine. In embodiments, $R^2$ is a side chain of valine and $R^3$ is a side chain of valine. In embodiments, $R^2$ is a side chain of valine and $R^3$ is a side chain of phenylalanine. In embodiments, $R^2$ is a side chain of valine and $R^3$ is a side chain of tryptophan. In embodiments, $R^2$ is a side chain of valine and $R^3$ is a side chain of tyrosine. In embodiments, $R^2$ is a side chain of valine and $R^3$ is a side chain of asparagine. In embodiments, $R^2$ is a side chain of valine and $R^3$ is a side chain of cysteine. In embodiments, $R^2$ is a side chain of valine and $R^3$ is a side chain of glutamine. In embodiments, $R^2$ is a side chain of valine and $R^3$ is a side chain of serine. In embodiments, $R^2$ is a side chain of valine and $R^3$ is a side chain of threonine.

In embodiments, $R^2$ is a side chain of valine and $R^3$ is a side chain of aspartic acid. In embodiments, $R^2$ is a side chain of valine and $R^3$ is a side chain of glutamic acid. In embodiments, $R^2$ is a side chain of valine and $R^3$ is a side chain of arginine. In embodiments, $R^2$ is a side chain of valine and $R^3$ is a side chain of histidine. In embodiments, $R^2$ is a side chain of valine and $R^3$ is a side chain of lysine. In embodiments, $R^2$ is a side chain of valine and $R^3$ is a side chain of glycine (e.g., H). In embodiments, $R^2$ is a side chain of phenylalanine and $R^3$ is a side chain of alanine. In embodiments, $R^2$ is a side chain of phenylalanine and $R^3$ is a side chain of isoleucine. In embodiments, $R^2$ is a side chain of phenylalanine and $R^3$ is a side chain of leucine. In embodiments, $R^2$ is a side chain of phenylalanine and $R^3$ is a side chain of methionine. In embodiments, $R^2$ is a side chain of phenylalanine and $R^3$ is a side chain of valine. In embodiments, $R^2$ is a side chain of phenylalanine and $R^3$ is a side chain of phenylalanine. In embodiments, $R^2$ is a side chain of phenylalanine and $R^3$ is a side chain of tryptophan. In embodiments, $R^2$ is a side chain of phenylalanine and $R^3$ is a side chain of tyrosine. In embodiments, $R^2$ is a side chain of phenylalanine and $R^3$ is a side chain of asparagine. In embodiments, $R^2$ is a side chain of phenylalanine and $R^3$ is a side chain of cysteine. In embodiments, $R^2$ is a side chain of phenylalanine and $R^3$ is a side chain of glutamine. In embodiments, $R^2$ is a side chain of phenylalanine and $R^3$ is a side chain of serine. In embodiments, $R^2$ is a side chain of phenylalanine and $R^3$ is a side chain of threonine. In embodiments, $R^2$ is a side chain of phenylalanine and $R^3$ is a side chain of aspartic acid. In embodiments, $R^2$ is a side chain of phenylalanine and $R^3$ is a side chain of glutamic acid. In embodiments, $R^2$ is a side chain of phenylalanine and $R^3$ is a side chain of arginine. In embodiments, $R^2$ is a side chain of phenylalanine and $R^3$ is a side chain of histidine. In embodiments, $R^2$ is a side chain of phenylalanine and $R^3$ is a side chain of lysine. In embodiments, $R^2$ is a side chain of phenylalanine and $R^3$ is a side chain of glycine (e.g., H). In embodiments, $R^2$ is a side chain of tryptophan and $R^3$ is a side chain of alanine. In embodiments, $R^2$ is a side chain of tryptophan and $R^3$ is a side chain of isoleucine. In embodiments, $R^2$ is a side chain of tryptophan and $R^3$ is a side chain of leucine. In embodiments, $R^2$ is a side chain of tryptophan and $R^3$ is a side chain of methionine. In embodiments, $R^2$ is a side chain of tryptophan and $R^3$ is a side chain of valine. In embodiments, $R^2$ is a side chain of tryptophan and $R^3$ is a side chain of phenylalanine. In embodiments, $R^2$ is a side chain of tryptophan and $R^3$ is a side chain of tryptophan. In embodiments, $R^2$ is a side chain of tryptophan and $R^3$ is a side chain of tyrosine. In embodiments, $R^2$ is a side chain of tryptophan and $R^3$ is a side chain of asparagine. In embodiments, $R^2$ is a side chain of tryptophan and $R^3$ is a side chain of cysteine. In embodiments, $R^2$ is a side chain of tryptophan and $R^3$ is a side chain of glutamine. In embodiments, $R^2$ is a side chain of tryptophan and $R^3$ is a side chain of serine. In embodiments, $R^2$ is a side chain of tryptophan and $R^3$ is a side chain of threonine. In embodiments, $R^2$ is a side chain of tryptophan and $R^3$ is a side chain of aspartic acid. In embodiments, $R^2$ is a side chain of tryptophan and $R^3$ is a side chain of glutamic acid. In embodiments, $R^2$ is a side chain of tryptophan and $R^3$ is a side chain of arginine. In embodiments, $R^2$ is a side chain of tryptophan and $R^3$ is a side chain of histidine. In embodiments, $R^2$ is a side chain of tryptophan and $R^3$ is a side chain of lysine. In embodiments, $R^2$ is a side chain of tryptophan and $R^3$ is a side chain of glycine (e.g., H). In embodiments, $R^2$ is a side chain of tyrosine and $R^3$ is a side chain of alanine. In embodiments, $R^2$ is a side chain of tyrosine and $R^3$ is a side chain of isoleucine. In embodiments, $R^2$ is a side chain of tyrosine and $R^3$ is a side chain of leucine. In embodiments, $R^2$ is a side chain of tyrosine and $R^3$ is a side chain of methionine. In embodiments, $R^2$ is a side chain of tyrosine and $R^3$ is a side chain of valine. In embodiments, $R^2$ is a side chain of tyrosine and $R^3$ is a side chain of phenylalanine. In embodiments, $R^2$ is a side chain of tyrosine and $R^3$ is a side chain of tryptophan. In embodiments, $R^2$ is a side chain of tyrosine and $R^3$ is a side chain of tyrosine. In embodiments, $R^2$ is a side chain of tyrosine and $R^3$ is a side chain of asparagine. In embodiments, $R^2$ is a side chain of tyrosine and $R^3$ is a side chain of cysteine. In embodiments, $R^2$ is a side chain of tyrosine and $R^3$ is a side chain of glutamine. In embodiments, $R^2$ is a side chain of tyrosine and $R^3$ is a side chain of serine. In embodiments, $R^2$ is a side chain of tyrosine and $R^3$ is a side chain of threonine. In embodiments, $R^2$ is a side chain of tyrosine and $R^3$ is a side chain of aspartic acid. In embodiments, $R^2$ is a side chain of tyrosine and $R^3$ is a side chain of glutamic acid. In embodiments, $R^2$ is a side chain of tyrosine and $R^3$ is a side chain of arginine. In embodiments, $R^2$ is a side chain of tyrosine and $R^3$ is a side chain of histidine. In embodiments, $R^2$ is a side chain of tyrosine and $R^3$ is a side chain of lysine. In embodiments, $R^2$ is a side chain of tyrosine and $R^3$ is a side chain of glycine (e.g., H). In embodiments, $R^2$ is a side chain of asparagine and $R^3$ is a side chain of alanine. In embodiments, $R^2$ is a side chain of asparagine and $R^3$ is a side chain of isoleucine. In embodiments, $R^2$ is a side chain of asparagine and $R^3$ is a side chain of leucine. In embodiments, $R^2$ is a side chain of asparagine and $R^3$ is a side chain of methionine. In embodiments, $R^2$ is a side chain of asparagine and $R^3$ is a side chain of valine. In embodiments, $R^2$ is a side chain of asparagine and $R^3$ is a side chain of phenylalanine. In embodiments, $R^2$ is a side chain of asparagine and $R^3$ is a side chain of tryptophan. In embodiments, $R^2$ is a side chain of asparagine and $R^3$ is a side chain of tyrosine. In embodiments, $R^2$ is a side chain of asparagine and $R^3$ is a side chain of asparagine. In embodiments, $R^2$ is a side chain of asparagine and $R^3$ is a side chain of cysteine. In embodiments, $R^2$ is a side chain of asparagine and $R^3$ is a side chain of glutamine. In embodiments, $R^2$ is a side chain of asparagine and $R^3$ is a side chain of serine. In embodiments, $R^2$ is a side chain of asparagine and R³ is a side chain of threonine. In embodiments, R² is a side chain of asparagine and R³ is a side chain of aspartic acid. In embodiments, R² is a side chain of asparagine and R³ is a side chain of glutamic acid. In embodiments, R² is a side chain of asparagine and R³ is a side chain of arginine. In embodiments, R² is a side chain of asparagine and R³ is a side chain of histidine. In embodiments, R² is a side chain of asparagine and R³ is a side chain of lysine. In embodiments, R² is a side chain of asparagine and R³ is a side chain of glycine (e.g., H). In embodiments, R² is a side chain of cysteine and R³ is a side chain of alanine. In embodiments, R² is a side chain of cysteine and R³ is a side chain of isoleucine. In embodiments, R² is a side chain of cysteine and R³ is a side chain of leucine. In embodiments, R² is a side chain of cysteine and R³ is a side chain of methionine. In embodiments, R² is a side chain of cysteine and R³ is a side chain of valine. In embodiments, R² is a side chain of cysteine and R³ is a side chain of phenylalanine. In embodiments, R² is a side chain of cysteine and R³ is a side chain of tryptophan. In embodiments, R² is a side chain of cysteine and R³ is a side chain of tyrosine. In embodiments, R² is a side chain of cysteine and R³ is a side chain of asparagine. In embodiments, R² is a side chain of cysteine and R³ is a side chain of cysteine. In embodiments, R² is a side chain of cysteine and R³ is a side chain of glutamine. In embodiments, R² is a side chain of cysteine and R³ is a side chain of serine. In embodiments, R² is a side chain of cysteine and R³ is a side chain of threonine. In embodiments, R² is a side chain of cysteine and R³ is a side chain of aspartic acid. In embodiments, R² is a side chain of cysteine and R³ is a side chain of glutamic acid. In embodiments, R² is a side chain of cysteine and R³ is a side chain of arginine. In embodiments, R² is a side chain of cysteine and R³ is a side chain of histidine. In embodiments, R² is a side chain of cysteine and R³ is a side chain of lysine. In embodiments, R² is a side chain of cysteine and R³ is a side chain of glycine (e.g., H). In embodiments, R² is a side chain of glutamine and R³ is a side chain of alanine. In embodiments, R² is a side chain of glutamine and R³ is a side chain of isoleucine. In embodiments, R² is a side chain of glutamine and R³ is a side chain of leucine. In embodiments, R² is a side chain of glutamine and R³ is a side chain of methionine. In embodiments, R² is a side chain of glutamine and R³ is a side chain of valine. In embodiments, R² is a side chain of glutamine and R³ is a side chain of phenylalanine. In embodiments, R² is a side chain of glutamine and R³ is a side chain of tryptophan. In embodiments, R² is a side chain of glutamine and R³ is a side chain of tyrosine. In embodiments, R² is a side chain of glutamine and R³ is a side chain of asparagine. In embodiments, R² is a side chain of glutamine and R³ is a side chain of cysteine. In embodiments, R² is a side chain of glutamine and R³ is a side chain of glutamine. In embodiments, R² is a side chain of glutamine and R³ is a side chain of serine. In embodiments, R² is a side chain of glutamine and R³ is a side chain of threonine. In embodiments, R² is a side chain of glutamine and R³ is a side chain of aspartic acid. In embodiments, R² is a side chain of glutamine and R³ is a side chain of glutamic acid. In embodiments, R² is a side chain of glutamine and R³ is a side chain of arginine. In embodiments, R² is a side chain of glutamine and R³ is a side chain of histidine. In embodiments, R² is a side chain of glutamine and R³ is a side chain of lysine. In embodiments, R² is a side chain of glutamine and R³ is a side chain of glycine (e.g., H). In embodiments, R² is a side chain of serine and R³ is a side chain of alanine. In embodiments, R² is a side chain of serine and R³ is a side chain of isoleucine. In embodiments, R² is a side chain of serine and R³ is a side chain of leucine. In embodiments, R² is a side chain of serine and R³ is a side chain of methionine. In embodiments, R² is a side chain of serine and R³ is a side chain of valine. In embodiments, R² is a side chain of serine and R³ is a side chain of phenylalanine. In embodiments, R² is a side chain of serine and R³ is a side chain of tryptophan. In embodiments, R² is a side chain of serine and R³ is a side chain of tyrosine. In embodiments, R² is a side chain of serine and R³ is a side chain of asparagine. In embodiments, R² is a side chain of serine and R³ is a side chain of cysteine. In embodiments, R² is a side chain of serine and R³ is a side chain of glutamine. In embodiments, R² is a side chain of serine and R³ is a side chain of serine. In embodiments, R² is a side chain of serine and R³ is a side chain of threonine. In embodiments, R² is a side chain of serine and R³ is a side chain of aspartic acid. In embodiments, R² is a side chain of serine and R³ is a side chain of glutamic acid. In embodiments, R² is a side chain of serine and R³ is a side chain of arginine. In embodiments, R² is a side chain of serine and R³ is a side chain of histidine. In embodiments, R² is a side chain of serine and R³ is a side chain of lysine. In embodiments, R² is a side chain of serine and R³ is a side chain of glycine (e.g., H). In embodiments, R² is a side chain of threonine and R³ is a side chain of alanine. In embodiments, R² is a side chain of threonine and R³ is a side chain of isoleucine. In embodiments, R² is a side chain of threonine and R³ is a side chain of leucine. In embodiments, R² is a side chain of threonine and R³ is a side chain of methionine. In embodiments, R² is a side chain of threonine and R³ is a side chain of valine. In embodiments, R² is a side chain of threonine and R³ is a side chain of phenylalanine. In embodiments, R² is a side chain of threonine and R³ is a side chain of tryptophan. In embodiments, R² is a side chain of threonine and R³ is a side chain of tyrosine. In embodiments, R² is a side chain of threonine and R³ is a side chain of asparagine. In embodiments, R² is a side chain of threonine and R³ is a side chain of cysteine. In embodiments, R² is a side chain of threonine and R³ is a side chain of glutamine. In embodiments, R² is a side chain of threonine and R³ is a side chain of serine. In embodiments, R² is a side chain of threonine and R³ is a side chain of threonine. In embodiments, R² is a side chain of threonine and R³ is a side chain of aspartic acid. In embodiments, R² is a side chain of threonine and R³ is a side chain of glutamic acid. In embodiments, R² is a side chain of threonine and R³ is a side chain of arginine. In embodiments, R² is a side chain of threonine and R³ is a side chain of histidine. In embodiments, R² is a side chain of threonine and R³ is a side chain of lysine. In embodiments, R² is a side chain of threonine and R³ is a side chain of glycine (e.g., H). In embodiments, R² is a side chain of aspartic acid and R³ is a side chain of alanine. In embodiments, R² is a side chain of aspartic acid and R³ is a side chain of isoleucine. In embodiments, R² is a side chain of aspartic acid and R³ is a side chain of leucine. In embodiments, R² is a side chain of aspartic acid and R³ is a side chain of methionine. In embodiments, R² is a side chain of aspartic acid and R³ is a side chain of valine. In embodiments, R² is a side chain of aspartic acid and R³ is a side chain of phenylalanine. In embodiments, R² is a side chain of aspartic acid and R³ is a side chain of tryptophan. In embodiments, R² is a side chain of aspartic acid and R³ is a side chain of tyrosine. In embodiments, R² is a side chain of aspartic acid and R³ is a side chain of asparagine. In embodiments, R² is a side chain of aspartic acid and R³ is a side chain of cysteine. In embodiments, R² is a side chain of aspartic acid and R³ is a side chain of glutamine. In embodiments, $R^2$ is a side chain of aspartic acid and $R^3$ is a side chain of serine. In embodiments, $R^2$ is a side chain of aspartic acid and $R^3$ is a side chain of threonine. In embodiments, $R^2$ is a side chain of aspartic acid and $R^3$ is a side chain of aspartic acid. In embodiments, $R^2$ is a side chain of aspartic acid and $R^3$ is a side chain of glutamic acid. In embodiments, $R^2$ is a side chain of aspartic acid and $R^3$ is a side chain of arginine. In embodiments, $R^2$ is a side chain of aspartic acid and $R^3$ is a side chain of histidine. In embodiments, $R^2$ is a side chain of aspartic acid and $R^3$ is a side chain of lysine. In embodiments, $R^2$ is a side chain of aspartic acid and $R^3$ is a side chain of glycine (e.g., H). In embodiments, $R^2$ is a side chain of glutamic acid and $R^3$ is a side chain of alanine. In embodiments, $R^2$ is a side chain of glutamic acid and $R^3$ is a side chain of isoleucine. In embodiments, $R^2$ is a side chain of glutamic acid and $R^3$ is a side chain of leucine. In embodiments, $R^2$ is a side chain of glutamic acid and $R^3$ is a side chain of methionine. In embodiments, $R^2$ is a side chain of glutamic acid and $R^3$ is a side chain of valine. In embodiments, $R^2$ is a side chain of glutamic acid and $R^3$ is a side chain of phenylalanine. In embodiments, $R^2$ is a side chain of glutamic acid and $R^3$ is a side chain of tryptophan. In embodiments, $R^2$ is a side chain of glutamic acid and $R^3$ is a side chain of tyrosine. In embodiments, $R^2$ is a side chain of glutamic acid and $R^3$ is a side chain of asparagine. In embodiments, $R^2$ is a side chain of glutamic acid and $R^3$ is a side chain of cysteine. In embodiments, $R^2$ is a side chain of glutamic acid and $R^3$ is a side chain of glutamine. In embodiments, $R^2$ is a side chain of glutamic acid and $R^3$ is a side chain of serine. In embodiments, $R^2$ is a side chain of glutamic acid and $R^3$ is a side chain of threonine. In embodiments, $R^2$ is a side chain of glutamic acid and $R^3$ is a side chain of aspartic acid. In embodiments, $R^2$ is a side chain of glutamic acid and $R^3$ is a side chain of glutamic acid. In embodiments, $R^2$ is a side chain of glutamic acid and $R^3$ is a side chain of arginine. In embodiments, $R^2$ is a side chain of glutamic acid and $R^3$ is a side chain of histidine. In embodiments, $R^2$ is a side chain of glutamic acid and $R^3$ is a side chain of lysine. In embodiments, $R^2$ is a side chain of glutamic acid and $R^3$ is a side chain of glycine (e.g., H). In embodiments, $R^2$ is a side chain of arginine and $R^3$ is a side chain of alanine. In embodiments, $R^2$ is a side chain of arginine and $R^3$ is a side chain of isoleucine. In embodiments, $R^2$ is a side chain of arginine and $R^3$ is a side chain of leucine. In embodiments, $R^2$ is a side chain of arginine and $R^3$ is a side chain of methionine. In embodiments, $R^2$ is a side chain of arginine and $R^3$ is a side chain of valine. In embodiments, $R^2$ is a side chain of arginine and $R^3$ is a side chain of phenylalanine. In embodiments, $R^2$ is a side chain of arginine and $R^3$ is a side chain of tryptophan. In embodiments, $R^2$ is a side chain of arginine and $R^3$ is a side chain of tyrosine. In embodiments, $R^2$ is a side chain of arginine and $R^3$ is a side chain of asparagine. In embodiments, $R^2$ is a side chain of arginine and $R^3$ is a side chain of cysteine. In embodiments, $R^2$ is a side chain of arginine and $R^3$ is a side chain of glutamine. In embodiments, $R^2$ is a side chain of arginine and $R^3$ is a side chain of serine. In embodiments, $R^2$ is a side chain of arginine and $R^3$ is a side chain of threonine. In embodiments, $R^2$ is a side chain of arginine and $R^3$ is a side chain of aspartic acid. In embodiments, $R^2$ is a side chain of arginine and $R^3$ is a side chain of glutamic acid. In embodiments, $R^2$ is a side chain of arginine and $R^3$ is a side chain of arginine. In embodiments, $R^2$ is a side chain of arginine and $R^3$ is a side chain of histidine. In embodiments, $R^2$ is a side chain of arginine and $R^3$ is a side chain of lysine. In embodiments, $R^2$ is a side chain of arginine and $R^3$ is a side chain of glycine (e.g., H). In embodiments, $R^2$ is a side chain of histidine and $R^3$ is a side chain of alanine. In embodiments, $R^2$ is a side chain of histidine and $R^3$ is a side chain of isoleucine. In embodiments, $R^2$ is a side chain of histidine and $R^3$ is a side chain of leucine. In embodiments, $R^2$ is a side chain of histidine and $R^3$ is a side chain of methionine. In embodiments, $R^2$ is a side chain of histidine and $R^3$ is a side chain of valine. In embodiments, $R^2$ is a side chain of histidine and $R^3$ is a side chain of phenylalanine. In embodiments, $R^2$ is a side chain of histidine and $R^3$ is a side chain of tryptophan. In embodiments, $R^2$ is a side chain of histidine and $R^3$ is a side chain of tyrosine. In embodiments, $R^2$ is a side chain of histidine and $R^3$ is a side chain of asparagine. In embodiments, $R^2$ is a side chain of histidine and $R^3$ is a side chain of cysteine. In embodiments, $R^2$ is a side chain of histidine and $R^3$ is a side chain of glutamine. In embodiments, $R^2$ is a side chain of histidine and $R^3$ is a side chain of serine. In embodiments, $R^2$ is a side chain of histidine and $R^3$ is a side chain of threonine. In embodiments, $R^2$ is a side chain of histidine and $R^3$ is a side chain of aspartic acid. In embodiments, $R^2$ is a side chain of histidine and $R^3$ is a side chain of glutamic acid. In embodiments, $R^2$ is a side chain of histidine and $R^3$ is a side chain of arginine. In embodiments, $R^2$ is a side chain of histidine and $R^3$ is a side chain of histidine. In embodiments, $R^2$ is a side chain of histidine and $R^3$ is a side chain of lysine. In embodiments, $R^2$ is a side chain of histidine and $R^3$ is a side chain of glycine (e.g., H). In embodiments, $R^2$ is a side chain of lysine and $R^3$ is a side chain of alanine. In embodiments, $R^2$ is a side chain of lysine and $R^3$ is a side chain of isoleucine. In embodiments, $R^2$ is a side chain of lysine and $R^3$ is a side chain of leucine. In embodiments, $R^2$ is a side chain of lysine and $R^3$ is a side chain of methionine. In embodiments, $R^2$ is a side chain of lysine and $R^3$ is a side chain of valine. In embodiments, $R^2$ is a side chain of lysine and $R^3$ is a side chain of phenylalanine. In embodiments, $R^2$ is a side chain of lysine and $R^3$ is a side chain of tryptophan. In embodiments, $R^2$ is a side chain of lysine and $R^3$ is a side chain of tyrosine. In embodiments, $R^2$ is a side chain of lysine and $R^3$ is a side chain of asparagine. In embodiments, $R^2$ is a side chain of lysine and $R^3$ is a side chain of cysteine. In embodiments, $R^2$ is a side chain of lysine and $R^3$ is a side chain of glutamine. In embodiments, $R^2$ is a side chain of lysine and $R^3$ is a side chain of serine. In embodiments, $R^2$ is a side chain of lysine and $R^3$ is a side chain of threonine. In embodiments, $R^2$ is a side chain of lysine and $R^3$ is a side chain of aspartic acid. In embodiments, $R^2$ is a side chain of lysine and $R^3$ is a side chain of glutamic acid. In embodiments, $R^2$ is a side chain of lysine and $R^3$ is a side chain of arginine. In embodiments, $R^2$ is a side chain of lysine and $R^3$ is a side chain of histidine. In embodiments, $R^2$ is a side chain of lysine and $R^3$ is a side chain of lysine. In embodiments, $R^2$ is a side chain of lysine and $R^3$ is a side chain of glycine (e.g., H). In embodiments, $R^2$ is a side chain of glycine (e.g., H) and $R^3$ is a side chain of alanine. In embodiments, $R^2$ is a side chain of glycine (e.g., H) and $R^3$ is a side chain of isoleucine. In embodiments, $R^2$ is a side chain of glycine (e.g., H) and $R^3$ is a side chain of leucine. In embodiments, $R^2$ is a side chain of glycine (e.g., H) and $R^3$ is a side chain of methionine. In embodiments, $R^2$ is a side chain of glycine (e.g., H) and $R^3$ is a side chain of valine. In embodiments, $R^2$ is a side chain of glycine (e.g., H) and $R^3$ is a side chain of phenylalanine. In embodiments, $R^2$ is a side chain of glycine (e.g., H) and $R^3$ is a side chain of tryptophan. In embodiments, $R^2$ is a side chain of glycine (e.g., H) and $R^3$ is a side chain of tyrosine. In embodiments, $R^2$ is a side chain of glycine (e.g., H) and $R^3$ is a side chain of asparagine. In embodiments, $R^2$ is a side chain of glycine (e.g., H) and $R^3$ is a side chain of cysteine. In embodiments, $R^2$ is a side chain of glycine (e.g., H) and $R^3$ is a side chain of glutamine. In embodiments, $R^2$ is a side chain of glycine (e.g., H) and $R^3$ is a side chain of serine. In embodiments, $R^2$ is a side chain of glycine (e.g., H) and $R^3$ is a side chain of threonine. In embodiments, $R^2$ is a side chain of glycine (e.g., H) and $R^3$ is a side chain of aspartic acid. In embodiments, $R^2$ is a side chain of glycine (e.g., H) and $R^3$ is a side chain of glutamic acid. In embodiments, $R^2$ is a side chain of glycine (e.g., H) and $R^3$ is a side chain of arginine. In embodiments, $R^2$ is a side chain of glycine (e.g., H) and $R^3$ is a side chain of histidine. In embodiments, $R^2$ is a side chain of glycine (e.g., H) and $R^3$ is a side chain of lysine. In embodiments, $R^2$ is a side chain of glycine (e.g., H) and $R^3$ is a side chain of glycine (e.g., H).

In embodiments, $R^4$ is —C(O)H. In embodiments, when $R^4$ is —C(O)H, $R^1$ is —C(O)$R^{1C}$, or —C(O)—O$R^{1C}$. In embodiments, when $R^4$ is —C(O)H, $R^{1C}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl. In embodiments, when $R^4$ is —C(O)H, $R^{1C}$ is hydrogen, substituted or unsubstituted alkyl, substituted or unsubstituted heteroalkyl. In embodiments, when $R^4$ is —C(O)H, $R^{1C}$ is hydrogen or substituted or unsubstituted alkyl. In embodiments, when $R^4$ is —C(O)H, $R^{1C}$ is substituted or unsubstituted $C_1$-$C_{10}$ alkyl. In embodiments, when $R^4$ is —C(O)H, $R^{1C}$ is substituted or unsubstituted $C_2$-$C_8$ alkyl. In embodiments, when $R^4$ is —C(O)H, $R^{1C}$ is substituted or unsubstituted $C_4$-$C_8$ alkyl. In embodiments, when $R^4$ is —C(O)H, $R^{1C}$ is hydrogen or unsubstituted alkyl. In embodiments, when $R^4$ is —C(O)H, $R^{1C}$ is hydrogen. In embodiments, when $R^4$ is —C(O)H, $R^{1C}$ is unsubstituted $C_4$-$C_8$ alkyl.

In embodiments, when $R^4$ is —B(OH)$_2$, $R^1$ is independently hydrogen, —C(O)$R^{1C}$, or —C(O)—O$R^{1C}$; and $R^{1C}$ is hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl. In embodiments, when $R^4$ is —B(OH)$_2$, $R^{1C}$ is hydrogen, substituted or unsubstituted alkyl, substituted or unsubstituted heteroalkyl. In embodiments, when $R^4$ is —B(OH)$_2$, $R^{1C}$ is hydrogen or substituted or unsubstituted alkyl. In embodiments, when $R^4$ is —B(OH)$_2$, $R^{1C}$ is substituted or unsubstituted $C_1$-$C_{10}$ alkyl. In embodiments, when $R^4$ is —B(OH)$_2$, $R^{1C}$ is substituted or unsubstituted $C_2$-$C_8$ alkyl. In embodiments, when $R^4$ is —B(OH)$_2$, $R^{1C}$ is substituted or unsubstituted $C_4$-$C_8$ alkyl. In embodiments, when $R^4$ is —B(OH)$_2$, $R^{1C}$ is hydrogen or unsubstituted alkyl. In embodiments, when $R^4$ is —B(OH)$_2$, $R^{1C}$ is hydrogen. In embodiments, when $R^4$ is —B(OH)$_2$, $R^{1C}$ is unsubstituted $C_4$-$C_8$ alkyl. In embodiments, when $R^4$ is —B(OH)$_2$, $R^1$ is not —C(O)$R^{1C}$, or —C(O)—O$R^{1C}$. In embodiments, when $R^4$ is —B(OH)$_2$, $R^{1C}$ is not substituted or unsubstituted aryl, or substituted or unsubstituted heteroaryl.

In embodiments, at least one N is $^{15}$N, at least one C is $^{13}$C, and/or at least one H is $^2$H.

$R^5$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^6$-substituted or unsubstituted alkyl (e.g., $C_1$-$C_8$ alkyl, $C_1$-$C_6$ alkyl, or $C_1$-$C_4$ alkyl), $R^6$-substituted or unsubstituted heteroalkyl (e.g., 2 to 8 membered heteroalkyl, 2 to 6 membered heteroalkyl, or 2 to 4 membered heteroalkyl), $R^6$-substituted or unsubstituted cycloalkyl (e.g., $C_3$-$C_8$ cycloalkyl, $C_3$-$C_6$ cycloalkyl, or $C_5$-$C_6$ cycloalkyl), $R^6$-substituted or unsubstituted heterocycloalkyl (e.g., 3 to 8 membered heterocycloalkyl, 3 to 6 membered heterocycloalkyl, or 5 to 6 membered heterocycloalkyl), $R^6$-substituted or unsubstituted aryl (e.g., $C_6$-$C_{10}$ aryl, $C_{10}$ aryl, or phenyl), or $R^6$-substituted or unsubstituted heteroaryl (e.g., 5 to 10 membered heteroaryl, 5 to 9 membered heteroaryl, or 5 to 6 membered heteroaryl).

In embodiments, $R^5$ is $R^6$-substituted or unsubstituted alkyl (e.g., $C_1$-$C_8$ alkyl, $C_1$-$C_6$ alkyl, or $C_1$-$C_4$ alkyl). In embodiments, $R^5$ is $R^6$-substituted alkyl (e.g., $C_1$-$C_8$ alkyl, $C_1$-$C_6$ alkyl, or $C_1$-$C_4$ alkyl). In embodiments, $R^5$ is an unsubstituted alkyl (e.g., $C_1$-$C_8$ alkyl, $C_1$-$C_6$ alkyl, or $C_1$-$C_4$ alkyl).

In embodiments, $R^5$ is $R^6$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^6$-substituted heteroalkyl (e.g., 2 to 8 membered heteroalkyl, 2 to 6 membered heteroalkyl, or 2 to 4 membered heteroalkyl). In embodiments, $R^5$ is an unsubstituted heteroalkyl (e.g., 2 to 8 membered heteroalkyl, 2 to 6 membered heteroalkyl, or 2 to 4 membered heteroalkyl).

In embodiments, $R^5$ is $R^6$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is $R^6$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is $R^6$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^6$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is $R^6$-substituted or unsubstituted aryl (e.g., $C_6$-$C_{10}$ aryl, $C_{10}$ aryl, or phenyl). In embodiments, $R^5$ is $R^6$-substituted aryl (e.g., $C_6$-$C_{10}$ aryl, $C_{10}$ aryl, or phenyl). In embodiments, $R^5$ is an unsubstituted aryl (e.g., $C_6$-$C_{10}$ aryl, $C_{10}$ aryl, or phenyl).

In embodiments, $R^5$ is $R^6$-substituted or unsubstituted heteroaryl (e.g., 5 to 10 membered heteroaryl, 5 to 9 membered heteroaryl, or 5 to 6 membered heteroaryl). In embodiments, $R^5$ is $R^6$-substituted heteroaryl (e.g., 5 to 10 membered heteroaryl, 5 to 9 membered heteroaryl, or 5 to 6 membered heteroaryl). In embodiments, $R^5$ is an unsubstituted heteroaryl (e.g., 5 to 10 membered heteroaryl, 5 to 9 membered heteroaryl, or 5 to 6 membered heteroaryl).

$R^{5A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{6A}$-substituted or unsubstituted alkyl (e.g., $C_1$-$C_8$ alkyl, $C_1$-$C_6$ alkyl, or $C_1$-$C_4$ alkyl), $R^{6A}$-substituted or unsubstituted heteroalkyl (e.g., 2 to 8 membered heteroalkyl, 2 to 6 membered heteroalkyl, or 2 to 4 membered heteroalkyl), $R^{6A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{6A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{6A}$-substituted or unsubstituted aryl (e.g., $C_6$-$C_{10}$ aryl, $C_{10}$ aryl, or phenyl), or $R^{6A}$-substituted or unsubstituted heteroaryl (e.g., 5 to 10 membered heteroaryl, 5 to 9 membered heteroaryl, or 5 to 6 membered heteroaryl).

$R^{5B}$ is independently oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{6B}$-substituted or unsubstituted alkyl (e.g., $C_1$-$C_8$ alkyl, $C_1$-$C_6$ alkyl, or $C_1$-$C_4$ alkyl), $R^{6B}$-substituted or unsubstituted heteroalkyl (e.g., 2 to 8 membered heteroalkyl, 2 to 6 membered heteroalkyl, or 2 to 4 membered heteroalkyl), $R^{6B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{6B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{6B}$-substituted or unsubstituted aryl (e.g., $C_6$-$C_{10}$ aryl, $C_{10}$ aryl, or phenyl), or $R^{6B}$-substituted or unsubstituted heteroaryl (e.g., 5 to 10 membered heteroaryl, 5 to 9 membered heteroaryl, or 5 to 6 membered heteroaryl).

$R^{5C}$ is independently oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{6C}$-substituted or unsubstituted alkyl (e.g., $C_1$-$C_8$ alkyl, $C_1$-$C_6$ alkyl, or $C_1$-$C_4$ alkyl), $R^{6C}$-substituted or unsubstituted heteroalkyl (e.g., 2 to 8 membered heteroalkyl, 2 to 6 membered heteroalkyl, or 2 to 4 membered heteroalkyl), $R^{6C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{6C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{6C}$-substituted or unsubstituted aryl (e.g., $C_6$-$C_{10}$ aryl, $C_{10}$ aryl, or phenyl), or $R^{6C}$-substituted or unsubstituted heteroaryl (e.g., 5 to 10 membered heteroaryl, 5 to 9 membered heteroaryl, or 5 to 6 membered heteroaryl).

$R^{5D}$ is independently oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{6D}$-substituted or unsubstituted alkyl (e.g., $C_1$-$C_8$ alkyl, $C_1$-$C_6$ alkyl, or $C_1$-$C_4$ alkyl), $R^{6D}$-substituted or unsubstituted heteroalkyl (e.g., 2 to 8 membered heteroalkyl, 2 to 6 membered heteroalkyl, or 2 to 4 membered heteroalkyl), $R^{6D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{6D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{6D}$-substituted or unsubstituted aryl (e.g., $C_6$-$C_{10}$ aryl, $C_{10}$ aryl, or phenyl), or $R^{6D}$-substituted or unsubstituted heteroaryl (e.g., 5 to 10 membered heteroaryl, 5 to 9 membered heteroaryl, or 5 to 6 membered heteroaryl).

$R^6$ is independently oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^7$-substituted or unsubstituted alkyl (e.g., $C_1$-$C_8$ alkyl, $C_1$-$C_6$ alkyl, or $C_1$-$C_4$ alkyl), $R^7$-substituted or unsubstituted heteroalkyl (e.g., 2 to 8 membered heteroalkyl, 2 to 6 membered heteroalkyl, or 2 to 4 membered heteroalkyl), $R^7$-substituted or unsubstituted cycloalkyl (e.g., $C_3$-$C_8$ cycloalkyl, $C_3$-$C_6$ cycloalkyl, or $C_5$-$C_6$ cycloalkyl), $R^7$-substituted or unsubstituted heterocycloalkyl (e.g., 3 to 8 membered heterocycloalkyl, 3 to 6 membered heterocycloalkyl, or 5 to 6 membered heterocycloalkyl), $R^7$-substituted or unsubstituted aryl (e.g., $C_6$-$C_{10}$ aryl, $C_{10}$ aryl, or phenyl), or $R^7$-substituted or unsubstituted heteroaryl (e.g., 5 to 10 membered heteroaryl, 5 to 9 membered heteroaryl, or 5 to 6 membered heteroaryl).

In embodiments, $R^6$ is $R^7$-substituted or unsubstituted alkyl (e.g., $C_1$-$C_8$ alkyl, $C_1$-$C_6$ alkyl, or $C_1$-$C_4$ alkyl). In embodiments, $R^6$ is $R^7$-substituted alkyl (e.g., $C_1$-$C_8$ alkyl, $C_1$-$C_6$ alkyl, or $C_1$-$C_4$ alkyl). In embodiments, $R^6$ is an unsubstituted alkyl (e.g., $C_1$-$C_8$ alkyl, $C_1$-$C_6$ alkyl, or $C_1$-$C_4$ alkyl).

In embodiments, $R^6$ is $R^7$-substituted or unsubstituted heteroalkyl (e.g., 2 to 8 membered heteroalkyl, 2 to 6 membered heteroalkyl, or 2 to 4 membered heteroalkyl). In embodiments, $R^6$ is $R^7$-substituted heteroalkyl (e.g., 2 to 8 membered heteroalkyl, 2 to 6 membered heteroalkyl, or 2 to 4 membered heteroalkyl). In embodiments, $R^6$ is an unsubstituted heteroalkyl (e.g., 2 to 8 membered heteroalkyl, 2 to 6 membered heteroalkyl, or 2 to 4 membered heteroalkyl).

In embodiments, $R^6$ is IC-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is $R^7$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^6$ is $R^7$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is $R^7$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^6$ is $R^7$-substituted or unsubstituted aryl (e.g., $C_6$-$C_{10}$ aryl, $C_{10}$ aryl, or phenyl). In embodiments, $R^6$ is $R^7$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^6$ is R'-substituted or unsubstituted heteroaryl (e.g., 5 to 10 membered heteroaryl, 5 to 9 membered heteroaryl, or 5 to 6 membered heteroaryl). In embodiments, $R^6$ is $R^7$-substituted heteroaryl (e.g., 5 to 10 membered heteroaryl, 5 to 9 membered heteroaryl, or 5 to 6 membered heteroaryl). In embodiments, $R^6$ is an unsubstituted heteroaryl (e.g., 5 to 10 membered heteroaryl, 5 to 9 membered heteroaryl, or 5 to 6 membered heteroaryl).

$R^{6A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{7A}$-substituted or unsubstituted alkyl (e.g., C$_1$-C$_8$ alkyl, C$_1$-C$_6$ alkyl, or C$_1$-C$_4$ alkyl), $R^{7A}$-substituted or unsubstituted heteroalkyl (e.g., 2 to 8 membered heteroalkyl, 2 to 6 membered heteroalkyl, or 2 to 4 membered heteroalkyl), $R^{7A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{7A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7A}$-substituted or unsubstituted aryl (e.g., C$_6$-C$_{10}$ aryl, C$_{10}$ aryl, or phenyl), or $R^{7A}$-substituted or unsubstituted heteroaryl (e.g., 5 to 10 membered heteroaryl, 5 to 9 membered heteroaryl, or 5 to 6 membered heteroaryl).

$R^{6B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{7B}$-substituted or unsubstituted alkyl (e.g., C$_1$-C$_8$ alkyl, C$_1$-C$_6$ alkyl, or C$_1$-C$_4$ alkyl), $R^{7B}$-substituted or unsubstituted heteroalkyl (e.g., 2 to 8 membered heteroalkyl, 2 to 6 membered heteroalkyl, or 2 to 4 membered heteroalkyl), $R^{7B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{7B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7B}$-substituted or unsubstituted aryl (e.g., C$_6$-C$_{10}$ aryl, C$_{10}$ aryl, or phenyl), or $R^{7B}$-substituted or unsubstituted heteroaryl (e.g., 5 to 10 membered heteroaryl, 5 to 9 membered heteroaryl, or 5 to 6 membered heteroaryl).

$R^{6C}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{7C}$-substituted or unsubstituted alkyl (e.g., C$_1$-C$_8$ alkyl, C$_1$-C$_6$ alkyl, or C$_1$-C$_4$ alkyl), $R^{7C}$-substituted or unsubstituted heteroalkyl (e.g., 2 to 8 membered heteroalkyl, 2 to 6 membered heteroalkyl, or 2 to 4 membered heteroalkyl), $R^{7C}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{7C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7C}$-substituted or unsubstituted aryl (e.g., C$_6$-C$_{10}$ aryl, C$_{10}$ aryl, or phenyl), or $R^{7C}$-substituted or unsubstituted heteroaryl (e.g., 5 to 10 membered heteroaryl, 5 to 9 membered heteroaryl, or 5 to 6 membered heteroaryl).

$R^{6D}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{7D}$-substituted or unsubstituted alkyl (e.g., C$_1$-C$_8$ alkyl, C$_1$-C$_6$ alkyl, or C$_1$-C$_4$ alkyl), $R^{7D}$-substituted or unsubstituted heteroalkyl (e.g., 2 to 8 membered heteroalkyl, 2 to 6 membered heteroalkyl, or 2 to 4 membered heteroalkyl), $R^{7D}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{7D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7D}$-substituted or unsubstituted aryl (e.g., C$_6$-C$_{10}$ aryl, C$_{10}$ aryl, or phenyl), or $R^{7D}$-substituted or unsubstituted heteroaryl (e.g., 5 to 10 membered heteroaryl, 5 to 9 membered heteroaryl, or 5 to 6 membered heteroaryl).

$R^{7A}$, $R^{7B}$, $R^{7C}$, $R^{7D}$, and $R^7$ are independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{7A}$, $R_{7B}$, $R^{7C}$, $R^{7D}$, and $R^7$ are independently unsubstituted alkyl, unsubstituted heteroalkyl, unsubstituted cycloalkyl, unsubstituted heterocycloalkyl, unsubstituted aryl, or unsubstituted heteroaryl.

In embodiments, the compound, or pharmaceutically acceptable salt thereof, has the formula:

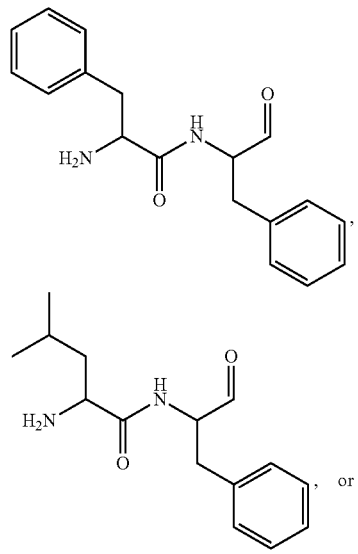

, or

-continued
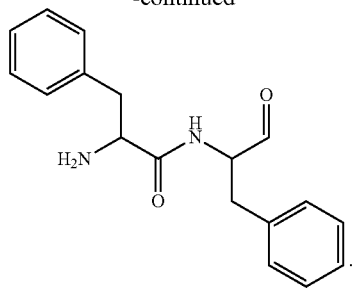
In embodiments, the compound is
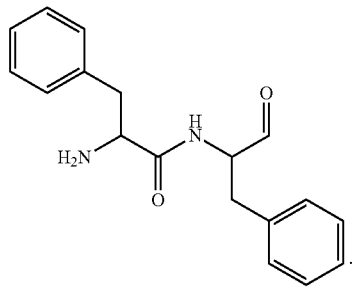 [SMILES: NC(Cc1ccccc1)C(=O)NC(C=O)Cc1ccccc1]
In embodiments, the compound is
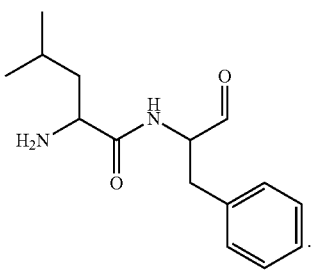 [SMILES: CC(C)CC(N)C(=O)NC(C=O)Cc1ccccc1]
In embodiments, the compound is
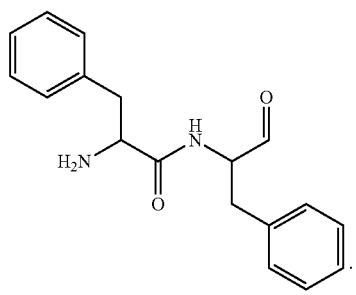 [SMILES: NC(Cc1ccccc1)C(=O)NC(C=O)Cc1ccccc1]
In embodiments, the compound, or pharmaceutically acceptable salt thereof, has the formula:
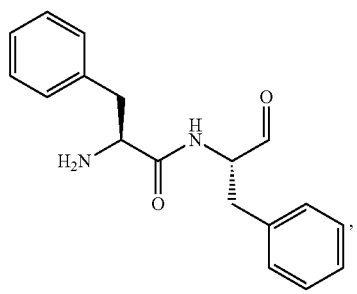
-continued
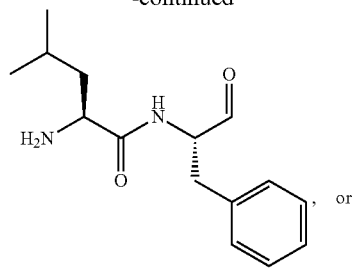, or
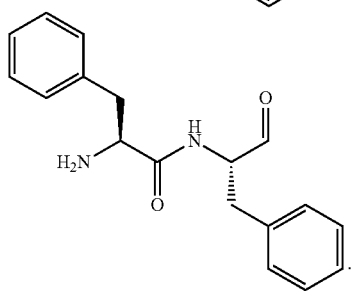
In embodiments, the compound is
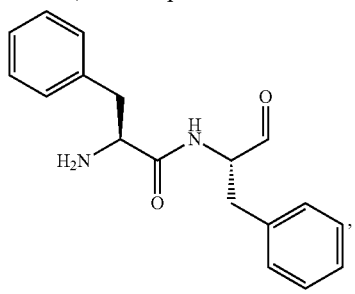
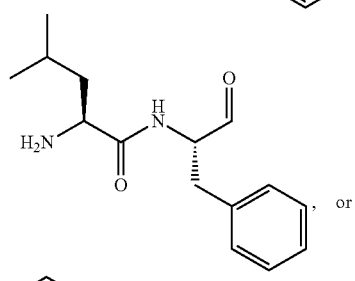, or
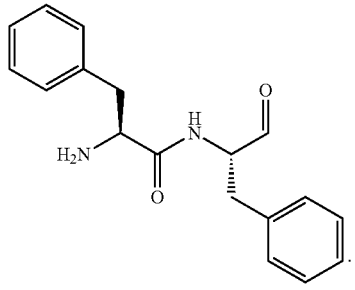
In embodiments, the compound is
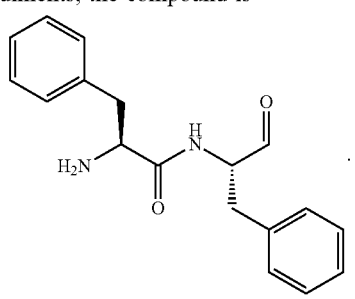

In embodiments, the compound is

[Structure: H2N-CH(iBu)-C(=O)-NH-CH(CH2Ph)-CHO]

In embodiments, the compound is

[Structure: H2N-CH(CH2Ph)-C(=O)-NH-CH(CH2Ph)-CHO]

In an aspect is provided a compound, or pharmaceutically acceptable salt thereof, having the formula:

[Structure IIa: pyrazinone with R² and R³]  (IIa)

[Structure IIb: pyrazinone with R² and R³]  (IIb)

[Structure IIc: pyrazinone with R² and R³]  (IIc)

wherein R² and R³ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or an amino acid side chain.

In embodiments of formula IIa, IIb, or IIc, when R² is

[isobutyl group],

R³ is not

[isobutyl], [benzyl], or

[4-hydroxybenzyl].

In embodiments of formula IIa, IIb, or IIc, when R² is

[isopropyl],

R³ is not

[isobutyl],

In embodiments of formula IIa, IIb, or IIc, when R² is

[isopropyl],

R³ is not

[benzyl].

In embodiments of formula IIa, IIb, or IIc, when R² is

[isopropyl],

R³ is not

[4-hydroxybenzyl].

In embodiments of formula IIa, IIb, or IIc, when R² is

[benzyl],

R³ is not
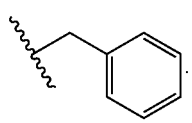
In embodiments, the compound, or pharmaceutically acceptable salt thereof, has the formula:
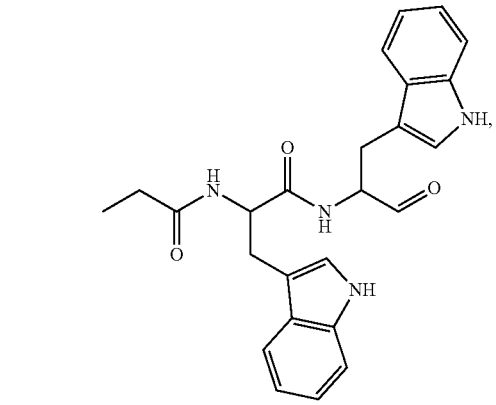
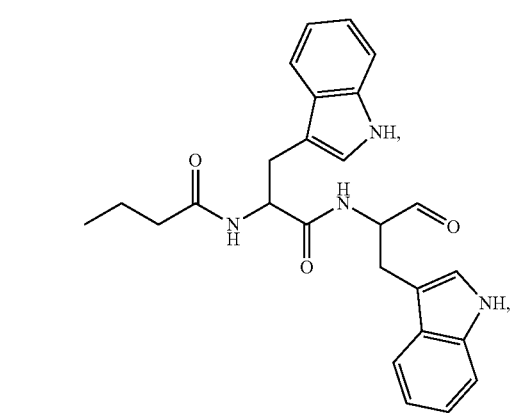
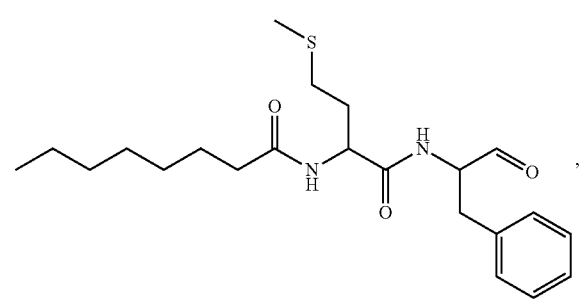
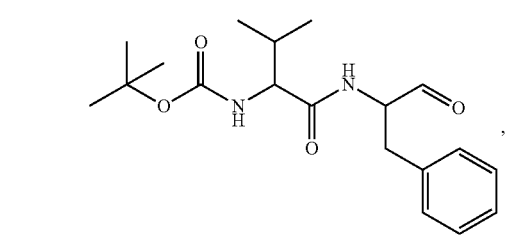
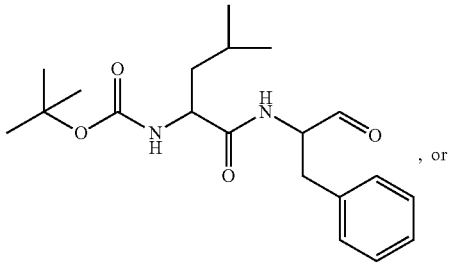, or
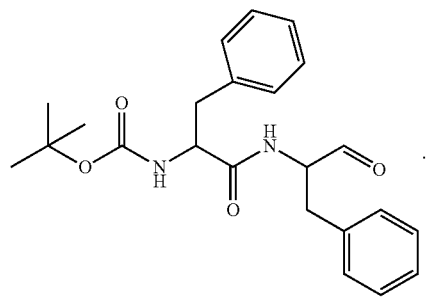 [SMILES: CC(C)(C)OC(=O)NC(Cc1ccccc1)C(=O)NC(C=O)Cc1ccccc1]
In embodiments, the compound, or pharmaceutically acceptable salt thereof, has the formula:
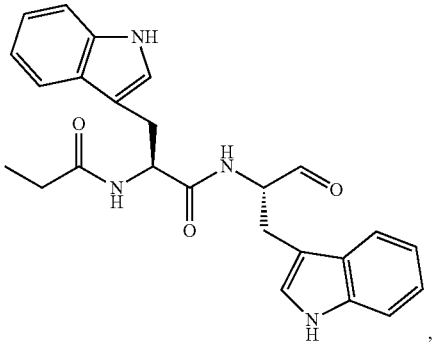
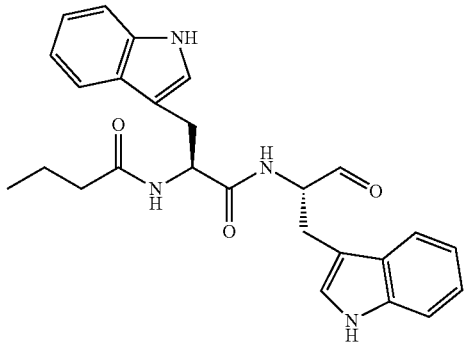
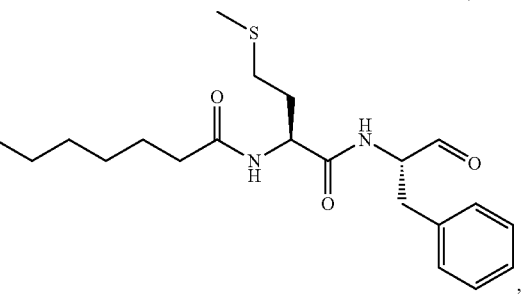

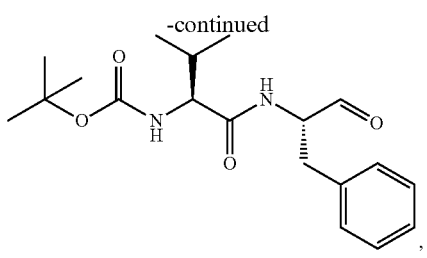
,
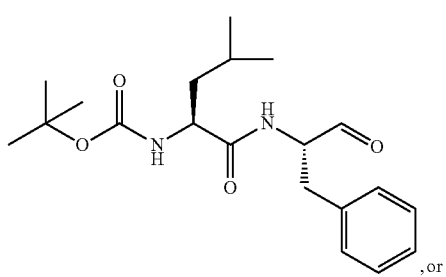
, or
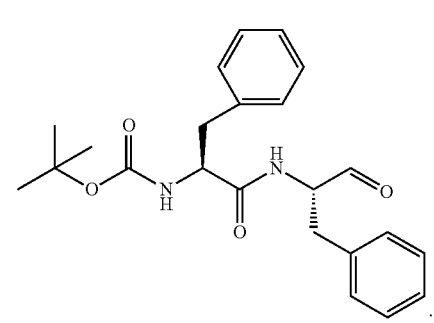 [SMILES: CC(C)(C)OC(=O)N[C@@H](Cc1ccccc1)C(=O)N[C@H](C=O)Cc1ccccc1]
.
In embodiments, the compound, or pharmaceutically acceptable salt thereof, has the formula:
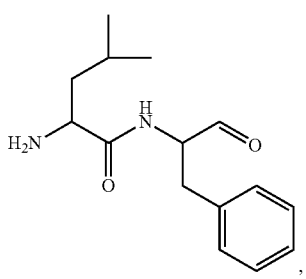
,
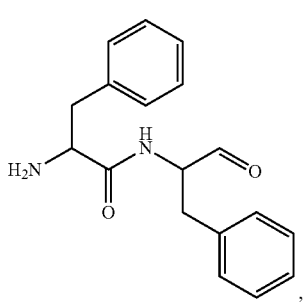
,
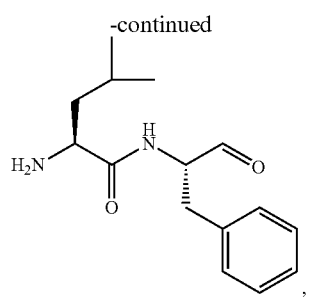
,
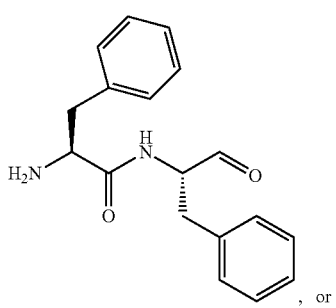
, or
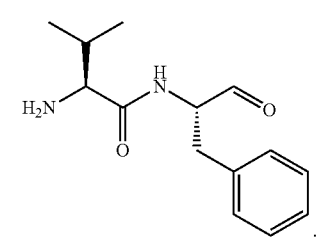
.
In embodiments, the compound, or pharmaceutically acceptable salt thereof, has the formula:
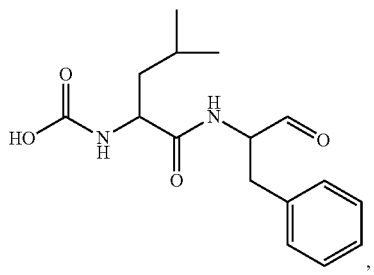
,
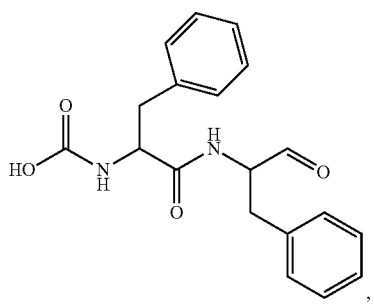
, -continued In embodiments, the compound, or pharmaceutically acceptable salt thereof, has the formula:

-continued

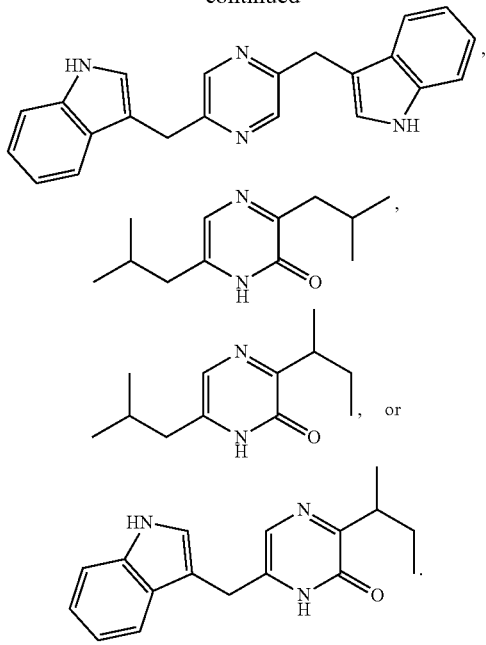

In embodiments the compound is cell permeable. In embodiments, the compound is a compound described herein, including embodiments, formula, tables, claims, examples, and/or figures.

In embodiments, when $R^4$ is —B(OH)$_2$, $R^{1C}$ is not

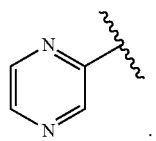 [SMILES: *c1cnccn1]

In embodiments, when $R^4$ is —B(OH)$_2$, $R^{1C}$ is not unsubstituted pyrazine. In embodiments, when $R^4$ is —B(OH)$_2$, $R^{1C}$ is not substituted or unsubstituted 6 membered heteroaryl. In embodiments, when $R^4$ is —B(OH)$_2$, $R^{1C}$ is not substituted or unsubstituted heteroaryl. In embodiments, when $R^4$ is —B(OH)$_2$, $R^{1C}$ is not a substituted heteroaryl. In embodiments, when $R^4$ is —B(OH)$_2$, $R^{1C}$ is not an unsubstituted heteroaryl. In embodiments, when $R^4$ is —B(OH)$_2$, $R^{1C}$ is not substituted or unsubstituted cycloalkyl, substituted or unsubstituted heterocycloalkyl, substituted or unsubstituted aryl, or substituted or unsubstituted heteroaryl.

In embodiments, $R^{1C}$ is not

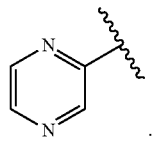 [SMILES: *c1cnccn1]

In embodiments, $R^{1C}$ is not unsubstituted pyrazine. In embodiments, $R^{1C}$ is not substituted or unsubstituted 6 membered heteroaryl. In embodiments, $R^{1C}$ is not substituted or unsubstituted heteroaryl. In embodiments, $R^{1C}$ is not a substituted heteroaryl. In embodiments, $R^{1C}$ is not an unsubstituted heteroaryl. In embodiments, $R^{1C}$ is not substituted or unsubstituted cycloalkyl, substituted or unsubstituted heterocycloalkyl, substituted or unsubstituted aryl, or substituted or unsubstituted heteroaryl.

In embodiments, when $R^4$ is —B(OH)$_2$, $R^{1C}$ is substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), or substituted or unsubstituted aryl (e.g., $C_6$-$C_{10}$ aryl, $C_{10}$ aryl, or phenyl).

In embodiments, $R^1$ is not

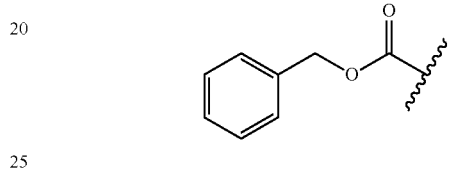

In embodiments, $R^1$ is not

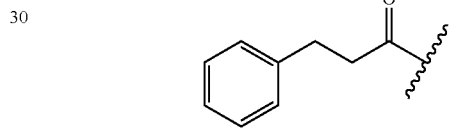

In embodiments, $R^{1C}$ is not

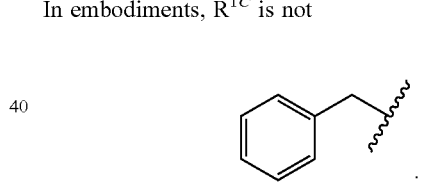

III. Pharmaceutical Compositions

In an aspect is provided a pharmaceutical composition comprising the compound as described herein and a pharmaceutically acceptable excipient.

In embodiments of the pharmaceutical compositions, the compound (e.g. as described herein, including embodiments), or a pharmaceutically acceptable salt, solvate or hydrate thereof, is included in a therapeutically effective amount. In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an agent for treating acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases, malnutrition or obesity. In embodiments, the compound is about 0.01% w/v to about 70% w/v of said composition. In embodiments, the compound is about 0.05% w/v of said composition. In embodiments, the compound is about 0.10% w/v of said composition. In embodiments, the compound is about 0.25% w/v of said composition. In embodiments, the compound is about 0.50% w/v of said composition. In embodiments, the compound is about 1% w/v of said composition. In embodiments, the compound is about 5% w/v of said composition.

In embodiments, the compound is about 10% w/v of said composition. In embodiments, the compound is about 20% w/v of said composition. In embodiments, the compound is about 25% w/v of said composition. In embodiments, the compound is about 35% w/v of said composition. In embodiments, the compound is about 45% w/v of said composition. In embodiments, the compound is about 50% w/v of said composition. In embodiments, the compound is about 55% w/v of said composition. In embodiments, the compound is about 65% w/v of said composition. In embodiments, the compound is about 70% w/v of said composition.

In embodiments, the pharmaceutical composition is in oral, intravenous, parenteral, subcutaneous, intramuscular, transdermal, intraperitoneal, intranasal, aerosol, intracranial, intrathecal, or topical dosage form. In embodiments, the pharmaceutical composition is formulated for administration daily, once every two days, once every three days, once a week, bi-weekly, or once a month.

IV. Methods of Use

In an aspect is provided a method of treating cancer, the method including administering to a subject in need thereof an effective amount of a compound as described herein.

In an aspect is provided a method of inhibiting protease activity, the method including contacting the protease with a compound as described herein. In embodiments, the protease is a serine protease, cysteine protease, or aspartyl protease. In embodiments, the protease is a serine protease. In embodiments, the protease is a cysteine protease. In embodiments, the protease is an aspartyl protease. In embodiments, the protease is a lysosomal protease. In embodiments, the protease is a cathepsin (e.g., cathepsin A, cathepsin B, cathepsin C, cathepsin D, cathepsin E, cathepsin F, cathepsin G, cathepsin H, cathepsin K, cathepsin L, cathepsin O, cathepsin S, cathepsin W, cathepsin Z). In embodiments, the protease is a cathepsin, calpain, or trypsin.

In an aspect is provided a method of inhibiting cathepsin activity, the method including contacting the cathepsin with a compound as described herein. In embodiments, the cathepsin is cathepsin A. In embodiments, the cathepsin is cathepsin B. In embodiments, the cathepsin is cathepsin C. In embodiments, the cathepsin is cathepsin D. In embodiments, the cathepsin is cathepsin E. In embodiments, the cathepsin is cathepsin F. In embodiments, the cathepsin is cathepsin G. In embodiments, the cathepsin is cathepsin H. In embodiments, the cathepsin is cathepsin K. In embodiments, the cathepsin is cathepsin L (e.g., cathepsin L1 or cathepsin L2). In embodiments, the cathepsin is cathepsin L1. In embodiments, the cathepsin is cathepsin L2. In embodiments, the cathepsin is cathepsin O. In embodiments, the cathepsin is cathepsin S. In embodiments, the cathepsin is cathepsin W. In embodiments, the cathepsin is cathepsin Z. In embodiments, the cathepsin is cathepsin B, cathepsin L, cathepsin C, or cathepsin S. In embodiments, the cathepsin is cathepsin B. In embodiments, the cathepsin is cathepsin L. In embodiments, the cathepsin is cathepsin C. In embodiments, the cathepsin is cathepsin S.

In embodiments, the compound (e.g., described herein) inhibits cathespin S more potently (e.g., preferentially or with greater affinity or with comparable level of inhibition at a lower concentration) than a different cathespin (e.g., cathepsin B, cathepsin L, or cathepsin C). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits cathespin S at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a different cathespin (e.g., cathepsin B, cathepsin L, or cathepsin C).

In embodiments, the compound (e.g., described herein) inhibits cathespin L more potently (e.g., preferentially or with greater affinity or with comparable level of inhibition at a lower concentration) than a different cathespin (e.g., cathepsin B, cathepsin S, or cathepsin C). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits cathespin L at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a different cathespin (e.g., cathepsin B, cathepsin S, or cathepsin C).

In embodiments, the compound (e.g., described herein) inhibits cathespin B more potently (e.g., preferentially or with greater affinity or with comparable level of inhibition at a lower concentration) than a different cathespin (e.g., cathepsin S, cathepsin L, or cathepsin C). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits cathespin B at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a different cathespin (e.g., cathepsin S, cathepsin L, or cathepsin C).

In embodiments, the compound (e.g., described herein) inhibits cathespin C more potently (e.g., preferentially or with greater affinity or with comparable level of inhibition at a lower concentration) than a different cathespin (e.g., cathepsin B, cathepsin L, or cathepsin S). In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits cathespin C at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a different cathespin (e.g., cathepsin B, cathepsin L, or cathepsin S).

In an aspect is provided a method of reducing cathepsin activity, the method including contacting the cathepsin with a compound as described herein, wherein the reduction is quantified (e.g., level of cathespin or cathespin activity) relative to the absence of the compound. In embodiments, the cathepsin is cathepsin B, cathepsin L, cathepsin C, or cathepsin S. In embodiments, the activity of cathepsin S is reduced greater than the activity of cathepsin L. In embodiments, the activity of cathepsin L is reduced greater than the activity of cathepsin C. In embodiments, the activity of cathepsin L is reduced greater than the activity of cathepsin S. In embodiments, the activity of cathepsin L is reduced greater than the activity of cathepsin Z. In embodiments, the activity of cathepsin S is reduced greater than the activity of cathepsin B. In embodiments, the activity of cathepsin C is reduced greater than the activity of cathepsin S. In embodiments, the activity of cathepsin C is reduced greater than the activity of cathepsin Z. In embodiments, the activity of cathepsin C is reduced greater than the activity of cathepsin S. In embodiments, the activity of cathepsin C is reduced greater than the activity of cathepsin B. In embodiments, the activity of cathepsin S is reduced greater than the activity of cathepsin Z. In embodiments, the activity of cathepsin S is reduced greater than the activity of cathepsin B. In embodiments, the activity of cathepsin S is reduced greater than the activity of cathepsin C.

In embodiments, the compound contacts a cysteine amino acid of the cathepsin (e.g., Cys135 of cathepsin L, Cys138 of cathepsin L, Cys255 of cathepsin C, Cys258 of cathepsin C, Cys136 of cathepsin S, Cys139 of cathepsin S, Cys105 of cathepsin B, or Cys108 of cathepsin B). In embodiments, the compound contacts Cys135 of cathepsin L. In embodiments, the compound contacts Cys138 of cathepsin L. In embodiments, the compound contacts Cys255 of cathepsin C. In embodiments, the compound contacts Cys258 of cathepsin C. In embodiments, the compound contacts Cys136 of cathepsin S. In embodiments, the compound contacts Cys139 of cathepsin S. In embodiments, the compound contacts Cys105 of cathepsin B. In embodiments, the compound contacts Cys108 of cathepsin B. In embodiments, the compound contacts Cys89 of cathepsin Z. In embodiments, the compound contacts Cys92 of cathepsin Z. In embodiments, the compound contacts Cys108 of cathepsin B. In embodiments, the compound contacts Cys138 of cathepsin H. In embodiments, the compound contacts Cys141 of cathepsin H.

In embodiments, the compound contacts one or more cysteines on the same tryptic peptide (e.g. Cys135/Cys138 of cathepsin L, Cys255/Cys258 of cathepsin C, Cys136/Cys139 of cathepsin S, Cys89/Cys92 of cathepsin Z, Cys105/Cys108 of cathepsin B, or Cys138/Cys141 of cathepsin H). In embodiments, the compound contacts Cys135 or Cys138 of cathepsin L. In embodiments, the compound contacts Cys255 or Cys258 of cathepsin C. In embodiments, the compound contacts Cys136 or Cys139 of cathepsin S. In embodiments, the compound contacts Cys89 or Cys92 of cathepsin Z. In embodiments, the compound contacts Cys105 or Cys108 of cathepsin B. In embodiments, the compound contacts Cys138 or Cys141 of cathepsin H. In embodiments, the compound contacts Cys135 and Cys138 of cathepsin L. In embodiments, the compound contacts Cys255 and Cys258 of cathepsin C. In embodiments, the compound contacts Cys136 and Cys139 of cathepsin S. In embodiments, the compound contacts Cys89 and Cys92 of cathepsin Z. In embodiments, the compound contacts Cys105 and Cys108 of cathepsin B. In embodiments, the compound contacts Cys138 and Cys141 of cathepsin H.

In another aspect, there is provided a method of treating a disease or disorder associated with microbiome imbalance in a subject in need thereof. In embodiments the treatment may be of a pediatric subject. In embodiments, the treatment may be of a non-pediatric or an adult subject. The method includes administering to the subject an effective amount of a compound as described herein and embodiments thereof disclosed herein. The term "microbiome" (e.g., "human microbiome") refers, in the usual and customary sense, to the assemblage of microorganisms and genome information thereof which reside on the surface or inside a body (e.g., a human body). The term "microbiome imbalance" and the like refers to a disruption in the normal levels of microorganisms within a microbiome. A microbiome imbalance may be observed in a disease or disorder, e.g., acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases (including Crohn's Disease (CD)), malnutrition, obesity, or other diseases or disorders.

In embodiments, the disease or disorder is acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases, malnutrition or obesity. In embodiments the disease or disorder is acne. In embodiments the disease or disorder is antibiotic-associated diarrhea. In embodiments the disease or disorder is asthma/allergies. In embodiments the disease or disorder is autism. In embodiments the disease or disorder is autoimmune diseases. In embodiments the disease or disorder is cancer. In embodiments the disease or disorder is dental cavities. In embodiments the disease or disorder is depression and anxiety. In embodiments the disease or disorder is diabetes. In embodiments the disease or disorder is eczema. In embodiments the disease or disorder is liver disease. In embodiments the disease or disorder is heart disease. In embodiments the disease or disorder is gastric ulcers. In embodiments the disease or disorder is hardening of the arteries. In embodiments the disease or disorder is inflammatory bowel diseases. In embodiments the disease or disorder is malnutrition. In embodiments the disease or disorder is obesity.

TABLE 1

Examples of microbes and associated disease/disorder

| Disease | Microbes Associated with Disease |
| --- | --- |
| Psoriasis | Increased ratio of Firmicutes to Actinobacteria |
| Reflux oesophagitis | Oesophageal microbiota dominated by gram-negative anaerobes; gastric microbiota with low or absent *Helicobacter pylori* |
| Obesity | Reduced ratio of Bacteroidetes to Firmicutes |
| Childhood-onset asthma | Absent gastric *H. pylori* (especially the cytotoxin-associated gene A (cagA) genotype) |
| Inflammatory bowel disease (colitis) | Larger populations of Enterobacteriaceae |
| Functional bowel diseases | Larger populations of *Veillonella* and *Lactobacillus* |
| Colorectal carcinoma | Larger populations of *Fusobacterium* spp. |
| Cardiovascular disease | Gut-microbiota-dependent metabolism of phosphatidylcholine |

In embodiments, the present disclosure includes treating Crohn's disease (CD), which is associated with increased abundance in bacteria which include Enterobacteriaceae, Pasteurellacaea, Veillonellaceae, and Fusobacteriaceae, and decreased abundance in Erysipelotrichales, Bacteroidales, and Clostridiales, correlates strongly with disease status, by altering the relative abundance of the associated bacterial population. Thus, in the disclosed method, treatment can refer to about 10%, about 20%, about 30%, about 40%, about 50%, about 60%, about 70%, about 80%, about 90%, or about 100% reduction in the severity of an established disease, condition, or symptom of the disease or condition. For example, a method for treating a disease is considered to be a treatment if there is about 10% reduction in one or more symptoms of the disease in a subject as compared to a control. Thus, the reduction can be about 10%, about 20%, about 30%, about 40%, about 50%, about 60%, about 70%, about 80%, about 90%, about 100%, or any percent reduction in between about 10% and about 100% as compared to native or control levels. It is understood that treatment does not necessarily refer to a cure or complete ablation of the disease, condition, or symptoms of the disease or condition. Further, as used herein, references to decreasing, reducing, or inhibiting include a change of about 10%, about 20%, about 30%, about 40%, about 50%, about 60%, about 70%, about 80%, about 90% or greater as compared to a control level and such terms can include but do not necessarily include complete elimination.

In embodiments, the dominant species increased in CD may be *Escherichia coli, Fusobacterium nucleatum, Haemophilus parainfluenzae* (Pasteurellaceae), *Veillonella parvula, Eikenella corrodens* (Neisseriaceae), and *Gemella moribillum*. The dominant species decreased in CD may be *Bacteroides vulgatus, Bacteroides caccae, Bifidobacterium bifidum, Bifidobacterium longum, Bifidobacterium adolescentis, Bifidobacterium dentum, Blautia hansenii, Ruminococcus gnavus, Clostridium nexile, Faecalibacterium prausnitzii, Ruminoccus torques, Clostridium bolteae, Eubacterium rectale, Roseburia intestinalis*, and *Coprococcus comes*.

In another aspect, there is provided a method of restoring an imbalance of a microbial population of a subject in need thereof. The method includes administering to the subject an effective amount of a compound as described herein and embodiments thereof disclosed herein. In embodiments the restoration may be of a pediatric subject. In embodiments, the restoration may be of a non-pediatric or an adult subject. The term "restoring an imbalance of a microbial population" refers to a modulation of the assemblage of microorganisms within a microbiome such that the microbial population returns to a normal or near normal state. Restoring an imbalance of a microbial population can be associated with treatment or amelioration of a disease or disorder.

In the disclosed method, restoring an imbalance can refer to restoring to about 10%, about 20%, about 30%, about 40%, about 50%, about 60%, about 70%, about 80%, about 90%, or about 100% of the normal state of the microbial population. For example, restoring an imbalance can refer to restoring to about 10%, about 20%, about 30%, about 40%, about 50%, about 60%, about 70%, about 80%, about 90%, about 100%, or any percent in between 10% and 100% as compared to native or control levels.

In another aspect, there is provided a method of reducing a harmful bacterial load of a subject in need thereof. The method includes administering to the subject an effective amount of a compound as described herein and embodiments thereof disclosed herein. In embodiments the reduction of harmful bacterial may be in a pediatric subject. In embodiments, the reduction of harmful bacteria may be in a non-pediatric or an adult subject. The terms "harmful bacterial," "harmful bacterial load" and the like refer, in the usual and customary sense, to bacterial members of a microbiome which cause or are associated with a disease or disorder in the subject.

In the disclosed method, reducing a harmful bacterial load can refer to reducing by about 10%, about 20%, about 30%, about 40%, about 50%, about 60%, about 70%, about 80%, about 90%, or about 100% of harmful microbial population. For example, reducing a harmful bacterial population can refer to reducing by about 10%, about 20%, about 30%, about 40%, about 50%, about 60%, about 70%, about 80%, about 90%, about 100%, or any percent in between 10% and 100% as compared to the high level or baseline level.

In embodiments, the method reduces the harmful bacterial population without substantially affecting other microbial populations. In embodiments, the harmful bacterial load causes or is associated with acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases, malnutrition or obesity.

In another aspect, there is provided a method of promoting growth of a microbial population in a subject in need thereof. The method includes administering to the subject an effective amount of a compound as described herein and embodiments thereof disclosed herein. In embodiments the promotion of desired microbial population may be in a pediatric subject. In embodiments, the promotion of desired microbial population may be in a non-pediatric or an adult subject. In embodiments, the method promotes growth of the desired microbial population and reduces growth of other microbial populations. In embodiments, the desired microbial population reduces risk of acne, antibiotic-associated diarrhea, asthma/allergies, autism, autoimmune diseases, cancer, dental cavities, depression and anxiety, diabetes, eczema, liver disease, heart disease, gastric ulcers, hardening of the arteries, inflammatory bowel diseases, malnutrition or obesity.

In the disclosed method, promoting growth of a microbial population can refer to promoting growth by about 10%, about 20%, about 30%, about 40%, about 50%, about 60%, about 70%, about 80%, about 90%, or about 100% of the baseline state of the microbial population. For example, promoting growth of a microbial population can refer to promoting growth by about 10%, about 20%, about 30%, about 40%, about 50%, about 60%, about 70%, about 80%, about 90%, about 100%, or any percent in between 10% and 100% as compared to the baseline levels.

Further to any method disclosed herein, in embodiments the effective amount of the compound or a pharmaceutically acceptable salt, hydrate, solvate thereof, is about 0.001 mg/kg to about 200 mg/kg. In embodiments the effective amount is about 0.001 mg/kg. In embodiments the effective amount is about 0.005 mg/kg. In embodiments the effective amount is about 0.01 mg/kg. In embodiments the effective amount is about 0.02 mg/kg. In embodiments the effective amount is about 0.05 mg/kg. In embodiments the effective amount is about 0.075 mg/kg. In embodiments the effective amount is about 0.100 mg/kg. In embodiments the effective amount is about 0.500 mg/kg. In embodiments the effective amount is about 1 mg/kg. In embodiments the effective amount is about 2 mg/kg. In embodiments the effective amount is about 5 mg/kg. In embodiments the effective amount is about 10 mg/kg. In embodiments the effective amount is about 25 mg/kg. In embodiments the effective amount is about 50 mg/kg. In embodiments the effective amount is about 100 mg/kg. In embodiments the effective amount is about 150 mg/kg. In embodiments the effective amount is about 200 mg/kg.

In embodiments, the compound is administered in oral, intravenous, parenteral, subcutaneous, intramuscular, transdermal, intraperitoneal, intranasal, aerosol, intracranial, intrathecal, or topical dosage form. In embodiments, the compound is formulated for administration daily, once every two days, once every three days, once a week, bi-weekly, or once a month.

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. For a given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

V. Kits

In various aspects, a kit is envisioned containing one or more compounds described herein. The kit may contain one or more sealed containers, such as a vial, containing any of the compounds described herein and/or reagents for preparing any of the compounds described herein. In some embodiments, the kit may also contain a suitable container means, which is a container that will not react with components of the kit, such as an Eppendorf tube, an assay plate, a syringe, a bottle, or a tube. The container may be made from sterilizable materials such as plastic or glass.

The kit may further include instructions that outline the procedural steps for methods of treatment or prevention of disease, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of one or more compounds described herein

VI. Provisional Embodiments

Embodiment P1. A compound, or pharmaceutically acceptable salt thereof, having the formula:

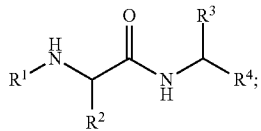

wherein $R^1$ is independently hydrogen, halogen, —C(O)$R^{1C}$, —C(O)—O$R^{1C}$, —C(O)N$R^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, and $R^{1C}$ are each independently hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^3$ are independently an amino acid side chain; $R^4$ is —C(O)H, or —B(OH)$_2$; when $R^4$ is —B(OH)$_2$, $R^1$ is not

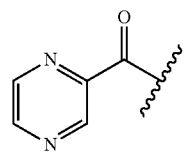

Embodiment P2. The compound, of embodiment P1, wherein when $R^4$ is —B(OH)$_2$, $R^1$ is independently hydrogen, —C(O)$R^{1C}$, or —C(O)—O$R^{1C}$; and $R^{1C}$ is hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl.

Embodiment P3. The compound of embodiments P1 or P2, wherein when $R^4$ is —B(OH)$_2$, $R^{1C}$ is hydrogen, substituted or unsubstituted alkyl, substituted or unsubstituted heteroalkyl.

Embodiment P4. The compound of embodiments P1 or P2, wherein when $R^4$ is —B(OH)$_2$, $R^{1C}$ is hydrogen or substituted or unsubstituted alkyl.

Embodiment P5. The compound of embodiments P1 or P2, wherein when $R^4$ is —B(OH)$_2$, $R^{1C}$ is substituted or unsubstituted $C_1$-$C_{10}$ alkyl.

Embodiment P6. The compound of embodiments P1 or P2, wherein when $R^4$ is —B(OH)$_2$, $R^{1C}$ is substituted or unsubstituted $C_2$-$C_8$ alkyl.

Embodiment P7. The compound of embodiments P1 or P2, wherein when $R^4$ is —B(OH)$_2$, $R^{1C}$ is substituted or unsubstituted $C_4$-$C_8$ alkyl.

Embodiment P8. The compound of embodiments P1 or P2, wherein when $R^4$ is —B(OH)$_2$, $R^{1C}$ is hydrogen or unsubstituted alkyl.

Embodiment P9. The compound of embodiments P1 or P2, wherein when $R^4$ is —B(OH)$_2$, $R^{1C}$ is hydrogen.

Embodiment P10. The compound of embodiments P1 or P2, wherein when $R^4$ is —B(OH)$_2$, $R^{1C}$ is unsubstituted $C_4$-$C_8$ alkyl.

Embodiment P11. The compound of embodiments P1 or P2, wherein when $R^4$ is —B(OH)$_2$, $R^1$ is not —C(O)$R^{1C}$, or —C(O)—O$R^{1C}$.

Embodiment P12. The compound of embodiments P1 or P2, wherein when $R^4$ is —B(OH)$_2$, $R^{1C}$ is not substituted or unsubstituted aryl, or substituted or unsubstituted heteroaryl.

Embodiment P13. The compound of embodiment P1 having the formula:

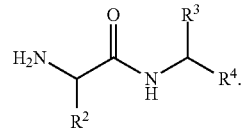

Embodiment P14. The compound of embodiment P1, wherein $R^4$ is —C(O)H.

Embodiment P15. The compound of embodiment P1 or P14, wherein when $R^4$ is —C(O)H, $R^1$ is —C(O)$R^{1C}$, or —C(O)—O$R^{1C}$.

Embodiment P16. The compound of embodiment P1 or P14, wherein when $R^4$ is —C(O)H, $R^{1C}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl.

Embodiment P17. The compound of embodiment P1 or P14, wherein when $R^4$ is —C(O)H, $R^{1C}$ is hydrogen, substituted or unsubstituted alkyl, substituted or unsubstituted heteroalkyl.

Embodiment P18. The compound of embodiment P1 or P14, wherein when $R^4$ is —C(O)H, $R^{1C}$ is hydrogen or substituted or unsubstituted alkyl.

Embodiment P19. The compound of embodiment P1 or P14, wherein when $R^4$ is —C(O)H, $R^{1C}$ is substituted or unsubstituted $C_1$-$C_{10}$ alkyl.

Embodiment P20. The compound of embodiment P1 or P14, wherein when $R^4$ is —C(O)H, $R^{1C}$ is substituted or unsubstituted $C_2$-$C_8$ alkyl.

Embodiment P21. The compound of embodiment P1 or P14, wherein when $R^4$ is —C(O)H, $R^{1C}$ is substituted or unsubstituted $C_4$-$C_8$ alkyl.

Embodiment P22. The compound of embodiment P1 or P14, wherein when $R^4$ is —C(O)H, $R^{1C}$ is hydrogen or unsubstituted alkyl.

Embodiment P23. The compound of embodiment P1 or P14, wherein when $R^4$ is —C(O)H, $R^{1C}$ is hydrogen.

Embodiment P24. The compound of embodiment P1 or P14, wherein when $R^4$ is —C(O)H, $R^{1C}$ is unsubstituted $C_4$-$C_8$ alkyl.

Embodiment P25. The compound of embodiment P1 or P14, having the formula:

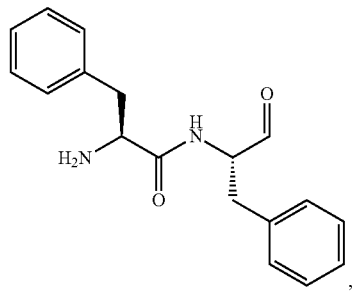

,

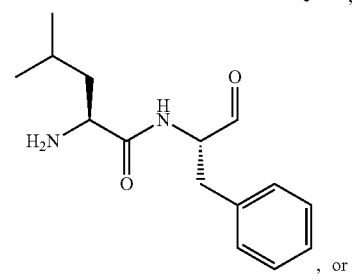

, or

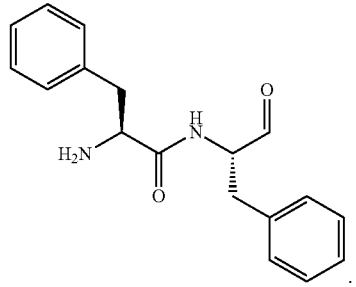

.

Embodiment P26. A compound, or pharmaceutically acceptable salt thereof, having the formula:

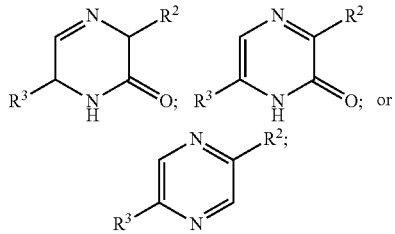

wherein
$R^1$ is independently hydrogen, halogen, —C(O)$R^{1C}$, —C(O)—O$R^{1C}$, —C(O)N$R^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, and $R^{1C}$ are each independently hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are independently an amino acid side chain;
when $R^2$ is

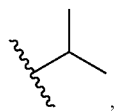

, $R^3$ is not

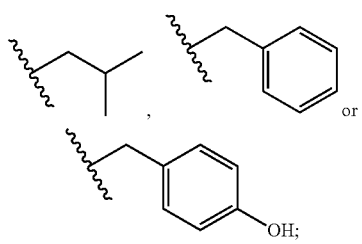

;

and when $R^2$ is

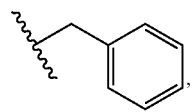

, $R^3$ is not

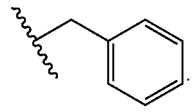 [SMILES: *Cc1ccccc1]

.

Embodiment P27. The compound of any one of embodiments P1 to P25, wherein $R^2$ and $R^3$ are independently selected from the group consisting of H,

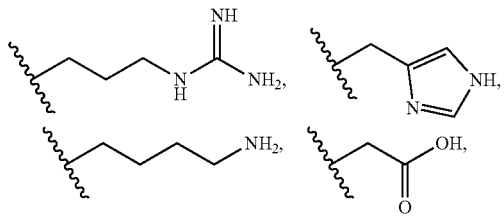

-continued

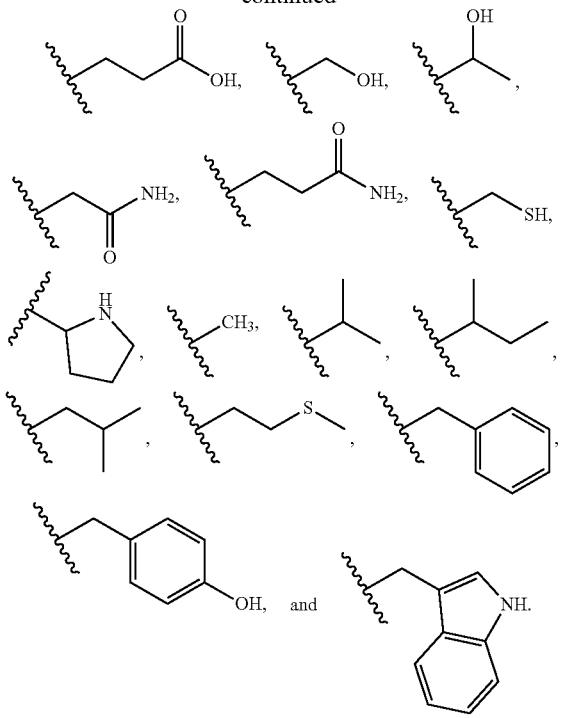

Embodiment P28. The compound of any one of embodiments P1 to P25, wherein $R^2$ is selected from the group consisting of

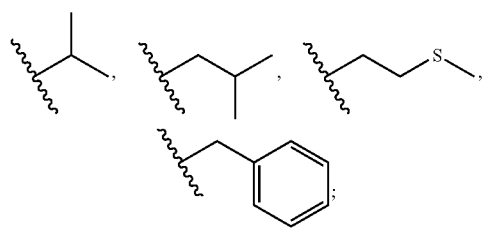

and $R^3$ is

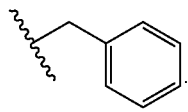 [SMILES: *Cc1ccccc1]

Embodiment P29. The compound of any one of embodiments P1 to P25, wherein $R^2$ and $R^3$ are independently selected from the group consisting of

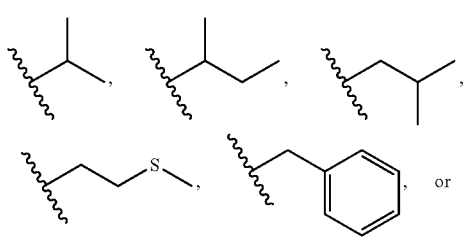

-continued

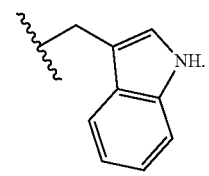

Embodiment P30. The compound of any one of embodiments P1 to P25, wherein $R^2$ is and $R^3$ is Embodiment P31. The compound of any one of embodiments P1 to P25, wherein $R^2$ is and $R^3$ is

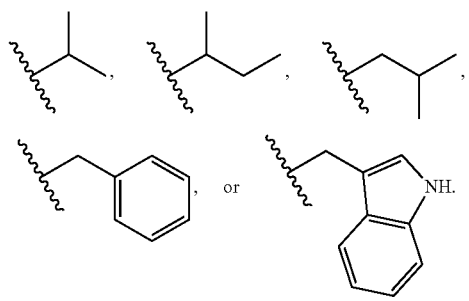

Embodiment P32. The compound of embodiment P1, having the formula:

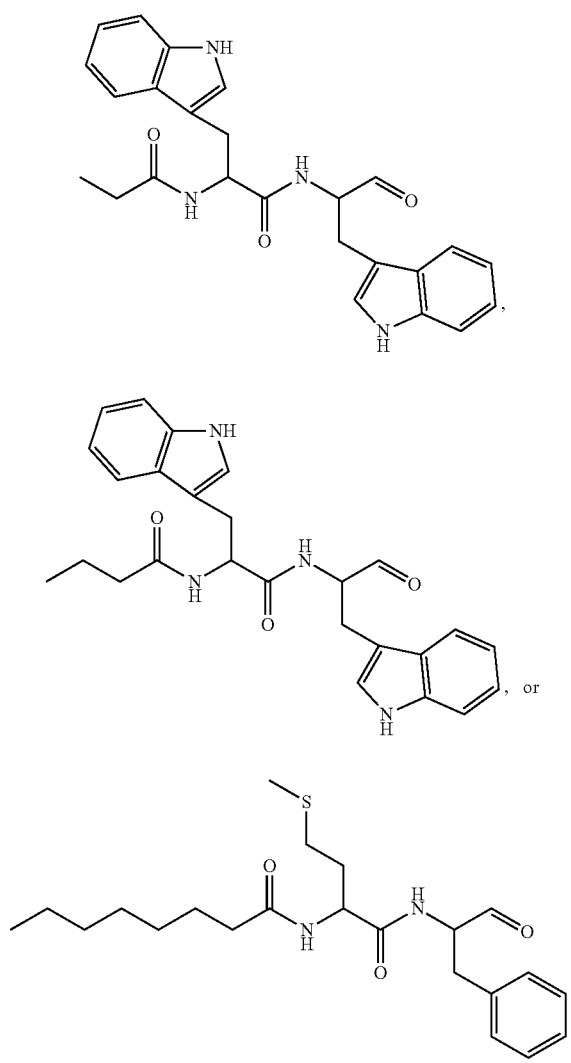
Embodiment P33. The compound of embodiment P26, having the formula:
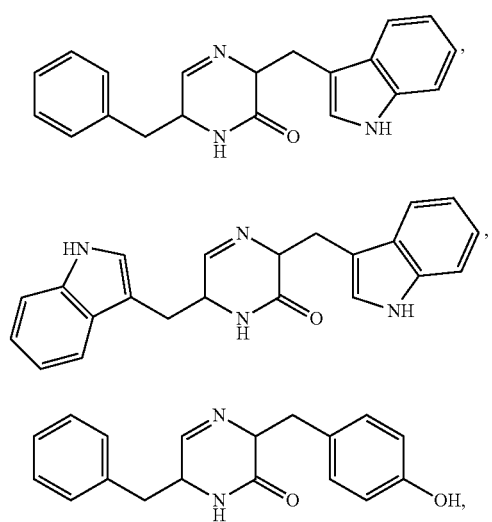
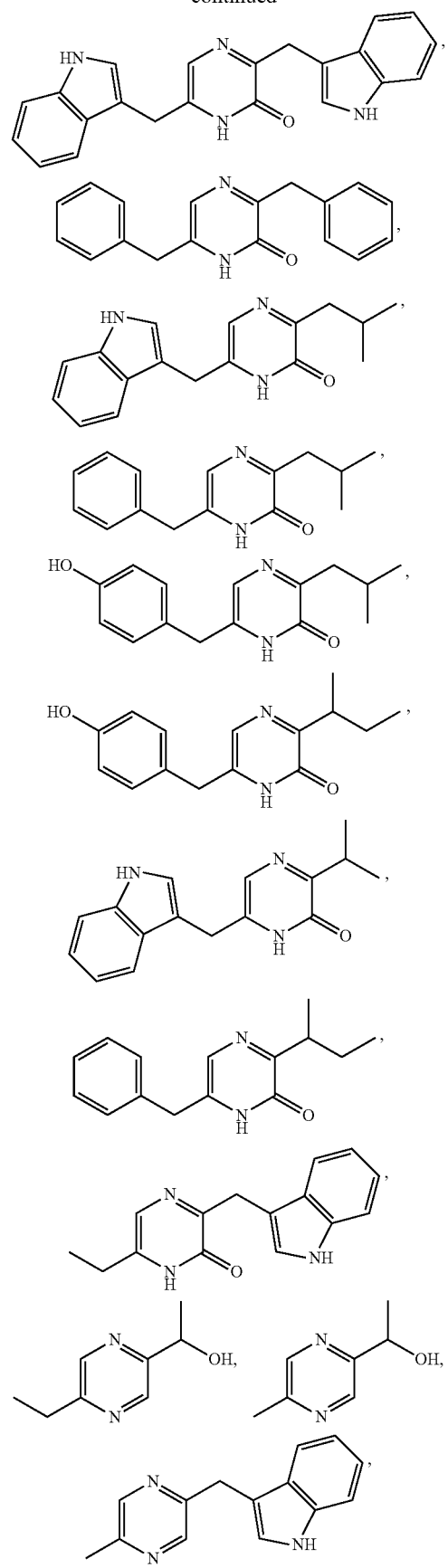

-continued

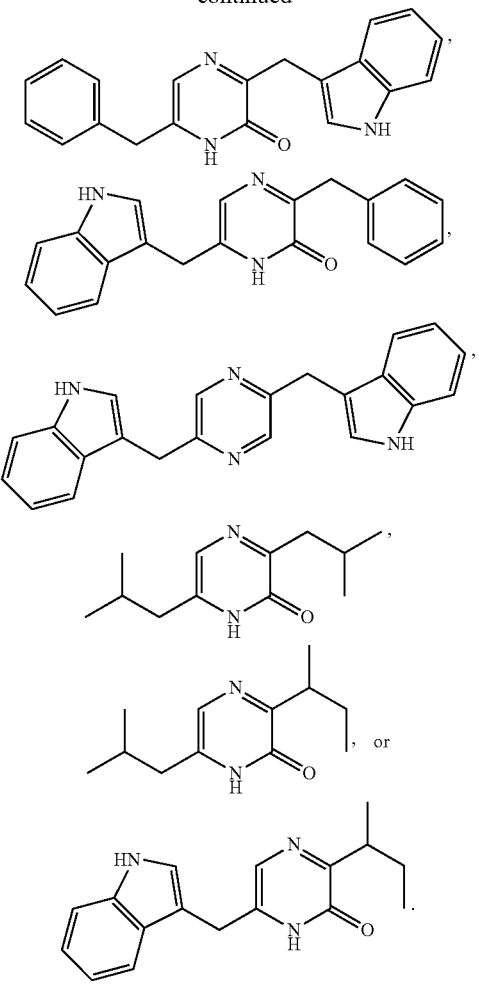

Embodiment P34. The compound of any one of embodiments P1 to P31, wherein at least one N is $^{15}$N, at least one C is $^{13}$C, or at least one H is $^{2}$H.

Embodiment P35. A pharmaceutical composition comprising the compound of any one of embodiments P1 to P34 and a pharmaceutically acceptable excipient.

Embodiment P36. A method of treating cancer, said method comprising administering to a subject in need thereof an effective amount of a compound of one of embodiments P1 to P34.

Embodiment P37. A method of inhibiting cathepsin activity, said method comprising: contacting the cathepsin with a compound of one of embodiments P1 to P34.

Embodiment P38. The method of embodiment P37, wherein the cathepsin is cathepsin B, cathepsin L, cathepsin C, or cathepsin S.

Embodiment P39. A method of reducing cathepsin activity, said method comprising: contacting the cathepsin with a compound of one of embodiments P1 to P34.

Embodiment P40. The method of embodiment P37, wherein the cathepsin is cathepsin B, cathepsin L, cathepsin C, or cathepsin S.

Embodiment P41. The method of embodiment P40, wherein the activity of cathepsin S is reduced greater than the activity of cathepsin L.

Embodiment P42. A method of inhibiting protease activity, said method comprising: contacting the protease with a compound of one of embodiments P1 to P34.

Embodiment P43. The method of embodiment P42, wherein the protease is a serine protease, cysteine protease, or aspartyl protease.

Embodiment P44. The method of embodiment P42, wherein the protease is a cysteine protease.

Embodiment P45. The method of embodiment P42, wherein the protease is a lysosomal protease.

VII. Additional Embodiments

Embodiment 1. A compound, or pharmaceutically acceptable salt thereof, having the formula:

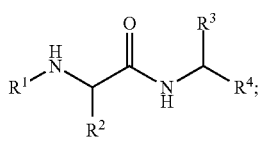

wherein
$R^1$ is independently hydrogen, halogen, —C(O)$R^{1C}$, —C(O)—OR$^{1C}$, —C(O)NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, and $R^{1C}$ are each independently
hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ and $R^3$ are independently an amino acid side chain;
$R^4$ is —C(O)H, or —B(OH)$_2$;
when $R^4$ is —B(OH)$_2$, $R^1$ is not

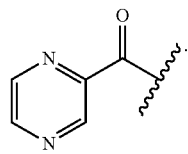 [SMILES: *C(=O)c1cnccn1]

Embodiment 2. The compound, of embodiment 1, wherein when $R^4$ is —B(OH)$_2$, $R^1$ is independently hydrogen, —C(O)$R^{1C}$, or —C(O)—OR$^{1C}$; and $R^{1C}$ is hydrogen, —CF$_3$, —Cl$_3$, —CI$_3$, —CBr$_3$, —COOH, —CONH$_2$, —CHF$_2$, —CHCl$_2$, —CHI$_2$, —CHBr$_2$, —OCH$_2$F, —OCH$_2$Cl, —OCH$_2$I, substituted or unsubstituted alkyl, substituted or unsubstituted heteroalkyl, substituted or unsubstituted cycloalkyl, substituted or unsubstituted heterocycloalkyl, substituted or unsubstituted aryl.

Embodiment 3. The compound of embodiments 1 or 2, wherein when $R^4$ is —B(OH)$_2$, $R^{1C}$ is hydrogen, substituted or unsubstituted alkyl, substituted or unsubstituted heteroalkyl.

Embodiment 4. The compound of embodiments 1 or 2, wherein when $R^4$ is —B(OH)$_2$, $R^{1C}$ is hydrogen or substituted or unsubstituted alkyl.

Embodiment 5. The compound of embodiments 1 or 2, wherein when $R^4$ is —B(OH)$_2$, $R^{1C}$ is substituted or unsubstituted $C_1$-$C_{10}$ alkyl.

Embodiment 6. The compound of embodiments 1 or 2, wherein when $R^4$ is —B(OH)$_2$, $R^{1C}$ is substituted or unsubstituted $C_2$-$C_8$ alkyl.

Embodiment 7. The compound of embodiments 1 or 2, wherein when $R^4$ is —B(OH)$_2$, $R^{1C}$ is substituted or unsubstituted $C_4$-$C_8$ alkyl.

Embodiment 8. The compound of embodiments 1 or 2, wherein when $R^4$ is —B(OH)$_2$, $R^{1C}$ is hydrogen or unsubstituted alkyl.

Embodiment 9. The compound of embodiments 1 or 2, wherein when $R^4$ is —B(OH)$_2$, $R^{1C}$ is hydrogen.

Embodiment 10. The compound of embodiments 1 or 2, wherein when $R^4$ is —B(OH)$_2$, $R^{1C}$ is unsubstituted $C_4$-$C_8$ alkyl.

Embodiment 11. The compound of embodiments 1 or 2, wherein when $R^4$ is —B(OH)$_2$, $R^1$ is not —C(O)$R^{1C}$, or —C(O)—O$R^{1C}$.

Embodiment 12. The compound of embodiments 1 or 2, wherein when $R^4$ is —B(OH)$_2$, $R^{1C}$ is not substituted or unsubstituted aryl, or substituted or unsubstituted heteroaryl.

Embodiment 13. The compound of embodiment 1 having the formula:

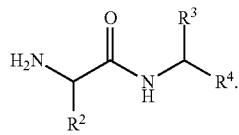

Embodiment 14. The compound of embodiment 1, wherein $R^4$ is —C(O)H.

Embodiment 15. The compound of embodiment 1 or 14, wherein when $R^4$ is —C(O)H, $R^1$ is —C(O)$R^{1C}$, or —C(O)—O$R^{1C}$.

Embodiment 16. The compound of embodiment 1 or 14, wherein when $R^4$ is —C(O)H, $R^{1C}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl.

Embodiment 17. The compound of embodiment 1 or 14, wherein when $R^4$ is —C(O)H, $R^{1C}$ is hydrogen, substituted or unsubstituted alkyl, substituted or unsubstituted heteroalkyl.

Embodiment 18. The compound of embodiment 1 or 14, wherein when $R^4$ is —C(O)H, $R^{1C}$ is hydrogen or substituted or unsubstituted alkyl.

Embodiment 19. The compound of embodiment 1 or 14, wherein when $R^4$ is —C(O)H, $R^{1C}$ is substituted or unsubstituted $C_1$-$C_{10}$ alkyl.

Embodiment 20. The compound of embodiment 1 or 14, wherein when $R^4$ is —C(O)H, $R^{1C}$ is substituted or unsubstituted $C_2$-$C_8$ alkyl.

Embodiment 21. The compound of embodiment 1 or 14, wherein when $R^4$ is —C(O)H, $R^{1C}$ is substituted or unsubstituted $C_4$-$C_8$ alkyl.

Embodiment 22. The compound of embodiment 1 or 14, wherein when $R^4$ is —C(O)H, $R^{1C}$ is hydrogen or unsubstituted alkyl.

Embodiment 23. The compound of embodiment 1 or 14, wherein when $R^4$ is —C(O)H, $R^{1C}$ is hydrogen.

Embodiment 24. The compound of embodiment 1 or 14, wherein when $R^4$ is —C(O)H, $R^{1C}$ is unsubstituted $C_4$-$C_8$ alkyl.

Embodiment 25. The compound of embodiment 1 or 14, having the formula:

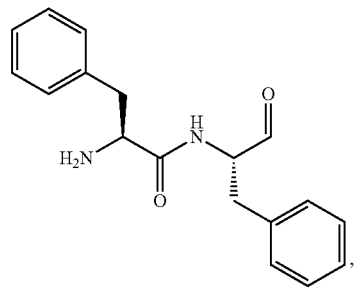

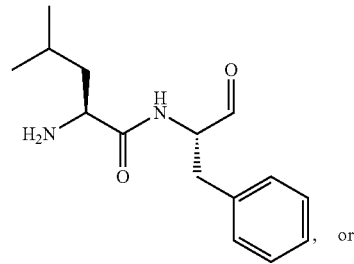

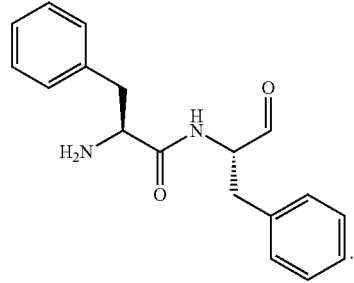

Embodiment 26. A compound, or pharmaceutically acceptable salt thereof, having the formula:

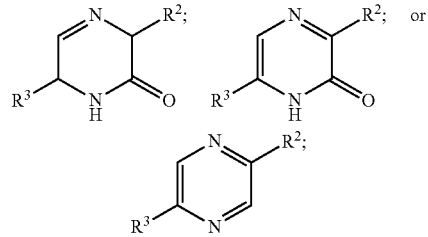

wherein $R^2$ and $R^3$ are independently an amino acid side chain;

when $R^2$ is

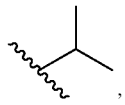

$R^3$ is not

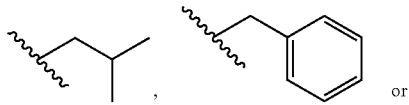

-continued

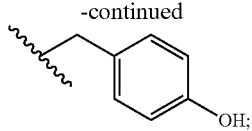

and when R² is

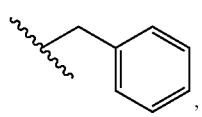 [SMILES: *Cc1ccccc1]

R³ is not

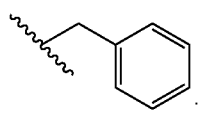 [SMILES: *Cc1ccccc1].

Embodiment 27. The compound of any one of embodiments 1 to 25, wherein R² and R³ are independently selected from the group consisting of H,

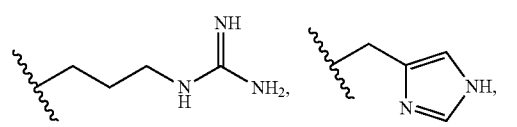

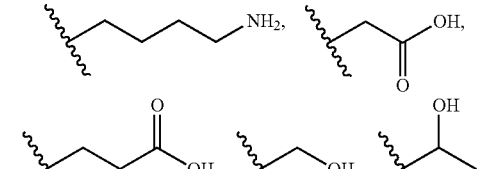

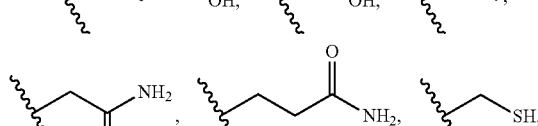

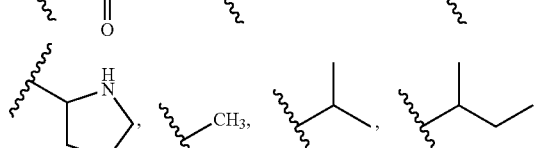

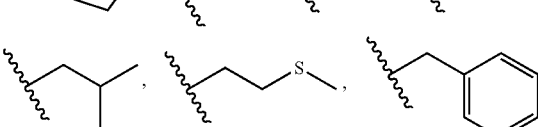

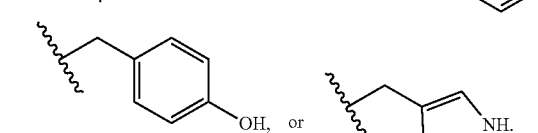

Embodiment 28. The compound of any one of embodiments 1 to 25, wherein R² is selected from the group consisting of

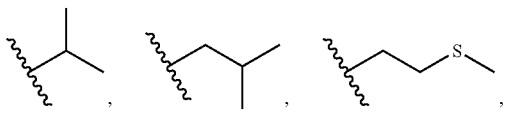

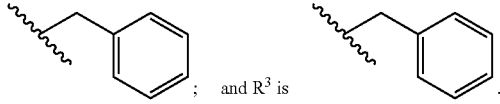; and R³ is

Embodiment 29. The compound of any one of embodiments 1 to 25, wherein R² and R³ are independently selected from the group consisting of

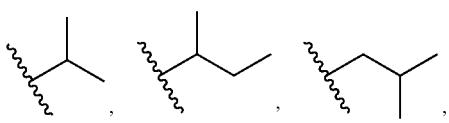

, or

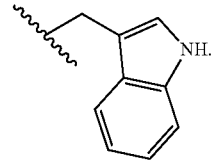

Embodiment 30. The compound of any one of embodiments 1 to 25, wherein R² is

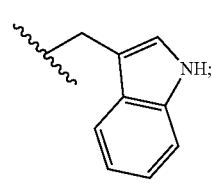 [SMILES: *Cc1c[nH]c2ccccc12]

and R³ is

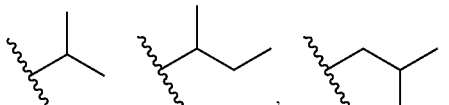

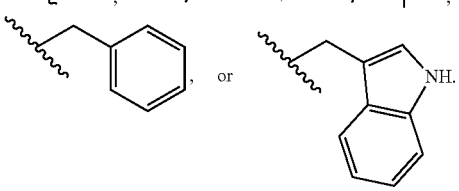

Embodiment 31. The compound of any one of embodiments 1 to 25, wherein R² is

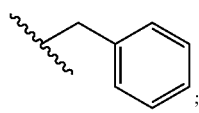 [SMILES: *Cc1ccccc1]
and R³ is
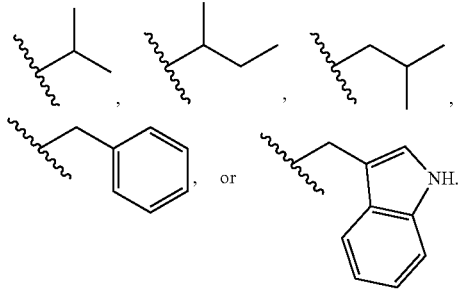
Embodiment 32. The compound of embodiment 1, having the formula:
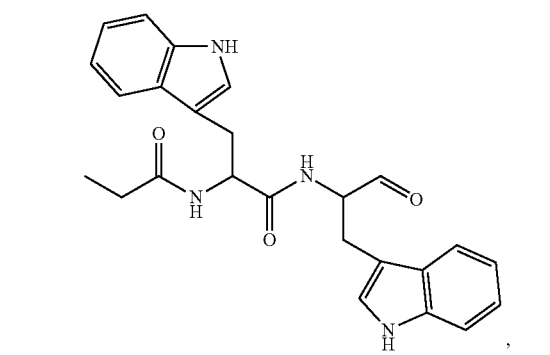
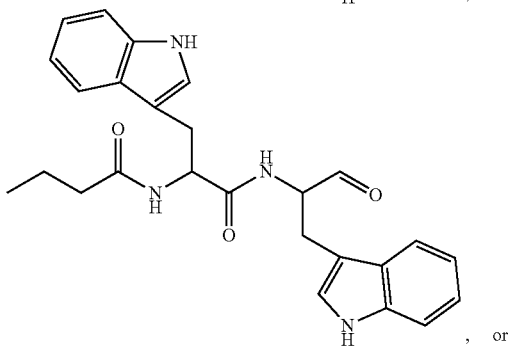
, or
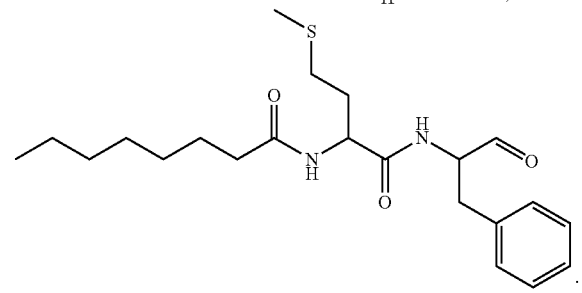
Embodiment 33. The compound of embodiment 26, having the formula:
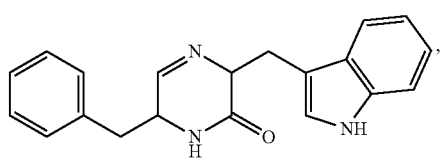
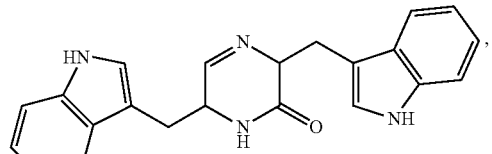
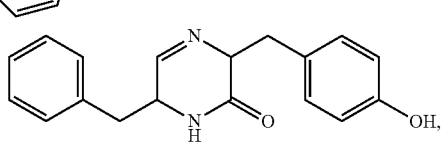
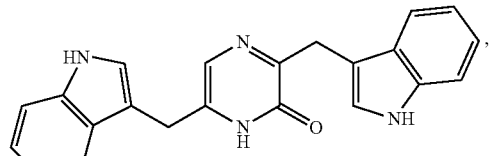
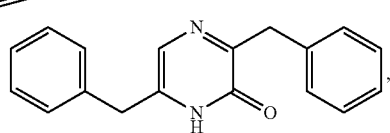
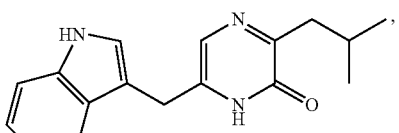
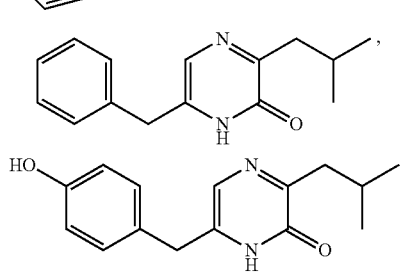
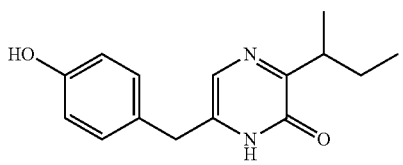
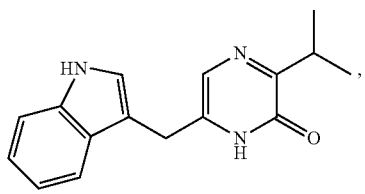
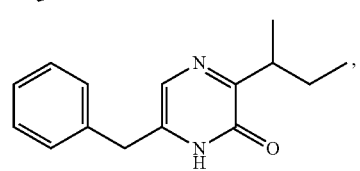

-continued

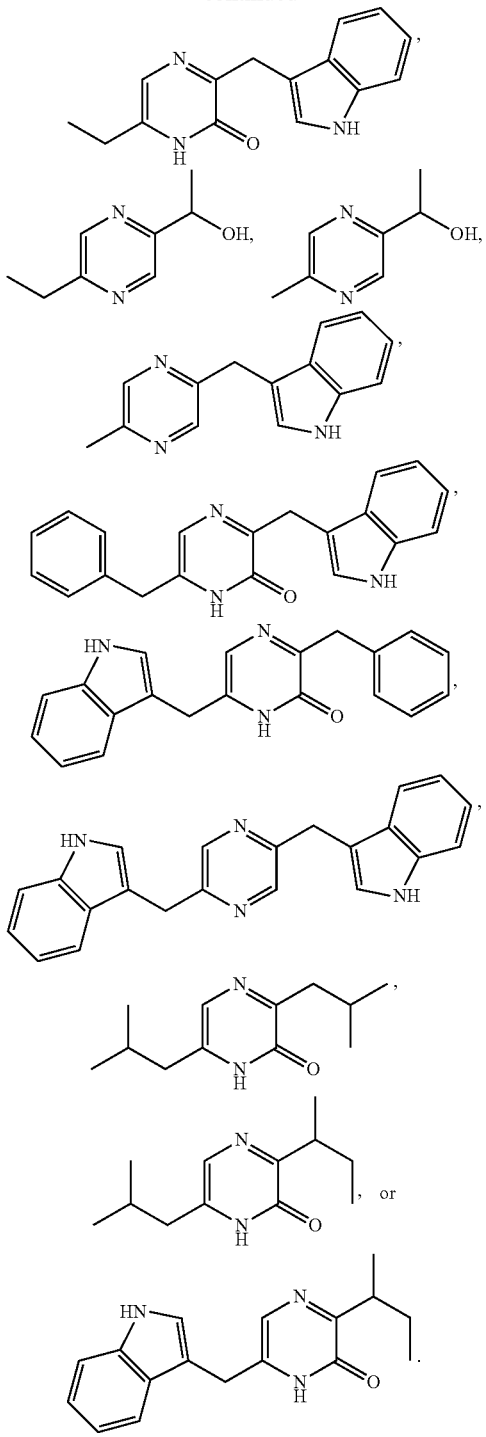

Embodiment 34. The compound of any one of embodiments 1 to 31, wherein at least one N is $^{15}$N, at least one C is $^{13}$C, or at least one H is $^{2}$H.

Embodiment 35. A pharmaceutical composition including the compound of any one of embodiments 1 to 34 and a pharmaceutically acceptable excipient.

Embodiment 36. A method of treating cancer, the method including administering to a subject in need thereof an effective amount of a compound of one of embodiments 1 to 34.

Embodiment 37. A method of inhibiting cathepsin activity, the method including: contacting the cathepsin with a compound of one of embodiments 1 to 34.

Embodiment 38. The method of embodiment 37, wherein the cathepsin is cathepsin B, cathepsin L, cathepsin C, or cathepsin S.

Embodiment 39. A method of reducing cathepsin activity, the method including: contacting the cathepsin with a compound of one of embodiments 1 to 34.

Embodiment 40. The method of embodiment 39, wherein the cathepsin is cathepsin B, cathepsin L, cathepsin C, or cathepsin S.

Embodiment 41. The method of embodiment 40, wherein the activity of cathepsin S is reduced greater than the activity of cathepsin L.

Embodiment 42. A method of inhibiting protease activity, the method including: contacting the protease with a compound of one of embodiments 1 to 34.

Embodiment 43. The method of embodiment 42, wherein the protease is a serine protease, cysteine protease, or aspartyl protease.

Embodiment 44. The method of embodiment 42, wherein the protease is a cysteine protease.

Embodiment 45. The method of embodiment 42, wherein the protease is a lysosomal protease.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1. Peptide Aldehydes from a Family of Widely Distributed Gene Clusters in Gut Bacteria The gut microbiota modulate host biology in numerous ways, but little is known about the molecular mediators of these interactions. In previous work, we found a widely distributed family of nonribosomal peptide synthetase gene clusters in gut bacteria. Here, by a subset of these clusters in Escherichia coli or Bacillus subtilis, we show that they encode pyrazinones and dihydropyrazinones. At least one of the 47 clusters is present in 88% of the NIH HMP stool samples, and they are transcribed under native conditions of host colonization. We present evidence that the active form of these molecules is the initially released peptide aldehyde, which bears potent protease inhibitory activity and selectively targets a subset of cathespsins in human cell proteomes. Our study reveals a large family of previously unknown microbiota-derived metabolites, and it shows that merging synthetic biology with chemistry can close large gaps in our knowledge of the metabolic potential of the microbiota.

The microbiota influence host biology in numerous ways, very few of which are understood at the level of molecular mechanism (Donia and Fischbach, 2015; Lee and Hase, 2014; Nicholson et al., 2012). In a previous survey of biosynthetic gene clusters from the human microbiome, we reported the presence of thousands of biosynthetic loci of unknown function, including large families that are present in >50% of the subjects from the NIH Human Microbiome Project (Donia et al., 2014). The small molecule products of these genetic elements represent large gaps in our knowledge of what the microbiota are capable of producing, and constitute an enticing opportunity to discover new mediators of interspecies interactions.

As a test case for expanding our knowledge of the biosynthetic capacity of the microbiota, we set out to characterize a family of nonribosomal peptide synthetase (NRPS) gene clusters that are found in a variety of gut bacterial genome sequences (Donia et al., 2014). These clusters attracted our attention for two reasons: First, they are present in >90% of the stool samples from the HMP, suggesting that the metabolites they encode are widely distributed among healthy humans. Second, they reside almost exclusively in gut bacterial genome sequences; only a few environmental isolates harbor a cluster in the family, raising the possibility that their small molecule products play a role in interspecies signaling in the gut.

Computational analysis of the gut NRPS cluster family. We began by performing a multi-gene BLAST search (Medema et al., 2013) to identify new clusters in the family from genome sequences that had been deposited since our previous analysis. This search yielded 19 new clusters at a threshold of 30% average sequence identity, increasing the size of the family to 47 (FIG. 1). The resulting reanalysis shows a family that has the following characteristics: 1) It consists of four clades: one featuring a three-module NRPS (e.g., bgc52), another with a two-module NRPS and a loading module on a separate protein (e.g., bgc35), a third consisting solely of a two-module NRPS (e.g., bgc26), and a fourth containing NRPSs of variable domain architecture. In every case, the NRPS features a terminal reductase (R) domain. 2) Almost all of the gene clusters are found in anaerobic Firmicutes from the class Clostridia, although a few of the clusters are found in Gram-negative organisms (Bacteroides and Desulfovibrio). 3) Nearly all of the clusters reside in isolates from the human gut and that of other mammals (FIG. 1). Very few of the clusters are found in relatives of these organisms that are free-living or inhabit a non-intestinal host-associated niche, implying a function that is relevant to the biology of host colonization. 4) Each clade contains clusters from hosts that have never been isolated; genome sequences of the hosts from which these clusters derive were assembled from metagenomic samples in a recent study (Nielsen et al., 2014). As such, the only way to access these clusters is to synthesize them, a problem of increasing importance as the volume of metagenomic sequence data increases and tools are developed for assembling short-read metagenomic data into cluster-size fragments.

We selected 14 of these clusters for analysis: The BGCs characterized experimentally where products were obtained include bgc52, bgc39, bgc38, bgc 34, bgc34, bgc35, bgc33, and bgc86. Experimentally characterized but no products observed include bgc28, bgc30, bgc32, bgc37, bgc45, bgc43, and bgc41; see FIG. 1 for details. Clusters were chosen to represent the diversity of sequences and domain architectures from the four clades of the family. Since none of the host organisms have been manipulated genetically and most are from a bacterial class (Clostridia) that is largely refractory to genetic manipulation, we decided not to make targeted genetic deletions in any of the native host strains. Instead, we expressed gene clusters heterologously in two commonly used laboratory hosts, *Escherichia coli* and *Bacillus subtilis*. The host organisms of three of the clusters (bgc34, bgc35, bgc52) were available from laboratories or culture collections; clusters from these hosts were cloned in their native form (omitting regulatory genes) into *E. coli* or *B. subtilis* vectors in which expression was driven by a strong promoter (see FIGS. 5A-5B for more details). The remaining clusters were either from organisms that could not be obtained or from metagenomic sequence data, so the host organism was never isolated; these clusters were synthesized with optimized codons and expressed in the *E. coli* and *B. subtilis* vectors.

Figure 2A:
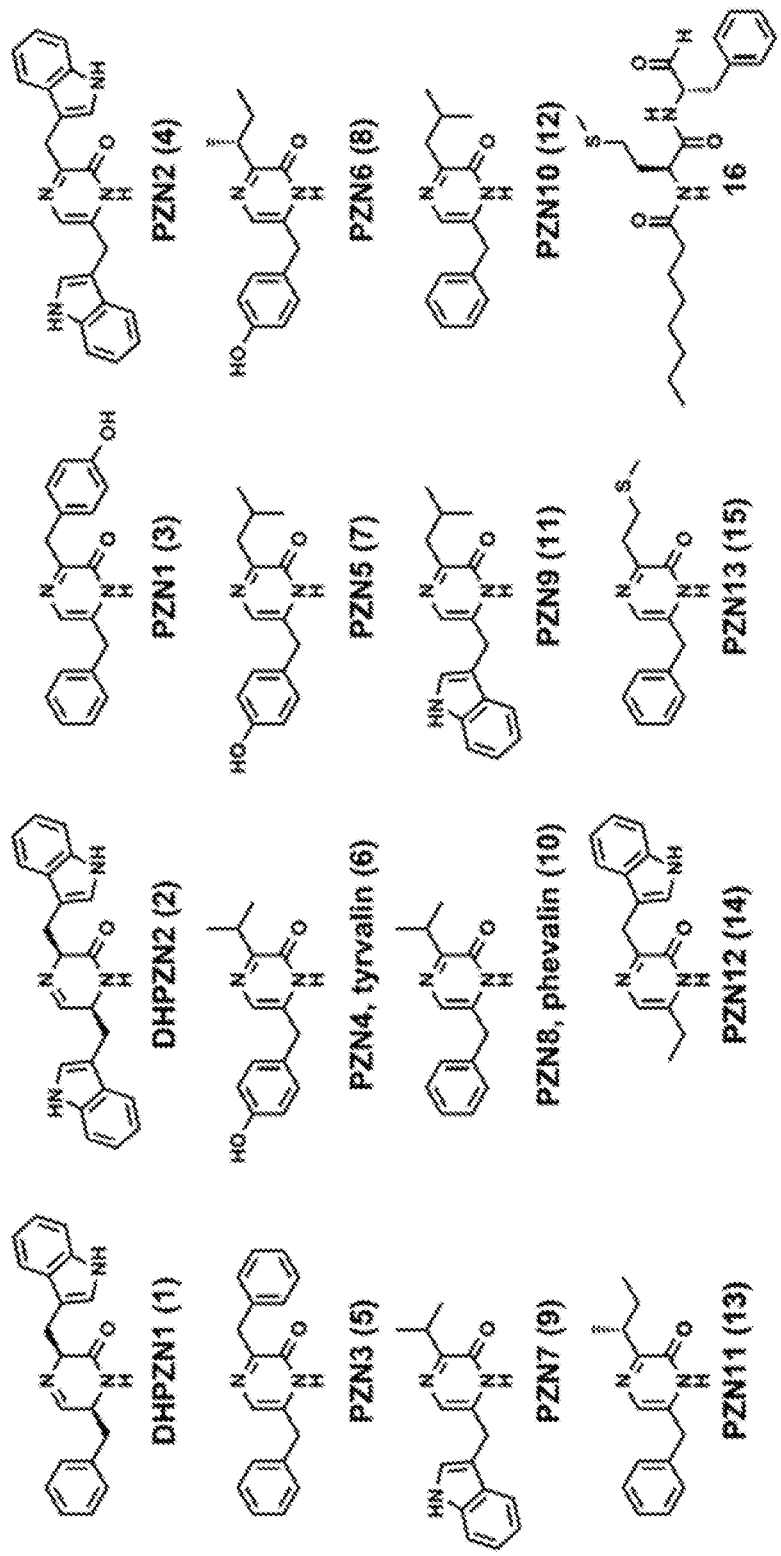
FIGS. 2A-2C: Chemical and biochemical analysis of the gut NRPS BGCs. FIG. A: Chemical structures of the small molecule products of the gut NRPS gene clusters.
Figure 2B:
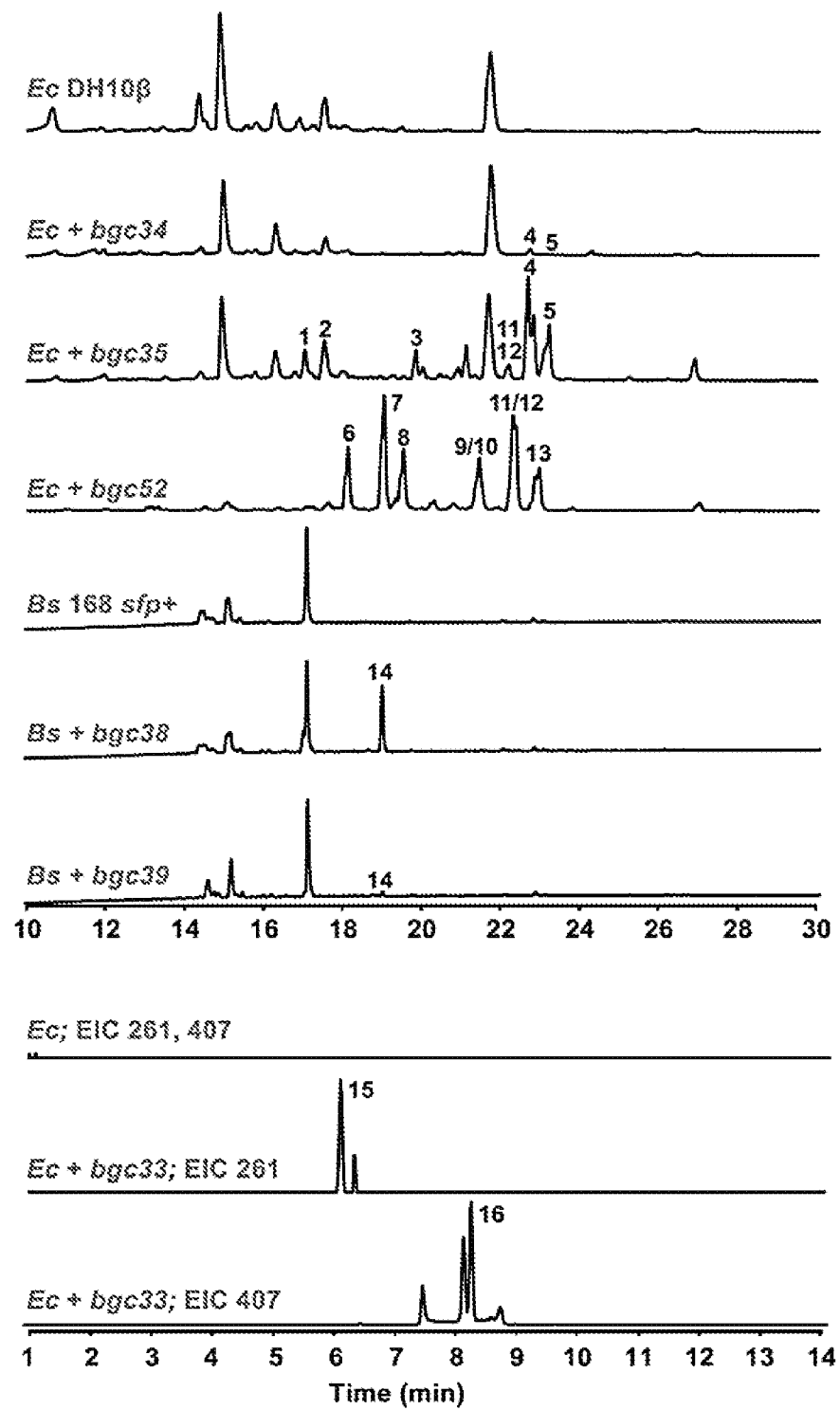
Figure 2C:
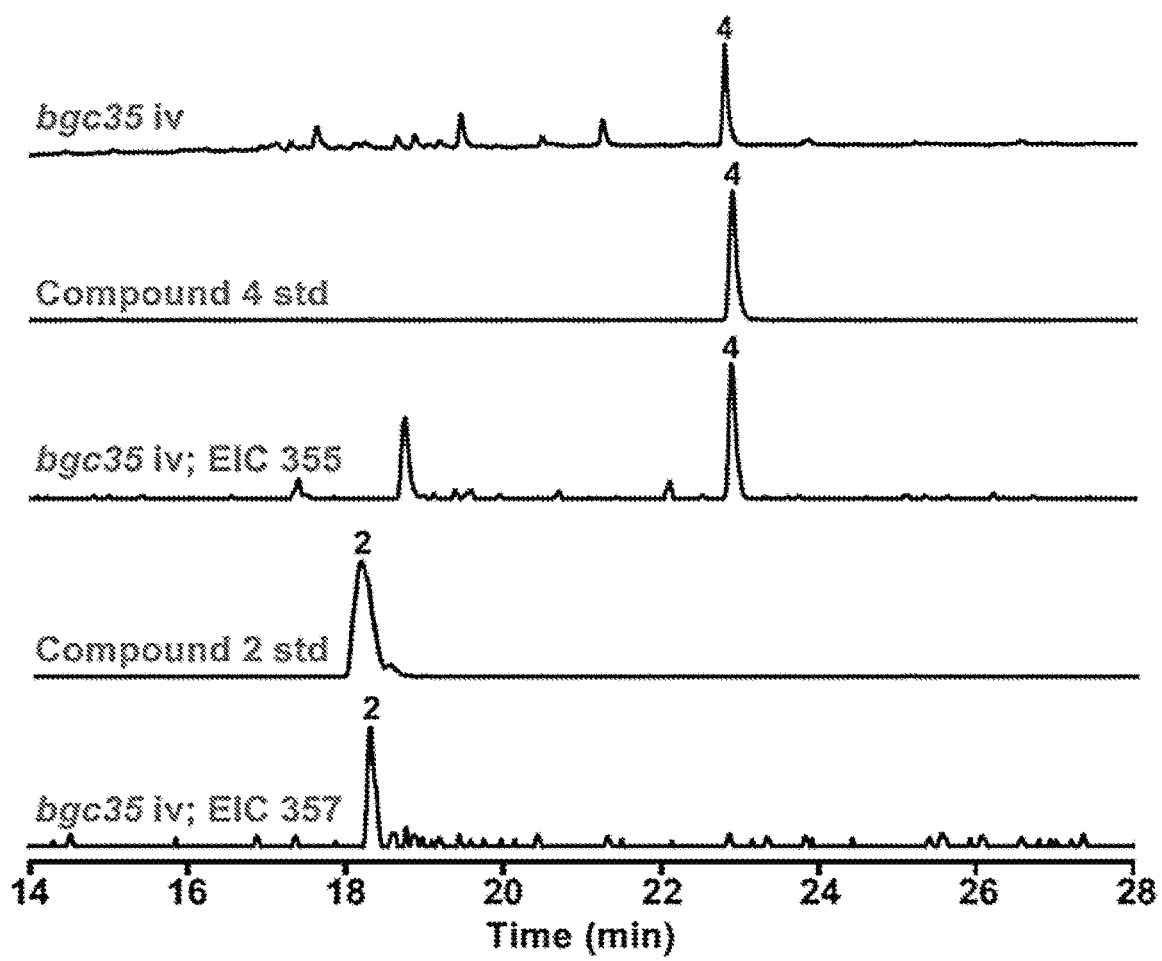

Experimental analysis of the gut NRPS gene clusters. LC-MS analysis of culture fluid extract from *E. coli* strains harboring bgc35 and bgc52 showed evidence of seven and eight new peaks, respectively (FIG. 2), which is notable since both clusters are from Gram-positive hosts. From 4 L of culture fluid, we purified multi-milligram quantities of each compound (FIG. 2). Three lines of evidence reveal that these molecules are a family of pyrazinones and dihydropyrazinones: 1) The purified compounds have UV absorption maxima 220 and 300 nm, consistent with a pyrazinone core. 2) High-resolution LC-MS analysis of the compounds yields masses and empirical formulae consistent with a series of α-amino-acid-derived pyrazinones and dihydropyrazinones with variable sidechains at both positions (FIG. 6). 3) 1D and 2D NMR experiments show chemical shifts and correlations characteristic of pyrazinones (MacDonald et al., 1976). An *E. coli* strain harboring bgc34 produced a subset of the bgc35 products, but at a level so low it would not have been observed without a targeted mass ion search.

Figure 8A:
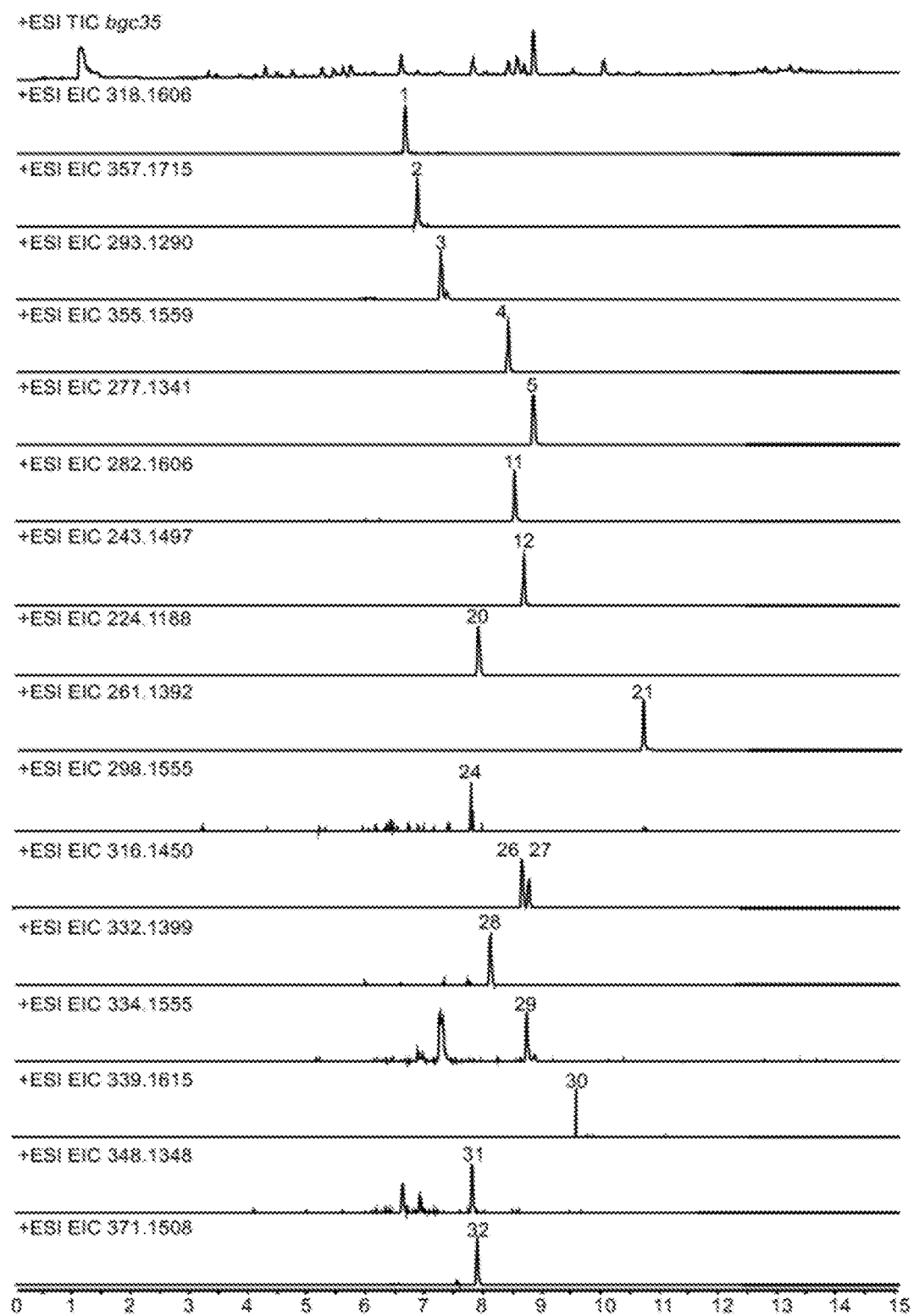
FIGS. 8A-8C. HRESIMS analyses of the organic extracts of the mutant strains carrying bgc35 (FIG. 8A), bgc52 (FIG. 8B), bgc38 (FIG. 9C). TIC stands for total ion current. The exact MS of each individual compound was extracted and the traces are shown. The numbering of the peaks corresponds to the compounds shown in FIG. 6.
Figure 8B:
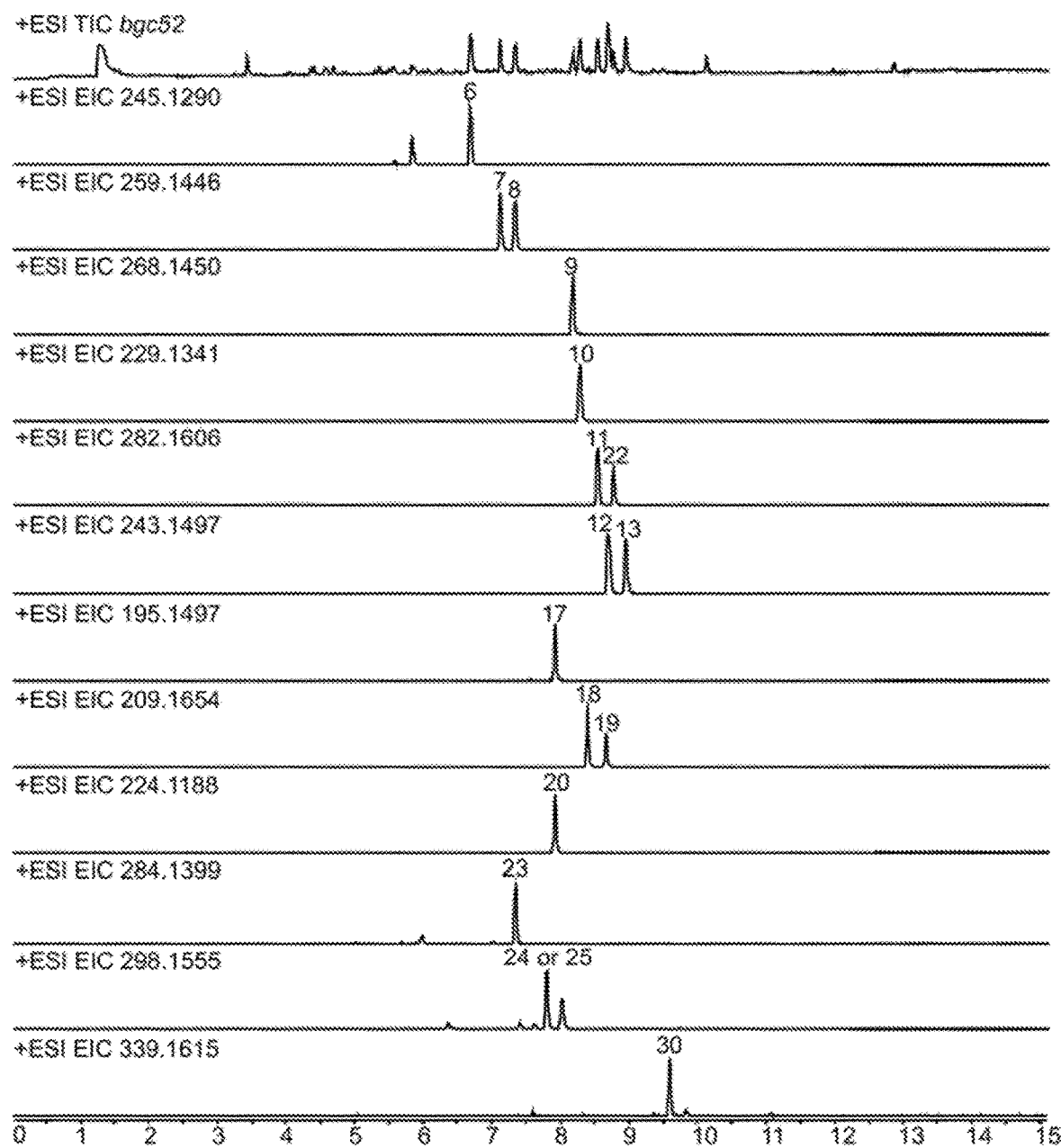
Figure 8C:
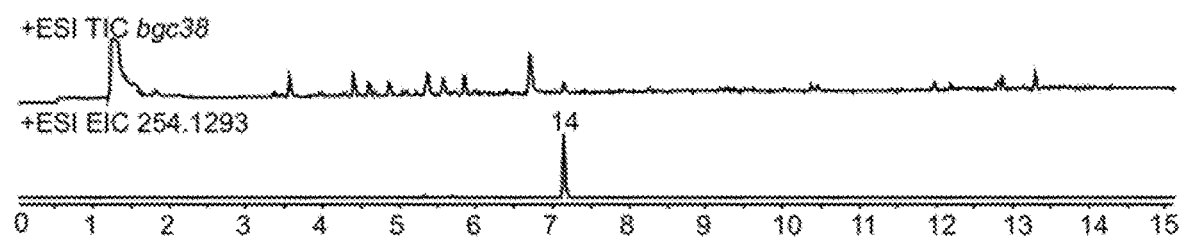

Results from two other clusters showed additional modes of diversity in the family. When bgc38 was expressed in *B. subtilis*, we observed one new peak corresponding to a pyrazinone with ethyl and methylindole side chains, indicating that α-aminobutyrate (or an unknown precursor) can be a native monomer; bgc39 was a low-level producer of the bgc38 products. bgc33 and bgc86 were of particular interest: these clusters were discovered from a metagenomic sample, so their host organisms were never isolated (FIG. 1). An *E. coli* strain carrying a synthetic, codon-optimized version of bgc33 yielded two classes of molecules: a pyrazinone that derives from methionine and valine (15), and a corresponding set of N-acylated dipeptide aldehydes (FIG. 8), including one that bears an N-octanoyl acyl chain (16). In comparison, only the pyrazinone product (15) can be identified from the *E. coli* strain harboring bgc86.

In addition to the 16 molecules that were produced at a titer sufficient to purify milligram quantities for NMR experiments, we identified 16 additional pathway-dependent molecules from bgc35 and bgc52. These metabolites are produced at a lower titer and their structures are proposed on the basis of diagnostic high-resolution MS/MS fragmentation patterns. In addition to the seven clusters from which we observed products, seven additional clusters were synthesized and expressed in *E. coli* DH103, *E. coli* BAP1, or *B. subtilis* 168 (bgc28, bgc30, bgc32, bgc37, bgc45, bgc43, and bgc41 identified in FIG. 1); no high-titer products were observed from any of these BGCs using an LC-MS trace comparison. In total, from 7 of 14 heterologously expressed clusters, we discovered 32 compounds (FIG. 6).

Figure 9:
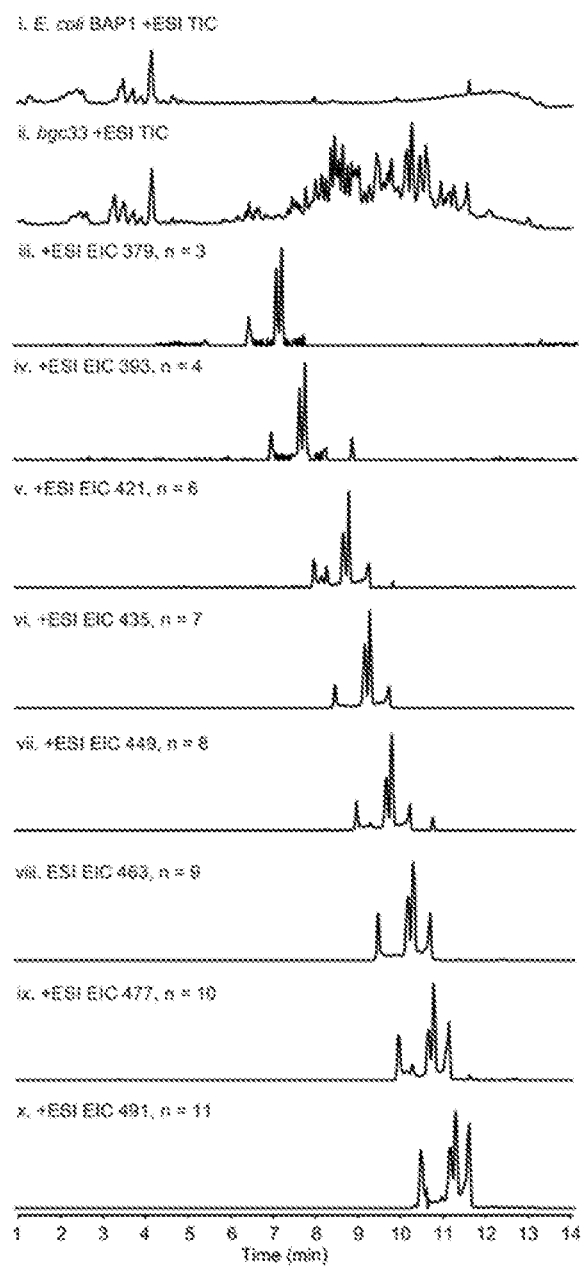
FIG. 9. HRMS analyses of pathway dependent molecules from bgc33. i. TIC of E. coli BAP1. ii. TIC trace of E. coli BAP1 expressing bgc33. Peptidyl aldehydes with different acyl chain lengths can be identified by EIC. iii. n=3, HRESIMS $[M+H]^+$ m/z found 379.2050, calcd for $C_{20}H_{31}N_2O_3S$ 379.2055; iv. n=4, HRESIMS $[M+H]^+$ m/z found 393.2206, calcd for $C_{21}H_{33}N_2O_3S$ 393.2212; v. n=6, HRESIMS

The results from our heterologous expression experiments raise an important question: Are the molecules we isolated the native products of the cluster or artifacts of expression in *E. coli* or *B. subtilis*? To address this question, we used two complementary approaches. First, we cultivated the bgc52 producer, *Ruminococcus* sp. 5_1_39BFAA, in ten different culture media in an effort to find a condition under which we could observe production of the bgc52 products. LC-MS analysis of cell-free culture extracts from one of the media, M17, revealed peaks identical to five of the most prominent compounds produced under conditions of heterologous expression in *E. coli* (FIG. 9), suggesting that these pyrazinones are the native products of bgc52 (it is unlikely these compounds derive from a different biosynthetic pathway in the same organism, since *Ruminococcus* sp. 5_1_39BFAA harbors only one additional nonribosomal peptide synthetase in its genome, a condensation-thiolation di-domain protein).

Using a similar approach, we could not find a condition under which the bgc35 producer, *Clostridium* sp. KLE 1755, produced the molecules we observed from *E. coli*-bgc35. As an alternative approach, we overexpressed the 280 kDa, two-module bgc35 NRPS in *E. coli* and purified it as an N-terminal His6 fusion protein. We then attempted to reconstitute the biosynthetic pathway by incubating the NRPS with Sfp and coenzyme A (to 4'-phosphopantetheinylate both thiolation domains), amino acid substrates (either all 20 proteinogenic amino acids or aromatic amino acids only), ATP for monomer activation, and NADH as a cofactor for the terminal reductase domain. LC-MS analysis of a time course of this reaction showed the formation of two products identical to compounds 2 and 4, suggesting that these are native products of bgc35 (FIG. 2).

The gut NRPS family is widely distributed in healthy humans. Having identified the small molecule products of a subset of the gut NRPS family, we next turned to the question of how widely distributed this cluster family is in the human population. In previous work, we showed that of the smaller subset of 28 clusters that was known at the time, at least one cluster was present in >90% of the ~100 stool metagenomic samples from the HMP phase I. These data were derived from a global analysis that involved mapping metagenomic reads to proteins from 14,000 BGCs using the fast, metagenomics-optimized algorithm mBLASTx (Donia et al., 2014). Here, we used two complementary methods to determine the abundance of the gut NRPS family in publicly available metagenomic data sets. First, since we had a smaller set of BGCs to map, we developed a highly sensitive and specific analytical method in which we used BLASTn to map quality-filtered metagenomic reads from the 149 metagenomic stool samples from HMP Phase I to the large NRPS gene in each BGC. Using this analysis, we found that at least one of the clusters is present in >88% of the 149 stool samples. Second, we used a recently developed approach that leverages a large gene catalog of >9 million gut microbiome genes (Nayfach et al., 2015), and found that at least one of the clusters was present in >93% of 1,267 publicly available stool samples. Together, these results confirm that this gene cluster family is widely distributed in healthy human subjects.

Gut NRPS clusters are actively transcribed under conditions of host colonization.

Figures 3A, 3B:
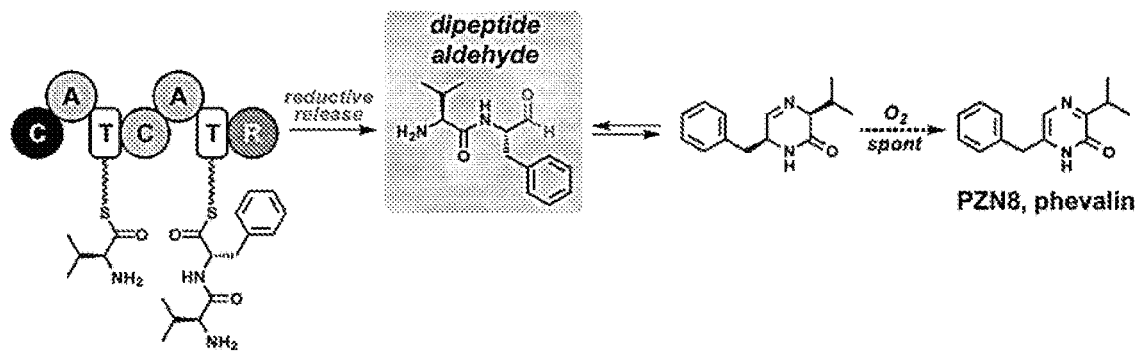
FIGS. 3A-C: Functional analyses of the gut NRPS cluster and its small molecule products. Seven of eight publicly available gut metatranscriptomic data sets harbored an actively transcribed gene cluster from the gut NRPS family. Typical cluster tiling is shown for bgc52; a sample with unusually robust transcription of bgc71 is also shown.

A cluster might be present in a metagenomic sample but not expressed in the gut1 indeed, many metabolic pathways present in metagenomic samples are expressed at very low levels in corresponding metatranscriptomic data sets (Franzosa et al., 2014; Gosalbes et al., 2011). To address whether the gut NRPS clusters are transcribed under conditions of native host colonization, we recruited reads from publicly available RNA sequencing (RNA-seq) data sets from the stool samples of eight healthy subjects (Franzosa et al., 2014). Illumina reads from several runs on each sample were combined and used to construct a BLAST database, which we then searched using the 47 full-length gut NRPS BGCs as query sequences. Seven of the eight samples (87.5%) harbored at least one actively transcribed gene cluster from this family, and the robust level of transcription observed in most samples is notable, given that the anaerobic Firmicutes from which the gut NRPS clusters derive are often lower abundance members of the community. (FIGS. 3A-3B).

Figure 3C:
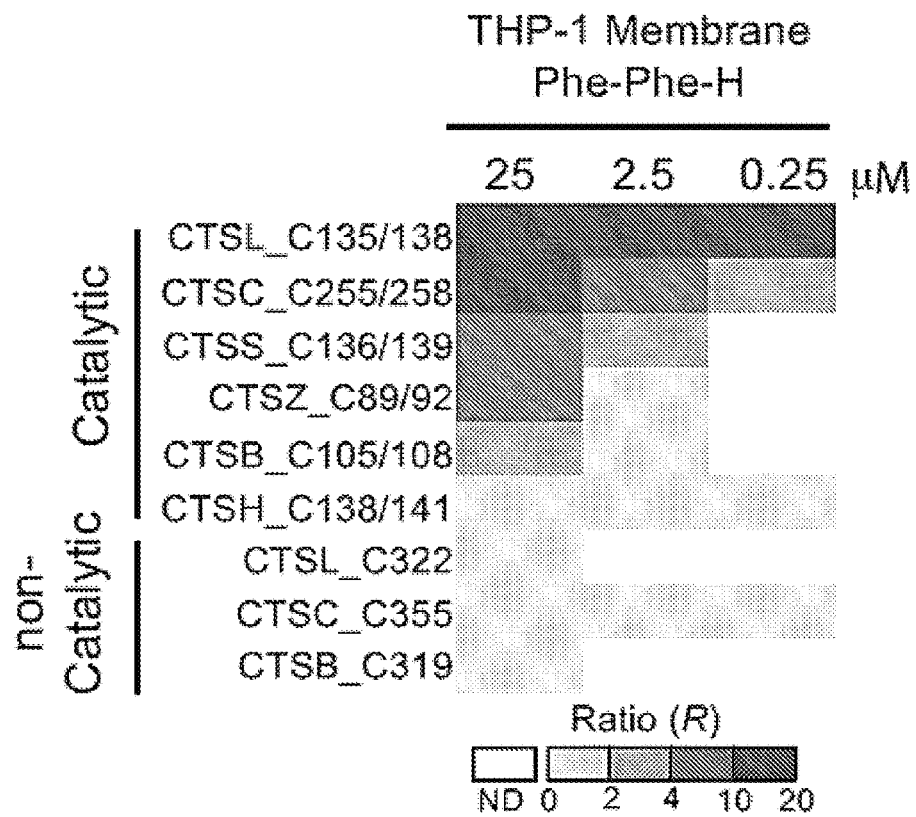

The active gut NRPS product may be the initially released dipeptide aldehydes. The NRPSs in this family harbor a C-terminal reductase domain that catalyzes the chain-terminating release of a C-terminal aldehyde (FIGS. 1 and 3). The newly liberated dipeptide aldehydes exist in equilibrium with the cyclic imine; in the presence of oxygen, this dihydropyrazinone oxidizes spontaneously and irreversibly to the fully aromatic pyrazinone. Three lines of evidence suggest that the active form of the gut NRPS product is the initially released dipeptide aldehyde: First, under physiological conditions, the peptide aldehydes are stable for long enough to be active. We measured the half-life of oxidation for three compounds—the peptide aldehyde versions of 5, 10, and 12—in vitro at physiological pH: they ranged from 3-28 hr (FIGS. 10A-10C), which would provide sufficient time for systemic distribution in the host. Indeed, compounds 1 and 2 are stable enough that we isolate milligram quantities of the cyclic imine after >24 hr of aerobic *E. coli* culture. Moreover, these molecules are produced in the gut, which is anaerobic, so the slow process of spontaneous oxidation would not begin until the compounds encounter oxygenated host tissues. Notably, the major product of bgc33, N-octanoyl-Met-Phe-H (16), is N-acylated, preventing it from cyclizing and oxidizing to a pyrazinone. These findings raise the possibility that peptide aldehydes are the predominant active product of every cluster in the family.

Second, peptide aldehydes have a long history in the literature of being highly potent, cell permeable protease inhibitors. Starting with the discovery of the leupeptins from soil isolates of *Streptomyces* almost four decades ago (Aoyagi et al., 1969a; 1969b), numerous peptide aldehydes—mostly N-carboxybenzyl (Cbz) protected di-, tri-, and tetrapeptide aldehydes—have been synthesized and shown in vitro and in vivo to have potent inhibitory activity against serine and cysteine proteases and the proteasome (Lee and Goldberg, 1998; Otto and Schirmeister, 1997; Thompson, 1973; Westerik and Wolfenden, 1972). Dipeptide aldehydes were the starting point for the development of the clinically used dipeptide boronate proteasome inhibitor bortezomib (FIGS. 3A-3B) (Adams et al., 1998). Cbz-protected versions of multiple gut NRPS products, including Cbz-Val-Phe-H, have been synthesized and shown to inhibit various cysteine proteases (Mehdi et al., 1988; Woo et al., 1995).

Third, since dipeptide aldehydes with a free amino group have not been tested as protease inhibitors, we assessed the activity of three of the bgc52 and bgc35 products (Val-Phe-H, Leu-Phe-H, and Phe-Phe-H) and the bgc33-derived compound 16 against a panel of proteases in vitro, comparing them to the corresponding pyrazinones and N-tert-butyloxycarbonyl (N-Boc) protected dipeptide aldehydes (FIGS. 3A-3B and FIGS. 11A-11B). Consistent with previous reports on N-Cbz-protected dipeptide aldehydes (Mehdi et al., 1988; Woo et al., 1995), the N-Boc protected dipeptide aldehydes were active at low- to mid-nanomolar against the lysosomal cysteine proteases cathepsins B and L. The free-amino dipeptide aldehydes had similarly potent (single-digit nanomolar) activity against cathepsin L but greatly reduced activity against cathepsin B, showing that they are capable of highly potent inhibitory activity and exhibit selectivity not seen in their N-Boc protected counterparts (FIGS. 3A-3B and FIGS. 11A-11B). This difference in selectivity was also seen in compound 16, which had undetectable activity against cathepsin L but 13 nM activity against cathepsin S. None of the compounds tested here had quantifiable activity against trypsin, chymotrypsin, or the proteasome at the concentrations tested. Overall, these data suggest that the dipeptide aldehydes harbor potent and selective protease inhibitory activity, as assessed in vitro.

Figure 3D:
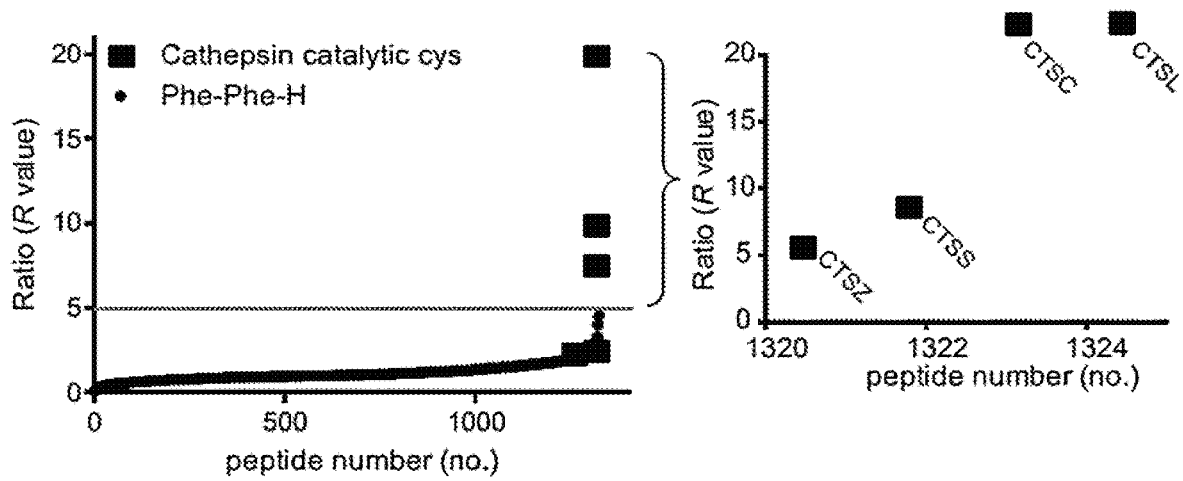
Figure 4:
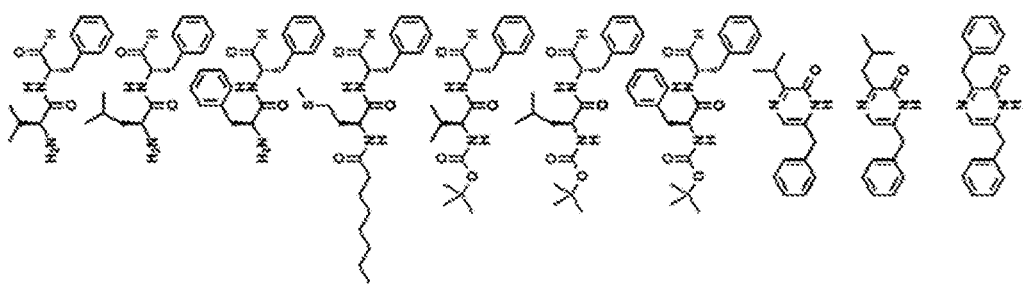
FIG. 4. Protease activity data for a selection of compounds.

The proteases we assayed were chosen based on literature precedent. To determine the target of the peptide aldehydes in an unbiased way, we applied a quantitative chemical proteomic method, termed isoTOP-ABPP (Weerapana et al. 2010, Backus et al., 2016) to measure the global interactions of a representative dipeptide aldehyde, bgc35 product Phe-Phe-H, with cysteine residues in the human cell lysates. We treated membrane preparations of the human innate immune (monocytic) cell line THP-1 with the bgc35 product Phe-Phe-H or vehicle, and then these samples were treated with a cysteine reactive iodoacetamide-alkyne (IA-alkyne) probe and conjugated to an isotopically differentiated (heavy or light, respectively) TEV protease-cleavable biotin tag using copper-catalyzed azide-alkyne cycloaddition (CuAAC or click) chemistry. Vehicle- and peptide-treated samples were then combined, enriched, subjected to sequential trypsin and TEV digests and evaluated by LC-MS/MS. Site-specific blockade of IA-alkyne labeling as measured by quantitation of heavy/light MS1 chromatographic peaks designates cysteine residues that are targeted by Phe-Phe-H (heavy/light ratios, or R values>5; line, FIG. 3D). Treatment of THP-1 membranes with 250 nM Phe-Phe-H, the lowest concentration tested, fully blocked IA-alkyne labeling of the catalytic cysteine of cathepsin L (CTSL1; Cys138, R >20), while showing only partial (cathepsin C (CTSC) R >2.78 for catalytic cysteine Cys258) or negligible (R<2.0; cathepsins B (CTSB), H (CTSH), S (CTSS), and Z (CTSZ)) cross-reactivity with other cathepsins (FIG. 3D). Phe-Phe-H also interacted with a subset of additional cathepsin targets when tested at higher concentrations (25 μM; R>5 for CTSC, CTSS, CTSZ) in THP-1 (FIGS. 3D-3E) and other human cell proteomes (Ramos, H1975). Phe-Phe-H showed remarkable selectivity for cathepsins, exhibiting no additional targets across the more than 3500 total quantified cysteines across three different human cell proteomes (R<2.0). Additional experiments at the characteristic acidic pH of the lysosome (pH 5 or 5.5), where cathepsin reside, produced similar results. Together, these data designate the cathepsins (specifically cathepsin L) as principal targets of the gut NRPS product Phe-Phe-H.

We have found 32 compounds that represent a subset of the molecular output from this family of NRPSs. The discovery approach we used—to express cloned or synthetic BGCs in E. coli or B. subtilis—revealed two unanticipated findings that may be relevant to similar discovery efforts in the future. First, bgc35 and bgc52 were functional in E. coli in their native form (driven by an E. coli promoter); this is notable, given that these clusters are from a Gram-positive host. E. coli might therefore be an appropriate heterologous host for a broader range of gene clusters than previously imagined. Second, the E. coli strain harboring bgc34 produced a subset of the bgc35 products, but at a level so low it would not have been observed without a targeted mass ion search; likewise, bgc39 was a low-level producer of the bgc38 products. Importantly, the amino acid sequences NRPS genes from the bgc34-bgc35 and bgc38-bgc39 pairs share 70% and 51% identity, respectively, pointing to the potential importance of subtle changes in primary sequence that alter expression level as a determinant of whether an NRPS will work in a heterologous host. Gene clusters in this family are widely distributed in the human gut microbiome, and they are transcribed robustly under conditions of host colonization. Notably, of the 4 out of 32 molecules that were previously known, three are produced by an unrelated NRPS conserved across all known skin-associated species of Staphylococcus. Thus, the gut and Staphylococcus NRPSs are an example of convergent evolution toward a common scaffold, suggesting that the same compounds might play a biological role in more than one host-associated niche (Wyatt and Magarvey, 2013; Wyatt et al., 2012a; Zimmermann and Fischbach, 2010a).

We presented three lines of evidence suggesting that the active small molecule products are peptide aldehydes: 1) The free amino dipeptide aldehydes have a half-life of hours, and some compounds in the family are stabilized by N-acylation; 2) peptide aldehydes have a long history in the literature as potent, cell permeable protease inhibitors; and 3) four of our compounds exhibit potent and selective protease inhibitory activity in vitro. From studies of peptide aldehydes and other C-terminally modified peptide protease inhibitors, it has become clear that the sidechains in the inhibitor help occupy the P1 and P2 pockets (Siklos et al., 2015) and a free amino terminus can form specific charge contacts in the active site (Katunuma, 2011; Laine and Busch-Petersen, 2010). Thus, side chain identity and N-terminal acylation state are key determinants of selectivity, potentially helping to explain the breadth of chemical diversity in this family. Mutational experiments with bgc35 show that both adenylation domains participate in generating sidechain chemical diversity (FIG. 12). Likewise, an analysis of products from bgc86, a version of bgc33 with a truncated NRPS system, suggests that the starting condensation domain of bgc33 NRPS is responsible for N-acylation (FIG. 13).

Our unbiased chemical proteomics experiments suggest that dipeptide aldehydes, e.g., Phe-Phe-H, targets the catalytic cysteines of multiple cathepsins, showing the highest potency for cathepsin L. Our substrate assay data with recombinant proteases generally matched our proteomic data, with the exception of CTSC, which was more potently inhibited in proteomes by Phe-Phe-H. This result could indicate that endogenously expressed CTSC is post-translationally regulated to create a form of the protease that is more sensitive to peptide aldehyde inhibition. Our chemical proteomic studies also revealed that Phe-Phe-H exhibits very high selectivity for cathepsins, as we did not detect any additional cysteines targeted by this peptide aldehyde in human cell lysates. Although these data do not prove a mammalian (rather than bacterial) target for the peptide aldehydes, they raise the possibility that the gut NRPS product acts in the host lysosome. Further support for this premise comes from a recently reported screen for Staphylococcus aureus genes required for survival in and escape from the phagosome (Blättner et al., 2016). Among the top hits was the Staphylococcus NRPS described above (Wyatt and Magarvey, 2013; Wyatt et al., 2012b; Zimmermann and Fischbach, 2010b), which is unrelated to the gut NRPS enzymes but produces two of the same compounds. Although the authors were unaware that the NRPS product is likely a dipeptide aldehyde rather than a pyrazinone, these data provide independent evidence that the dipeptide aldehydes and the NRPS genes that encode them might play a role in an intracellular niche for bacteria in the phagolysosome.

Taken together, these two lines of evidence raise the intriguing possibility of a previously unknown interaction between the commensal gut microbiota and a cysteine protease system in the host lysosome. Since cathepsins play an important role in antigen processing and presentation in intestinal epithelial cells (Hershberg et al., 1997) and TLR9 activation in macrophages and dendritic cells (Matsumoto et al., 2008; Park et al., 2008), their inhibition by dipeptide aldehydes might block adaptive or innate immune recognition of a subset of anaerobic Firmicutes in the gut.

Another possibility is that dipeptide aldehyde-mediated cathepsin inhibition enables gut mutualists to stably occupy and emerge from a niche in the phagolysosome. Intracellular pathogens commonly inhabit the phagolysosome (Rosenberger and Finlay, 2003), and a subset of Gram-negative pathobionts including Alcaligenes are found in Peyer's patches and other gut lymphoid tissues (Fung et al., 2014; Maslowski et al., 2009; Obata et al., 2010). Our data raise the possibility that dipeptide aldehydes enables a broad set of mutualistic Gram-positive species to reside in gut epithelial or immune cells. If borne out by subsequent studies, either possibility (cathepsin inhibition by extracellular or intracellular mutualists) would represent a novel form of immune modulation by the gut microbiota Our findings show that an approach combining bioinformatics and synthetic biology can rapidly expand our knowledge of the metabolic potential of the microbiota while avoiding the challenges of cultivating fastidious commensals. Given the large number of biosynthetic gene clusters of unknown function in the human microbiome, such an approach holds great potential for discovering, in a scalable fashion, small molecule mediators of microbe-host and microbe-microbe interactions relevant to the biology of the microbiome.

Assembly of Expression Vectors. A general scheme of all the experiments and analyses performed in this study can be found in Table 2. Details of the characterized NRPSs, including their host organisms, putative substrates, and products can be found in Table 3. Primers and strains used in this study are listed in Tables 4 and 5, respectively. BGCs expressed in *E. coli* (The BGCs characterized experimentally where products were obtained include bgc52, bgc39, bgc38, bgc 34, bgc34, bgc35, bgc33, and bgc86. Experimentally characterized but no products observed include bgc28, bgc30, bgc32, bgc37, bgc45, bgc43, and bgc41) were regulated by the lac promoter except bgc33 (T7 promoter). BGCs expressed in *B. subtilis* 168 are regulated by the hyper-Pspac promoter. bgc34, bgc35, bgc41, bgc43, and bgc52 were assembled in the vector pGFP-UV and verified by sequencing (FIG. 6). Synthetic, codon-optimized versions of bgc33 and bgc86 were assembled in the vector pET28a and verified by sequencing. Synthetic, codon-optimized versions of bgc28, bgc30, bgc32, bgc37, bgc38, bgc39, and bgc45 were synthesized in pMSD and verified by sequencing. To verify that clusters integrated properly into the chromosome of *B. subtilis*, we performed diagnostic PCR according to a scheme detailed in FIGS. 5A-5B.

Fermentation and LC-MS Analysis. A single colony of each mutant strain was used to inoculate a 5 mL LB broth culture (10 g tryptone, 5 g yeast extract, 10 g NaCl, 100 µg/mL of the corresponding antibiotic), which was incubated at 30° C. with shaking at 225 rpm. After 48 hr, the culture supernatant was extracted with 5 ml ethyl acetate (EA). The EA layer was evaporated in vacuo and re-dissolved in 200 µL of 20% DMSO/MeOH, 10 µL of which was examined by LC-MS analysis. LC-MS was carried out using an Agilent 6120 quadrupole mass spectrometer with a reverse-phase C18 column (Agilent Zorbax SB-C18 3.0 mm by 100 mm, 1.8 micron, 600 bar) at a flow rate of 400 µL/min. For HR-ESI-MS analysis of bgc35, bgc38, and bgc52, the DMSO/MeOH extract was diluted to ~1 ng/µL, 10 µL of which was used for an MS-MS fragmentation analysis (Thermo Orbitrap Velos).

Isolation and Characterization of Secondary Metabolites. For structure elucidation, each mutant strain was cultivated in 4×1 L LB medium (with the exception of bgc33, which was cultivated on 16 L scale) containing 100 µg/mL of the corresponding antibiotic and incubated at 30° C. (25° C. for bgc33) with shaking at 225 rpm. After 48 hr (28 hr for bgc33), the culture supernatant was extracted 2× with an equal volume of EA, and the solvent was removed from the combined extracts by rotary evaporation. The dried material was dissolved in 80% MeOH/DMSO and separated by reverse-phase HPLC (Agilent 1200 series) for small molecule purification. NMR spectra were collected on either a Bruker Avance DRX500 or a Bruker AvanceIII 600-I spectrometer (see also Extended Experimental Procedures).

Biochemical Reconstitution of bgc35. See Extended Experimental Procedures (below) for detailed procedures for the purification of the large NRPS enzyme in bgc35. Its activity was assayed by comparing the LC-MS profiles of the reaction with and without the biosynthetic enzymes. A typical 220 µL assay solution contained 75 mM Tris-HCl buffer (pH 8.0), 10 mM MgCl2, 1 mM NADPH, 5 mM ATP, 0.1 mM CoA, 1 mM amino acid substrate, 0.1 µM Sfp, and 10 µM NRPS. The reactions were performed at 30° C. for 12 hr. Reactions were terminated by extracting with an equal volume of EA. The EA layer was evaporated and the dried material was dissolved in 40 µL 20% DMSO in MeOH. A 10 µL aliquot was examined by LC-MS using the same conditions used for analyzing the metabolite profiles of the *E. coli* strain expressing bgc35.

Analysis of Metatranscriptomic Data. We recruited reads from publicly available RNA sequencing (RNA-seq) data sets from the stool samples of eight healthy subjects (Franzosa et al., 2014). Illumina reads from several runs on each sample were combined, and used to construct a BLAST database that was then searched using the 47 full-length gut NRPS BGCs as query sequences. For this search, we used BLASTn using the default parameters to identify all reads recruited to the BGCs, then used the following parameters to map them back to individual BGCs (minimum number of reads: 100, minimum overlap: 50 bp, minimum percent identity at overlap: 90%, and maximum percentage of mismatch per read: 20%), and finally displayed them using Geneious. The BGCs identified were bgc41, bgc44, bgc45/48/71, and bgc52/53/73 (the latter two sets are too similar in amino acid sequence to be differentiated in this analysis).

Protease Inhibition Assays. Detailed information about synthesis of N-Boc-protected peptidyl aldehydes and their deprotection for protease inhibition activity tests are available in the Extended Experimental Procedures. For protease inhibition assays, all fluorescence measurements were made on a Biotek H4 instrument. Buffering reagents were purchased from Sigma-Aldrich and sterile-filtered prior to use. Compounds and substrates were diluted from DMSO stocks into water/DMSO such that final DMSO plate concentrations were below 5% during the reaction. All reactions were started by the addition of substrate to the enzyme/compound solutions (see also Extended Experimental Procedures).

Target Identification by chemical proteomics. The experiments were performed as described in Backus, Nature 2016 with minor modifications detailed in the Supplementary Information.

Detailed information about refactoring and synthesizing BGCs in this study. Since the bacterial species shown in FIG. 1 have not been manipulated genetically, we decided not to use a targeted gene deletion strategy. Instead, we expressed these BGCs heterologously in hosts whose genetic systems have been well developed. Each BGC contains a core biosynthetic gene encoding an NRPS. Two extra genes, which putatively encode an A domain and a T domain (e.g., bgc35) are in close proximity to their core NRPS genes. In addition, a 4'-phosphopantetheinyltransferase (PPTase) gene is located at 3' end of some of the BGCs. PPTase enzymes, such as Sfp from *B. subtilis*, catalyze an essential posttranslational modification in NRP biosynthesis (Reuter et al., 1999). The targeted BGCs were reconstructed by excising regulatory genes which, we presumed, are not directly involved in the biochemical steps of the biosynthetic pathway. Other genes, including those code for the core NRPS, the extra A and T domains, the PPTase, and some transporter genes, remain intact in our assembled BGCs.

Figure 5:
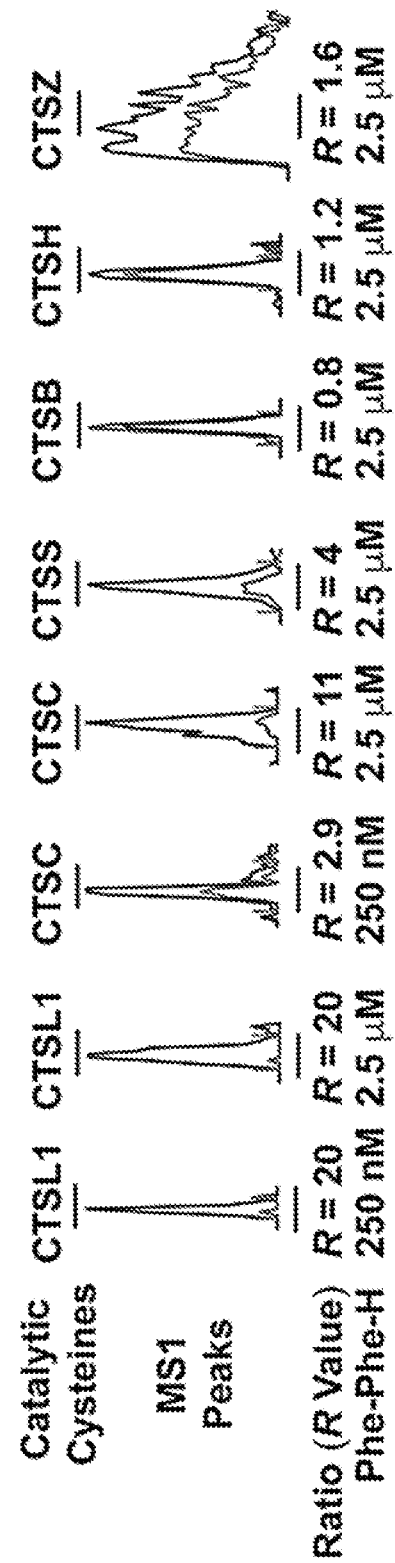
FIG. 5. MS1 chromatographic peaks for peptides in target identification analyses. This figure shows representative MS1 chromatographic peaks for peptides containing the catalytic cysteines from CTSL1, CTSC, CTSS, CTSB, CTSH and CTSZ. The membrane fraction of THP1 cells was treated with Phe-Phe-H at the indicated concentrations and evaluated by isoTOP-ABPP.
Figure 7:
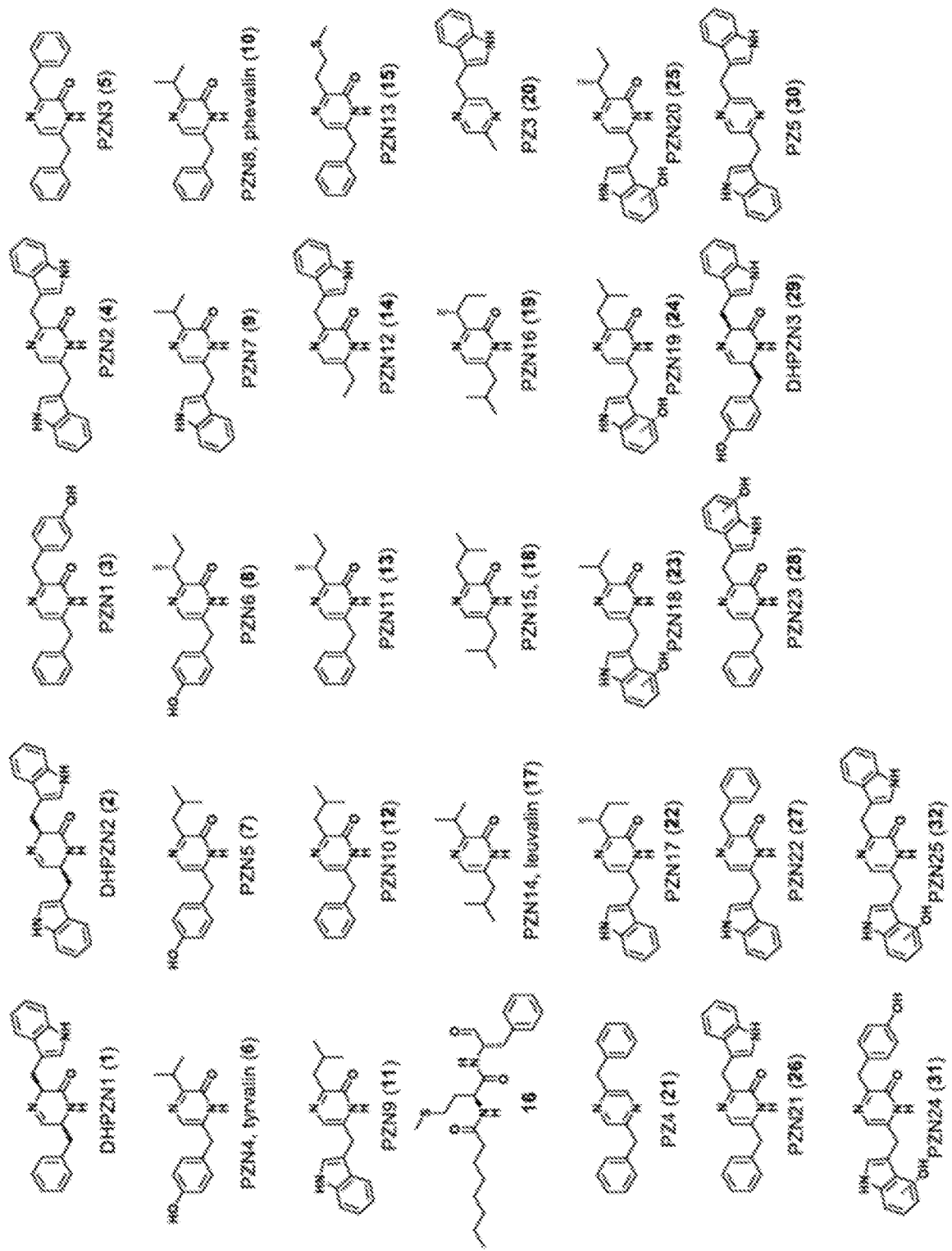
FIG. 7. Compounds identified in this study. (1) Compounds 1 to 16 are characterized by HRESIMS and NMR experiments. The structures of compounds 17 to 32 are proposed on the basis of HRESIMS experiments, HRESIMS MS-MS analyses, and the structural data from compounds 1 to 16.

For molecular cloning experiments, BGCs are divided into two categories. BGCs from hosts we could obtain were assembled in the pGFP-UV vector and heterologously expressed in *E. coli* DH10β (FIGS. 5A-5B). BGCs from hosts that were not accessible were synthesized by GenScript. For any BGCs without a PPTase gene, we included a PPTase at the 3' end of the assembled cluster. The synthesized clusters were codon-optimized for their expression host (either *E. coli* or *B. subtilis*) and assembled into their respective vectors for heterologous expression.

Structural characterization of purified compounds. Compounds identified in this study can be grouped into three classes: dihydropyrazinones (compounds 1 and 2, for example), pyrazinones (compounds 3-15), and N-acyl peptide aldehydes (compound 16) (FIG. 2). Their biosynthetic origin, from a group of NRPSs which take amino acids as substrates, facilitates the structural elucidation process. For dihyropyrazinones, compound 1 was purified as amorphous yellowish solid and its molecular formula was determined to be C20H19N3O by its HRMS spectral data, suggesting thirteen indices of hydrogen deficiency (IHD). The $^1H$, $^{13}C$, gHMQC, and gHIVIBC NMR spectroscopic data of compound 1 (Table 6) including the six phenyl carbons [δC 138.3 (C-4), δC 128.6 (C-5 and C-9), δC 129.4 (C-6 and C-8), the five aromatic protons [H-5 and H-9, δH 7.38 (2H, d, J=12.0 Hz); H-6 and H-8, δH 7.29 (2H, m); H-7, δH 7.28 (1H, m)], the CH2-3 methylene group [δH 3.03 (1H, d, J=12.0 Hz), δH 3.03 (1H, d, J=12.0 Hz), and δC 40.6] exhibit a typical phenylalanine side chain. A tryptophan side chain was also established from the $^1H$, $^{13}C$, gHMQC, and gHMBC NMR spectroscopic data. The $^{13}C$ spectrum exhibits eight aromatic carbons (C-4' to C-11'). The $^1H$ spectrum shows four aromatic protons exhibiting a typical coupling pattern of an indole ring (H-7' to H-10'). The gHMBC correlations between the indole 5'-NH [δH 10.73 (1H, s)] and four aromatic carbons (C-4', 5', 6', and 11') and the gHMBC correlations between the CH2-3' methylene group [δH 2.88 (1H, dd, J=12.0, 6.0 Hz), δH 2.77 (1H, d, J=12.0 Hz), and δC 26.4] and C-4' and 11' further suggests that compound 1 contains a tryptophan side chain moiety. The phenylalanine and tryptophan side chains, in combined, contributed 10 IHDs. The dihydropyrazinone core (and how these two side chains are connected to the core) was set up based on the following evidence: 1. The gHMBC correlations between the H2-3' and C2' (δC 53.1) and one amide carbon C-1' (δC 171.5); 2. The gHMBC correlations between H2-3 and C-2 (δC 58.6); 3. The gCOSY correlations between one imine proton H-1 (δH 7.44, m) and H-2 (δH 3.53, m). Thus, the structure of compound 1 was assigned as shown in FIG. 2, also referred to herein as DHPZN1.

For compounds within the pyrazinone class, the verification of amino acid side chains are comparable to that of compound 1. Taking compound 7 (Table 12) as an example, its molecular formula was determined to be C15H18N2O2 by its HRESIMS spectral data, suggesting eight indices of hydrogen deficiency (IHD). The tyrosine side chain takes up four IHDs. The pyrazinone core (and how tyrosine and leucine side chains are connected to the core) was set up based on the following evidence: 1. Comparison to the published literature (MacDonald et al., 1976; Zimmermann and Fischbach, 2010); 2. The gHMBC correlations between the H2-3' [δH 2.60 (2H, d, J=10.0 Hz)] and C-2' (δC 156.6) and one amide carbon C-1' (δC 157.3); 3. The gHMBC correlations between H2-3 [δH 3.76 (2H, s)] and C-2 (δC 139.3) and C-1 (δC 121.6). Thus, the structure of compound 7 was assigned as shown in FIG. 2A also referred to herein as PZNS.

Both adenylation domains participate in generating side-chain chemical diversity. Given that pyrazinones appear to be the native products of bgc35 and bgc52, we next turned to the question of how a three-module NRPS gives rise to a diverse family of dimeric nonribosomal peptides. To address this question, we individually mutagenized the first and second adenylation domains (A1 and A2) from the NRPS in bgc35, expressed the mutagenized protein in *E. coli*, and profiled its culture extract by LC-MS (FIG. 12). To our surprise, both individual mutants retained the production of a subset of the bgc35 products. Reasoning that the residual activity could be due to A domain mutations that did not eliminate amino acid substrate binding, we constructed and profiled an A1-A2 double mutant. LC-MS analysis of its culture extract revealed that activity had been completely abolished, indicating that each single domain mutant had effectively eliminated substrate binding. Collectively, these data suggest that each module in the NRPS is capable of acting iteratively. Consistent with this view, a truncated form of the bgc35 NRPS consisting of only the second module (C2-A2-T2-R) is capable of synthesizing a subset of the pyrazinone and pyrazine products observed from bgc35 (FIG. 6 and FIG. 12). These data suggest that both modules of the bgc35 NRPS contribute to the diversity in product structure. Moreover, the observation that the product spectrum of the single A domain mutants is skewed toward pyrazines is consistent with the possibility that in iterative format, the terminal reductase favors the release of individual α-aminoaldehyde monomers rather than a dipeptide aldehyde.

Assembling bgc34, bgc35, and bgc52 with pGFP-UV vector. Due to the relatively large size of these BGCs, regulatory components in these BGCs were omitted. The genes essential for biosynthesis were PCR amplified using Q5 hot start high-fidelity DNA polymerase (See Table 4 and FIGS. 5A-5B). Three fragments for each BGC were synthesized and assembled with pGFP-UV vector using either In-Fusion cloning kit (bgc34 and bgc35) or Gibson assembly kit (bgc52). The assembled reaction mixture was further purified using Zymo DNA Clean and Concentrator kit and transformed into commercial *E. coli* DH10β competent cells. Upon transformation, transformants that are resistant to carbenicillin (carb) were first streaked on LB agar supplemented with carb (100 µg/ml) followed by diagnostic PCR using primer set F3 (Bgc34_F3 for bgc34) and pGFP-Diag-R (Table 4). Positive hits (mutants carrying assembled plasmids) were then cultivated in 10 ml LB+carb at 30° C., 225 rpm for 24 hours for plasmid extraction. The assembled plasmids were extracted using Qiagen Miniprep Kits and further verified by sequencing.

TABLE 2

Experiments and analyses performed in this study. BGC numbers in bold and italics are those that we were able to characterize and identify their products in this study.

| BGCs | 28 | 30 | 32 | *33* | *34* | *35* | 37 | *38* | *39* | 41 | 43 | 45 | *52* | *86* |
|---|---|---|---|---|---|---|---|---|---|---|---|---|---|---|
| Cloning from gDNA | | | | | X | X | | | | | | | X | |
| Synthesized for E. coli | | | X | | | | | | | X | X | | | X |
| Synthesized for B. subtillis | X | X | X | | | | X | X | X | | | X | | |
| HPLC-MS | X | X | X | X | X | X | X | X | X | X | X | X | X | X |
| HPLC-qTOF-HRMS/MS | X | X | X | X | X | X | X | X | X | X | X | X | X | X |
| XCMS | X | X | X | X | X | X | X | X | X | X | X | X | X | X |
| Scaled-up culture and NMR | | | | X | | X | | X | | | | | X | |
| Protein purification | | | | | X | | | | X | | | | | |
| In vitro reconstitution | | | | | X | | | | X | | | | | |

TABLE 3

Details of the characterized BGCs in this study.

| Gene clusters | Species | Substrates for NRPs | Products |
|---|---|---|---|
| bgc33 | *Clostridium* sp. CAG: 567 | Met, Phe, fatty acyl-CoA | Cpds 15, 16 |
| bgc34 | *Lachnospiraceae* sp. 3_1_57FAA | Phe, Trp, Tyr | Cpds 4, 5 |
| bgc35 | *Clostridium* sp. KLE1755 | Phe, Trp, Tyr, Leu | Cpds 1 to 5, 11, 12, 20, 21, 24, 26 to 32 |
| bgc38 | *Blautia producta* ATCC 27340 | Trp, α-Aminobutyric acid | Cpd 14 |
| bgc39 | *Clostridium* sp. D5 | Trp, α-Aminobutyric acid | Cpd 14 |
| bgc52 | *Ruminococcus* sp. 5_1_39BFAA | Val, Leu, Ile, Phe, Trp, Tyr | Cpds 6 to 13, 17 to 20, 22 to 25, 30 |
| bgc86 | *Clostridium* sp. CAG: 273 | Met, Phe | Cpd 15 |

Heterologous expression (HE) of bgc28, bgc30, bgc32, bgc37, bgc38, bgc39, and bgc45 in *B. subtilis* and transformation of bgc41 and bgc43 in *E. coli*. These BGCs were synthesized and codon optimized for their specific expression strains. For transformation of *B. subtilis*, the synthesized BGCs were assembled into the pMSD vector (see FIGS. 5A-5B) and around 80 ng of total DNA was added into 1 ml of protoplast solution for each individual transformation. The transformants were then further verified by diagnostic PCR using primer set BS_amyE_F and BS_amyE_R (Table 4). The transformant with correct single insertion at amyE locus should amplify a much larger fragment (~10 kb) in comparison to that of the host strain without an insertion (see FIGS. 5A-5B). For transformation of bgc41 and bgc43, the procedures are similar to those described above.

TABLE 4

Primers used in this study.

| primer | Sequence (5'→3') |
|---|---|
| Primers used in the assembly of bgc34 with pGFP-UV vector | |
| Bgc34_F1 | CAC ACA GGAAAC AGC TAT GGA TTT TGG AGG GAT AAC AGT (SEQ ID NO: 1) |
| Bgc34_R2 | CAG CAC CAG CTC AAT AAA CA (SEQ ID NO: 2) |
| Bgc34_F3 | TGT TTA TTG AGC TGG TGC TG (SEQ ID NO: 3) |
| Bgc34_R4 | TTG CCT TCC CCC TTC TCA (SEQ ID NO: 4) |
| Bgc34_F5 | TAA GAC GTG AGA AGG GGG AAG GCA A AA AAT GAA GAA TTT TCC ACG (SEQ ID NO: 5) |
| Bgc34_R6 | ACC GGC GCT CAG TTG GAA TTC AAG CAT TTT CAT AAT AAA (SEQ ID NO: 6) |

TABLE 4-continued

Primers used in this study.

| primer | Sequence (5'→3') |
|---|---|
| Primers used in the assembly of bgc35 with pGFP-UV vector | |
| Bgc35_F1 | CAC ACA GGAAAC AGC TAT GCA TAA TAG ACA GCG TCT CC (SEQ ID NO: 7) |
| Bgc35_R2 | GCC AAT AAG CGT AAT CCA GA (SEQ ID NO: 8) |
| Bgc35_F3 | GGG ACG TGG ATT ATC TGG AT (SEQ ID NO: 9) |
| Bgc35_R4 | CCG CCC GCT TTA GTG GGC AT (SEQ ID NO: 10) |
| Bgc35_F5 | ATG CCC ACT AAA GCG GGC GGA TGA AAA ATT TCC CGC GCA (SEQ ID NO: 11) |
| Bgc35_R6 | ACC GGC GCT CAG TTG GAA TTC ACT GTG TTT CGT AAT GAA (SEQ ID NO: 12) |
| Primers used in the assembly of bgc52 with pGFP-UV vector | |
| Bgc52_F1 | CAC ACA GGAAAC AGC TAT GAA AAA TAT TAA TGA AAG G (SEQ ID NO: 13) |
| Bgc52_R2 | AGA GAT GTA CCA TCG GCA AC (SEQ ID NO: 14) |
| Bgc52_F3 | TGG ACC TTC ACC ACA TTG TT (SEQ ID NO: 15) |
| Bgc52_R4 | TCA TAC ATAAAT ATC GTC GA (SEQ ID NO: 16) |
| Bgc52_F5 | TCG ACG ATA TTT ATG TAT GAA TGG AAG AGA GAA ATAACA G (SEQ ID NO: 17) |
| Bgc52_R6 | ACC GGC GCT CAG TTG GAA TTC AAA AAG ATA TTA TGG TAT TAT (SEQ ID NO: 18) |
| Primers used in the assembly of bgc33 with pET28a vector | |
| pET28a-BsaI-F | CAGTCAGTGGTCTCACATATGGCTGCCGCGCG |
| pET28a-BsaI-R | CAGTCAGTGGTCTCAAAGTCGACAAGCTTGCGGCC |
| Diagnostic PCR primer used in the initial screen of mutants carrying bgc assembled with pGFP-UV vector | |
| pGFP_Diag_R | TGC ATG TGT CAG AGG TTT TC |
| Primers used in in vitro reconstitution of bgc35 NRPS | |
| C.sp_KLE_NRPS1_pET28_fwd | CCT GGT GCC GCG CGG CAG CCA TAT GCA TAA TAG ACA GCG TCT CCC TGA GGG (SEQ ID NO: 19) |
| C.sp_KLE_NRPS1_pET28_rev | GAG TGC GGC CGC AAG CTT GTC GAC TTA TTC ACC GGA AAA AAG TCC GGC (SEQ ID NO: 20) |
| pET28_SalI_fwd | GTC GAC AAG CTT GCG GCC G (SEQ ID NO: 21) |
| pET28_NdeI_rev | CAT ATG GCT GCC GCG CGG (SEQ ID NO: 22) |
| C.sp_KLE_NRPS1_pET28_fwd | CCT GGT GCC GCG CGG CAG CCA TAT GCA TAA TAG ACA GCG TCT CCC TGA GGG (SEQ ID NO: 23) |
| Primer used in the point mutation protein truncation experiments of the NRPS in bgc35 | |
| 35_N_A1_F | TGT GGG CTT TGC CGC GTT TAC CC (SEQ ID NO: 24) |
| 35_N_A1_R | TTG CAGACG GAA AGA ACC GC (SEQ ID NO: 25) |
| 35_N_A2_F | CAT GAT GTT TGC CAT TTT TAT AGT GGAAAG (SEQ ID NO: 26) |
| 35_N_A2_R | TTG GCG GTA CAC AGT ACC (SEQ ID NO: 27) |
| pGFP_trun_R | CAT AGC TGT TTC CTG TGT GAAATT G (SEQ ID NO: 28) |
| 35_$T_1C_2A_2T_2R$_F | CCT GCG CCG GAG GAAAAG (SEQ ID NO: 29) |
| 35_$C_2A_2T_2R$_F | GGC GGG GAAAAG GAA GCG (SEQ ID NO: 30) |

TABLE 4-continued

Primers used in this study.

| primer | Sequence (5'→3') |
|---|---|
| Diagnostic PCR primers for *Bacillus subtilis* transformation | |
| BS_amyE_F | AAC TGG ACA CAT GGAAAC AC (SEQ ID NO: 31) |
| BS_amyE_R | CCG CTC CAG CTT TAT TGT (SEQ ID NO: 32) |

Assembling bgc33 and bgc86 with pET28a vector and HE in *E. coli* BAP1. The coding sequence (CDS) of the bgc33 and bgc86 NRPS biosynthetic genes were synthesized with BsaI flanking sites by GeneArt (Thermo Fisher Scientific) with *E. coli* codon optimization using the GeneOptimizer algorithm. The synthesized gene was cloned by Golden Gate assembly into *E. coli* expression vector under T7 promoter control. In brief, PCR fragment of expression vector pET28a (Novagen) was generated with Q5 High-Fidelity DNA Polymerase (New England Biolabs) following manufacturer protocol with primers pET28a-BsaI-F and pET28a-BsaI-R (Table 3). PCR fragment of pET28a was ligated to synthesized bgc33 or bgc86 construct in a 5 μl one-pot digestion/ligation reaction mix consisting of 10 fmol of bgc33 construct, 10 fmol of pET28a PCR product, 2.5 u of BsaI (New England Biolabs) and 2.5 u of T4 DNA ligase HC (Promega). Reaction conditions: 1 cycle of 37° C. for 5 hr; 10 cycles of 37° C. for 2 min, 16° C. for 5 min; 1 cycle of 50° C. for 15 min; 1 cycle of 80° C. for 15 min; 4° C. hold. The resulting construct bgc33-pET28a was verified by complete plasmid sequencing service (Massachusetts General Hospital DNA core facility). bgc33-pET28a and bgc86-pET28a were transformed into *E. coli* BAP1 containing T7 DNA polymerase and sfp phosphopantetheinyl transferase.

TABLE 5

Bacterial strains used in this example.

| Bacterial strains | Gene mutation(s) | Genotype |
|---|---|---|
| *E. coli* DH10β | — | — |
| *E. coli* BL21 | — | — |
| MFCJ1 (*E. coli* DH10β) | None | Carrying pGFP-UV assembled with bgc34 |
| MFCJ2 (*E. coli* DH10β) | None | Carrying pGFP-UV assembled with bgc35 |
| MFCJ3 (*E. coli* DH10β) | None | Carrying pGFP-UV assembled with bgc41 |
| MFCJ4 (*E. coli* DH10β) | None | Carrying pGFP-UV assembled with bgc43 |
| MFCJ5 (*E. coli* DH10β) | None | Carrying pGFP-UV assembled with bgc52 |
| CVFY1 (*E. coli* BAP1) | None | Carrying pET28 assembled with bgc33 |
| CVFY2 (*E. coli* BAP1) | None | Carrying pET28 assembled with bgc86 |
| *B. subtilis* 168 | sfp+ | sfp+ |
| MFCJ6 (*B. subtilis* 168 sfp+) | sfp+, pspac(p)-bgc28 | sfp+, amyE:: pspac(p)-bgc28-spec |
| MFCJ7 (*B. subtilis* 168 sfp+) | sfp+, pspac(p)-bgc30 | sfp+, amyE:: pspac(p)-bgc30-spec |
| MFCJ8 (*B. subtilis* 168 sfp+) | sfp+, pspac(p)-bgc32 | sfp+, amyE:: pspac(p)-bgc32-spec |
| MFCJ9 (*B. subtilis* 168 sfp+) | sfp+, pspac(p)-bgc37 | sfp+, amyE:: pspac(p)-bgc37-spec |
| MFCJ10 (*B. subtilis* 168 sfp+) | sfp+, pspac(p)-bgc38 | sfp+, amyE:: pspac(p)-bgc38-spec |
| MFCJ11 (*B. subtilis* 168 sfp+) | sfp+, pspac(p)-bgc39 | sfp+, amyE:: pspac(p)-bgc39-spec |
| MFCJ12 (*B. subtilis* 168 sfp+) | sfp+, pspac(p)-bgc45 | sfp+, amyE:: pspac(p)-bgc45-spec |

LCMS analysis using an Agilent 6120 quadrupole mass spectrometer. Solvent system: A: 100% H2O with 0.1% formic acid; B: MeCN with 0.1% formic acid. For ethyl acetate (EA) extraction of bacterial culture, as described in the manuscript, the gradient for HPLC-MS analysis is 0-5 min 100% A, 5-35 min 100-0% A, 35-37 min 0% A, 37-39 min 0-100% A, 39-41 min 100% A at a flow rate of 0.4 ml/min. For analysis of the purified Boc-protected aldehydes and estimation of the stability of those deprotected peptidyl aldehydes, the gradient is 0-8 min 95-5% A, 8-10 min 5% A at a flow rate of 1.0 ml/min using a Cadenza CD-C18 column (75×4.6 mm, 3 μm).

HRMS and HRMS-MS analyses. The analysis of pathway dependent molecules from bgc33, bgc35, bgc38, bgc52, and bgc86 was performed on an Agilent 6530 Q-TOF LC/MS equipment and a C18 column. The HPLC gradient for bgc35, bgc38, and bgc52 is 0-1 min 99.9% A, 1-7 min 99.9-50% A, 7-11 min 50-15% A, 11-13 min 15-0.1% A, 13-25 min 0.1% A, 25-25.5 min 0.1-99.9% A, 25.5-28 min 99.9% A at a flow rate of 0.4 ml/min. The gradient for bgc33 and bgc86 is 0-1 min 90% A; 1-12 min 90-0% A; 12-14 min 100% B at a flow rate of 0.3 mL/min. The column was a Phenomenex Kinetex EVO C18 (2.6 um, 100×2.1 mm). (Solvent A: 100% H2O with 0.1% formic acid; B: MeCN with 0.1% formic acid).

The HR MS-MS fragmentation analysis for pathway dependent molecules was performed on a Thermo Q-exactive Orbitrap Velos MS equipped with a nanospray ESI source using the following gradient: 0-5 min 100% A, 5-35 min 100-0% A, 35-37 min 0% A, 37-39 min 0-100% A, 39-41 min 100% A. Pathway dependent molecules were analyzed in auto MS/MS mode with a collision energy of 35 eV.

The HR MS and HR MS-MS analyses for examining the deprotection reaction of boc-protected peptidyl aldehydes were carried out on an Agilent 6530 Accurate-Mass Q-TOF LC/MS. We used the following gradient: 0-8 min 95-5% A, 8-10 min 5% A at a flow rate of 0.4 ml/min using a C18 column (Agilent Zorbax SB-C18 3.0 mm by 100 mm, 1.8-Micron, 600 Bar). The MS-MS analysis was performed in auto MS-MS mode with a collision energy of 20 eV.

Cloning of bgc35 NRPS into pET28a. *Clostridium* sp. KLE1755 was grown in an anaerobic chamber at 37° C. in Brain Heart Infusion agar with 0.1% cysteine, 0.5% yeast extract, and 15 mg/L hemin, pH 7.0. Genomic DNA was extracted from the bacteria using ZR bacterial DNA miniprep kit (Zymo). C.sp_KLE_NRPS1_pET28_fwd and rev primers were used to amplify the NRPS gene from genomic DNA and pET28_SalI_fwd and pET28_NdeI_rev were used to amplify the vector. (Table 4) The gene was assembled into pET28a with an N-terminus His tag using Circular Polymerase Extension Cloning (CPEC) and transformed into *E. coli* BL21. (Quan and Tian, 2009)

Purification of bgc35 NRPS. *E. coli* BL21 harboring bgc35 NRPS in pET28a was grown in 20 mL of LB+50 µg/mL Kanamycin at 30° C. overnight and diluted to fresh 1 L of LB+50 µg/mL Kanamycin the next morning until early log phase (OD 600~0.4). The diluted culture was moved to 16° C. incubator and shaken overnight without IPTG induction. The next day, cells were pelleted at 6000 g for 10 minutes, and resuspended in Lysis Buffer (300 mM NaCl, 10 mM Imidazole, 50 mM NaH2PO4, pH 8.0) with EDTA-free Protease Inhibitors (Roche). Cells were lysed using the EmulsiFlex (~10 minutes continuous flow, ~15,000 psi). Lysed cells were centrifuged at 16,000 rpm for 20 minutes. The supernatant was added to pre-equilibrated Ni-NTA beads (Qiagen) and rocked on the Nutator at 4° C. for 1 hour. The beads were spun down at 1000 rpm for 3 minutes. 20 mL of Wash Buffer (300 mM NaCl, 20 mM Imidazole, 100 mM NaH2PO4) was added and the mixture was transferred to an equilibrated column. Three 20 mL washes were performed and finally eluted in 4 mL of Elution Buffer (300 mM NaCl, 250 mM Imidazole, 50 mM NaH2PO4). The eluted protein was dialyzed using a Dialysis Cassette (20K MWCO, Pierce) against a Dialysis Buffer (25 mM Tris pH 8.0, 50 mM NaCl, 1 mM DTT, 10% (v/v) glycerol).

When we performed SDS-PAGE on the eluent, we noticed that along with the expected full size band at 280 kDa, there were other lower bands present. We performed a western blot with anti-His antibody and found that these lower bands also bound to anti-His antibody, suggesting they were degradation products of the full length bgc35 NRPS. In order to verify that the full length NRPS was present in the eluent, we cut out the highest band that ran above the 212 kDa ladder in the SDS-PAGE gel and submitted it for MS analysis. The MS results showed a tryptic peptide that matched the N-terminus beginning and the C-terminus end of the amino acid sequence of the NRPS. Therefore we concluded that the full length NRPS is present in the eluent, and proceeded with the in vitro reconstitution using this full length and degraded NRPS mixture.

In vitro reconstitution of bgc35. The in vitro reconstitution reaction was set up as follows: 75 mM Tris-HCl pH 8.0, 10 mM MgCl2, 0.1 mM CoA, 1 mM Amino Acid Mixture, 1 mM NADPH, 10 µM NRPS enzyme, 0.1 µM sfp and 5 mM ATP in a total volume of 200 µL. The entire reaction excluding ATP was incubated at 37° C. for 30 minutes before adding the ATP. After addition of ATP, the reaction was incubated at 37° C. overnight. The next day, the reaction was quenched by addition 200 µL EA and mixing vigorously on the vortex. The mixture was spun at 10,000×g for 5 minutes, and the top layer (EA) was collected and removed by rotary evaporation. The dried crude was resuspended in 40 µL of 20% DMSO in 80% MeOH and spun at 21,000 g for 10 minutes on the microcentrifuge. A 10 µL portion of the supernatant was sent for LC-MS for analysis.

Identification of compounds from the native organism harboring the gene cluster. Glycerol stocks containing *Clostridium* sp. KLE1755 and *Ruminococcus* sp. 5_1_39BFAA were streaked on pre-reduced EG blood agar plates (Recipe for 1L: 2.8 g Lab Lemco Powder, 10 g Protease Peptone No. 3, 5 g Yeast Extract, 4 g Na2HPO4, 1.5 g D(+)-Glucose, 0.5 g Soluble Starch, 0.2 g L-cystine, 0.5 g L-cysteine.HCl.H2O, 0.5 g Tween 80, 16 g Bacto Agar, 5% Horse Blood, pH 7.6-7.8) and grown for 2 days at 37° C. in an anaerobic chamber. After 2 days, the resulting colonies were inoculated into 6 mL of twelve different pre-reduced liquid media (Anaerobic Basal Broth, BHI Broth, Casman Broth Base, Columbia Broth, Cooked Meat Medium, M17 Broth, Marine Broth, Nutrient Basal Broth, Reinforced Clostridium Media, Tryptic Soy Broth, TYG broth, Wilkins Chalgren Anaerobic Base Broth) and incubated for another 2 days at 37° C. anaerobically. Media without the reducing agent L-cysteine in the ingredients were supplemented with L-cysteine for a final concentration of 0.05% (w/v). After another 2 days, some of the liquid cultures showed turbidity (not all media resulted in growth): *Clostridium* sp. KLE1755 grew in TYG, TSB, RCM and M17. *Ruminococcus* sp. 5_1_39BFAA grew in RCM, TYG, ABB, Columbia, M17, WCABB, Casman and TSB. Cultures in which the bacterial species grew were centrifuged at 3200 g for 5 minutes, and 5 ml of the supernatant was extracted with 5 ml of EA. This mixture was spun down for 10 minutes at 3200 g. The top layer was transferred to 5 ml glass vials and solvent was removed by rotary evaporation. The crude was resuspended in 100 µL 20% DMSO in MeOH. The resuspended extract was centrifuged at 21,000 g for 10 minutes on the microcentrifuge and a 10 µL portion of the supernatant was injected for LC-MS analysis.

Detailed procedure for isolation of secondary metabolites. Purification of EA fraction was carried on by gradient HPLC on a C18 reverse phase column (Phenomenex Luna 5 µm C18 (2), 250×10 mm) with a flow rate of 5.0 ml/min. The gradient system was MeCN (solvent B) and H2O (solvent A).

Purification of compounds 1-5 from bgc35. Compounds 1 to 5 were identified in the metabolite profiles of the *E. coli* mutant strains heterologously expressing bgc35. The gradient condition for semi-preparative HPLC separation of the crude of the bgc35 heterologous expressing strain was 0-5 min 100% A, 5-29 min 100-20% A, 29-30 min 20-0% A, 30-31 min 0-100% A, 31-32 min 100% A. Compound 3 (1.68 mg/L of culture) was eluted at 20.11 min. Compounds 1 (0.45 mg/L of culture) and 2 (1.20 mg/L of culture) are in a mixed fraction which was further purified using gradient 0-2 min 100% A, 2-3 min 100-67% A, 3-21 min 67% A, 21-22 min 67-0% A, 22-23 min 0% A, 23-24 min 100% A. Compounds 4 and 5 were eluted at 14.0 and 15.7 min, respectively. Compounds 4 and 5 are mixed and the gradient for further purification is 0-2 min 100% A, 2-3 min 100-62.5% A, 3-20 min 62.5% A, 20-21 min 62.5-0% A, 21-22 min 0-100% A. Compounds 4 (2.05 mg/L of culture) and 5 (2.78 mg/L of culture) were eluted at 18.09 and 19.59 min, respectively.

Purifications of compounds 6-13 from bgc52. The gradient for purifying compounds from bgc52 was the same as that was used for bgc35. Compound 6 (1.00 mg/L of culture) was eluted at 18.71 min. Compound 7 (3.13 mg/L of culture) was eluted at 19.59 min. Compound 8 (1.64 mg/L of culture) was eluted at 20.11 min. Compound 13 was eluted at 23.60 min. Compounds 9 and 10 were eluted in the same fraction which was further purified using gradient 0-3 min 100% A, 3-5 min 100-44% A, 5-10 min 44-43% A, 10-11 min 0% A, 11-12 min 0-100% A, 12-13 min 100% A. The same gradient was used to purify fraction containing compounds 11 and 12. The four compounds [9 (1.13 mg/L of culture), 10 (1.19 mg/L of culture), 11 (1.12 mg/L of culture), 12 (1.25 mg/L of culture)] were eluted at 8.90, 9.12, 9.35, 9.70 min, respectively.

Purifications of compound 14 from bgc38. The gradient purifying the crude from the mutant strains carrying bgc38 is 0-5 min 100% A, 5-23 min 100-40% A, 23-24 min 40-0% A, 24-25 min 0-100% A, 25-26 min 100% A. Compound 14 (1.23 mg/L of culture) was eluted at 20.10 min.

Purifications of compounds 15 and 16 from bgc33. Sixteen L of bgc33 were extracted with EA and dried by rotary evaporation. The EA extract was purified by reversed-phase preparative HPLC using a gradient of 10% acetonitrile/90% H2O containing 0.1% acetic acid to 100% acetonitrile in 24 minutes (10 mL/min). Fractions containing 15 and 16 were purified by reversed-phase HPLC (Phenomenex Luna C18, 250×10 mm, 5 μm) using a gradient of 10% methanol/90% H2O containing 0.1% acetic acid to 40%/60% in 3 minutes, followed by a gradient to 100% methanol in 22 minutes. Fractions containing 15 and 16 were subjected to additional reversed-phase HPLC (Phenomenex Kinetex Biphenyl C18, 250×10 mm, 5 μm) using a gradient of 10% acetonitrile/90% H2O containing 0.1% acetic acid to 70%/30% in 25 minutes, followed by 100% acetonitrile in 1 minute, yielding 15 (RT 18.5 min, 0.09 mg/L of culture) and 16 (RT 22.6 min, 0.31 mg/L of culture).

Synthesis of Boc-Val-Phe-H, Boc-Leu-Phe-H, and Boc-Phe-Phe-H. Boc-Val-OH (286.7 mg, 1.32 mmol, 1.0 equiv.) and 2-amino-3-phenyl-1-propanol (200 mg, 1.32 mmol, 1.0 equiv.) were dissolved in DMF (10 mL) and then EtN(iPr)2 (0.5 ml, 2.9 mmol, 2.2 equiv.) and HATU (500 mg, 1.32 mmol, 1 equiv.) were added. The reaction was stirred for 2 h at room temperature. 50 ml ddH2O was added to quench the reaction and the mixture was extracted with equal amount of EA, twice. The EA layer was washed by brine, dried by adding anhydrous Na2SO4, followed by concentration using rotary evaporation. The crude was purified by flash column chromatography on silica gel to give Boc-Val-Phe-OH (256.5 mg). Boc-Val-Phe-OH (99 mg, 0.28 mmol, 1.0 equiv.) was dissolved in DMF (2 ml) and Dess-Martin periodinane (360 mg, 0.85 mmol, 3.0 equiv.) was added. The reaction was stirred for 3 h at room temperature. 50 ml water was added to quench the reaction and the mixture was extracted with equal volume of EA twice. The EA layer was washed by brine and dried by anhydrous Na2SO4. The concentrated EA crude was further purified by HPLC using Phenomenex Luna C18 (250×10 mm, 5 μm). The HPLC gradient for purification is 0-3 min 80% A, 3-10 min 80-5% A, 10-13 min 5-80% A at a flow rate of 5 ml/min (Solvent A: H2O; Solvent B: MeCN). Fractions were collected in a time-based manner and individual fraction was examined by LCMS. Fractions containing targeted aldehyde compounds were collected and concentrated via freeze-drying to yield Boc-Val-Phe-H (white powder, 21.0 mg).

The aforementioned procedure was applied to synthesize and purify Boc-Leu-Phe-H and Boc-Phe-Phe-H. Boc-Leu-OH (305.3 mg, 1.32 mmol, 1.0 equiv.) was used as a starting material to give 267.1 mg Boc-Leu-Phe-OH. Then 100 mg of Boc-Leu-Phe-OH was oxidized to give Boc-Leu-Phe-H (white powder, 75.3 mg). For the synthesis of Boc-Phe-Phe-H, Boc-Phe-OH (350.2 mg, 1.32 mmol, 1.0 equiv.) was used as a starting material and 197.9 mg of Boc-Phe-Phe-OH was obtained. 100 mg of Boc-Phe-Phe-OH was then oxidized to give Boc-Phe-Phe-H (white powder, 66.5 mg).

Deprotection of Boc-protected dipeptide aldehyde compounds. All the deprotection experiments were performed in an anaerobic chamber. Trifluoroacetic acid (TFA) was added to the purified Boc-protected dipeptidyl aldehydes. 1 μL of the reaction was added to 100 μL 80% DMSO in ddH2O and a 0.5 μL portion of the solution was examined by an Agilent 6530 qTOF LC/MS. For preparing dipeptide aldehyde solution for protease inhibition assays, the deprotection reaction was left at 30° C. for 15 mins. Then ddH2O was added to quench the reaction and give a 2.5 mM peptidyl aldehydes in 1% TFA solution. Some side products like isobutylene and their corresponding imine and pyrazinone products have poor water solubility. The imine and pyrazinone compounds will precipitate in the solution. The reaction was centrifuged for 5 min at 16,000 g and the supernatant was given for protease assay immediately.

HRESIMS analyses of peptidyl aldehydes after deprotection (FIGS. 10A-10C). Val-Phe-H (aldehyde): HRESIMS [M+H]$^+$ m/z found 249.1609, calcd for C14H21N2O2 249.1603; Val-Phe-DHPZN (imine): HRESIMS [M+H]$^+$ m/z found 231.1491, calcd for C14H19N2O 231.1497; Val-Phe-PZN (pyrazinone, compound 10): HRESIMS [M+H]$^+$ m/z found 229.1348, calcd for C14H17N2O 229.1341.Leu-Phe-H: HRESIMS [M+H]$^+$ m/z found 263.1787, calcd for C15H23N2O2 263.1760; Leu-Phe-DHPZN (imine): HRESIMS [M+H]$^+$ m/z found 245.1679, calcd for C15H21N2O 245.1654; Leu-Phe-PZN (compound 12): HRESIMS [M+H]$^+$ m/z found 243.1518, calcd for C15H19N2O 243.1497. Phe-Phe-H: HRESIMS [M+H]$^+$ m/z found 297.1600, calcd for C18H21N2O2 297.1603; Phe-Phe-DHPZN (imine): HRESIMS [M+H]$^+$ m/z found 279.1498, calcd for C18H19N2O 279.1497; N (compound 5): HRESIMS [M+H]$^+$ m/z found 277.1348, calcd for C18H17N2O 277.1341. The structures of peptide aldehydes after deprotection were verified by HRMS and HRMS-MS analyses. These compounds will fragment in a characterized manner as shown in FIGS. 10A-10C.

To estimate the stability (half-life) of deprotected peptide aldehyde compounds, 50% aqueous DMSO (for dissolving pyrazinone compounds with poor water solubility) in 50 mM potassium phosphate buffer (pH 7.2) was prepared. 1% of the reaction solution (in TFA) was added to the prepared buffer to yield a 1% TFA solution (pH 7.0). At different time points, 20 μL of the mixed solution was injected into LCMS using the method as aforementioned. The amount of pyrazinone type compounds was measured by EIC as shown in FIGS. 10A-10C.

Detailed procedures for protease inhibition assays. Enzymes: cathepsin L, cathepsin B, cathepsin C and cathepsin S were purchased from R&D Systems trypsin, chymotrypsin and calpain I were purchased from Sigma-Aldrich. Calpain I was also purchased from Abcam. Human 20s proteasome was purchased from Boston Biochem.

Substrates: z-FR-AMC, Boc-IEGR-AMC, Suc-ALPF-AMC and GR-AMC were purchased from Bachem. Suc-LLVY-AMC was purchased from Anaspec. Substrates were used without further purification.

Inhibitors: Carfilzomib was a generous gift from Onyx Pharmaceuticals and was used as a positive control in the proteasome inhibition assay. Pefabloc was purchased from Sigma-Aldrich and used as a positive control in the inhibition assays of trypsin and chymotrypsin. Leupeptin and Chymostatin were purchased from Research Products International. Leupeptin was used as a positive control in the inhibition assays of cathepsin B, cathepsin L, cathepsin S, and human calpain I. Chymostatin, as a positive control, was used in the inhibition assay of cathepsin C.

Enzyme assays: cathepsin L (0.02 μg/ml) and cathepsin B (0.2 μg/ml) were assayed in 50 mM MES buffer (pH 5.5) containing 5 mM DTT, using z-FR-AMC at 20 μM. Trypsin (3 μg/ml) was assayed in 40 mM Tris (pH 7.8), 0.01 M CaCl2 using Boc-IEGR-AMC (10 μM). Chymotrypsin (30 ng/μl) was assayed in 40 mM Tris (pH 7.8), 0.1 M CaCl2 with Suc-ALPF-AMC (10 μM) Human 20S proteasome was pre-activated for 1 hr in 20 mM Tris (pH 8.0), 0.5 mM EDTA, and 0.03% SDS at 10 nM prior to dilution to 1 nM for assays with Suc-LLVY-AMC (10 µM) Calpain I (10 µg/ml) was assayed in 20 mM Imidazole (pH 7.5), 5 mM DTT, 5 mM CaCl2 with Suc-LLVY-AMC (10 µM) Cathepsin S was pre-activated for two hours at 10 µg/ml in 50 mM MES buffer (pH 5.5), 5 mM DTT, and then diluted to 100 ng/ml for assays with z-FR-AMC (10 µM) Cathepsin C/DPPI (200 µg/ml) was incubated with cathepsin L (20 µg/ml) in 25 mM MES (pH 5.5) 5 mM DTT for 1 hour prior to dilution to 0.25 ng/µl in 25 mM MES (pH 5.5), 5 mM DTT, 50 mM NaCl for assays with GR-AMC (10 Normalized enzyme activity data were fit using GraphPad Prism version 5.0 for Windows, GraphPad Software, La Jolla Calif. USA, www.graphpad.com.

References: Adams, J., Behnke, M., Chen, S., Cruickshank, A. A., Dick, L. R., Grenier, L., Klunder, J. M., Ma, Y.-T., Plamondon, L., and Stein, R. L. (1998). Potent and selective inhibitors of the proteasome: Dipeptidyl boronic acids. Bioorganic & Medicinal Chemistry Letters 8, 333-338. Aoyagi, T., Miyata, S., Nanbo, M., Kojima, F., Matsuzaki, M., Ishizuka, M., Takeuchi, T., and Umezawa, H. (1969a). Biological activities of leupeptins. The Journal of Antibiotics 22, 558-568. Aoyagi, T., Takeuchi, T., Matsuzaki, A., Kawamura, K., Kondo, S., Hamada, M., Maeda, K., and Umezawa, H. (1969b). Leupeptins, new protease inhibitors from actinomycetes. The Journal of Antibiotics 22, 283-286. Backus, K. M., Correia, B. E., Lum, K. M., Forli, S., Horning, B. D., Gonzalez-Paez, G. E., Chatterjee, S., Lanning, B. R., Teijaro, J. R., Olson, A. J., et al. (2016). Proteome-wide covalent ligand discovery in native biological systems. Nature 534, 570-574. Blattner, S., Das, S., Paprotka, K., Eilers, U., Krischke, M., Kretschmer, D., Remmele, C. W., Dittrich, M., Müller, T., Schuelein-Voelk, C., et al. (2016). *Staphylococcus aureus* Exploits a Non-ribosomal Cyclic Dipeptide to Modulate Survival within Epithelial Cells and Phagocytes. PLoS Pathog 12, e1005857-23. Correia, B. E., Lum, K. M., Forli, S., Horning, B. D., Gonzalez-Páez, G. E., Chatterjee, S., Lanning, B. R., Teijaro, J. R., Olson, A. J., Wolan, D. W., et al. (2016). Proteome-wide covalent ligand discovery in native biological systems. Nature 534, 570-574. Donia, M. S., and Fischbach, M. A. (2015). HUMAN MICROBIOTA. Small molecules from the human microbiota. Science (New York, N.Y. 349, 1254766-1254766. Donia, M. S., Cimermancic, P., Schulze, C. J., Wieland Brown, L. C., Martin, J., Mitreva, M., Clardy, J., Linington, R. G., and Fischbach, M. A. (2014). A Systematic Analysis of Biosynthetic Gene Clusters in the Human Microbiome Reveals a Common Family of Antibiotics. Cell 158, 1402-1414. Franzosa, E. A., Morgan, X. C., Segata, N., Waldron, L., Reyes, J., Earl, A. M., Giannoukos, G., Boylan, M. R., Ciulla, D., Gevers, D., et al. (2014). Relating the metatranscriptome and metagenome of the human gut. Proceedings of the National Academy of Sciences of the United States of America 111, E2329-E2338. Fung, T. C., Artis, D., and Sonnenberg, G. F. (2014). Anatomical localization of commensal bacteria in immune cell homeostasis and disease. Immunological Reviews 260, 35-49. Gosalbes, M. J., Durbán, A., Pignatelli, M., Abellan, J. J., Jiménez-Hernández, N., Pérez-Cobas, A. E., Latorre, A., and Moya, A. (2011). Metatranscriptomic Approach to Analyze the Functional Human Gut Microbiota. PLoS ONE 6, e17447-e17449. Hershberg, R. M., Framson, P. E., Cho, D. H., Lee, L. Y., Kovats, S., Beitz, J., Blum, J. S., and Nepom, G. T. (1997). Intestinal epithelial cells use two distinct pathways for HLA class II antigen processing. J Clin Invest 100, 204-215. Katunuma, N. (2011). Structure-based development of specific inhibitors for individual cathepsins and their medical applications. Proc. Jpn. Acad., Ser. B 87, 29-39. Laine, D. I., and Busch-Petersen, J. (2010). Inhibitors of cathepsin C (dipeptidyl peptidase I). Expert Opinion on Therapeutic Patents 20, 497-506. Lee, D. H., and Goldberg, A. L. (1998). Proteasome inhibitors: valuable new tools for cell biologists. Trends in Cell Biology 8, 397-403. Lee, W.-J., and Hase, K. (2014). Gut microbiota-generated metabolites in animal health and disease. Nature Chemical Biology 10, 416-424. MacDonald, J. C., Bishop, G. G., and Mazurek, M. (1976). 13C and proton NMR spectra of 2(1H)pyrazinones. Tetrahedron 32, 655-660. Maslowski, K. M., Vieira, A. T., Ng, A., Kranich, J., Sierro, F., Yu, D., Schilter, H. C., Rolph, M. S., Mackay, F., Artis, D., et al. (2009). Regulation of inflammatory responses by gut microbiota and chemoattractant receptor GPR43. Nature 461, 1282-1286. Matsumoto, F., Saitoh, S.-I., Fukui, R., Kobayashi, T., Tanimura, N., Konno, K., Kusumoto, Y., Akashi-Takamura, S., and Miyake, K. (2008). Cathepsins are required for Toll-like receptor 9 responses. Biochemical and Biophysical Research Communications 367, 693-699. Medema, M. H., Takano, E., and Breitling, R. (2013). Detecting sequence homology at the gene cluster level with MultiGeneBlast. Mol Biol Evol 30, 1218-1223. Mehdi, S., Angelastro, M. R., Wiseman, J. S., and Bey, P. (1988). Inhibition of the proteolysis of rat erythrocyte membrane proteins by a synthetic inhibitor of calpain. Biochemical and Biophysical Research Communications 157, 1117-1123. Nayfach, S., Fischbach, M. A., and Pollard, K. S. (2015). MetaQuery: a web server for rapid annotation and quantitative analysis of specific genes in the human gut microbiome. Bioinformatics 31, 3368-3370. Nicholson, J. K., Holmes, E., Kinross, J., Burcelin, R., Gibson, G., Jia, W., and Pettersson, S. (2012). Host-Gut Microbiota Metabolic Interactions. Science (New York, N.Y. 336, 1262-1267. Nielsen, H. B., Almeida, M., Juncker, A. S., Rasmussen, S., Li, J., Sunagawa, S., Plichta, D. R., Gautier, L., Pedersen, A. G., Le Chatelier, E., et al. (2014). Identification and assembly of genomes and genetic elements in complex metagenomic samples without using reference genomes. Nature Biotechnology 32, 822-828. Obata, T., Goto, Y., Kunisawa, J., Sato, S., Sakamoto, M., Setoyama, H., Matsuki, T., Nonaka, K., Shibata, N., Gohda, M., et al. (2010). Indigenous opportunistic bacteria inhabit mammalian gut-associated lymphoid tissues and share a mucosal antibody-mediated symbiosis. Proceedings of the National Academy of Sciences of the United States of America 107, 7419-7424. Otto, H.-H., and Schirmeister, T. (1997). Cysteine Proteases and Their Inhibitors. Chemical Reviews 97, 133-172. Park, B., Brinkmann, M. M., Spooner, E., Lee, C. C., Kim, Y.-M., and Ploegh, H. L. (2008). Proteolytic cleavage in an endolysosomal compartment is required for activation of Toll-like receptor 9. Nat Immunol 9, 1407-1414. Rosenberger, C. M., and Finlay, B. B. (2003). Phagocyte sabotage: disruption of macrophage signalling by bacterial pathogens. Nature Reviews 4, 385-396. Siklos, M., BenAissa, M., and Thatcher, G. R. J. (2015). Cysteine proteases as therapeutic targets: does selectivity matter? A systematic review of calpain and cathepsin inhibitors. Acta Pharmaceutica Sinica B 5, 506-519. Thompson, R. C. (1973). Use of peptide aldehydes to generate transition-state analogs of elastase. Biochemistry 12, 47-51. Westerik, J. O., and Wolfenden, R. (1972). Aldehydes as inhibitors of papain. The Journal of Biological Chemistry 247, 8195-8197. Woo, J.-T., Sigeizumi, S., Yamaguchi, K., Sugimoto, K., Kobori, T., Tsuji, T., and Kondo, K. (1995). Peptidyl aldehyde derivatives as potent and selective inhibitors of cathepsin L. Bioorganic &

Medicinal Chemistry Letters 5, 1501-1504. Wyatt, M. A., and Magarvey, N. A. (2013). Optimizing dimodular nonribosomal peptide synthetases and natural dipeptides in an *Escherichia coli* heterologous host. Biochemistry and Cell Biology 91, 203-208. Wyatt, M. A., Mok, M. C. Y., Junop, M., and Magarvey, N. A. (2012a). Heterologous Expression and Structural Characterisation of a Pyrazinone Natural Product Assembly Line. Chembiochem 13, 2408-2415. Wyatt, M. A., Mok, M. C. Y., Junop, M., and Magarvey, N. A. (2012b). Heterologous expression and structural characterisation of a pyrazinone natural product assembly line. Chembiochem 13, 2408-2415. Zimmermann, M., and Fischbach, M. A. (2010a). A family of pyrazinone natural products from a conserved nonribosomal peptide synthetase in *Staphylococcus aureus*. Chemistry & Biology 17, 925-930. Zimmermann, M., and Fischbach, M. A. (2010b). A Family of Pyrazinone Natural Products from a Conserved Nonribosomal Peptide Synthetase in *Staphylococcus aureus*. Chemistry & Biology 17, 925-930.

NMR Tables

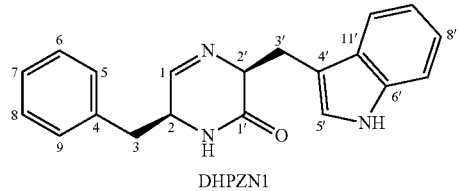

DHPZN1

TABLE 6

NMR data for compound 1 (600 and 100 MHz in DMSO-$d_6$)

| Position | δH (J in Hz) | δC | HMBC[a] | COSY |
|---|---|---|---|---|
| 1 | 7.44, m | 128.6, CH | 2' | H-2, |
| 2 | 3.53, m | 58.6, CH | | H-1, H$_2$-3 |
| 3 | 3.16, dd (12.0, 6.0) 3.03, dd (12.0, 6.0) | 40.6, CH$_2$ | 2, 4, 5, 6, 8, 9, 11 | H-2 |
| 4 | — | 138.3, C | | |
| 5 | 7.38, d (12.0) | 128.6, CH | 4, 6 | H-6 |
| 6 | 7.29, m | 129.4, CH | 5, 7 | H-5, H-7 |
| 7 | 7.28, m | 126.4, CH | 6, 8 | H-6, H-8 |
| 8 | 7.29, m | 129.4, CH | 7, 9 | H-7, H-9 |
| 9 | 7.38, d (12.0) | 128.6, CH | 4, 8 | H-8 |
| 1' | | 171.5, C | | |
| 2' | 3.71, m | 53.11, CH | 1', 3, 4' | H$_2$-3' |
| 3' | 2.77, d (12.0) 2.88, dd (12.0, 6.0) | 26.4, CH$_2$ | 1', 2', 4', 11' | H-2' |
| 4' | — | 107.8, C | | |
| 5' | 7.29, s | 126.6, CH | 3' | |
| 6' | — | 135.6, C | | |
| 7' | 7.24, d (12.0) | 111.2, CH | 6', 8', 9', | H-8' |
| 8' | 7.00, t (12.0) | 120.7, CH | 6', 7' | H-7' |
| 9' | 6.95, t (12.0) | 118.4, CH | 10', 11' | H-8' |
| 10' | 7.34, br d (12.0) | 117.4, CH | 9', 11' | H-9' |
| 11' | — | 134.9, C | | |
| 5'-NH | 10.73, s | — | 4', 5', 6', 11' | |

The absolute configuration was inferred from its biosynthetic origin.
[a]HMBC correlations are from proton(s) to the indicated carbon.
[b]The carbon can be identified in the HMBC spectrum.

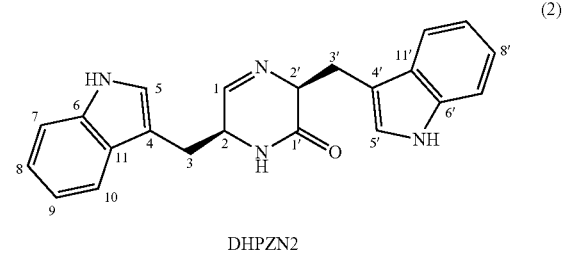 [SMILES: O=C1N[C@@H](Cc2c[nH]c3ccccc23)C=N[C@H]1Cc1c[nH]c2ccccc12]

DHPZN2

TABLE 7

NMR data for compound 2 (600 and 100 MHz in DMSO-$d_6$)

| Position | δH (J in Hz) | δC | HMBC[a] | COSY |
|---|---|---|---|---|
| 1 | 7.56, m | 119.3, CH | 2' | H-2 |
| 2 | 3.53, m | 58.8, CH | | H-1, H$_2$-3 |
| 3 | 3.33 3.08, dd (12.0, 6.0) | 30.8, CH$_2$ | 2, 4, 5, 11 | H-2 |
| 4 | — | 111.2, C | | |
| 5 | 7.29, s | 123.9, CH | 4, 6, 11 | |
| 6 | — | 136.7, C | | |
| 7 | 7.39, d (12.0) | 111.9, CH | 6, 9 | H-8 |
| 8 | 7.10, t (12.0) | 121.5, CH | 10, 11 | H-7, H-9 |
| 9 | 7.02, t (12.0) | 118.9, CH | 6, 8 | H-8, H-10 |
| 10 | 7.66, d (12.0) | 119.0, CH | 8, 11 | H-9 |
| 11 | — | 128.3, C | | |
| 1' | — | 172.0, C | | |
| 2' | 3.75, d (6.0) | 53.6, CH | 1', 3', 4' | H$_2$-3' |
| 3' | 2.77, d (12.0) 2.90, dd (12.0, 6.0) | 26.8, CH$_2$ | 1', 2', 4', 6' | H-2' |
| 4' | — | 107.1, C | | |
| 5' | 7.29, s | 123.9, CH | | |
| 6' | — | 136.0, C | | |
| 7' | 7.22, d (12.0) | 111.6, CH | 6', 9' | H-8' |
| 8' | 7.00, t (12.0) | 121.1, CH | 10', 11' | H-7', H-9' |
| 9' | 6.92, t (12.0) | 118.7, CH | 6, 8' | H-8', H-10' |
| 10' | 7.35, d (12.0) | 117.9, CH | 8', 11' | H-9' |
| 11' | — | 127.1, C | | |
| 5-NH | 10.94, s | — | 4, 5, 6, 11 | |
| 5'-NH | 10.72, s | — | 4', 5', 6', 11' | |

The absolute configuration was inferred from its biosynthetic origin.
[a]HMBC correlations are from proton(s) to the indicated carbon.
[b]The carbon can be identified in the HMBC spectrum.

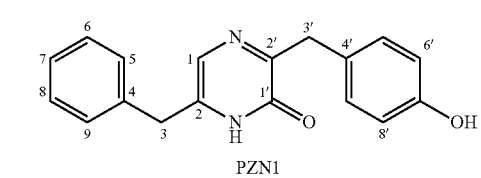

PZN1

TABLE 8

NMR data for compound 3 (500 and 100 MHz in DMSO-$d_6$)

| Position | δH (J in Hz) | δC | HMBC[a] | COSY |
|---|---|---|---|---|
| 1 | 6.95, br s | 120.4 CH[b] | 2, 4 | |
| 2 | — | 128.1, C | | |
| 3 | 3.75, s | 36.1, CH$_2$[b] | 1, 2, 4, 5, 9 | |
| 4 | — | 137.6, C | | |

TABLE 8-continued

NMR data for compound 3 (500 and 100 MHz in DMSO-$d_6$)

| Position | δH (J in Hz) | δC | HMBC[a] | COSY |
|---|---|---|---|---|
| 5 | 7.31, m | 128.5, CH | 4, 6, 7, 8 | H-6 |
| 6 | 7.31, m | 128.7, CH | | H-5, H-7 |
| 7 | 7.23, m | 126.7, CH | 6, 8 | H-6, H-8 |
| 8 | 7.32, m | 128.7, CH | | H-7, H-9 |
| 9 | 7.31, m | 128.5, CH | 4, 6, 7, 8 | H-8 |
| 1' | — | 155.7, C | | |
| 2' | — | 155.7, C | | |
| 3' | 3.80, s | 37.5, CH$_2$ | 1', 2', 5', 9' | |
| 4' | — | 135.7, C[b] | | |
| 5' | 7.03, dd (10.0, 5.0) | 129.9, CH | 3', 4', 6', 7' | H-6' |
| 6' | 6.63, dd (10.0, 5.0) | 114.9, CH | 5', 7', 8' | H-5', H-7' |
| 7' | — | 156.1, C | — | H-6', H-8' |
| 8' | 6.63, dd (10.0, 5.0) | 114.9, CH | 6', 7', 9' | H-7', H-9' |
| 9' | 7.03, dd (10.0, 5.0) | 129.9, CH | 3', 4', 7', 8' | H-8' |
| 7'-OH | 9.15, s | — | | |

[a]HMBC correlations are from proton(s) to the indicated carbon.
[b]The carbon can be identified in the HSQC or HMBC spectrum.

(4)

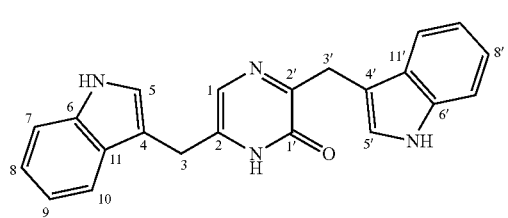

PZN2

TABLE 9

NMR data for compound 4 (500 and 100 MHz in DMSO-$d_6$)

| Position | δH (J in Hz) | δC | HMBC[a] | COSY |
|---|---|---|---|---|
| 1 | 7.12, br s[c] | 124.0, CH | | |
| 2 | — | 139.0, C[b] | | |
| 3 | 3.74, s | 26.3, CH$_2$ | 1, 2, 4, 5, 11 | |
| 4 | — | 110.0, C[b] | | |
| 5 | 7.26, br s | 124.5, CH | 4, 6, 11 | |
| 6 | — | 136.6, C | | |
| 7 | 7.34, d (10.0) | 112.0, CH | 8, 9 | H-8 |
| 8 | 6.96, m | 119.0, CH | 7, 9 | H-7, H-9 |
| 9 | 7.06, m | 121.2, CH | 10 | H-8, H-10 |
| 10 | 7.51, d (10.0) | 118.8, CH | 4, 6, 9, 11 | H-9 |
| 11 | — | 127.0, C | | |
| 1' | — | 156.5, C | | |
| 2' | — | 156.5, C | | |
| 3' | 4.01, s | 28.9, CH$_2$ | 1', 4', 5', 11' | |
| 4' | — | 111.0, C | | |
| 5' | 7.10, br s[c] | 124.0, CH | 3', 4', 6', 11' | |
| 6' | — | 136.5, C | | |
| 7' | 7.31, m | 111.7, CH | 8' | H-8' |
| 8' | 6.90, m | 118.7, CH | 7' | H-7', H-9' |
| 9' | 7.01, m | 121.6, CH | 10', 6' | H-8', H-10' |
| 10' | 7.54, d (10.0) | 119.3, CH | 4', 6', 9' | H-9' |
| 11' | — | 127.8, C | | |
| 2-NH | 12.22, s | — | | |
| 5-NH | 10.93 br s | — | 4, 5, 6, 11 | |
| 5'-NH | 10.80, br s | — | 4', 5', 6', 11' | |

[a]HMBC correlations are from proton(s) to the indicated carbon.
[b]The carbon can be identified in the HMBC spectrum.
[c]These signals are interchangeable in the NMR spectrum.

(5)

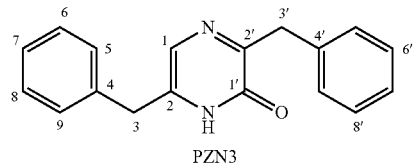

PZN3

TABLE 10

NMR data for compound 5 (500 and 100 MHz in DMSO-$d_6$)

| Position | δH (J in Hz) | δC | HMBC[a] | COSY |
|---|---|---|---|---|
| 1 | 7.10, s | 122.0, CH | 2, 3, 4 | |
| 2 | — | 139.4, C[b] | | |
| 3 | 3.77, s | 36.1, CH$_2$ | 2, 4, 5, 9 | |
| 4 | — | 137.9, C | | |
| 5 | 7.31, m | 129.2, CH | 3, 4, 6, 7 | H-6 |
| 6 | 7.32, m | 128.6, CH | 5, 7, 8 | H-5, H-7 |
| 7 | 7.23, m | 127.2, CH | 6, 8 | H-6, H-8 |
| 8 | 7.32, m | 128.6, CH | 6, 7, 9 | H-7, H-9 |
| 9 | 7.31, m | 129.2, CH | 3, 4, 7, 8 | H-8 |
| 1' | — | 156.7, C | | |
| 2' | — | 155.6, C[b] | | |
| 3' | 3.92, s | 38.7, CH$_2$ | 2', 4', 5', 9' | |
| 4' | — | 138.7, C | | |
| 5' | 7.25, m | 129.4, CH | 3', 4', 6', 7' | H-6' |
| 6' | 7.26, m | 129.0, CH | 5', 7', 8' | H-5', H-7' |
| 7' | 7.17, m | 126.6, CH | 6', 8' | H-6', H-8' |
| 8' | 7.26, m | 129.0, CH | 6', 7', 9' | H-7', H-9' |
| 9' | 7.25, m | 129.4, CH | 3', 4', 7', 8' | H-8' |

[a]HMBC correlations are from proton(s) to the indicated carbon.
[b]The carbon can be identified in the HSQC and HMBC spectrum.

(6)

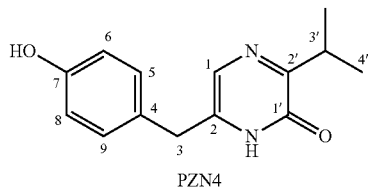

PZN4

TABLE 11

NMR data for compound 6 (500 and 100 MHz in DMSO-$d_6$)

| Position | δH (J in Hz) | δC |
|---|---|---|
| 1 | 7.07, br s | 120.0, CH |
| 2 | — | 138.3, C[a] |
| 3 | 3.61, s | 34.6, CH$_2$ |
| 4 | — | 130.2, C |
| 5 | 7.09, d, (10.0) | 129.7, CH |
| 6 | 6.69, d, (10.0) | 115.3, CH |
| 7 | — | 156.1, C |
| 8 | 6.69, d, (10.0) | 115.3, CH |
| 9 | 7.09, d, (10.0) | 129.7, CH |
| 1' | — | 155.6, C |
| 2' | — | 161.0, C[a] |
| 3' | 3.22, m | 29.2, CH |
| 4' | 1.09, dd (10.0, 5.0) | 20.0, CH$_3$ |
| 5' | 1.09, dd (10.0, 5.0) | 20.0, CH$_3$ |
| 7-OH | 9.30, s | — |
| 2-NH | 12.14, s | — |

[a]The carbon can be identified in the HSQC and HMBC spectrum.

(7)

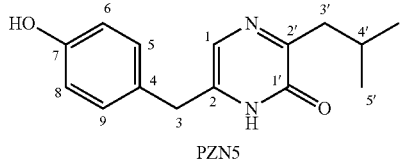

PZN5

TABLE 12

NMR data for compound 7 (500 and 100 MHz in CD₃OD)

| Position | δH (J in Hz) | δC | HMBC[a] | COSY | NOESY |
|---|---|---|---|---|---|
| 1 | 7.08, s | 121.6, CH | 2, 3 | | |
| 2 | — | 139.3, C | | | |
| 3 | 3.76, s | 34.8, CH₂ | 1, 2, 4, 5, 9 | | |
| 4 | — | 126.9, C | | | |
| 5 | 7.09, d, (10.0) | 129.6, CH | 3, 6, 7 | H-6 | |
| 6 | 6.77, d, (10.0) | 115.2, CH | 4, 7, 8 | H-5 | |
| 7 | — | 156.3, C | | | |
| 8 | 6.77, d, (10.0) | 115.2, CH | 4, 6, 7 | H-9 | |
| 9 | 7.09, d, (10.0) | 129.6, CH | 3, 7, 8 | H-8 | |
| 1' | — | 157.3, C | | | |
| 2' | — | 156.6, C | | | |
| 3' | 2.60, d (10.0) | 41.1, CH₂ | 1', 2', 4', 5', 6' | H-4' | |
| 4' | 2.16, sep (10.0) | 26.7, CH | 2', 3', 5', 6' | H₂-3', H₃-5', H₃-6' | |
| 5' | 0.95, d (10.0) | 21.5, CH₃ | 3', 4', 6' | H-4', H₃-6' | H₂-3', H-4' |
| 6' | 0.95, d (10.0) | 21.5, CH₃ | 3', 4', 5' | H-4', H₃-5' | H₂-3', H-4' |

[a]HMBC correlations are from proton(s) to the indicated carbon.

(8)

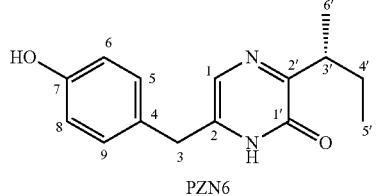

PZN6

TABLE 13

NMR data for compound 8 (600 and 100 MHz in DMSO-d₆)

| Position | δH (J in Hz) | δC | HMBC[a] | COSY | NOESY |
|---|---|---|---|---|---|
| 1 | 7.07, br s | 120.7, CH[b] | 3, 4 | | |
| 2 | — | 139.2, C | | | |
| 3 | 3.62, s | 35.2, CH₂ | 1, 2, 4, 5, 9 | | |
| 4 | — | 127.6, C | | | |
| 5 | 7.11, d (12.0) | 129.8, CH | 3, 4, 6, 7, 9 | H-6 | |
| 6 | 6.70, d (12.0) | 115.3, CH | 4, 5, 7, 8 | H-5 | |
| 7 | — | 156.6, C | | | |
| 8 | 6.70, d (12.0) | 115.3, CH | 4, 5, 7, 8 | H-9 | |
| 9 | 7.11, d (12.0) | 129.8, CH | 3, 4, 5, 7, 8 | H-8 | |
| 1' | — | 156.2, C | | | |
| 2' | — | 160.3, C | | | |
| 3' | 3.07, m | 35.7, CH | 1', 2', 4', 5', 6' | H₂-4', H₃-6' | H₂-4', H₃-5', H₃-6' |
| 4' | 1.68, m / 1.40, m | 27.0, CH₂ | 3', 5', 6' | H-3', H₃-5' | H-3', H₃-5' |
| 5' | 0.79, td (12.0, 6.0) | 11.9, CH₃ | 3', 4' | H-4' | H₂-4' |
| 6' | 1.06, dd (12.0, 6.0) | 17.8, CH₃ | 2', 3', 4' | H₂-4', H₃-6' | H-3' |

The absolute configuration was inferred from its biosynthetic origin.
[a]HMBC correlations are from proton(s) to the indicated carbon.
[b]The carbon can be identified in the HMBC spectrum.

(9)

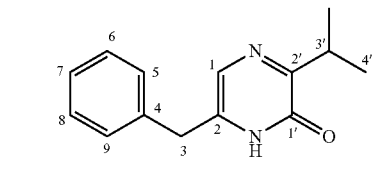

PZN7

TABLE 14

NMR data for compound 9 (600 and 100 MHz in DMSO-d₆)

| Position | δH (J in Hz) | δC | HMBC[a] | COSY |
|---|---|---|---|---|
| 1 | 7.13, br s | 120.5, CH | 2, 2', 3 | |
| 2 | — | 138.8, C[b] | | |
| 3 | 3.85, s | 26.0, CH₂ | 1, 2, 4, 5, 11 | |
| 4 | — | 109.8, C | | |
| 5 | 7.28, br s | 124.0, CH | 4, 6, 11 | 5-NH |
| 6 | — | 136.2, C | | |
| 7 | 7.35, d (12.0) | 111.5, CH | 9, 10, 11 | H-8 |
| 8 | 7.07, t (12.0) | 121.2, CH | 6, 9, 10 | H-7, H-9 |
| 9 | 6.98, t (12.0) | 118.6, CH | 7, 11 | H-8, H-10 |
| 10 | 7.55, d (12.0) | 118.4, CH | 4, 5, 6, 11 | H-9 |
| 11 | — | 126.7, C | | |
| 1' | — | 155.9, C | | |
| 2' | — | 160.1, C[b] | | |
| 3' | 3.23, m | 29.2, CH | 1', 2', 4', 5' | H₃-4', H₃-5' |
| 4' | 1.07, d (12.0) | 20.1, CH₃ | 2', 3', 5' | H₃-3' |
| 5' | 1.07, d (12.0) | 20.1, CH₃ | 2', 3', 4' | H₃-4' |
| 5-NH | 10.94, s | | | H-5 |

[a]HMBC correlations are from proton(s) to the indicated carbon.
[b]The carbon can be identified in the HMBC spectrum.

(10)

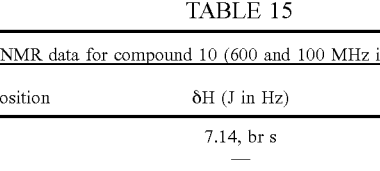

PZN8

TABLE 15

NMR data for compound 10 (600 and 100 MHz in DMSO-d₆)

| Position | δH (J in Hz) | δC |
|---|---|---|
| 1 | 7.14, br s | 121.7, CH |
| 2 | — | 138.5, C[a] |

TABLE 15-continued

NMR data for compound 10 (600 and 100 MHz in DMSO-$d_6$)

| Position | δH (J in Hz) | δC |
|---|---|---|
| 3 | 3.76, s | 36.0, $CH_2$ |
| 4 | — | 138.1, C |
| 5 | 7.32, m | 129.2, CH |
| 6 | 7.32, m | 129.0, CH |
| 7 | 7.24, m | 127.1, CH |
| 8 | 7.32, m | 129.0, CH |
| 9 | 7.32, m | 129.2, CH |
| 1' | — | 156.1, C |
| 2' | — | 161.0, $C^a$ |
| 3' | 3.23, sep (10.0) | 29.8, CH |
| 4' | 1.10, d (10.0) | 20.5, $CH_3$ |
| 5' | 1.10, d (10.0) | 20.5, $CH_3$ |
| 2-NH | 12.08, s | |

$^a$The carbon can be identified in the HMBC spectrum.

(11)

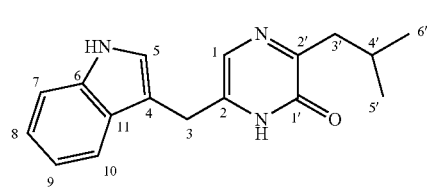

PZN9

TABLE 16

NMR data for compound 11 (600 and 100 MHz in DMSO-$d_6$)

| Position | δH (J in Hz) | δC | HMBC$^a$ | COSY |
|---|---|---|---|---|
| 1 | 7.10, br s | 121.1, CH | 2, 3, 5, 2' | |
| 2 | — | 139.7, $C^b$ | | |
| 3 | 3.85, s | 26.3, $CH_2$ | 1, 2, 4, 5, 11 | |
| 4 | — | 109.9, C | | |
| 5 | 7.26, br s | 123.9, CH | 4, 6, 11 | 5-NH |
| 6 | — | 136.2, CH | | |
| 7 | 7.37, d (12.0) | 111.5, CH | 9, 10, 11 | H-8 |
| 8 | 7.08, t (12.0) | 121.1, CH | 6, 9, 10 | H-7, H-9 |
| 9 | 6.98, t (12.0) | 118.5, CH | 7, 11 | H-8, H-10 |
| 10 | 7.54, d (12.0) | 118.3, CH | 4, 5, 6, 11 | H-9 |
| 11 | — | 126.7, C | | |
| 1' | — | 155.0, $C^b$ | | |
| 2' | — | 157.5, $C^b$ | | |
| 3' | 2.44, d (6.0) | 41.0, $CH_2$ | 1', 2', 4', 5', 6' | H-4' |
| 4' | 2.07, sep (6.0) | 26.0, CH | 3', 5', 6' | H-3', $H_3$-5', $H_3$-6' |
| 5' | 0.85, d (6.0) | 22.5, $CH_3$ | 3', 4', 6' | H-4', $H_3$-6' |
| 6' | 0.85, d (6.0) | 22.5, $CH_3$ | 3', 4', 5' | $H_2$-4', $H_3$-5' |
| 5-NH | 10.95, s | | 4, 6, 11 | H-5 |

$^a$HMBC correlations are from proton(s) to the indicated carbon.
$^b$The carbon can be identified in the HMBC spectrum.

(12)

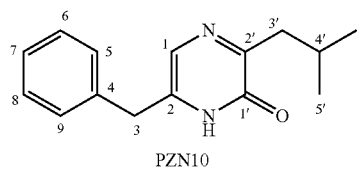

PZN10

TABLE 17

NMR data for compound 12 (600 and 100 MHz in DMSO-$d_6$)

| Position | δH (J in Hz) | δC | HMBC$^a$ | COSY |
|---|---|---|---|---|
| 1 | 7.12, s | 121.6, CH | | |
| 2 | — | 139.5, $C^b$ | | |
| 3 | 3.75, s | 36.1, $CH_2$ | 1, 2, 4, 5, 9 | |
| 4 | — | 138.0, C | | |
| 5 | 7.31, m | 129.2, CH | 3, 4, 6, 7, 9 | H-6 |
| 6 | 7.31, m | 129.0, CH | 4, 5, 7, 8 | H-5, H-7 |
| 7 | 7.24, m | 127.2, CH | 5, 6, 8, 9 | H-6, H-8 |
| 8 | 7.31, m | 129.0, CH | 4, 5, 7, 8 | H-7, H-9 |
| 9 | 7.31, m | 129.2, CH | 3, 4, 5, 7, 8 | H-8 |
| 1' | — | 156.8, C | | |
| 2' | — | 156.5, $C^b$ | | |
| 3' | 2.46 d (10.0) | 41.0, $CH_2$ | 1', 2', 4', 5', 6' | H-4' |
| 4' | 2.09, m | 26.0, CH | 3', 5', 6' | H-3', $H_3$-5', $H_3$-6' |
| 5' | 0.86, d (10.0) | 23.0, $CH_3$ | 3', 4', 6' | H-4' |
| 6' | 0.86, d (10.0) | 23.0, $CH_3$ | 3', 4', 6' | H-4' |
| 2-NH | 12.15, s | — | | |

$^a$HMBC correlations are from proton(s) to the indicated carbon.
$^b$The carbon can be identified in the HMBC spectrum.

(13)

PZN11

TABLE 18

NMR data for compound 13 (600 and 100 MHz in DMSO-$d_6$)

| Position | δH (J in Hz) | δC | HMBC$^a$ | COSY | NOESY |
|---|---|---|---|---|---|
| 1 | 7.14, br s | 121.5, CH | | | |
| 2 | — | 138.0, C | | | |
| 3 | 3.76, s | 36.1, $CH_2$ | 1, 2, 4, 5, 9 | | H-5, H-9 |
| 4 | — | 138.0, C | | | |
| 5 | 7.31, m | 129.2, CH | 3, 4, 6, 7, 9 | H-6 | $H_2$-3 |
| 6 | 7.31, m | 129.0, CH | 4, 5, 7, 8 | H-5, H-7 | |
| 7 | 7.24, m | 127.2, CH | 5, 6, 8, 9 | H-6, H-8 | |
| 8 | 7.31, m | 129.0, CH | 4, 5, 7, 8 | H-7, H-9 | |
| 9 | 7.31, m | 129.2, CH | 3, 4, 5, 7, 8 | H-8 | $H_2$-3 |
| 1' | — | 156.4, C | | | |
| 2' | — | 160.2, $C^b$ | | | |
| 3' | 3.07, m | 36.2, CH | 1', 2', 4', 5', 6' | $H_2$-4', $H_3$-6' | |
| 4' | 1.40, m<br>1.68, m | 27.5, $CH_2$ | 2', 3', 5', 6' | H-3', $H_3$-5' | |
| 5' | 0.79, t (10.0) | 12.3, $CH_3$ | 3', 4' | H-4' | |
| 6' | 1.07, d (5.0) | 18.2, $CH_3$ | 2', 3', 4' | $H_2$-4', $H_3$-6' | |
| 2-NH | 12.12, s | — | | | |

$^a$HMBC correlations are from proton(s) to the indicated carbon.
$^b$The carbon can be identified in the HMBC spectrum.

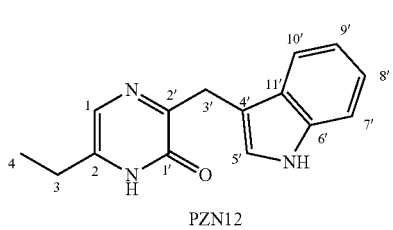

PZN12 (14)

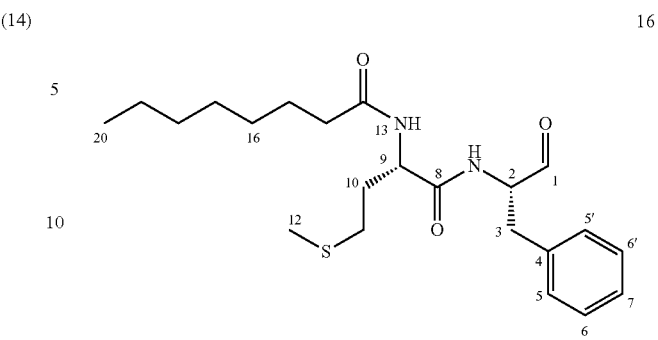

16

TABLE 19

NMR data for compound 14 (600 and 100 MHz in DMSO-$d_6$)

| Position | δH (J in Hz) | δC | HMBC[a] | COSY |
|---|---|---|---|---|
| 1 | 7.04, br s | 120.8, CH | | |
| 2 | — | 140.2, C | | |
| 3 | 2.39, q (12.0) | 23.0, $CH_2$ | 1, 2, 4 | $H_3$-4 |
| 4 | 1.12, t (12.0) | 12.9, $CH_3$ | 2, 3 | $H_2$-3 |
| 1' | — | 156.1, C | | |
| 2' | — | 158.6, C | | |
| 3' | 4.01, s | 28.4, $CH_2$ | 1', 2', 4', 5', 6' | |
| 4' | — | 110.6, CH | | |
| 5' | 7.13, br s | 123.6, CH | 4', 6', 11' | 5'-NH |
| 6' | — | 136.0, C | | |
| 7' | 7.31, d (12.0) | 111.2, CH | 10', 11' | H-8' |
| 8' | 7.03, t (12.0) | 120.8, CH | 6', 10 | H-7', H-9' |
| 9' | 6.93, t (12.0) | 118.2, CH | 7', 11 | H-8', H-10' |
| 10' | 7.55, d (12.0) | 118.8, CH | 4', 5', 6', 11' | H-9' |
| 11' | — | 127.3, C | | |
| 5'-NH | 10.80, s | — | | |

[a]HMBC correlations are from proton(s) to the indicated carbon.

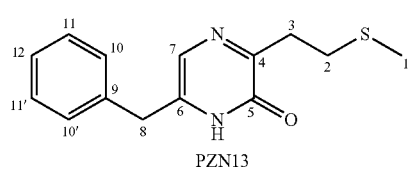

PZN13 (15)

TABLE 20

NMR data for compound 15 (500 and 125 MHz in $CDCl_3$)

| Position | δH (J in Hz) | δC | HMBC[a] | COSY |
|---|---|---|---|---|
| 1 | 2.14, s | 15.5, $CH_3$ | 2 | |
| 2 | 2.88, t (7.3) | 30.9, $CH_2$ | 1, 3, 4 | 3 |
| 3 | 3.06, t (7.3) | 32.5, $CH_2$ | 2, 5 | 2 |
| 4 | — | 156.0, C | | |
| 5 | — | 156.1, C | | |
| 6 | — | 137.0, C | | |
| 7 | 7.23, s | 122.3, CH | 4, 6 | |
| 8 | 3.82, s | 36.6, $CH_2$ | 6, 7, 9, 10, 10' | |
| 9 | — | 135.3, C | | |
| 10, 10' | 7.27, m | 129.2, CH | 8, 12 | |
| 11, 11' | 7.31, m | 129.1, CH | 9, 10, 10', 11, 11' | |
| 12 | 7.27, m | 128.0, C | 10, 10' | |

[a]HMBC correlations are from proton(s) to the indicated carbon.

TABLE 21

NMR data for compound 16 (500 and 125 MHz in $CDCl_3$)

| Position | δH (J in Hz) | δC | HMBC[a] | COSY |
|---|---|---|---|---|
| 1 | 9.59, s | 198.4, CH | | |
| 2 | 4.67, q (7.3) | 59.7, CH | 1, 3, 4, 8 | 3, 8-NH |
| 3 | 3.17, dd (6.2, 14.3) | 34.9, $CH_2$ | 1, 2, 4, 5, 5' | 2 |
|   | 3.03, dd (6.2, 14.3) | | | |
| 4 | — | 135.4, C | | |
| 5, 5' | 7.14, m | 129.1, CH | 3, 6, 6', 7 | 6, 6' |
| 6, 6' | 7.29, m | 129.0, CH | 4, 5, 5' | 5, 5' |
| 7 | 7.23, m | 127.3, CH | 5, 5', 6, 6' | |
| 8-NH | 6.86, m | | 8 | 2 |
| 8 | | 171.3, C | | |
| 9 | 4.60, q (7.3) | 51.8, CH | 8, 10, 13 | 10, 13-NH |
| 10 | 1.95, m | 31.2, $CH_2$ | 8, 9, 11 | 9, 11 |
|   | 1.85, m | | | |
| 11 | 2.42, m | 29.9, $CH_2$ | 9, 10, 12 | 10 |
|   | 2.26, m | | | |
| 12 | 2.03, s | 15.2, $CH_3$ | 11 | |
| 13-NH | 6.22, d (7.7) | | 13 | 9 |
| 13 | — | 173.1, C | | |
| 14 | 2.15, m | 36.4, $CH_2$ | 13, 15, 16 | 15 |
| 15 | 1.57, m | 25.5, $CH_2$ | 13, 14, 16 | 14, 16 |
| 16 | 1.25, m | 28.9, $CH_2$ | | 15 |
| 17 | 1.25, m | 28.9, $CH_2$ | | |
| 18 | 1.23, m | 31.6, $CH_2$ | | |
| 19 | 1.25, m | 22.6, $CH_2$ | 17, 19, 20 | 20 |
| 20 | 0.82, m | 14.0, $CH_3$ | 18, 19 | 19 |

[a]HMBC correlations are from proton(s) to the indicated carbon.

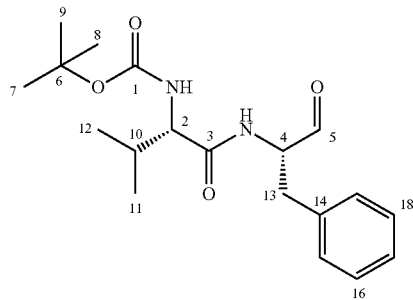

16

-continued

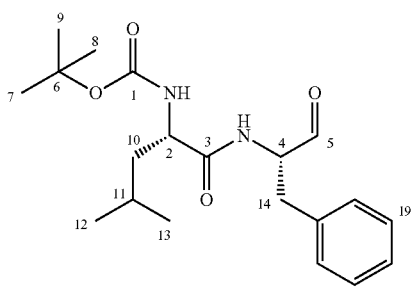

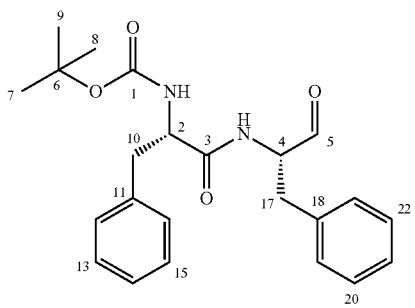

TABLE S22

NMR data for Boc-Val-Phe-H, Boc-Leu-Phe-H, and Boc-Phe-Phe-H (600 MHz in DMSO-d$_6$)

| Position | δH (J in Hz) | δH (J in Hz) | δH (J in Hz) |
|---|---|---|---|
| 1 | — | — | — |
| 2 | 4.35, br s | 4.28, br s | 4.75, br s |

TABLE S22-continued

NMR data for Boc-Val-Phe-H, Boc-Leu-Phe-H, and Boc-Phe-Phe-H (600 MHz in DMSO-d$_6$)

| Position | δH (J in Hz) | δH (J in Hz) | δH (J in Hz) |
|---|---|---|---|
| 3 | — | — | — |
| 4 | 3.99, m | 3.96, m | 4.19, m |
| 5 | 9.45, s | 9.44, s | 9.38, s |
| 6 | — | — | — |
| 7 | 1.38, s | 1.37, s | 1.28, br s |
| 8 | 1.38, s | 1.37, s | 1.28, br s |
| 9 | 1.38, s | 1.37, s | 1.28, br s |
| 10 | 1.86, m | 1.99, m | 3.00, m$^a$ 2.65, m |
| 11 | 0.76, d (12.0)$^a$ | 1.47, m | — |
| 12 | 0.68, d (12.0)$^a$ | 0.86, d (12.0)$^a$ | 7.20, m |
| 13 | 2.92, m 2.82, m | 0.80, d (12.0)$^a$ | 7.20, m |
| 14 | — | 3.15, m 2.82, m | 7.20, m |
| 15 | 7.23, m | — | 7.20, m |
| 16 | 7.23, m | 7.23, m | 7.20, m |
| 17 | 7.23, m | 7.23, m | 3.00, m$^a$ 2.65, m |
| 18 | 7.23, m | 7.23, m | — |
| 19 | 7.23, m | 7.23, m | 7.20, m |
| 20 | NA | 7.23, m | 7.20, m |
| 21 | NA | NA | 7.20, m |
| 22 | NA | NA | 7.20, m |
| 23 | NA | NA | 7.20, m |
| 1-NH | 8.31, br s | 8.25, br s | 8.42, br s |
| 3-NH | 6.63, br s | 6.87, br s | 6.97, br s |

$^a$These signals are interchangeable.
NA: not available

What is claimed is:

1. A method of treating cancer, said method comprising administering to a subject in need thereof an effective amount of a compound, or pharmaceutically acceptable salt thereof, having the formula:

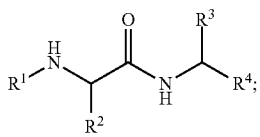

wherein R¹ is independently hydrogen, —C(O)R¹ᶜ, unsubstituted alkyl, unsubstituted cycloalkyl, unsubstituted heterocycloalkyl, unsubstituted aryl, or unsubstituted heteroaryl;
R¹ᶜ is unsubstituted alkyl;
R² is independently an amino acid side chain,
R³ is independently an amino acid side chain, wherein R³ is not

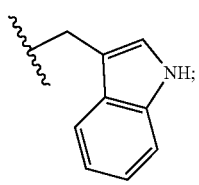 [SMILES: *Cc1c[nH]c2ccccc12]

R⁴ is —C(O)H, or —B(OH)₂.

2. A method of inhibiting cathepsin activity, said method comprising: contacting the cathepsin with a compound, or pharmaceutically acceptable salt thereof, having the formula:

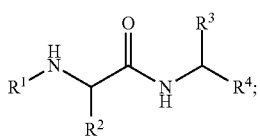

wherein R¹ is independently hydrogen, —C(O)R¹ᶜ, —C(O)—OR¹ᶜ, unsubstituted alkyl, unsubstituted cycloalkyl, unsubstituted heterocycloalkyl, unsubstituted aryl, or unsubstituted heteroaryl;
R¹ᶜ is unsubstituted alkyl;
R² is independently an amino acid side chain,
R³ is independently an amino acid side chain, wherein R³ is not

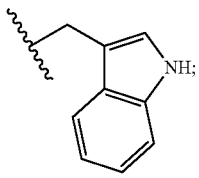 [SMILES: *Cc1c[nH]c2ccccc12]

R⁴ is —C(O)H, or —B(OH)₂.

3. A method of reducing cathepsin activity, said method comprising: contacting the cathepsin with a compound or pharmaceutically acceptable salt thereof, having the formula:

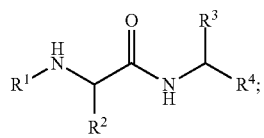

wherein R¹ is independently hydrogen, —C(O)R¹ᶜ, —C(O)—OR¹ᶜ, unsubstituted alkyl, unsubstituted cycloalkyl, unsubstituted heterocycloalkyl, unsubstituted aryl, or unsubstituted heteroaryl;
R¹ᶜ is unsubstituted alkyl;
R² is independently an amino acid side chain,
R³ is independently an amino acid side chain, wherein R³ is not

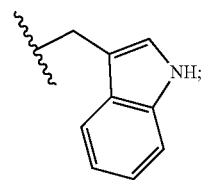

R⁴ is —C(O)H, or —B(OH)₂.

4. A method of inhibiting protease activity, said method comprising: contacting the protease with a compound or pharmaceutically acceptable salt thereof, having the formula:

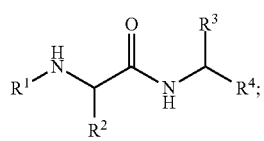

wherein R¹ is independently hydrogen, —C(O)R¹ᶜ, unsubstituted alkyl, unsubstituted cycloalkyl, unsubstituted heterocycloalkyl, unsubstituted aryl, or unsubstituted heteroaryl;
R¹ᶜ is unsubstituted alkyl;
R² is independently an amino acid side chain,
R³ is independently an amino acid side chain, wherein R³ is not

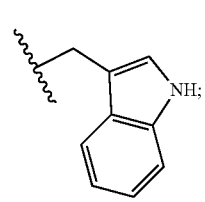 [SMILES: *Cc1c[nH]c2ccccc12]

R⁴ is —C(O)H, or —B(OH)₂.

5. The method of claim 1, wherein the compound has the formula:

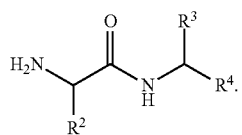

6. The method of claim 1, wherein $R^2$ is independently selected from the group consisting of H,

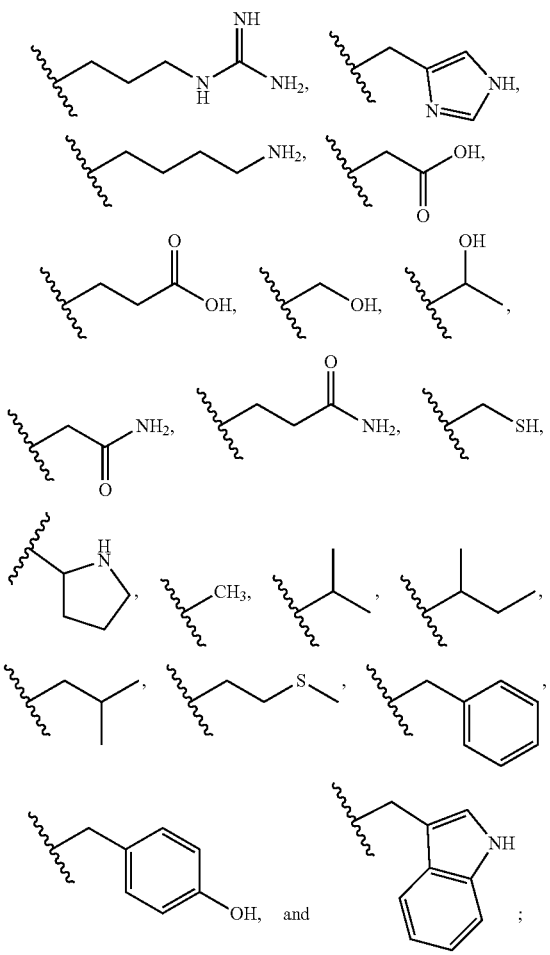

and $R^3$ is independently selected from the group consisting of H,

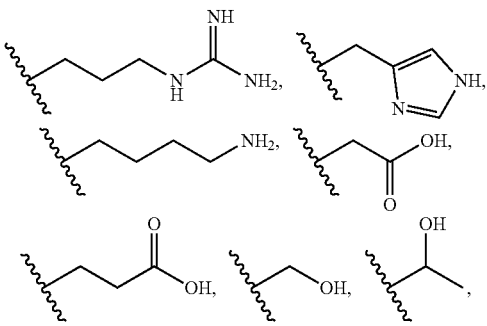

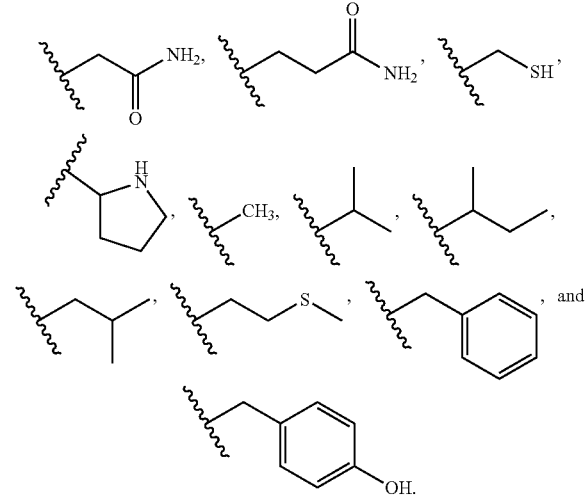

7. The method of claim 1, wherein $R^2$ is selected from the group consisting of

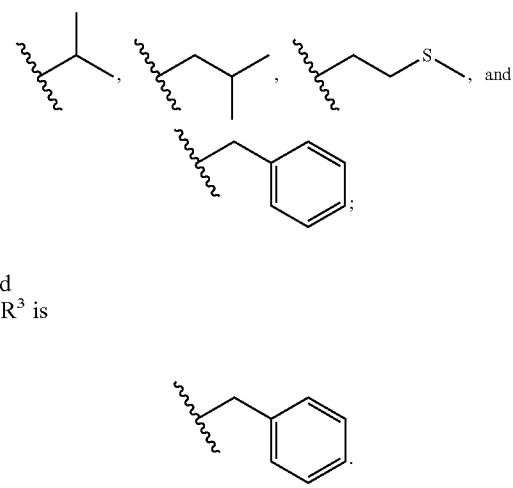

and
$R^3$ is

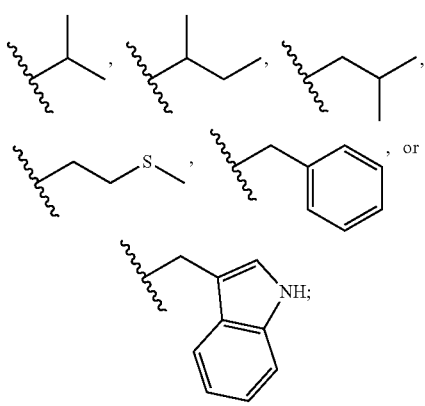

8. The method of claim 1, wherein $R^2$ is independently selected from the group consisting of and $R^3$ is independently selected from the group consisting of

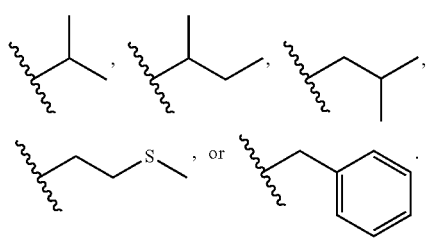
9. The method of claim 1, wherein the compound has the formula:
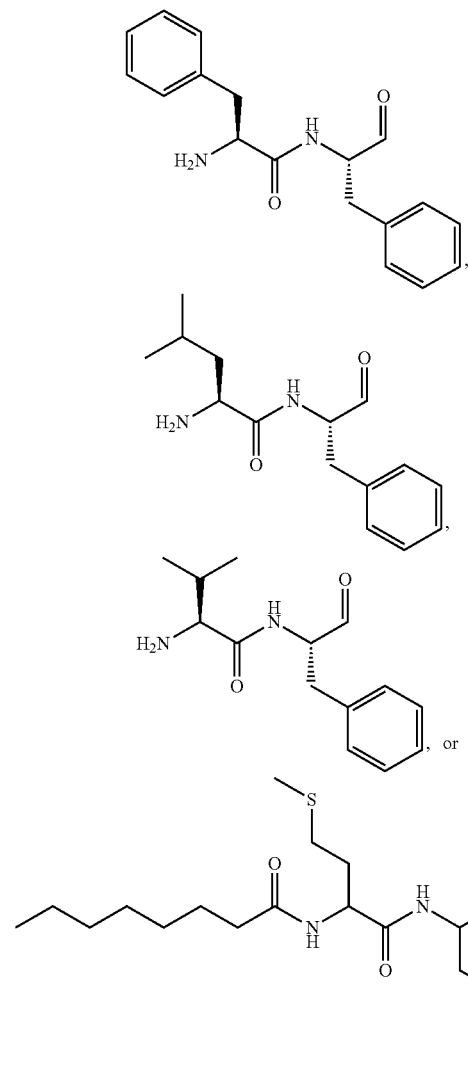
10. The method of claim 2, wherein the compound has the formula:
11. The method of claim 2, wherein $R^2$ is independently selected from the group consisting of H,
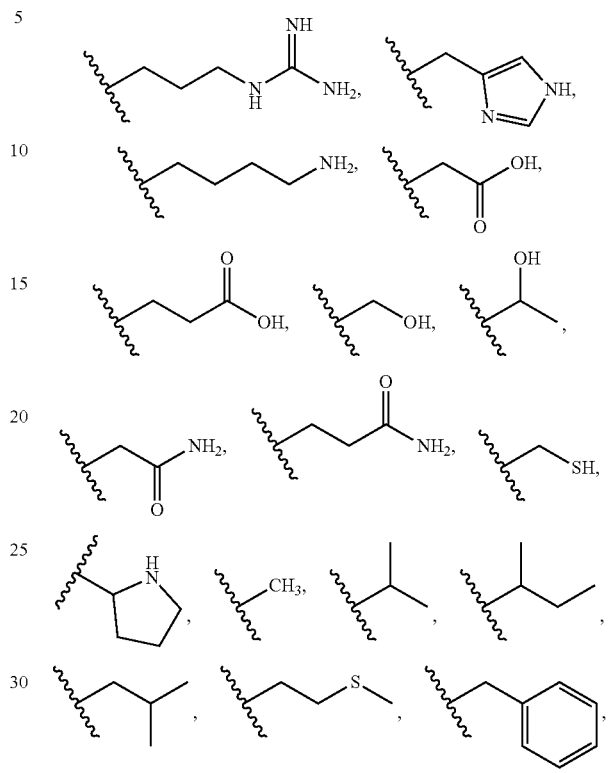
and $R^3$ is independently selected from the group consisting of H,
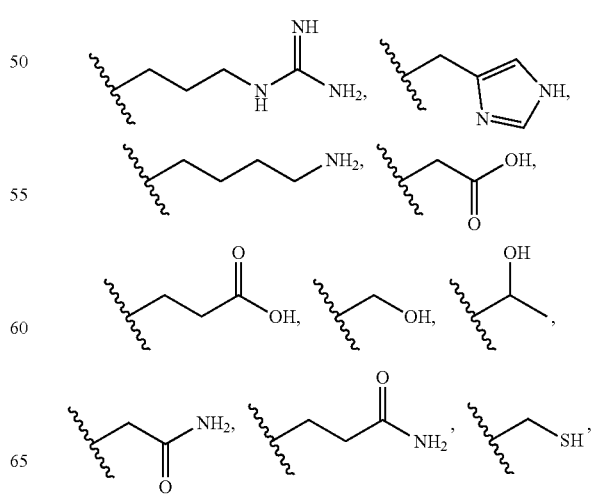

-continued
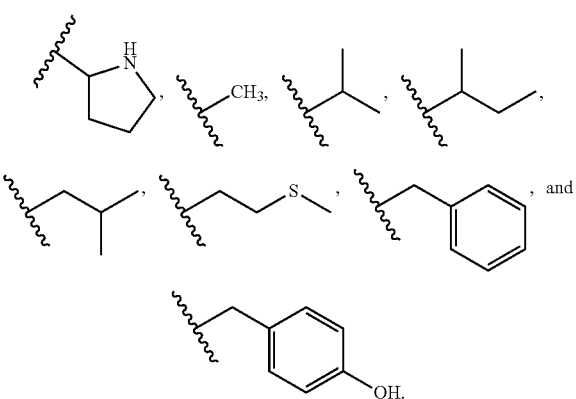
12. The method of claim 2, wherein R² is selected from the group consisting of
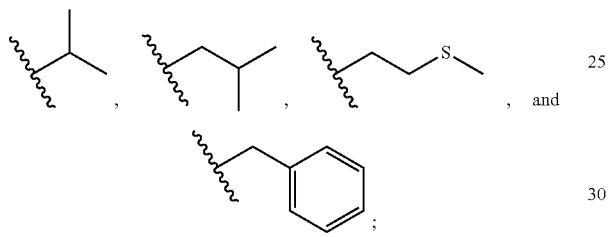
and
R³ is
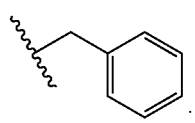
.
13. The method of claim 2, wherein R² is independently selected from the group consisting of
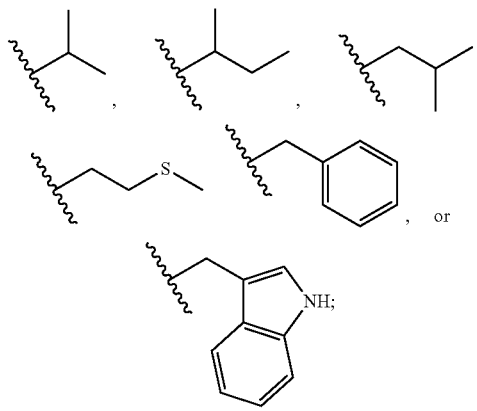
and R³ is independently selected from the group consisting of
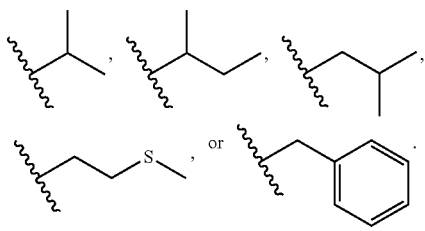
14. The method of claim 2, wherein the compound has the formula:
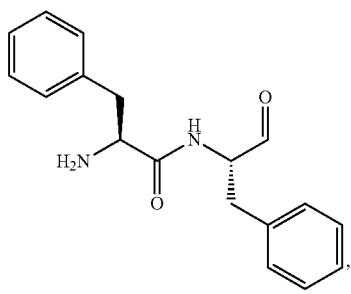
,
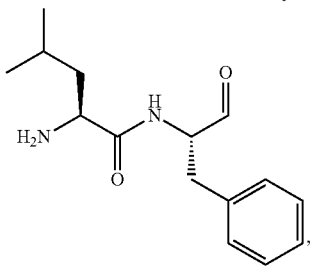
,
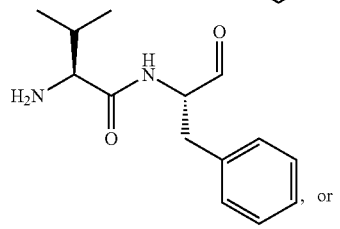
, or
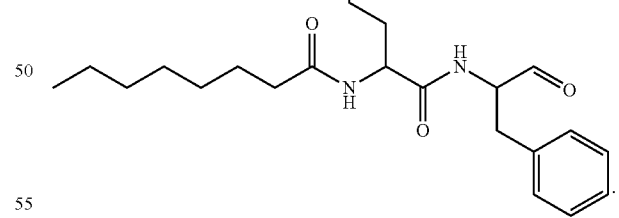
.
15. The method of claim 3, wherein the compound has the formula:
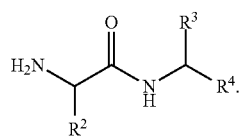

16. The method of claim 3, wherein $R^2$ is independently selected from the group consisting of H,

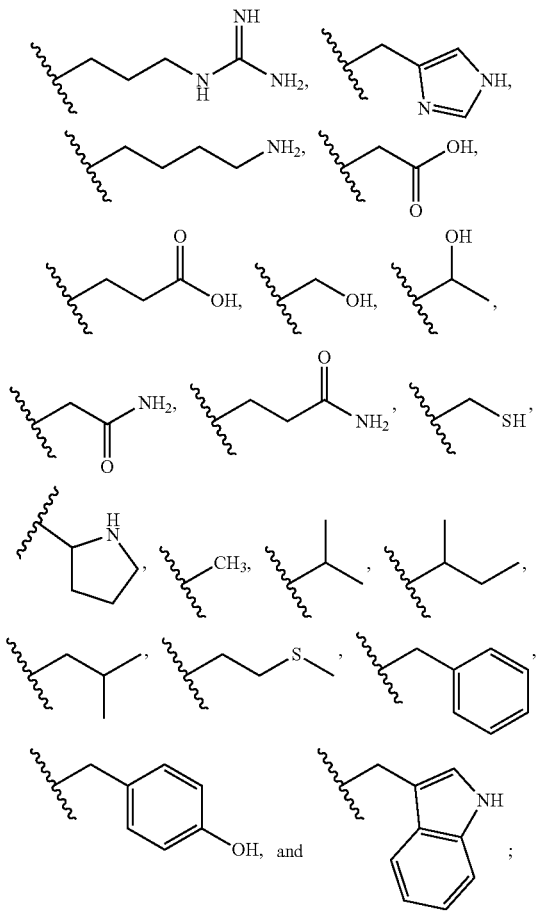

and $R^3$ is independently selected from the group consisting of H,

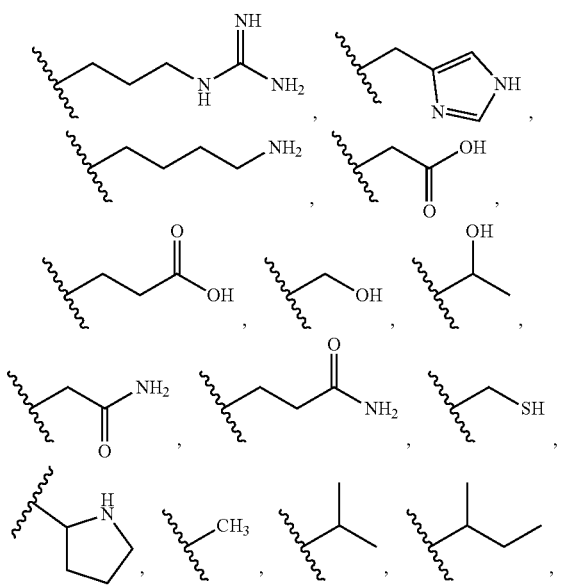

-continued

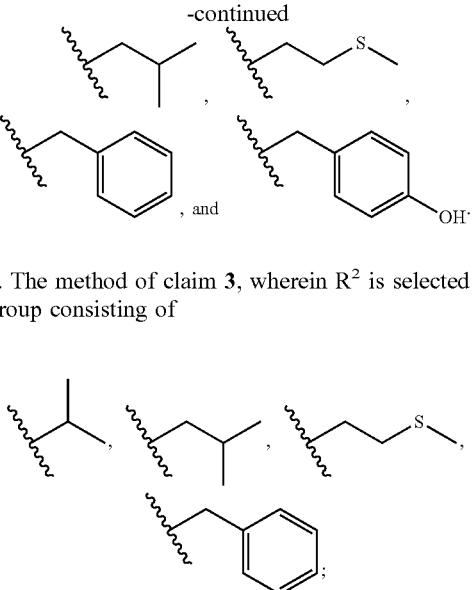

, and

17. The method of claim 3, wherein $R^2$ is selected from the group consisting of

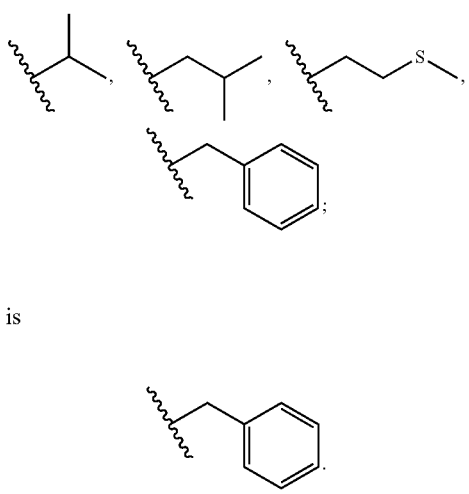

and
$R^3$ is

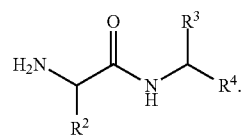

.

18. The method of claim 4, wherein the compound has the formula:

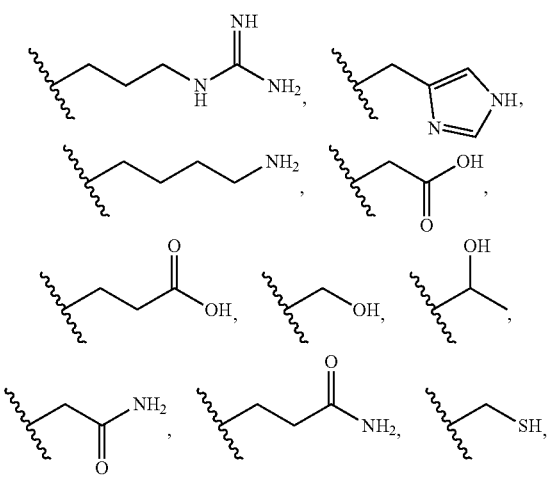

19. The method of claim 4, wherein $R^2$ is independently selected from the group consisting of H, -continued
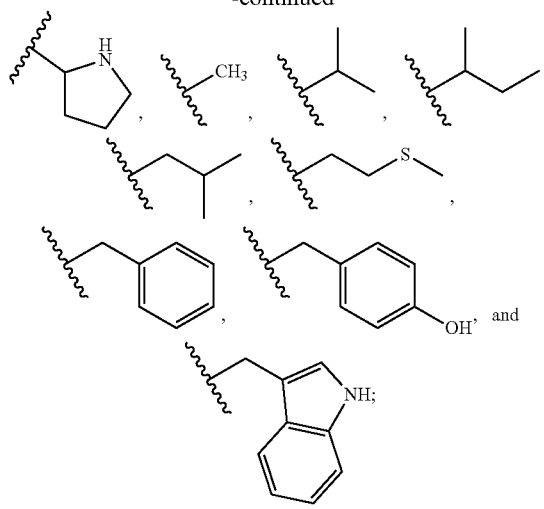
and R³ is independently selected from the group consisting of H,
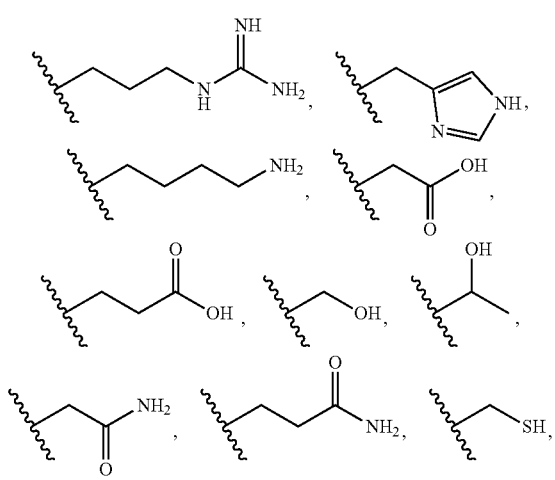
-continued
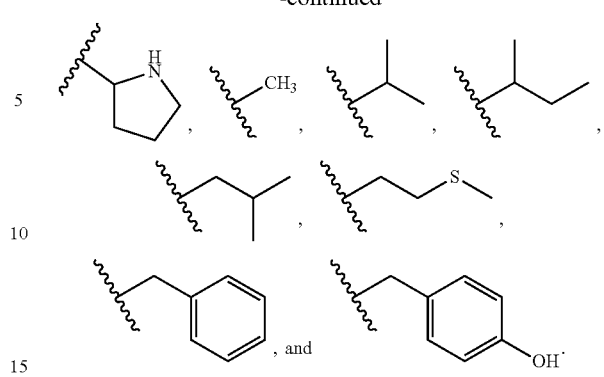
20. The method of claim 4, wherein R² is selected from the group consisting of
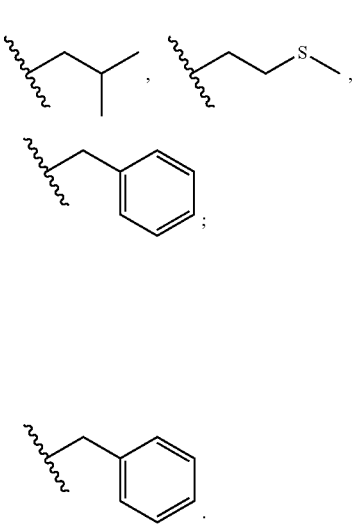
and
R³ is
* * * * *